US010993995B2

(12) United States Patent
van der Wal et al.

(10) Patent No.: US 10,993,995 B2
(45) Date of Patent: May 4, 2021

(54) ENZYMATIC REPLACEMENT THERAPY AND ANTISENSE THERAPY FOR POMPE DISEASE

(71) Applicant: Erasmus University Medical Center Rotterdam, Rotterdam (NL)

(72) Inventors: Erik van der Wal, Rotterdam (NL); Atze Jacobus Bergsma, Rotterdam (NL); Wilhelmus Wenceslaus Matthias Pijnappel, Rotterdam (NL); Antje Tjitske van der Ploeg, Rotterdam (NL); Arnoldus Reuser, Rotterdam (NL)

(73) Assignee: Erasmus University Medical Center Rotterdam, Rotterdam (NL)

( * ) Notice: Subject to any disclaimer, the term of this patent is extended or adjusted under 35 U.S.C. 154(b) by 73 days.

(21) Appl. No.: 15/781,809

(22) PCT Filed: Dec. 7, 2015

(86) PCT No.: PCT/NL2015/050849
§ 371 (c)(1),
(2) Date: Jun. 6, 2018

(87) PCT Pub. No.: WO2017/099579
PCT Pub. Date: Jun. 15, 2017

(65) Prior Publication Data
US 2018/0360927 A1    Dec. 20, 2018

(51) Int. Cl.
*A61K 38/47*    (2006.01)
*C12N 15/11*    (2006.01)
*C12N 15/113*    (2010.01)
*A61P 21/00*    (2006.01)
*A61P 3/00*    (2006.01)
*A61K 31/352*    (2006.01)

(52) U.S. Cl.
CPC ............ *A61K 38/47* (2013.01); *A61K 31/352* (2013.01); *A61P 3/00* (2018.01); *A61P 21/00* (2018.01); *C12N 15/111* (2013.01); *C12N 15/1137* (2013.01); *C12Y 302/0102* (2013.01); *C12N 2310/11* (2013.01); *C12N 2320/33* (2013.01)

(58) Field of Classification Search
None
See application file for complete search history.

(56) References Cited

U.S. PATENT DOCUMENTS 9,404,100 B2 * 8/2016 Valenzano ............... A61P 25/00
2015/0148551 A1 * 5/2015 Wegrzyn ............... A61K 31/352
549/403

FOREIGN PATENT DOCUMENTS

| WO | 2013134530 A1 | 9/2013 | |
| WO | 2013134630 A1 | 9/2013 | |
| WO | 2013182906 A1 | 12/2013 | |
| WO | 2014130723 A1 | 8/2014 | |
| WO | 2015035231 A1 | 3/2015 | |
| WO | 2015036451 A1 | 3/2015 | |
| WO | 2015036461 A1 | 3/2015 | |
| WO | WO-2015035231 A1 * | 3/2015 | ............ C07F 9/6533 |

OTHER PUBLICATIONS

Adams, Elizabeth M., et al. "Glycogenosis Type II: A Juvenile-Specific Mutation With an Unusual Splicing Pattern and a Shared Mutation in African Americans" Human Mutation, vol. 10, Issue 2, pp. 128-134, 1997.
International Search Report and Written Opinion dated Sep. 2, 2016 in International (PCT) Application No. PCT/NL2015/050849.
Zampieri, Stefania, et al. "Splicing mutations in glycogen-storage disease type II: evaluation of the full spectrum of mutations and their relation to patients' phenotypes" European Journal of Human Genetics, No. 19, pp. 422-431, 2011.

* cited by examiner

*Primary Examiner* — Heidi Reese
(74) *Attorney, Agent, or Firm* — Dentons US LLP

(57) ABSTRACT

The present invention is direct to the treatment of Pompe disease by administration of an enzyme or nucleic acid encoding for said enzyme suitable for Enzyme Replacement Therapy for Pompe disease in combination with the administration of an antisense oligomeric compound that modulates the splicing of acid alpha-glucosidase (GAA) gene.

11 Claims, No Drawings
Specification includes a Sequence Listing.

ENZYMATIC REPLACEMENT THERAPY AND ANTISENSE THERAPY FOR POMPE DISEASE

RELATED APPLICATIONS

This application is a United States National Phase under 35 U.S.C. § 371 of International Application No. PCT/NL2015/050849, filed on Dec. 7, 2015, which is hereby incorporated by reference in its entirety for all purposes.

SEQUENCE LISTING

The instant application contains a Sequence Listing which has been submitted in ASCII format via EFS-Web and is hereby incorporated by reference in its entirety. Said ASCII copy, created on Jun. 5, 2018, is named "091876-0060_Sequence-Listing.txt" and is 352,256 bytes in size.

The invention is related to a combination of enzymatic replacement therapy (ERT) or gene therapy and antisense oligonucleotides for the treatment of Pompe disease and to pharmaceutical compositions comprising the antisense oligonucleotides and enzymes. The invention is also related to a method to modulate the splicing of pre-mRNA of the GAA gene and to treatment of Pompe disease.

BACKGROUND

Pompe disease also known as acid maltase deficiency or Glycogen storage disease type II is an autosomal recessive metabolic disorder which damages many cells throughout the body and in particular muscle cells and nerve cells, but also other cells throughout the body. The damage is caused by an accumulation of glycogen in the lysosome due to a deficiency of the lysosomal enzyme acid alpha-glucosidase. The build-up of glycogen and the consequences thereof affect various body tissues, particularly, skeletal muscles, heart muscles and smooth muscles of various organs and body parts such as blood vessels, gastrointestinal tract, uterus, bladder, the liver; and the central and perferal nervous system. As a consequence the clinical symptoms are broad. Progressive skeletal muscle weakness (myopathy) is a hallmark of the disease.

In Pompe disease, a protein, acid alpha-glucosidase (EC 3.2.1.20), also known as acid maltase, which is a lysosomal hydrolase, is defective. The protein is an enzyme that normally degrades the alpha-1,4 and alpha-1,6 linkages in glycogen, maltose and isomaltose and is required for the degradation of 1-3% of cellular glycogen. The deficiency of this enzyme results in the accumulation of structurally normal glycogen in lysosomes. The defective metabolism of glycogen in the lysosomes may also lead to (secondary) storage of glycogen in the cytoplasm and autophagic build-up. Excessive glycogen storage within lysosomes may interrupt normal functioning of other organelles and lead to cellular injury.

The defective alpha-glucosidase protein or reduced amount of alpha-glucosidase protein and activity is the result of mutations (or variations) with in the GAA gene. Some of these GAA mutations may lead to alternative splicing and thereby to absent or a reduced amount of alpha-glucosidase protein or activity. The GAA gene is located on long arm of chromosome 17 at 17q25.2-q25.3 (base pair 75,689,876 to 75,708,272). The gene spans approximately 20 kb and contains 20 exons with the first exon being noncoding.

Although over 460 GAA mutations have been described (http://cluster15.erasmusmc.nl/klgn/pompe/mutations.html), only a few splicing mutations have been characterized. Severe mutations that completely abrogate GAA enzyme activity cause the classic infantile form of Pompe disease with onset of symptoms shortly after birth, hypertrophic cardiomyopathy, general skeletal muscle weakness, and respiratory failure and death within the first 1.5 years of life if left untreated. Milder mutations leave partial GAA enzyme activity and result in a milder phenotype with onset of symptoms varying from childhood to adulthood. In general, a higher residual alpha-glucosidase activity in primary fibroblasts is associated with later onset of Pompe disease.

Enzyme replacement therapy (ERT) has been developed for Pompe disease, in which recombinant human GAA protein is administered intravenously every two weeks. This treatment is aimed to increase the intracellular level of alpha-glucosidase activity in affected cells and tissues and thereby reduce or prevent glycogen storage and eventually symptoms of the disease. The treatment can rescue the lives of classic infantile patients and delay disease progression of later onset patients, but the effects are heterogeneous.

Pompe disease is an autosomal recessive inheritable disorder. One of the most common mutation in Pompe disease is the IVS1 mutation, c.-32-13T>G, a transversion (T to G) mutation and occurs among infants, children, juveniles and adults with this disorder. This mutation interrupts a site of RNA splicing.

Antisense oligonucleotides (antisense oligomeric compounds) are currently being tested in clinical trials for their ability to modulate splicing. A classical example is Duchenne muscular dystrophy. In this disease, mutation hotspots are present in certain exons. Using antisense oligomeric compounds, the mutated exon is skipped and the mutation is bypassed. This results in a slightly shorter protein that is still partial functional. It is straightforward to induce exon skipping using antisense oligomeric compounds, because it is evident that the antisense oligomeric compound must be targeted to the relevant splice site. Also in Epidermolysis bullosa (WO2013053819) and in Leber congenital amaurosis symptoms (WO2012168435) antisense oligonucleotides are used for exon skipping.

For the IVS1 mutation in Pompe, such a strategy does not work. The IVS mutation causes a skipping of exon 2 resulting in the deletion of the canonical translation start side and leads to non-sense mediated decay and thus no protein is transcribed. For antisense therapy to work for the IVS1 mutation in Pompe disease, it needs to induce exon inclusion. However, it is very difficult to induce exon inclusion, because it relies on targeting a splicing repressor sequence, which cannot be reliably predicted. For the IVS1 mutation, an antisense oligomeric compound that blocks a splicing repressor sequence may promote exon 2 inclusion in the presence of the IVS1 mutation. It is known that such repressor sequences may be present anywhere in the gene, either in an exon (termed exonic splicing silencer or ESS) or in an intron (termed intronic splicing silencer or ISS) and maybe close to the mutation or far away or maybe close to the affected splice site or far away from it.

Although a number of antisense compounds that are capable of modulating splicing of a target gene in vitro have been reported, there remains a need to identify compounds that may modulate the splicing of the GAA gene.

Enzyme replacement therapy (ERT) with acid alpha-glucosidase (GAA), has been used for infantile, childhood and adult Pompe patients also called classic infantile or infantile onset and late onset forms. The ERT modifies the natural course of the disease, however targeting of the main target tissues and cells is a challenge. For example 15-40% of the body is composed of skeletal muscle and to be corrective each individual cell in the body needs to reached. The enzyme needs to be taken up by cells via endocytosis, which seems most efficient when it is targeted to receptors on the cell surface such as the mannose 6-phosphate/IGF II receptor. This mannose 6-phosphate/IGF II receptor recognizes various ligands such as mannose 6-phosphate, IGF II and Gluc-NAC. Thus ERT with these ligands show a better uptake. The current registered ERT is targeted at the M6P part of the M6P/IGF II receptor, but there is also ERT underdevelopment with an increased amount of M6P ligands or with IGF II linked to it. Another problem with ERT is that some patients develop antibodies to the administered GAA enzyme reducing the effect of ERT and these patients respond poorly to the treatment. In addition, ERT requires purified recombinant human GAA which is difficult to make and is expensive. Furthermore, recombinant human GAA is has a relative short half life ranging and therefore must be administered intravenously every 2 weeks (or every week), which is cumbersome for patients.

It is therefore an object of the invention to provide an improved treatment for Pompe Disease. Another object of the invention is to provide an improved ERT treatment of Pompe Disease. Another object of the invention is to provide an antisense compound that is capable of targeting exonic splicing silencer (ESS) or in an intronic splicing silencer (ISS). Yet another object of the invention is to provide a antisense compound that is capable of targeting the IVS-1 mutation. It is further an object of the invention to improve the enzyme replacement therapy of GAA enzyme in patients. The present invention meets one or more of the objects.

The present invention combines two strategies which are different. ERT or gene therapy enhances the activity of glycogen breakdown administration of administration of a foreign GAA enzyme, whereas antisense therapy improves or enhances the intracellular production of the patients own GAA enzyme.

SUMMARY OF THE INVENTION

The present invention is directed to a composition for use for the treatment of Pompe disease, said composition comprising an enzyme or nucleic acid encoding for said enzyme suitable for Enzyme Replacement Therapy for Pompe disease, wherein said treatment is a combination of the administration of said enzyme or said nucleic acid encoding for said enzyme and the administration of an antisense oligomeric that modulates the splicing of acid alpha-glucosidase (GAA) enzyme.

The present invention is directed to a treatment of Pompe disease by administration of an enzyme or nucleic acid encoding for said enzyme suitable for Enzyme Replacement Therapy for Pompe disease in combination with the administration of an antisense oligomeric compound that modulates the splicing of acid alpha-glucosidase (GAA) enzyme gene.

Optionally the enzyme suitable for Enzyme Replacement Therapy for Pompe disease is an enzyme that breaks down glycogen such as acid alpha glycosidase (GAA). The nucleic acid encoding for said enzyme suitable for Enzyme Replacement Therapy for Pompe disease may be used in gene therapy. Optionally the nucleic acid is in a vector or other means that enables the translation of the enzyme. Optionally the modulation of the splicing is to increase the activity of glycogen break-down. Optionally the modulation of the splicing is to increase the activity of acid alpha-glucosidase (GAA) enzyme gene. Optionally the modulation of the splicing is to increase the activity of GAA to at least 120% of the activity of GAA enzyme without the modulation of the splicing of the GAA gene. Optionally the modulation of the splicing is to increase the activity of GAA to at least 25%% of the activity of a wild type GAA enzyme.

Optionally the antisense oligomeric compound modulates abherant splicing of acid alpha-glucosidase (GAA) enzyme gene.

Optionally the antisense oligomeric compound modulates splicing by an activity selected from the group consisting of promotion of exon inclusion, inhibition of a cryptic splicing site, inhibition of intron inclusion, recovering of reading frame, inhibition of splicing silencer sequence, activation of spicing enhancer sequence or any combination thereof.

Optionally the antisense oligomeric compound modulates splicing by promotion of exon inclusion, optionally exon 2, or exon 6.

Optionally the antisense oligomeric compound modulates splicing by inhibition of a cryptic splicing site.

Optionally the antisense oligomeric compound modulates splicing by inhibition of intron inclusion.

Optionally the antisense oligomeric compound modulates splicing by recovering of the reading frame.

Optionally the antisense oligomeric compound modulates splicing by inhibition of splicing silencer sequence.

Optionally the antisense oligomeric compound modulates splicing by activation of spicing enhancer sequence.

Optionally the antisense oligomeric compound targets a nucleic acid sequence of the GAA gene selected from the group consisting of SEQ ID NO: 1, 37-40, 1584-1589 and nucleotide polymorphism of SEQ ID NO: 1, 37-40, 1584-1589.

Optionally said enzyme or said nucleic acid encoding for said enzyme and the antisense oligomeric compound is administered simultaneously or separately. Optionally said nucleic acid encoding for said enzyme and said antisense oligomeric compound are administered simultaneously or in one treatment composition. Optionally said enzyme and said antisense oligomeric compound are administered simultaneously or in one treatment composition. Optionally said nucleic acid encoding for said enzyme and said antisense oligomeric compound are administered on separate occasions or in separate treatment compositions. Optionally said enzyme and said antisense oligomeric compound are administered on separate occasions or in separate treatment compositions. Optionally the treatment uses said enzyme and said nucleic acid encoding for said enzyme. Optionally said enzyme and said nucleic acid encoding for said enzyme are administered simultaneously or in one treatment composition. Optionally the treatment uses said enzyme and said nucleic acid encoding for said enzyme. Optionally said enzyme and said nucleic acid encoding for said enzyme are administered on separate occasions or in separate treatment compositions. Optionally said enzyme and said nucleic acid encoding for said enzyme and said antisense oligomeric compound are administered simultaneously or in one treatment composition.

Optionally the administration route is selected from the group consisting of oral, parenteral, intravenous, intra-arterial, subcutaneous, intraperitoneal, ophthalmic, intramuscular, buccal, rectal, vaginal, intraorbital, intracerebral, intradermal, intracranial, intraspinal, intraventricular, intrathecal, intracisternal, intracapsular, intrapulmonary, intranasal, transmucosal, transdermal, or via inhalation, or combinations thereof. Optionally the administration route for the enzyme or the nucleic acid encoding for said enzyme is intravenous. Optionally the administration route of said enzyme or said nucleic acid encoding for said enzyme and the administration route of said antisense oligomeric compound are the same or different. Optionally the administration route for said antisense oligomeric compound is intravenous. Optionally the administration route for said antisense oligomeric compound is orally. Optionally the administration route for the enzyme or the nucleic acid encoding for said enzyme is orally. It is explicitly envisioned to combine various administration routes in the present invention.

Optionally said enzyme or said nucleic acid encoding for said enzyme is administered once every 1, 2, 3, 4, 5, 6, 7, 8, 9, 10, 11, 12, 13, 14, 15, 16, 17, 18, 19, 20, 21, 22, 23, 24, or 25 days. Optionally said enzyme or said nucleic acid encoding for said enzyme is administered once every 1, 2, 3, 4, 5, 6, 7, 8, 9, 10, 11, 12, 13, 14, 15, 16, 17, 18, 19, 20, 21, 22, 23, 24, or 25 weeks. Optionally said enzyme or said nucleic acid encoding for said enzyme is administered once every 1, 2, 3, 4, 5, 6, 7, 8, 9, 10, 11, 12, 13, 14, 15, 16, 17, 18, 19, 20, 21, 22, 23, 24, or 25 months. Optionally said enzyme or said nucleic acid encoding for said enzyme is administered once every 1, 2, 3, 4, 5, 6, 7, 8, 9, 10, years. It is explicitly envisioned that various frequencies of administration as indicated here are combined. For example 8 weeks of administration once every week and thereafter 24 weeks of administration of once every 2 weeks.

Optionally said antisense oligomeric compound is administered once every 1, 2, 3, 4, 5, 6, 7, 8, 9, 10, 11, 12, 13, 14, 15, 16, 17, 18, 19, 20, 21, 22, 23, 24, or 25 days. Optionally said antisense oligomeric compound is administered once every 1, 2, 3, 4, 5, 6, 7, 8, 9, 10, 11, 12, 13, 14, 15, 16, 17, 18, 19, 20, 21, 22, 23, 24, or 25 weeks. Optionally said antisense oligomeric compound is administered once every 1, 2, 3, 4, 5, 6, 7, 8, 9, 10, 11, 12, 13, 14, 15, 16, 17, 18, 19, 20, 21, 22, 23, 24, or 25 months. Optionally said antisense oligomeric compound is administered once every 1, 2, 3, 4, 5, 6, 7, 8, 9, 10, years. It is explicitly envisioned that various frequencies of administration as indicated here are combined. For example 8 weeks of administration once every week and thereafter 24 weeks of administration of once every 2 weeks. 10. Also various combinations of the frequencies of administration of the antisense oligomeric compound in combination with various combination of the frequencies of administration of the said enzyme or said nucleic acid encoding for said enzyme are explicitly envisioned in the present invention. For example said enzyme is administered once every two weeks and the antisense oligomeric compound is administered once every 4 weeks.

Optionally said enzyme or said nucleic acid encoding for said enzyme is administered in a dose of about 1-100 mg/kg, optionally 2-90 mg/kg, 3-80 mg/kg, 5-75 mg/kg, 7-70 mg/kg, 10-60 mg/kg, 12-55 mg/kg, 15-50 mg/kg, 17-45 mg/kg, 20-40 mg/kg, 22-35 mg/kg, 25-30 mg/kg.

Optionally said antisense oligomeric compound is administered in a dose of about 0.05 to 1000 mg/kg, optionally about 0.1 to 900 mg/kg, 1-800 mg/kg, 2-750 mg/kg, 3-700 mg/kg, 4-600 mg/kg, 5-500 mg/kg, 7 to 450 mg/kg, 10 to 400 mg/kg, 12 to 350 mg/kg, 15 to 300 mg/kg, 17 to 250 mg/kg, 20 to 220 mg/kg, 22 to 200 mg/kg, 25 to 180 mg/kg, 30 to 150 mg/kg, 35 to 125 mg/kg, 40 to 100 mg/kg, 45 to 75 mg/kg, 50-70 mg/kg.

Optionally said enzyme or said nucleic acid encoding for said enzyme or said antisense oligomeric compound is administered in combination with a chaperone such as an Active Site-Specific Chaperone (ASSC). Optionally said enzyme is administered in combination with a chaperone Optionally said nucleic acid encoding for said enzyme is administered in combination with a chaperone Optionally said antisense oligomeric compound is administered in combination with a chaperone Suitable chaperones are 1-deoxynojirimycin and derivatives thereof. Suitable examples of chaperones are 1-deoxynojirimycin N-(n-nonyl) deoxynojirimycin (NN-DNJ), N-(n-butyl) deoxynojirimycin (NB-DNJ), N-octyl-4-epi-ß-valienamine, N-acetylglucosamine-thiazoline, N-(7-oxadecyl)deoxynojirimycin (NO-DNJ) and N-(n-dodecyl)deoxynojirimycin (ND-DNJ), 1-deoxygalactonojirimycin, N-alkylderivative of 1-deoxynojirimycin. 1-deoxynojirimycin and derivatives thereof are also suitable for substrate reduction.

Optionally the administration is in combination with genistein. Optionally in a dose of genistein of 1-100 mg/kg per day, optionally of 5-90 mg/kg per day, optionally 10-80- mg/kg per day, optionally 15-75 mg/kg per day, optionally 20-70 mg/kg per day, optionally 25-60 mg/kg per day, 30-55 mg/kg per day, 35-50 mg/kg per day, 40-45 mg/kg per day. Optionally said enzyme or said nucleic acid encoding for said enzyme or said antisense oligomeric compound is administered in combination with a genistein. Optionally said enzyme is administered in combination with a genistein Optionally said nucleic acid encoding for said enzyme is administered in combination with a genistein Optionally said antisense oligomeric compound is administered in combination with a genistein.

Optionally the administration is in combination with cell penetrating peptides. Optionally the administration is in combination with a targeting ligand. Optionally said cell penetrating peptide and/or targeting ligand is present on the antisense oligomeric compound. Optionally said cell penetrating peptide and/or targeting ligand is present on said nucleic acid encoding for said enzyme. Optionally said cell penetrating peptide and/or targeting ligand is present on said enzyme.

Optionally the enzyme is an acid alpha-glucosidase (GAA) enzyme. Optionally said enzyme is a modification, variant, analogue, fragment, portion, or functional derivative, thereof. Optionally said enzyme is a modification, variant, analogue, fragment, portion, or functional derivative of GAA enzyme. The present invention explicitly encompasses all forms of recombinant human acid alpha-glucosidase which may be based on all natural or genetically modified forms of either human GAA cDNA, or human GAA gene, or combinations thereof, including those forms that are created by codon optimization. Suitable GAA enzyme include an enzyme selected from the group consisting of Myozyme and lysozyme, neo-GAA (carbohydrate modified forms of alglucosidase-alpha), BMN-701 (BioMarin: Gilt GAA for Pompe disease, in which rhGAA is fused with an IGF-II peptide) rhGGAA (Oxyrane: recombinant human acid alpha-glucosidase produced in genetically modified yeast cells and enriched in mannose 6-phosphate content), rhGAA modified by conjugation, for example to mannose-6-phosphate groups or to IGF-II peptides. said enzyme is selected from the group consisting of a recombinant human GAA, Myozyme, Lumizyme, neoGAA, Gilt GAA (BMN-701), or rhGGAA.

Optionally the composition or treatment comprises more than one antisense oligomeric compound. Optionally, 1, 2, 3, 4, 5, 6, 7, 8, 9, 10, 11, 12, 13, 14, 15, or more different antisense oligomeric compounds are used for the composition and/or treatment.

Optionally the antisense oligomeric compound is selected from the group comprising SEQ ID NO: 2-33, 541-1583, 1590-1594, and sequences having at least 80% identity thereof. Optionally the antisense oligomeric compound is is selected from the group comprising SEQ ID NO: 2-33 and sequences having at least 80% identity thereof. Optionally the antisense oligomeric compound is SEQ ID NO: 12 or SEQ ID NO: 33 and sequences having at least 80% identity thereof.

Optionally the antisense oligomeric compound is complementary to a sequence selected from the group comprising SEQ ID NO: 1, 37-40, 1584-1589, and sequences having at least 80% identity thereof.

Optionally at least one of the nucleotides of the is antisense oligomeric compound is modified. Optionally all of the nucleotides in the antisense oligomeric compound are modified. Optionally the modifications in the antisense oligomeric compound is the same for each nucleotide or different. Various combinations of modification of the nucleotides is explicitly envisioned in the present invention.

Optionally the sugar of one or more nucleotides of the is antisense oligomeric compound is modified. Optionally the sugar modification is 2'-O-methyl. Optionally the sugar modification 2'-O-methoxyethyl.

Optionally the base of one or more nucleotides of the antisense oligomeric compound is modified.

Optionally the backbone of the antisense oligomeric compound is modified, Optionally the backbone of the antisense oligomeric compound is a morpholino phosphorothioate. Optionally the backbone of the antisense oligomeric compound is a morpholino phosphorodiamidate. Optionally the backbone of the antisense oligomeric compound is a tricyclo-DNA.

Optionally the antisense oligomeric compound and/or the enzyme or nucleic acid coding for said enzyme is present in a carrier selected from the group of exosomes, nanoparticles, micelles, liposomes, or microparticles. The carrier may enhance the uptake of the antisense oligomeric compound and/or the enzyme or nucleic acid coding for said enzyme into the cells.

Optionally the composition or the treatment comprises compounds that enhance the uptake of the antisense oligomeric compound and/or the enzyme or nucleic acid coding for said enzyme into the cells. Suitable compounds that enhance the uptake into the cells are Polyethylimine, conjugated pluronic copolymers, lipids, e.g. patisiran, ICAM-targeted nanocariers, peptide Pip6a or cationic nanoemulsions. A skilled person is well suited to find compounds that enhance the uptake of the antisense oligomeric compound and/or the enzyme or nucleic acid coding for said enzyme into the cells.

The present invention is also directed to a pharmaceutical composition comprising at least one antisense oligomeric compound as defined in aspects of the present invention and/or embodiments thereof and a enzyme as defined in aspects of the present invention and/or embodiments thereof.

Optionally the pharmaceutical composition further comprises a pharmaceutical acceptable excipient and/or a cell delivery agent. Suitable cell delivery agents are carriers selected from the group of exosomes, nanop articles, micelles, liposomes, or microp articles. Optionally the pharmaceutical composition comprises compounds that enhance the uptake of the antisense oligomeric compound and/or the enzyme or nucleic acid coding for said enzyme into the cells. Suitable compounds that enhance the uptake into the cells are Polyethylimine, conjugated pluronic copolymers, lipids, e.g. patisiran, ICAM-targeted nanocariers. peptide Pip6a or cationic nanoemulsions. A skilled person is well suited to find compounds that enhance the uptake of the antisense oligomeric compound and/or the enzyme or nucleic acid coding for said enzyme into the cells.

Optionally the pharmaceutical composition further comprises a chaperone such as a Active Site-Specific Chaperone (ASSC). Suitable chaperones are 1-deoxynojirimycin and derivatives thereof. Suitable examples of chaperones are 1-deoxynojirimycin N-(n-nonyl)deoxynojirimycin (NN-DNJ), N-(n-butyl)deoxynojirimycin (NB-DNJ), N-octyl-4-epi-ß-valienamine, N-acetylglucosamine-thiazoline, N-(7-oxadecyl)deoxynojirimycin (NO-DNJ) and N-(n-dodecyl) deoxynojirimycin (ND-DNJ), 1-deoxygalactonojirimycin, N-alkylderivative of 1-deoxynojirimycin. 1-deoxynojirimycin and derivatives thereof are also suitable for substrate reduction.

Optionally the pharmaceutical composition further comprises genistein. Optionally the pharmaceutical composition further comprises genistein in a dose of of 1-100 mg/kg per day, optionally of 5-90 mg/kg per day, optionally 10-80-mg/kg per day, optionally 15-75 mg/kg per day, optionally 20-70 mg/kg per day, optionally 25-60 mg/kg per day, 30-55 mg/kg per day, 35-50 mg/kg per day, 40-45 mg/kg per day. Optionally the pharmaceutical composition comprises said enzyme or said nucleic acid encoding for said enzyme or said antisense oligomeric compound in combination with a genistein. Optionally the pharmaceutical composition comprises said enzyme in combination with a genistein Optionally the pharmaceutical composition comprises said nucleic acid encoding for said enzyme in combination with a genistein Optionally the pharmaceutical composition comprises said antisense oligomeric compound in combination with a genistein.

Optionally the pharmaceutical composition further comprises cell penetrating peptides. Optionally the pharmaceutical composition further comprises a targeting ligand. Optionally said cell penetrating peptide and/or targeting ligand is present on the antisense oligomeric compound.

Optionally said cell penetrating peptide and/or targeting ligand is present on said nucleic acid encoding for said enzyme. Optionally said cell penetrating peptide and/or targeting ligand is present on said enzyme.

Optionally in the pharmaceutical composition the enzyme is an acid alpha-glucosidase (GAA) enzyme. Optionally said enzyme is a modification, variant, analogue, fragment, portion, or functional derivative, thereof. Optionally said enzyme is a modification, variant, analogue, fragment, portion, or functional derivative of GAA enzyme. The present invention explicitly encompasses all forms of recombinant human acid alpha-glucosidase which may be based on all natural or genetically modified forms of either human GAA cDNA, or human GAA gene, or combinations thereof, including those forms that are created by codon optimization. Suitable GAA enzyme include an enzyme selected from the group consisting of Myozyme and lysozyme, neo-GAA (carbohydrate modified forms of alglucosidase-alpha), BMN-701 (BioMarin: Gilt GAA for Pompe disease, in which rhGAA is fused with an IGF-II peptide) rhGGAA (Oxyrane:

recombinant human acid alpha-glucosidase produced in genetically modified yeast cells and enriched in mannose 6-phosphate content), rhGAA modified by conjugation, for example to mannose-6-phosphate groups or to IGF-II peptides. said enzyme is selected from the group consisting of a recombinant human GAA, Myozyme, Lumizyme, neoGAA, Gilt GAA (BMN-701), or rhGGAA.

Optionally the pharmaceutical composition comprises the enzyme in an amount of about 1-50 mg/mL enzyme. Optionally the enzyme is present in the pharmaceutical composition in an amount of 2-45 mg/mL, 3-40 mg/mL, 5-35 mg/mL, 7-30 mg/mL, 10-25 mg/mL, 12-22 mg/mL, or 15-20, mg/mL.

Optionally the pharmaceutical composition comprises more than one antisense oligomeric compound. Optionally, the pharmaceutical composition comprises 1, 2, 3, 4, 5, 6, 7, 8, 9, 10, 11, 12, 13, 14, 15, or more different antisense oligomeric compounds.

Optionally the pharmaceutical composition comprises the antisense oligomeric compound in an amount of about 1-50 mg/mL enzyme. Optionally the antisense oligomeric compound is present in the pharmaceutical composition in an amount of 2-45 mg/mL, 3-40 mg/mL, 5-35 mg/mL, 7-30 mg/mL, 10-25 mg/mL, 12-22 mg/mL, or 15-20, mg/mL.

Optionally the pharmaceutical composition comprises a carrier selected from the group consisting of exosomes, nanoparticles, micelles, liposomes, and microparticles.

The present invention is also directed to a sequences selected from the group comprising SEQ ID NO: 1590-1594 and sequences having at least 80% identity thereof.

The present invention is also directed to a sequences selected from the group comprising SEQ ID NO: 1590-1594 and sequences having at least 80% identity thereof for use in the treatment Pompe disease.

The present invention is also directed to a method of modulating splicing of GAA pre-mRNA in a cell comprising:

contacting the cell with an antisense oligomeric compound selected from the group comprising SEQ ID NO: 1590-1594 and sequences having at least 80% identity thereof.

The present invention is also directed to a method for treating Pompe disease in a patient comprising administering said patient with an effective amount of an antisense oligomeric compound selected from the group comprising SEQ ID NO: 1590-1594 and sequences having at least 80% identity thereof.

The present invention is also directed to a method to restore the function of GAA in a cell wherein said method comprises the administration of an antisense oligomeric compound selected from the group comprising SEQ ID NO: 1590-1594 and sequences having at least 80% identity thereof. The present invention is also directed to a method of correcting abnormal gene expression in a cell, Optionally a muscular cell, of a subject, the method comprising administering to the subject an antisense oligomeric compound selected from the group comprising SEQ ID NO: 1590-1594 and sequences having at least 80% identity thereof. Optionally in said methods the cell or the patient comprises at least one mutation selected from the group c.-32-13T>G, c.-32-3C>G, c.547-6, c.1071, c.1254, and c.1552-30, Optionally the cell or patient comprises mutation c.-32-3C>G or c.-32-13T>G. Optionally in said methods exon inclusion is accomplished, optionally inclusion of exon 2.

The present invention is also directed to a pharmaceutical composition comprising at least one antisense oligomeric compound selected from the group comprising SEQ ID NO: 1590-1594 and sequences having at least 80% identity thereof. Optionally the pharmaceutical composition further comprises a pharmaceutical acceptable excipient and/or a cell delivery agent.

DETAILED DESCRIPTION

The principle behind antisense technology is that an antisense compound, which hybridizes to a target nucleic acid, modulates gene expression activities such as transcription, splicing or translation. This sequence specificity makes antisense compounds extremely attractive as tools for target validation and gene functionalization, as well as therapeutics to selectively modulate the expression of genes or gene products involved in disease.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence, resulting in exon-exon junctions at the site where exons are joined. Targeting exon-exon junctions can be useful in situations where aberrant levels of a normal splice product are implicated in disease, or where aberrant levels of an aberrant splice product are implicated in disease. Targeting splice sites, i.e., intron-exon junctions or exon-intron junctions can also be particularly useful in situations where aberrant splicing is implicated in disease, or where an overproduction of a particular splice product is implicated in disease. Aberrant fusion junctions due to rearrangements or deletions are also suitable targets. mRNA transcripts produced via the process of splicing of two (or more) mRNAs from different gene sources are known as "fusion transcripts" and are also suitable targets. It is also known that introns can be effectively targeted using antisense compounds targeted to, for example, DNA or pre-mRNA. Single-stranded antisense compounds such as oligonucleotide compounds that work via an RNase H mechanism are effective for targeting pre-mRNA. Antisense compounds that function via an occupancy-based mechanism are effective for redirecting splicing as they do not, for example, elicit RNase H cleavage of the mRNA, but rather leave the mRNA intact and promote the yield of desired splice product(s).

It is also known in the art that alternative RNA transcripts can be produced from the same genomic region of DNA. These alternative transcripts are generally known as "variants." More specifically, "pre-mRNA variants" are transcripts produced from the same genomic DNA that differ from other transcripts produced from the same genomic DNA in either their start or stop position and contain both intronic and exonic sequence. Upon excision of one or more exon or intron regions, or portions thereof during splicing, pre-mRNA variants produce smaller "mRNA variants."

Consequently, mRNA variants are processed pre-mRNA variants and each unique pre-mRNA variant must always produce a unique mRNA variant as a result of splicing. These mRNA variants are also known as "alternative splice variants." If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites.

As used herein, "antisense mechanisms" are all those involving hybridization of a compound with target nucleic acid, wherein the outcome or effect of the hybridization is either target degradation or target occupancy with concomitant stalling of the cellular machinery involving, for example, transcription or splicing.

As used herein, "to comprise" and its conjugations is used in its non-limiting sense to mean that items following the word are included, but items not specifically mentioned are not excluded. In addition the verb "to consist" may be replaced by "to consist essentially of" meaning that a compound or adjunct compound as defined herein may comprise additional component(s) than the ones specifically identified, said additional component(s) not altering the unique characteristic of the invention.

The articles "a" and "an" are used herein to refer to one or to more than one (i.e., to at least one) of the grammatical object of the article.

The terms "individual", "patient", and "subject" are used interchangeably herein and refer to mammals, in particular primates and Optionally humans.

The term "exon" refers to a portion of a gene that is present in the mature form of mRNA. Exons include the ORF (open reading frame), i.e., the sequence which encodes protein, as well as the 5' and 3' UTRs (untranslated regions). The UTRs are important for translation of the protein. Algorithms and computer programs are available for predicting exons in DNA sequences (Grail, Grail 2 and Genscan and US 20040219522 for determining an exon-intron junctions).

As used herein, the term "protein coding exon" refers to an exon which codes (or at least partially codes) for a protein (or part of a protein). The first protein coding exon in an mRNA is the exon which contains the start codon. The last protein encoding exon in an mRNA is the exon which contains the stop codon. The start and stop codons can be predicted using any number of well-known programs in the art.

As used herein, the term "internal exon" refers to an exon that is flanked on both its 5' and 3' end by another exon. For an mRNA comprising n exons, exon 2 to exon (n−1) are the internal exons. The first and last exons of an mRNA are referred to herein as "external exons".

The term "intron" refers to a portion of a gene that is not translated into protein and while present in genomic DNA and pre-mRNA, it is removed in the formation of mature mRNA.

The term "messenger RNA" or "mRNA" refers to RNA that is transcribed from genomic DNA and that carries the coding sequence for protein synthesis. Pre-mRNA (precursor mRNA) is transcribed from genomic DNA. In eukaryotes, pre-mRNA is processed into mRNA, which includes removal of the introns, i.e., "splicing", and modifications to the 5' and 3' end (e.g., polyadenylation). mRNA typically comprises from 5' to 3'; a 5' cap (modified guanine nucleotide), 5' UTR (untranslated region), the coding sequence (beginning with a start codon and ending with a stop codon), the 3' UTR, and the poly(A) tail.

The term "nucleic acid sequence" or "nucleic acid molecule" or polynucleotide are used interchangeably and refer to a DNA or RNA molecule in single or double stranded form. An "isolated nucleic acid sequence" refers to a nucleic acid sequence which is no longer in the natural environment from which it was isolated, e.g. the nucleic acid sequence in a cell.

A "mutation" in a nucleic acid molecule is a change of one or more nucleotides compared to the wild type sequence, e.g. by replacement, deletion or insertion of one or more nucleotides. A "point mutation" is the replacement of a single nucleotide, or the insertion or deletion of a single nucleotide.

Sequence identity" and "sequence similarity" can be determined by alignment of two peptide or two nucleotide sequences using global or local alignment algorithms. Sequences may then be referred to as "substantially identical" or "essentially similar" when they are optimally aligned by for example the programs GAP or BESTFIT or the Emboss program "Needle" (using default parameters, see below) share at least a certain minimal percentage of sequence identity (as defined further below). These programs use the Needleman and Wunsch global alignment algorithm to align two sequences over their entire length, maximising the number of matches and minimises the number of gaps. Generally, the default parameters are used, with a gap creation penalty=10 and gap extension penalty=0.5 (both for nucleotide and protein alignments). For nucleotides the default scoring matrix used is DNAFULL and for proteins the default scoring matrix is Blosum62 (Henikoff & Henikoff, 1992, PNAS 89, 10915-10919). Sequence alignments and scores for percentage sequence identity may for example be determined using computer programs, such as EMBOSS (http://www.ebi.ac.uk/Tools/psa/emboss_needle/). Alternatively sequence similarity or identity may be determined by searching against databases such as FASTA, BLAST, etc., but hits should be retrieved and aligned pairwise to compare sequence identity. Two proteins or two protein domains, or two nucleic acid sequences have "substantial sequence identity" if the percentage sequence identity is at least 70%, 75%, 80%, 85%, 90%, 95%, 98%, 99% or more, Optionally 90%, 95%, 98%, 99% or more (as determined by Emboss "needle" using default parameters, i.e. gap creation penalty=10, gap extension penalty=0.5, using scoring matrix DNAFULL for nucleic acids an Blosum62 for proteins). Such sequences are also referred to as 'variants' herein, e.g. other variants of antisense oligomeric compounds. It should be understood that sequence with substantial sequence identity do not necessarily have the same length and may differ in length. For example sequences that have the same nucleotide sequence but of which one has additional nucleotides on the 3'- and/or 5'-side are 100% identical.

The term "hybridisation" as used herein is generally used to mean hybridisation of nucleic acids at appropriate conditions of stringency as would be readily evident to those skilled in the art depending upon the nature of the probe sequence and target sequences. Conditions of hybridisation and washing are well known in the art, and the adjustment of conditions depending upon the desired stringency by varying incubation time, temperature and/or ionic strength of the solution are readily accomplished. See, for example, Sambrook, J. et al., Molecular Cloning: A Laboratory Manual, 2nd edition, Cold Spring Harbor Press, Cold Spring Harbor, N.Y., 1989. The choice of conditions is dictated by the length of the sequences being hybridised, in particular, the length of the probe sequence, the relative G-C content of the nucleic acids and the amount of mismatches to be permitted. Low stringency conditions are preferred when partial hybridisation between strands that have lesser degrees of complementarity is desired. When perfect or near perfect complementarity is desired, high stringency conditions are preferred. For typical high stringency conditions, the hybridisation solution contains 6×S.S.C., 0.01 M EDTA, 1×Denhardt's solution and 0.5% SOS. hybridisation is carried out at about 68° C. for about 3 to 4 hours for fragments of cloned DNA and for about 12 to about 16 hours for total eukaryotic DNA. For lower stringencies the temperature of hybridisation is reduced to about 42° C. below the melting temperature (TM) of the duplex. The TM is known to be a function of the G-C content and duplex length as well as the ionic strength of the solution.

The term "allele(s)" means any of one or more alternative forms of a gene at a particular locus, all of which alleles relate to one trait or characteristic at a specific locus. One allele is present on each chromosome of the pair of homologous chromosomes. These may be identical alleles of the gene (homozygous) or two different alleles (heterozygous).

Mutant allele" refers herein to an allele comprising one or more mutations in the coding sequence (mRNA, cDNA or genomic sequence) compared to the wild type allele. Such mutation(s) (e.g. insertion, inversion, deletion and/or replacement of one or more nucleotide(s)) may lead to the encoded protein having reduced in vitro and/or in vivo functionality (reduced function) or no in vitro and/or in vivo functionality (loss-of-function), e.g. due to the protein e.g. being truncated or having an amino acid sequence wherein one or more amino acids are deleted, inserted or replaced. Such changes may lead to the protein having a different conformation, being targeted to a different sub-cellular compartment, having a modified catalytic domain, having a modified binding activity to nucleic acids or proteins, etc, it may also lead to a different splicing event.

A "fragment" of the gene or nucleotide sequence or antisense oligomeric compound refers to any subset of the molecule, e.g., a shorter polynucleotide or oligonucleotide.

A "variant" refers to a molecule substantially similar to the antisense oligomeric compound or a fragment thereof, such as a nucleotide substitution variant having one or more substituted nucleotides, but which maintains the ability to hybridize with the particular gene. Optionally the variant comprises the mutations as identified by the invention. Variants also include longer sequences.

An "analogue" refers to a non-natural molecule substantially similar to or functioning in relation to either the entire molecule, a variant or a fragment thereof.

As used herein, the terms "precursor mRNA" or "pre-mRNA" refer to an immature single strand of messenger ribonucleic acid (mRNA) that contains one or more intervening sequence(s) (introns). Pre-mRNA is transcribed by an RNA polymerase from a DNA template in the cell nucleus and is comprised of alternating sequences of introns and coding regions (exons). Once a pre-mRNA has been completely processed by the splicing out of introns and joining of exons, it is referred to as "messenger RNA" or "mRNA," which is an RNA that is comprised exclusively of exons. Eukaryotic pre-mRNAs exist only transiently before being fully processed into mRNA. When a pre-mRNA has been properly processed to an mRNA sequence, it is exported out of the nucleus and eventually translated into a protein by ribosomes in the cytoplasm.

As used herein, the terms "splicing" and "processing" refers to the modification of a pre-mRNA following transcription, in which introns are removed and exons are joined. Pre-mRNA splicing involves two sequential biochemical reactions. Both reactions involve the spliceosomal transesterification between RNA nucleotides. In a first reaction, the 2'-OH of a specific branch-point nucleotide within an intron, which is defined during spliceosome assembly, performs a nucleophilic attack on the first nucleotide of the intron at the 5' splice site forming a lariat intermediate. In a second reaction, the 3'-OH of the released 5' exon performs a nucleophilic attack at the last nucleotide of the intron at the 3' splice site thus joining the exons and releasing the intron lariat. Pre-mRNA splicing is regulated by intronic silencer sequence (ISS), exonic silencer sequences (ESS) and terminal stem loop (TSL) sequences.

As used herein, the terms "intronic silencer sequences (ISS)" and "exonic silencer sequences (TSL)" refer to sequence elements within introns and exons, respectively, that control alternative splicing by the binding of trans-acting protein factors within a pre-mRNA thereby resulting in differential use of splice sites. Typically, intronic silencer sequences are less conserved than the splice sites at exon-intron junctions.

As used herein, "modulation of splicing" refers to altering the processing of a pre-mRNA transcript such that there is an increase or decrease of one or more splice products, or a change in the ratio of two or more splice products. Modulation of splicing can also refer to altering the processing of a pre-mRNA transcript such that a spliced mRNA molecule contains either a different combination of exons as a result of exon skipping or exon inclusion, a deletion in one or more exons, or additional sequence not normally found in the spliced mRNA (e.g., intron sequence).

As used herein, "splice site" refers to the junction between an exon and an intron in a pre-mRNA (unspliced RNA) molecule (also known as a "splice junction"). A "cryptic splice site" is a splice site that is not typically used but may be used when the usual splice site is blocked or unavailable or when a mutation causes a normally dormant site to become an active splice site. An "aberrant splice site" is a splice site that results from a mutation in the native DNA and pre-mRNA.

As used herein, "splice products" or "splicing products" are the mature mRNA molecules generated from the process of splicing a pre-mRNA. Alternatively spliced pre-mRNAs have at least two different splice products. For example, a first splicing product may contain an additional exon, or portion of an exon, relative to a second splicing product. Splice products of a selected pre-mRNA can be identified by a variety of different techniques well known to those of skill in the art.

As used herein "splice donor site" refers to a splice site found at the 5' end of an intron, or alternatively, the 3' end of an exon. Splice donor site is used interchangeably with "5' splice site." As used herein "splice acceptor site" refers to a splice site found at the 3' end of an intron, or alternatively, the 5' end of an exon. Splice acceptor site is used interchangeably with "3' splice site."

As used herein, "targeting" or "targeted to" refer to the process of designing an oligomeric compound such that the compound hybridizes with a selected nucleic acid molecule or region of a nucleic acid molecule. Targeting an oligomeric compound to a particular target nucleic acid molecule can be a multistep process. The process usually begins with the identification of a target nucleic acid whose expression is to be modulated. As used herein, the terms "target nucleic acid" and "nucleic acid encoding GAA" encompass DNA encoding GAA, RNA (including pre-mRNA and mRNA) transcribed from such DNA, and also cDNA derived from such RNA. For example, the target nucleic acid can be a cellular gene (or mRNA transcribed from the gene) whose expression is associated with a particular disorder or disease state, or a nucleic acid molecule from an infectious agent. As disclosed herein, the target nucleic acid encodes GAA.

The targeting process usually also includes determination of at least one target region, segment, or site within the target nucleic acid for the antisense interaction to occur such that the desired effect, e.g., modulation of expression, will result.

As used herein, "target mRNA" refers to the nucleic acid molecule to which the oligomeric compounds provided herein are designed to hybridize. In the context of the present disclosure, target mRNA is usually unspliced mRNA, or pre-mRNA. In the context of the present invention, the target mRNA is GAA mRNA or GAA pre-mRNA.

"Region" is defined as a portion of the target nucleic acid having at least one identifiable structure, function, or characteristic. Target regions may include, for example, a particular exon or intron, or may include only selected nucleotides within an exon or intron which are identified as appropriate target regions. Target regions may also be splicing repressor sites. Within regions of target nucleic acids are segments. "Segments" are defined as smaller or sub-portions of regions within a target nucleic acid. "Sites," as used in the present invention, are defined as unique nucleobase positions within a target nucleic acid. As used herein, the "target site" of an oligomeric compound is the 5'-most nucleotide of the target nucleic acid to which the compound binds.

Target degradation can include an RNase H, which is a cellular endonuclease which cleaves the RNA strand of an RNA:DNA duplex. It is known in the art that single-stranded antisense compounds which are "DNA-like" elicit cleavage by RNAse H. Occupancy-based antisense mechanisms, whereby antisense compounds hybridize yet do not elicit cleavage of the target, include inhibition of translation, modulation of splicing, modulation of poly(A) site selection and disruption of regulatory RNA structure. For the present invention "RNA-like" antisense compounds for use in occupancy-based antisense mechanisms are preferred.

In the context of the present disclosure, an oligomeric compound "targeted to a splice site" refers to a compound that hybridizes with at least a portion of a region of nucleic acid encoding a splice site or a compound that hybridizes with an intron or exon in proximity to a splice site, such that splicing of the mRNA is modulated.

The term "oligomeric compound" refers to a polymeric structure capable of hybridizing to a region of a nucleic acid molecule. This term includes oligonucleotides, oligonucleosides, oligonucleotide analogs, oligonucleotide mimetics and chimeric combinations of these. Oligomeric compounds are routinely prepared linearly but can be joined or otherwise prepared to be circular. Moreover, branched structures are known in the art. Oligomeric compounds can be introduced in the form of single-stranded, double-stranded, circular, branched or hairpins and can contain structural elements such as internal or terminal bulges or loops. Oligomeric double-stranded compounds can be two strands hybridized to form double-stranded compounds or a single strand with sufficient self complementarity to allow for hybridization and formation of a fully or partially double-stranded compound.

The term "antisense oligonucleotide, AON, or antisense oligomeric compound" refers to an oligonucleotide that is capable of interacting with and/or hybridizing to a pre-mRNA or an mRNA having a complementary nucleotide sequence thereby modifying gene expression and/or splicing. Enzyme-dependent antisense oligonucleotides include forms that are dependent on RNase H activity to degrade target mRNA, and include single-stranded DNA, RNA, and phosphorothioate antisense. Steric blocking antisense oligonucleotides (RNase-H independent antisense) interfere with gene expression or other mRNA-dependent cellular processes by binding to a target sequence of mRNA. Steric blocking antisense includes 2'-0 alkyl antisense oligonucleotides, Morpholino antisense oligonucleotides, and tricyclo- DNA antisense oligonucleotides. Steric blocking antisense oligonucleotides are preferred in the present invention.

As used herein, antisense oligonucleotides that are "RNase H-independent" are those compounds which do not elicit cleavage by RNase H when hybridized to a target nucleic acid. RNase H-independent oligomeric compounds modulate gene expression, such as splicing, by a target occupancy-based mechanism. Rnase H-independent antisense oligonucleotides are preferred in the present invention.

As used herein, "hybridization" means the pairing of complementary strands of oligomeric compounds. In the context of the present disclosure, an oligomeric compound is specifically hybridizable when there is a sufficient degree of complementarity to avoid non-specific binding of the oligomeric compound to non-target nucleic acid sequences. One of skill in the art will be able to determine when an oligomeric compound is specifically hybridizable.

As used herein, "complementary" refers to a nucleic acid molecule that can form hydrogen bond(s) with another nucleic acid molecule by either traditional Watson-Crick base pairing or other non-traditional types of pairing (e.g., Hoogsteen or reversed Hoogsteen hydrogen bonding) between complementary nucleosides or nucleotides. In reference to the antisense oligomeric compound of the present disclosure, the binding free energy for a antisense oligomeric compound with its complementary sequence is sufficient to allow the relevant function of the antisense oligomeric compound to proceed and there is a sufficient degree of complementarity to avoid non-specific binding of the antisense oligomeric compound to non-target sequences under conditions in which specific binding is desired, i.e., under physiological conditions in the case of ex vivo or in vivo therapeutic treatment. Determination of binding free energies for nucleic acid molecules is well known in the art (see e.g., Turner et ah, CSH Symp. Quant. Biol. 1/7:123-133 (1987); Frier et al, Proc. Nat. Acad. Sci. USA 83:9373-77 (1986); and Turner et al, J. Am. Chem. Soc. 109:3783-3785 (1987)). Thus, "complementary" (or "specifically hybridizable") are terms that indicate a sufficient degree of complementarity or precise pairing such that stable and specific binding occurs between a antisense oligomeric compound and a pre-mRNA or mRNA target. It is understood in the art that a nucleic acid molecule need not be 100% complementary to a target nucleic acid sequence to be specifically hybridizable. That is, two or more nucleic acid molecules may be less than fully complementary. Complementarity is indicated by a percentage of contiguous residues in a nucleic acid molecule that can form hydrogen bonds with a second nucleic acid molecule. For example, if a first nucleic acid molecule has 10 nucleotides and a second nucleic acid molecule has 10 nucleotides, then base pairing of 5, 6, 7, 8, 9, or 10 nucleotides between the first and second nucleic acid molecules represents 50%, 60%, 70%, 80%, 90%, and 100% complementarity, respectively. Percent complementarity of an oligomeric compound with a region of a target nucleic acid can be determined routinely using BLAST programs (basic local alignment search tools) and Power-BLAST programs known in the art (Altschul et al., J. Mol. Biol., 1990, 215, 403-410; Zhang and Madden, Genome Res., 1997, 7, 649-656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). "Perfectly" or "fully" complementary nucleic acid molecules means those in which all the contiguous residues of a first nucleic acid molecule will hydrogen bond with the same number of contiguous residues in a second nucleic acid molecule, wherein the nucleic acid molecules either both have the same number of nucleotides (i.e., have the same length) or the two molecules have different lengths.

As used herein, "uniformly modified" or "fully modified" refers to an oligomeric compound, an antisense oligonucleotide, or a region of nucleotides wherein essentially each nucleoside is a sugar modified nucleoside having uniform modification.

As used herein, a "chimeric oligomeric compound", "chimeric antisense compound" or "chimeric antisense oligonucleotide compound" is a compound containing two or more chemically distinct regions, each comprising at least one monomer unit (i.e., a nucleotide in the case of an oligonucleotide compound). The term "chimeric antisense compound" specifically refers to an antisense compound, having at least one sugar, nucleobase and/or internucleoside linkage that is differentially modified as compared to the other sugars, nucleotides and internucleoside linkages within the same oligomeric compound. The remainder of the sugars, nucleotides and internucleoside linkages can be independently modified or unmodified. In general a chimeric oligomeric compound will have modified nucleosides that can be in isolated positions or grouped together in regions that will define a particular motif. Chimeric oligomeric compounds typically contain at least one region modified so as to confer increased resistance to nuclease degradation, increased cellular uptake, and/or increased binding affinity for the target nucleic acid. In the context of the present disclosure, a "chimeric RNase H-independent antisense compound" is an antisense compound with at least two chemically distinct regions, but which is not susceptible to cleavage by RNase H when hybridized to a target nucleic acid.

As used herein, a "nucleoside" is a base-sugar combination and "nucleotides" are nucleosides that further include a phosphate group covalently linked to the sugar portion of the nucleoside.

As used herein, a nucleoside with a modified sugar residue is any nucleoside wherein the ribose sugar of the nucleoside has been substituted with a chemically modified sugar moiety. In the context of the present disclosure, the chemically modified sugar moieties include, but are not limited to, 2'-O-methoxyethyl, 2'-fluoro, 2'-dimethylaminooxyethoxy, 2'-dimethylaminoethoxyethoxy, 2'-guanidinium, 2'-O-guanidinium ethyl, 2'-carbamate, 2'-aminooxy, 2'-acetamido and locked nucleic acid.

As used herein, compounds "resistant to RNase H degradation" are antisense compounds having a least one chemical modification that increases resistance of the compound to RNase H cleavage. Such modifications include, but are not limited to, nucleotides with sugar modifications. As used herein, a nucleotide with a modified sugar includes, but is not limited to, any nucleotide wherein the 2'-deoxyribose sugar has been substituted with a chemically modified sugar moiety. In the context of the present invention, chemically modified sugar moieties include, but are not limited to, 2'-O-(2-methoxyethyl), 2'-fluoro, 2'-dimethylaminooxyethoxy, 2'-dimethylaminoethoxyethoxy, 2'-guanidinium, 2'-O-guanidinium ethyl, 2'-carbamate, 2'-aminooxy, 2'-acetamido, locked nucleic acid (LNA) and ethylene bridged nucleic acid (ENA). Modified compounds resistant to RNase H cleavage are thoroughly described herein and are well know to those of skill in the art.

In the context of the present disclosure, "cellular uptake" refers to delivery and internalization of oligomeric compounds into cells. The oligomeric compounds can be internalized, for example, by cells grown in culture (in vitro), cells harvested from an animal (ex vivo) or by tissues following administration to an animal (in vivo).

By "subject" is meant an organism, which is a donor or recipient of explanted cells or the cells themselves. "Subject" also refers to an organism to which the nucleic acid molecules of this disclosure can be administered. In one embodiment of the invention and/or embodiments thereof, a subject is a mammal or mammalian cell. In another embodiment, a subject is a human or human cell.

As used herein, the term "therapeutically effective amount" means an amount of antisense oligomeric compound that is sufficient, in the subject (e.g., human) to which it is administered, to treat or prevent the stated disease, disorder, or condition. The antisense oligomeric compound of the instant disclosure, individually, or in combination or in conjunction with other drugs, can be used to treat diseases or conditions discussed herein. For example, to treat a particular disease, disorder, or condition, the antisense oligomeric compound can be administered to a patient or can be administered to other appropriate cells evident to those skilled in the art, individually or in combination with one or more drugs, under conditions suitable for treatment. In the present invention the disease is Optionally Pompe disease.

As used herein, the phrase "pharmaceutically acceptable" refers to molecular entities and compositions that are physiologically tolerable and do not typically produce an allergic or similar untoward reaction, such as gastric upset, dizziness and the like, when administered to a human. Optionally, as used herein, the term "pharmaceutically acceptable" means approved by a regulatory agency of the Federal or a state government or listed in the U.S. Pharmacopeia or other generally recognized pharmacopeia for use in animals, and more particularly in humans.

As used herein, the term "isolated" means that the referenced material is removed from its native environment, e.g., a cell. Thus, an isolated biological material can be free of some or all cellular components, i.e. components of the cells in which the native material occurs naturally (e.g., cytoplasmic or membrane component).

The term "purified" as used herein refers to material that has been isolated under conditions that reduce or eliminate the presence of unrelated materials, i.e. contaminants, including native materials from which the material is obtained. For example, a purified tc-DNA antisense oligomeric compound is Optionally substantially free of cell or culture components, including tissue culture components, contaminants, and the like. As used herein, the term "substantially free" is used operationally, in the context of analytical testing of the material. Optionally, purified material substantially free of contaminants is at least 50% pure; more Optionally, at least 90% pure, and more Optionally still at least 99% pure. Purity can be evaluated by chromatography, gel electrophoresis, immunoassay, composition analysis, biological assay, and other methods known in the art.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, "about" or "consisting essentially of" mean+−20% of the indicated range, value, or structure, unless otherwise indicated.

As used herein, the terms "include" and "comprise" are used synonymously. It should be understood that the terms "a" and "an" as used herein refer to "one or more" of the enumerated components. The use of the alternative (e.g., "or") should be understood to mean either one, both, or any combination thereof of the alternatives.

The term "about" or "approximately" means within a statistically meaningful range of a value. Such a range can be within an order of magnitude, Optionally within 50%, more Optionally within 20%, more Optionally still within 10%, and even more Optionally within 5% of a given value or range. The allowable variation encompassed by the term "about" or "approximately" depends on the particular system under study, and can be readily appreciated by one of ordinary skill in the art. According to the invention, a "subject" or "patient" is a human or non-human animal.

Although the animal subject is Optionally a human, the compounds and compositions of the invention have application in veterinary medicine as well, e.g., for the treatment of domesticated species such as canine, feline, and various other pets; farm animal species such as bovine, equine, ovine, caprine, porcine, etc.; wild animals, e.g., in the wild or in a zoological garden; and avian species, such as chickens, turkeys, quail, songbirds, etc.

The term "enzyme replacement therapy" or "ERT" refers to the introduction of a non-native, purified enzyme into an individual having a deficiency in such enzyme. The administered enzyme can be obtained from natural sources or by recombinant expression. The term also refers to the introduction of a purified enzyme in an individual otherwise requiring or benefiting from administration of a purified enzyme, e.g., suffering from protein insufficiency. The introduced enzyme may be a purified, recombinant enzyme produced in vitro, or enzyme purified from isolated tissue or fluid, such as, e.g., placenta or animal milk, or from plants.

As used herein, the term "active site-specific chaperone" or ASSC refers to any molecule including a protein, peptide, nucleic acid, carbohydrate, etc. that specifically interacts reversibly with an active site of a protein and enhances formation of a stable molecular conformation. As used herein, "active site-specific chaperone" does not include endogenous general chaperones present in the ER of cells such as Bip, calnexin or calreticulin, or general, non-specific chemical chaperones such as deuterated water, DMSO, or TMAO.

The term "purified" as used herein refers to material that has been isolated under conditions that reduce or eliminate the presence of unrelated materials, i.e., contaminants, including native materials from which the material is obtained. For example, a purified protein is Optionally substantially free of other proteins or nucleic acids with which it is associated in a cell; a purified nucleic acid molecule is Optionally substantially free of proteins or other unrelated nucleic acid molecules with which it can be found within a cell. As used herein, the term "substantially free" is used operationally, in the context of analytical testing of the material Optionally, purified material substantially free of contaminants is at least 95% pure; more Optionally, at least 97% pure, and more Optionally still at least 99% pure. Purity can be evaluated by chromatography, gel electrophoresis, immunoassay, composition analysis, biological assay, and other methods known in the art. In a specific embodiment, purified means that the level of contaminants is below a level acceptable to regulatory authorities for safe administration to a human or non-human animal.

As used herein, the terms "mutant" and "mutation" mean any detectable change in genetic material, e.g., DNA, or any process, mechanism or result of such a change. This includes gene mutations, in which the structure (e.g., DNA sequence) of a gene is altered, any gene or DNA arising from any mutation process, and any expression product (e.g., RNA, protein or enzyme) expressed by a modified gene or DNA sequence.

As used herein the term "mutant protein" refers to proteins translated from genes containing genetic mutations that result in altered protein sequences. In a specific embodiment, such mutations result in the inability of the protein to achieve its native conformation under the conditions normally present in the ER. The failure to achieve this conformation results in these proteins being degraded, rather than being transported through their normal pathway in the protein transport system to their proper location within the cell. Other mutations can result in decreased activity or more rapid turnover.

As used herein the term "wild-type gene" refers to a nucleic acid sequences which encodes a protein capable of having normal biological functional activity in vivo. The wild-type nucleic acid sequence may contain nucleotide changes that differ from the known, published sequence, as long as the changes result in amino acid substitutions having little or no effect on the biological activity. The term wild-type may also include nucleic acid sequences engineered to encode a protein capable of increased or enhanced activity relative to the endogenous or native protein.

As used herein, the term "wild-type protein" refers to any protein encoded by a wild-type gene that is capable of having functional biological activity when expressed or introduced in vivo. The term "normal wild-type activity" refers to the normal physiological function of a protein in a cell. Such functionality can be tested by any means known to establish functionality of a protein. The term "genetically modified" refers to cells that express a particular gene product following introduction of a nucleic acid comprising a coding sequence which encodes the gene product, along with regulatory elements that control expression of the coding sequence. Introduction of the nucleic acid may be accomplished by any method known in the art including gene targeting and homologous recombination. As used herein, the term also includes cells that have been engineered to express or overexpress an endogenous gene or gene product not normally expressed by such cell, e.g., by gene activation technology.

The phrase "pharmaceutically acceptable", whether used in connection with the pharmaceutical compositions of the invention, refers to molecular entities and compositions that are physiologically tolerable and do not typically produce untoward reactions when administered to a human. Optionally, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils. Water or aqueous solution saline solutions and aqueous dextrose and glycerol solutions are Optionally employed as carriers, particularly for injectable solutions. Suitable pharmaceutical carriers are described in "Remington's Pharmaceutical Sciences" by E. W. Martin, 18th Edition.

The terms "therapeutically effective dose" and "effective amount" refer to the amount of the compound that is sufficient to result in a therapeutic response. In embodiments where an ASSC and enzyme such as GAA are administered in a complex, the terms "therapeutically effective dose" and "effective amount" may refer to the amount of the complex that is sufficient to result in a therapeutic response. A therapeutic response may be any response that a user (e.g., a clinician) will recognize as an effective response to the therapy. Thus, a therapeutic response will generally be an amelioration of one or more symptoms or sign of a disease or disorder.

It should be noted that a concentration of the chaperone that is inhibitory during in vitro production, transportation, or storage of the purified therapeutic protein may still constitute an "effective amount" for purposes of this invention because of dilution (and consequent shift in binding due to the change in equilibrium), bioavailability and metabolism of the chaperone upon administration in vivo.

The term 'alkyl' refers to a straight or branched hydrocarbon group consisting solely of carbon and hydrogen atoms, containing no unsaturation, and which is attached to the rest of the molecule by a single bond, e.g., methyl, ethyl, n-propyl, 1-methylethyl (isopropyl), n-butyl, n-pentyl, 1, 1-dimethylethyl (t-butyl).

The term "alkenyl" refers to a C2-C20 aliphatic hydrocarbon group containing at least one carbon-carbon double bond and which may be a straight or branched chain, e.g., ethenyl, 1-propenyl, 2-propenyl (allyl), iso-propenyl, 2-methyl-1-propenyl, 1-butenyl, 2-butenyl.

The term "cycloalkyl" denotes an unsaturated, non-aromatic mono- or multicyclic hydrocarbon ring system such as cyclopropyl, cyclobutyl, cyclopentyl, cyclohexyl. Examples of multicyclic cycloalkyl groups include perhydronaphthyl, adamantyl and norbornyl groups bridged cyclic group or sprirobicyclic groups, e.g., spiro (4,4) non-2-yl.

The term "aryl" refers to aromatic radicals having in the range of about 6 to about 14 carbon atoms such as phenyl, naphthyl, tetrahydronaphthyl, indanyl, biphenyl.

The term "heterocyclic" refers to a stable 3- to 15-membered ring radical which consists of carbon atoms and from one to five heteroatoms selected from the group consisting of nitrogen, oxygen and sulfur. For purposes of this invention, the heterocyclic ring radical may be a monocyclic or bicyclic ring system, which may include fused or bridged ring systems, and the nitrogen, carbon, oxygen or sulfur atoms in the heterocyclic ring radical may be optionally oxidized to various oxidation states. In addition, a nitrogen atom, where present, may be optionally quaternized; and the ring radical may be partially or fully saturated (e.g. heteroaromatic or heteroaryl aromatic). The heterocyclic ring radical may be attached to the main structure at any heteroatom or carbon atom that results in the creation of a stable structure.

The term "heteroaryl" refers to a heterocyclic ring wherein the ring is aromatic.

The substituents in the 'substituted alkyl', 'substituted alkenyl', 'substituted cycloalkyl', 'substituted aryl' and 'substituted heteroaryl' may be the same or different, with one or more selected from the groups hydrogen, halogen, acetyl, nitro, carboxyl, oxo (=O), $CF_3$, $-OCF_3$, $NH_2$, $-C(=O)-$ alkyl$_2$, $OCH_3$, or optionally substituted groups selected from alkyl, alkoxy and aryl. The term "halogen" refers to radicals of fluorine, chlorine, bromine and iodine.

GAA Enzyme

Human GAA is synthesized as a 110 kDal precursor (Wisselaar et al. (1993) J. Biol. Chem. 268(3): 2223-31). The mature form of the enzyme is a mixture of monomers of 70 and 76 kD (Wisselaar et al. (1993) J. Biol. Chem. 268(3): 2223-31). The precursor enzyme has seven potential glycosylation sites and four of these are retained in the mature enzyme (Wisselaar et al. (1993) J. Biol. Chem. 268(3): 2223-31). The proteolytic cleavage events which produce the mature enzyme occur in late endosomes or in the lysosome (Wisselaar et al. (1993) J. Biol. Chem. 268(3): 2223-31). The C-terminal 160 amino acids are absent from the mature 70 and 76 kD species. It has been reported that the C-terminal portion of the protein, although cleaved from the rest of the protein during processing, remains associated with the major species (Moreland et al. (Nov. 1, 2004) J. Biol. Chem. Manuscript 404008200).

The enzyme of GAA may be obtained from a cell endogenously expressing the enzyme or GAA, or the enzyme or GAA may be a recombinant human enzyme or GAA (rhGAA), as described herein. Optionally the recombinant human enzyme or rhGAA is a full length wild-type enzyme. Optionally the recombinant human enzyme or rhGAA comprises a subset of the amino acid residues present in a wild-type enzyme or GAA, wherein the subset includes the amino acid residues of the wild-type enzyme or GAA that form the active site for substrate binding and/or substrate reduction. As such, the present invention contemplates an recombinant human enzyme or rhGAA that is a fusion protein comprising the wild-type enzyme or GAA active site for substrate binding and/or substrate reduction, as well as other amino acid residues that may or may not be present in the wild type enzyme or GAA.

The enzyme or GAA may be obtained from commercial sources or may be obtained by synthesis techniques known to a person of ordinary skill in the art. The wild-type enzyme can be purified from a recombinant cellular expression system (e.g., mammalian cells or insect cells-see generally U.S. Pat. Nos. 5,580,757; 6,395,884 and 6,458,574, 6,461, 609, 6,210,666; 6,083,725; 6,451,600; 5,236,838; and 5,879,680), human placenta, or animal milk (see e.g. U.S. Pat. No. 6,188,045). After the infusion, the exogenous enzyme is expected to be taken up by tissues through non-specific or receptor-specific mechanism. In general, the uptake efficiency (without use of an chaperone) is not high, and the circulation time of the exogenous protein is short (Ioannu et al, Am. J. Hum. Genet. 2001; 68: 14-25). In addition, the exogenous protein is unstable and subject to rapid intracellular degradation in vitro. Other synthesis techniques for obtaining GAA suitable for pharmaceutical may be found, for example, in U.S. Pat. Nos. 7,560,424 and 7,396,811, U.S. Published Application Nos. 2009/0203575, 2009/0029467, 2008/0299640, 2008/0241118, 2006/0121018, and 2005/0244400, U.S. Pat. Nos. 7,423,135, 6,534,300, and 6,537,785; International Published Application No. 2005/077093 and U.S. Published Application Nos. 2007/0280925, and 2004/0029779. These references are hereby incorporated by reference in their entirety.

Optionally the GAA is alglucosidase alfa, which consists of the human enzyme acid alpha-glucosidase (GAA), encoded by any of nine observed haplotypes of this gene.

The GAA or enzyme suitable for ERT may be a modification, variant, analogue, fragment, portion, or functional derivative, thereof.

The uptake of the enzyme or GAA may be enhanced by functionalizing the enzyme or GAA by targets for receptors selected from the group consisting of mannose 6-phosphate receptor, insulin like growth factor II receptor, mannose receptor, galactose receptor, fucose receptor, N-Acetylglucosamine (GlcNAc) receptor, plasminogen activator receptor, IGF 1 receptor, insulin receptor; transferrin receptor, cation-dependent mannose-6-phosphate receptor (CD-MPR).

Functional derivatives" of the enzyme or GAA as described herein are fragments, variants, analogs, or chemical derivatives of the enzyme which retain at least a portion of the enzyme activity or immunological cross reactivity with an antibody specific for the enzyme.

A fragment or portion of enzyme refers to any subset of the molecule.

The enzyme or GAA may be modified with a compound selected from the group consisting of mannose 6-phosphate, peptide insulin-like growth factor-2.

Peptide insulin-like growth factor-2 is used in glycosylation-independent lysosomal targeting (GILT).

Optionally the enzyme or GAA is produced by recombinant DNA technology in a Chinese hamster ovary cell line.

Optionally the enzyme or GAA is produced by a glyco-engineered yeast platform (e.g. based on the yeast *Yarrowia lipolytica*).

Optionally the enzyme or GAA is produced by transgene rabbits and collected via the milk of these transgene rabbits.

GAA enzyme is available as Myozyme (Sanofi) Lumizyme (Sanofi) OXY2810 (Oxyrane), IGF2-GAA (Biomarin) BMN-701 (Biomarin), Reveglucosidase alfa (Biomarin).

Chaperone or ASSC (active site-specific chaperone) may be obtained using synthesis techniques known to one of ordinary skill in the art. For example, ASSC that may be used in the present application, such as 1-DNJ may be prepared as described in U.S. Pat. Nos. 6,274,597 and 6,583,158, and U.S. Published Application No. 2006/0264467, each of which is hereby incorporated by reference in its entirety.

Optionally, the ASSC is a—homonojirimycin and the GAA is hrGAA (e.g., Myozyme® or Lumizyme®). Optionally the ASSC is castanospermine and the GAA is hrGAA (e.g., Myozyme® or Lumizyme®). The ASSC (e.g. -homonojirimycin and castanospermine) may be obtained from synthetic libraries (see, e.g., Needels et al., Proc. Natl. Acad. Sci. USA 1993; 90: 10700-4; Ohlmeyer et al., Proc. Natl. Acad. Sci. USA 1993; 90: 10922-10926; Lam et al., PCT Publication No. WO 92/00252; Kocis et al., PCT Publication No. WO 94/28028) which provide a source of potential ASSC's. Synthetic compound libraries are commercially available from Maybridge Chemical Co. (Trevillet, Cornwall, UK), Comgenex (Princeton, N. J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from e.g. Pan Laboratories (Bothell, Wash.) or MycoSearch (NC), or are readily producible. Additionally, natural and synthetically produced libraries and compounds are readily modified through Res. 1986; 155:1 19-29. Optionally ASSC's useful for the present invention are inhibitors of lysosomal enzymes and include glucose and galactose imino-sugar derivatives as described in Asano et al., J. Med. Chem. 1994; 37:3701-06; Dale et al, Biochemistry 1985; 24:3530-39; Goldman et al., J. Nat. Prod. 1996; 59:1137-42; Legler et al, Carbohydrate Res. 1986; 155; 1 19-29. Such derivatives include those that can be purchased from commercial sources such as Toronto Research Chemicals, Inc. (North York, On. Canada) and Sigma.

Optionally, the route of administration is subcutaneous. Other routes of administration may be oral or parenteral, including intravenous, intraarterial, intraperitoneal, ophthalmic, intramuscular, buccal, rectal, vaginal, intraorbital, intracerebral, intradermal, intracranial, intraspinal, intraventricular, intrathecal, intracisternal, intracapsular, intrapulmonary, intranasal, transmucosal, transdermal, or via inhalation. Intrapulmonary delivery methods, apparatus and drug preparation are described, for example, in U.S. Pat. Nos. 5,785,049, 5,780,019, and 5,775,320, each incorporated herein by reference. In some embodiments, the method of intradermal delivery is by iontophoretic delivery via patches; one example of such delivery is taught in U.S. Pat. No. 5,843,015, which is incorporated herein by reference. Administration may be by periodic injections of a bolus of the preparation, or as a sustained release dosage form over long periods of time, or by intravenous or intraperitoneal administration, for example, from a reservoir which is external (e.g., an IV bag) or internal (e.g., a bioerodable implant, a bioartificial organ, or a population of implanted GAA production cells). See, e.g., U.S. Pat. Nos. 4,407,957 and 5,798,113, each incorporated herein by reference. Intrapulmonary delivery methods and apparatus are described, for example, in U.S. Pat. Nos. 5,654,007, 5,780,014, and 5,814,607, each incorporated herein by reference. Other useful parenteral delivery systems include ethylene-vinyl acetate copolymer particles, osmotic pumps, implantable infusion systems, pump delivery, encapsulated cell delivery, liposomal delivery, needle-delivered injection, needle-less injection, nebulizer, aeorosolizer, electroporation, and transdermal patch. Needle-less injector devices are described in U.S. Pat. Nos. 5,879,327; 5,520,639; 5,846,233 and 5,704,911, the specifications of which are herein incorporated by reference. Any of the GAA preparation described herein can administered in these methods.

Optionally the enzyme or GAA enzyme or nucleic acid encoding the enzyme or GAA enzyme and/or the antisense oligomeric compound may be administered in combination with an Active Site-Specific Chaperone (ASSC) for the GAA enzyme (e.g., 1-deoxynojirimycin (DNJ, 1-DNJ)). The ASSC enables higher concentrations of the enzyme or GAA enzyme or nucleic acid encoding the enzyme or GAA enzyme and/or the antisense oligomeric compound in a pharmaceutical composition. In combination with an ASSC the enzyme or GAA enzyme or nucleic acid encoding the enzyme or GAA enzyme and/or the antisense oligomeric compound may be administered at a concentration between about 5 and about 250 mg/mL. Optionally, the enzyme or GAA enzyme or nucleic acid encoding the enzyme or GAA enzyme and/or the antisense oligomeric compound is combined with an ASSC at a high concentration, for example, at a concentration selected from the group consisting of about 25-240 mg/mL, about 80-200 mg/mL, about 115-160 mg/mL. Optionally, the enzyme or GAA enzyme or nucleic acid encoding the enzyme or GAA enzyme and/or the antisense oligomeric compound is combined with an ASSC, wherein the ASSC is present at a concentration between about 5 mg/mL and about 200 mg/mL, optionally between about 32 mg/mL and about 160 mg/mL. Optionally, t the enzyme or GAA enzyme or nucleic acid encoding the enzyme or GAA enzyme and/or the antisense oligomeric compound is combined with an ASSC, wherein the ASSC is present at a concentration between about 0.5 mM and about 20 mM. GAA enzyme combined with an ASSC can remain soluble at a high concentration (e.g., 25 mg/mL) and remain non-aggregated while maintaining a viscosity suitable for injection (e.g., subcutaneous administration). Optionally the compositions of the present invention comprise more than about 5 mg/mL of the enzyme or GAA enzyme or nucleic acid encoding the enzyme or GAA enzyme and/or the antisense oligomeric compound.

Optionally, the compositions of the invention comprise about 5-25 mg/mL the enzyme or GAA enzyme or nucleic acid encoding the enzyme or GAA enzyme and/or the antisense oligomeric compound and about 1-10 mM DNJ.

Optionally, 1-deoxynojirimycin-HCL or a pharmaceutically acceptable salt thereof, may be administered to a subject in a dose of between about 10 mg/kg to 1000 mg/kg, Optionally administered orally, either prior to, concurrent with, or after administration of the the enzyme or GAA enzyme or nucleic acid encoding the enzyme or GAA enzyme and/or the antisense oligomeric compound.

Optionally the method of treating Pompe Disease comprises administering the enzyme or GAA enzyme or nucleic acid encoding the enzyme or GAA enzyme and/or the antisense oligomeric compound biweekly, weekly or once per two weeks for up to about 10 weeks in combination with from about 1 to about 5000 mg/kg of an ASSC (e.g., 1-DNJ-HCl) prior to, and in regular intervals after, the infusion of the enzyme or GAA enzyme or nucleic acid encoding the enzyme or GAA enzyme and/or the antisense oligomeric compound. For example, the ASSC could be administered within two hours of the infusion, and then administered at regular intervals once, twice, three-times, four-times, five-times or six-times within 24 hours post-infusion. Optionally, the GAA is Myozyme® and is administered via infusion once per week and the ASSC (e.g., 1-DNJ-HCl) is administered at 10 mg/kg, 100 mg/kg or 1000 mg/kg 30 minutes prior to infusion, and then 8, 16, and 24 hours after each Myozyme® infusion.

Optionally, the GAA is Lumizyme® and is administered via infusion once per week and the ASSC (e.g., 1-DNJ-HCl) is administered at

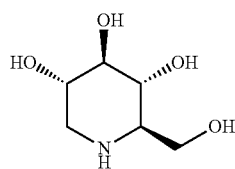 [SMILES: OC[C@H]1NC[C@H](O)[C@@H](O)[C@@H]1O]

10 mg/kg, 100 mg/kg or 1000 mg/kg 30 minutes prior to infusion, and then 8, 16, and 24 hours after each Lumizyme® infusion.

It is believed that acid alpha-glucosidase (GAA) functions to remove terminal glucose residues from lysosomal glycogen. Some genetic mutations reduce GAA trafficking and maturation. The pharmacological chaperone 1-DNJ increases GAA levels by selectively binding and stabilizing the enzyme in a proper conformation which restores proper protein trafficking to the lysosome. Optionally, the ASSC is administered as described in International Publication No. 2008/134628, which is hereby incorporated by reference in its entirety.

The ASSC is a small molecule inhibitor of the GAA enzyme, including reversible competitive inhibitors of the GAA enzyme. Optionally the ASSC may be represented by the formula:

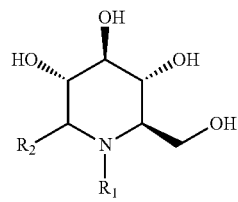

where $R_1$ is H or a straight or branched alkyl, cycloalkyl, alkoxyalkyl or aminoalkyl containing 1-12 carbon atoms optionally substituted with an —OH, —COOH, —Cl, —F, —CF$_3$, —OCF$_3$, —O—C(O)N-(alkyl)$_2$; and $R_2$ is H or a straight or branched alkyl, cycloalkyl, or alkoxylalkyl containing 1-9 carbon atoms; including pharmaceutically acceptable salts, esters and prodrugs thereof. Optionally the ASSC is 1-deoxynojirimycin (1-DNJ), which is represented by the following formula:

or a pharmaceutically acceptable salts, esters or prodrug of 1-deoxynojirimycin. Optionally, the salt is hydrochloride salt (i.e. 1-deoxynojirimycin-HCl). Optionally, the ASSC is N-butyl-deoxynojirimycin (NB-DNJ; Zavesca®, Actelion Pharmaceuticals Ltd, Switzerland), which is represented by the following formula:

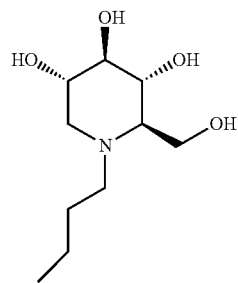

or a pharmaceutically acceptable salt, ester or prodrug of NB-DNJ.

Optionally the ASSC is $C_{10}H_{19}NO_4$, which is represented by the following formula:

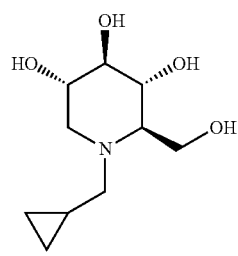 [SMILES: OC[C@@H]1[C@@H](O)[C@H](O)[C@@H](O)CN1CC1CC1]

or a pharmaceutically acceptable salt, ester or prodrug of C10H$_{19}$NO$_4$. Optionally the salt is hydrochloride salt.

Optionally, the ASSC is $C_{12}H_{23}NO_4$, which is represented by the following formula:

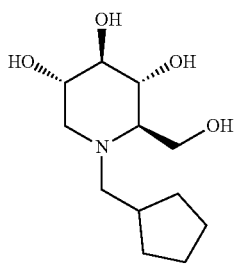 [SMILES: OC[C@@H]1[C@@H](O)[C@H](O)[C@@H](O)CN1CC1CCCC1]

or a pharmaceutically acceptable salt, ester or prodrug of $C_{12}H_{23}NO_4$. Optionally, the salt is hydrochloride salt.

Patients with complete absence of GAA enzyme are cross-reactive immunological material (CRIM) negative, and develop high titer antibody to rhGAA. Patients with GAA protein detectable by western blot are classified as CRIM-positive. Whereas the majority of CRIM-positive patients have sustained therapeutic responses to ERT, or gene therapy CRIM-negative patients almost uniformly do poorly, experiencing rapid clinical decline because of the development of sustained, high-titer antibodies to rhGAA.

A combination of rituximab with methotrexate with or without intravenous gammaglobulins (WIG) may be used to induce tolerance induction of CRIM negative patients. The treatment may be prophylactically to avoid antibody to rhGAA or may be given to patients that have already developed anti-rhGAA. Rituximab may be given in a dose of 100-1000 mg/kg, or in a dose of 150-900 mg/kg, or in a dose of 200-800 mg/kg, or in a dose of 250-750 mg/kg, or in a dose of 300-600 mg/kg, or in a dose of 350-500 mg/kg, or in a dose of 400-450 mg/kg.

Rituximab may be given once every 1, 2, 3, 4, 5, 6, 7, 8, 9, 10, 11, 12, 13, 14, 15, 16, 17, 18, 19, 20, 21, 22, 23, 24, or 25 days. Optionally Rituximab is administered once every 1, 2, 3, 4, 5, 6, 7, 8, 9, 10, 11, 12, 13, 14, 15, 16, 17, 18, 19, 20, 21, 22, 23, 24, or 25 weeks. Optionally Rituximab is administered once every 1, 2, 3, 4, 5, 6, 7, 8, 9, 10, 11, 12, 13, 14, 15, 16, 17, 18, 19, 20, 21, 22, 23, 24, or 25 months. Optionally Rituximab is administered once every 1, 2, 3, 4, 5, 6, 7, 8, 9, 10, years.

Methotrexate may be given in a dose of 0.1-10 mg/kg, or in a dose of 0.2-5 mg/kg, or in a dose of 0.3-2 mg/kg, or in a dose of 0.4-1 mg/kg or in a dose of 0.5-0.7 mg/kg. Methotrexate may be given once every 1, 2, 3, 4, 5, 6, 7, 8, 9, 10, 11, 12, 13, 14, 15, 16, 17, 18, 19, 20, 21, 22, 23, 24, or 25 days. Optionally Methotrexate is administered once every 1, 2, 3, 4, 5, 6, 7, 8, 9, 10, 11, 12, 13, 14, 15, 16, 17, 18, 19, 20, 21, 22, 23, 24, or 25 weeks. Optionally Methotrexate is administered once every 1, 2, 3, 4, 5, 6, 7, 8, 9, 10, 11, 12, 13, 14, 15, 16, 17, 18, 19, 20, 21, 22, 23, 24, or 25 months. Optionally Methotrexate is administered once every 1, 2, 3, 4, 5, 6, 7, 8, 9, 10, years. Administration of Methotrexate may be based on hematologic tolerance. WIG may be given in a dose of 0.1-10 mg/kg, or in a dose of 0.2-5 mg/kg, or in a dose of 0.3-2 mg/kg, or in a dose of 0.4-1 mg/kg or in a dose of 0.5-0.7 mg/kg. IVIG may be given once every 1, 2, 3, 4, 5, 6, 7, 8, 9, 10, 11, 12, 13, 14, 15, 16, 17, 18, 19, 20, 21, 22, 23, 24, or 25 days. Optionally IVIG is administered once every 1, 2, 3, 4, 5, 6, 7, 8, 9, 10, 11, 12, 13, 14, 15, 16, 17, 18, 19, 20, 21, 22, 23, 24, or 25 weeks. Optionally IVIG is administered once every 1, 2, 3, 4, 5, 6, 7, 8, 9, 10, 11, 12, 13, 14, 15, 16, 17, 18, 19, 20, 21, 22, 23, 24, or 25 months. Optionally WIG is administered once every 1, 2, 3, 4, 5, 6, 7, 8, 9, 10, years. Treatment may be given until rhGAA antibody titer is down to zero. Various combinations of administration of the enzyme or GAA and Rituximab, and/or Methotrexate and/or WIG is explicitly envisioned in the present invention.

In one aspect, the invention is directed to an antisense oligomeric compound. Previous work by others has resulted in the design of antisense oligomeric compounds that promote exon exclusion in several human disorders including Duchenne Muscular Dystrophy (DMD). The strategy is simple and straightforward and relies on blocking a well-defined splice site. This results in exon skipping, thereby removing the exon containing the pathogenic gene variant. The resulting mRNA is a little bit shorter resulting in expression of a truncated protein with considerable residual activity, sufficient to at least partially alleviate the disease. The strategy is simple because canonical splice sites are known for virtually all genes. The only requirement is to design an antisense oligomeric compound that binds to the canonical splice site in the pre-mRNA, which will result in blocking of that site and skipping of the exon involved.

A much more difficult task is the reverse process: to promote inclusion rather than exclusion of an exon. To promote exon inclusion, a splice repressor may be blocked using an antisense oligomeric compound. It is however unknown where splice repressors are located. These can be present in introns or in exons and are named intronic or exonic splice silencers (ISSs or ESSs, respectively). There is software available to predict the presence of such silences but these are very unreliable. This is further illustrated by our own experience using the minigene system containing GAA exon 1-3, which failed to confirm activity of predicted splice silencer motifs. The idea to promote exon 2 inclusion of GAA with an antisense oligomeric compound to treat Pompe disease is entirely novel.

sequences targeting SEQ ID NO: 1 are able to enhance inclusion of GAA exon 2. Also sequences targeting SEQ ID NO: 37, SEQ ID NO: 38, SEQ ID NO: 39, SEQ ID NO: 40, were found to be able to enhance inclusion of GAA exon 2. It is to be noted that targeting means that at least part of the sequence SEQ ID NO: 1 is targeted, e.g. by a sequence that hybridizes with at least a part or by the sequence SEQ ID NO: 1, or that binds to at least a part of SEQ ID NO: 1. Sequences that target may be shorter or longer than the target sequence.

| Sequence in cDNA to which AON anneals* | sequence of AON (5'-> 3'): | SEQ ID NO: |
|---|---|---|
| c-32-156_-210 | GCTCTGCACTCCCCTGCTGGAGCTTTT CTCGCCCTTCCTTCTGGCCCTCTCCCC A | 1 |
| c-32-156_-200 | GCTCTGCACTCCCCTGCTGGAGCTTTT CTCGCCCTTCCTTCTGGC | 37 |
| c-32-160_-190 | TGCACTCCCCTGCTGGAGCTTTTCTCG CCCT | 38 |
| c-32-160_195 | TGCACTCCCCTGCTGGAGCTTTTCTCG CCCTTCCTT | 39 |
| c-32-165_-195 | TCCCCTGCTGGAGCTTTTCTCGCCCTT CCTT | 40 |

Optionally the sequences targeting SEQ ID NO: 1 hybridize with at least a part of SEQ ID NO: 1. Sequences that hybridize may be shorter or longer than the target sequence.

Nucleotide sequences SEQ ID NO: 2-33 are oligomers that are able to enhance GAA exon 2 inclusion.

Two variant antisense oligomeric compounds, one of 21 nucleotides (SEQ ID NO: 33) and one of 25 nucleotides (SEQ ID NO: 12), were tested and both were found to enhance exon 2 inclusion. This was accompanied by enhanced GAA enzyme activity of at least 2 fold. It is known that patients with the IVS1 variant have ~15% leaky wild type splicing. The enhancement of 2 fold results in enzyme activities of ~30%, which are known to be above the disease threshold of 20% and thus are anticipated to restore at least a part, or even fully the lysosomal glycogen degradation.

In one aspect or embodiment of aspects and/or embodiments thereof, the invention is directed to an antisense oligomeric compound selected from the group comprising SEQ ID NO: 2-33 and variants and fragments having at least 80% identity thereof. The antisense oligomeric compound may also target single nucleotide polymorphism of SEQ ID NO: 1, 37, 38, 39, 40. It should be noted that it may not necessary to have the full length of SEQ ID NO: 2-33, fragments having a shorter or longer sequence are also envisioned. The inventors have found the target genomic sequence which enables the inclusion of exon 2 of GAA and a skilled person is capable of finding suitable sequences that target this target genomic sequence, such as SEQ ID NO: 1, 37, 38, 39, 40 and single nucleotide polymorphisms thereof. Exemplary sequences that target this target genomic sequence, such as SEQ ID NO: 1, 37, 38, 39, or 41 may be SEQ ID NO: 2-33, but also variants and fragments having at least 80% identity thereof. In particular shorter fragments such as fragments with 18, 19, 20, 21, 22, 23, or 24 nucleotides of SEQ ID NO: 2-33 are envisioned.

In one aspect or embodiment of aspects and/or embodiments thereof, the invention is directed to an antisense oligomeric compound complementary to a polynucleotide having a sequence selected from the group comprising SEQ ID NO: 1, 37-40 and single nucleotide polymorphisms thereof. Also sequences having at least 80% identity to antisense oligomeric compound complementary to a polynucleotide having a sequence selected from the group comprising SEQ ID NO: 1, 37-40 are envisioned. Antisense oligomeric compound that target one or more than one single nucleotide polymorphisms may be designed.

In one aspect or embodiment of aspects and/or embodiments thereof, the invention is directed to an antisense oligomeric compound targeting a sequence selected from the group comprising the genomic sequence c-32-156_-210.

In one aspect or embodiment of aspects and/or embodiments thereof, the invention is directed to an antisense oligomeric compound comprising sequences selected from the group comprising SEQ ID NO: 2-33, 41-1583, 1590-1594 and sequences having at least 80% identity thereof.

In one aspect or embodiment of aspects and/or embodiments thereof, the invention is directed to antisense oligomeric compound comprising a sequences selected from the group comprising SEQ ID NO: 2-33, and 41-540, 1590-1594.

In one aspect or embodiment of aspects and/or embodiments thereof the invention is directed to an antisense oligomeric compound complementary to a genomic nucleic acid sequence of GAA gene targeting the location that comprises the position of the following mutation c.-32-13T>G, c.-32-3C>G c.-32-102T>C, c.-32-56C>T, c.-32-46G>A, c.-32-28C>A, c.-32-28C>T, c.-32-21G>A, c.7G>A, c.11G>A, c.15_17AAA, c.17C>T, c.19_21AAA, c.26_28AAA, c.33_35AAA, c.39G>A, c.42C>T, c.90C>T, c.112G>A, c.137C>T, c.164C>T, c.348G>A, c.373C>T, c.413T>A, c.469C>T, c.476T>C, c.476T>G, c.478T>G, c.482C>T, c.510C>T, c.515T>A, c.520G>A, c.546+11C>T, c.546+14G>A, c.546+19G>A, c.546+23C>A, c.547-6, c.1071, c.1254, c.1552-30, c.1256A>T, c.1551+1G>T, c.546G>T, 0.17C>T, c.469C>T, c.546+23C>A, c.-32-102T>C, c.-32-56C>T, c.11G>A, c.112G>A, c.137C>T.

The above identified mutations have been found to modulate splicing. Targeting the location of the mutation may also modulate the splicing. It is therefore understood that the antisense oligomeric compound targets the location the mutation. The nomenclature of the mutation identifies the location and the mutation. It is understood that the antisense oligomeric compound targets the location of the mutation, and the mutation does not need to be present in the genomic sequence or in the pre-mRNA. The location of the mutation is thus the location of the mutated nucleotide, or the location of the wild type nucleotide of the mutation. The antisense oligomeric compound may be targeted to a sequence comprising nucleotides upstream and nucleotides downstream of the location of the mutation. Optionally the antisense oligomeric compound target a sequence comprising 2-50 nucleotides upstream, and/or 2-50 nucleotides downstream of the location of the mutation, more Optionally the antisense oligomeric compound target a sequence comprising 3-45 nucleotides upstream, and/or 3-45 nucleotides downstream of the location of the mutation, more Optionally the antisense oligomeric compound target a sequence comprising 5-40 nucleotides upstream, and/or 5-40 nucleotides downstream of the location of the mutation, more Optionally the antisense oligomeric compound target a sequence comprising 6-35 nucleotides upstream, and/or 6-35 nucleotides downstream of the location of the mutation, more Optionally the antisense oligomeric compound target a sequence comprising 7-33 nucleotides upstream, and/or 7-33 nucleotides downstream of the location of the mutation, more Optionally the antisense oligomeric compound target a sequence comprising 8-30 nucleotides upstream, and/or 8-30 nucleotides downstream of the location of the mutation, more Optionally the antisense oligomeric compound target a sequence comprising 9-28 nucleotides upstream, and/or 9-28 nucleotides downstream of the location of the mutation, more Optionally the antisense oligomeric compound target a sequence comprising 10-25 nucleotides upstream, and/or 10-25 nucleotides downstream of the location of the mutation, more Optionally the antisense oligomeric compound target a sequence comprising 11-22 nucleotides upstream, and/or 11-22 nucleotides downstream of the location of the mutation, more Optionally the antisense oligomeric compound target a sequence comprising 12-20 nucleotides upstream, and/or 12-20 nucleotides downstream of the location of the mutation, more Optionally the antisense oligomeric compound target a sequence comprising 13-18 nucleotides upstream, and/or 13-18 nucleotides downstream of the location of the mutation, more Optionally the antisense oligomeric compound target a sequence comprising 14-16 nucleotides upstream, and/or 14-16 nucleotides downstream of the location of the mutation.

The nomenclature is well known to a skilled person and can be found in Dunnen and Antonarakis Human mutation 15:7-12(2000) and Antonarakis SE, the Nomenclature Working Group. 1998. Recommendations for a nomenclature system for human gene mutations. Hum Mutat 11:1-3 and on the website (http://www.dmd.nl/mutnomen.html. Genomic positions may also be found on www.pompecenter.nl. All of these are incorporated by reference.

Optionally the genomic nucleic acid sequence is pre-mRNA.

These antisense oligomeric compound are useful in the treatment of glycogen storage disease type II/Pompe disease.

In one aspect or the target sequence is an intronic splicing silencer or ISS. Optionally of the invention and/or embodiments thereof of an aspect and/or embodiments of the invention the target sequence is the GCTCTGCACTCCCCTGCTGGAGCTTTTCTCGC-CCTTCCTTCTGGCCCTC TCCCCA (SEQ ID NO: 1). It should be noted that also naturally occurring single nucleotide polymorphism are included. Antisense oligomeric compounds targeting SEQ ID NO: 1 are a very suitable to treat Pompe patients. Exemplary antisense oligomeric compounds targeting SEQ ID NO: 1 are SEQ ID NO: 2-33 and in particular SEQ ID NO: 12 and SEQ ID NO 33. However the invention is not limited to these two sequences. A skilled person is capable of designing antisense oligomeric compounds against target sequence SEQ ID NO: 1, 37, 38, 39, or 40. The antisense oligomeric compounds against target sequenced SEQ ID NO: 1 may have length of 10 to 100 nucleotides, Optionally 11 to 75 nucleotides, Optionally 12 to 73 nucleotides, Optionally 13 to 70 nucleotides, Optionally 14 to 65 nucleotides, Optionally 15 to 60 nucleotides, Optionally 16 to 55 nucleotides, Optionally 17 to 50 nucleotides, Optionally 18 to 45 nucleotides, Optionally 19 to 40 nucleotides, Optionally 20 to 38 nucleotides, Optionally 21 to 35 nucleotides, Optionally 22 to 33 nucleotides, Optionally 23 to 30 nucleotides, Optionally 24 to 29 nucleotides, Optionally 25 to 28 nucleotides, Optionally 26 to 27 nucleotides.

Hereunder exemplary antisense oligomeric compounds targeting SEQ ID NO: 1 are given

| Sequence in cDNA to which AON anneals* | sequence of AON (5'-> 3'): | Seq ID |
|---|---|---|
| c.-32-180_-156 | TGGGGAGAGGGCCAGAAGGAAGGGC | 2 |
| c.-32-181_-157 | GGGGAGAGGGCCAGAAGGAAGGGCG | 3 |
| c.-32-182_-158 | GGGAGAGGGCCAGAAGGAAGGGCGA | 4 |
| c.-32-183_-159 | GGAGAGGGCCAGAAGGAAGGGCGAG | 5 |
| c.-32-184_-160 | GAGAGGGCCAGAAGGAAGGGCGAGA | 6 |
| c.-32-185_-161 | AGAGGGCCAGAAGGAAGGGCGAGAA | 7 |
| c.-32-186_-162 | GAGGGCCAGAAGGAAGGGCGAGAAA | 8 |
| c.-32-187_-163 | AGGGCCAGAAGGAAGGGCGAGAAAA | 9 |
| c.-32-188_-164 | GGGCCAGAAGGAAGGGCGAGAAAAG | 10 |
| c.-32-189_-165 | GGCCAGAAGGAAGGGCGAGAAAAGC | 11 |
| c.-32-190_-166 | GCCAGAAGGAAGGGCGAGAAAAGCT | 12 |
| c.-32-191_-167 | CCAGAAGGAAGGGCGAGAAAAGCTC | 13 |
| c.-32-192_-168 | CAGAAGGAAGGGCGAGAAAAGCTCC | 14 |
| c.-32-193_-169 | AGAAGGAAGGGCGAGAAAAGCTCCA | 15 |
| c.-32-194_-170 | GAAGGAAGGGCGAGAAAAGCTCCAG | 16 |
| c.-32-195_-171 | AAGGAAGGGCGAGAAAAGCTCCAGC | 17 |
| c.-32-196_-172 | AGGAAGGGCGAGAAAAGCTCCAGCA | 18 |
| c.-32-197_-173 | GGAAGGGCGAGAAAAGCTCCAGCAG | 19 |
| c.-32-198_-174 | GAAGGGCGAGAAAAGCTCCAGCAGG | 20 |
| c.-32-199_-175 | AAGGGCGAGAAAAGCTCCAGCAGGG | 21 |
| c.-32-200_-176 | AGGGCGAGAAAAGCTCCAGCAGGGG | 22 |
| c.-32-201_-177 | GGGCGAGAAAAGCTCCAGCAGGGGA | 23 |
| c.-32-202_-178 | GGCGAGAAAAGCTCCAGCAGGGGAG | 24 |
| c.-32-203_-179 | GCGAGAAAAGCTCCAGCAGGGGAGT | 25 |
| c.-32-204_-180 | CGAGAAAAGCTCCAGCAGGGGAGTG | 26 |
| c.-32-205_-181 | GAGAAAAGCTCCAGCAGGGGAGTGC | 27 |
| c.-32-206_-182 | AGAAAAGCTCCAGCAGGGGAGTGCA | 28 |
| c.-32-207_-183 | GAAAAGCTCCAGCAGGGGAGTGCAG | 29 |
| c.-32-208_-184 | AAAAGCTCCAGCAGGGGAGTGCAGA | 30 |
| c.-32-209_-185 | AAAGCTCCAGCAGGGGAGTGCAGAG | 31 |
| c.-32-210_-186 | AAGCTCCAGCAGGGGAGTGCAGAGC | 32 |
| c.-32-187_-167 | CCAGAAGGAAGGGCGAGAAAA | 33 |

In the above examples the sequences are 25 nucleotides long however longer variants or shorter fragment are also envisioned. Exemplary is SEQ ID NO: 33 which is only 21 nucleotides long and comprises the same nucleotides as SEQ ID NO: 12 but is shorter. Optionally of the invention and/or embodiments thereof of the present invention and/or embodiments thereof the antisense oligomeric compounds are selected from the group of SEQ ID NO: 2-33 and fragments and variants thereof having at least 80% sequence identity. Optionally of the invention and/or embodiments thereof of the present invention and/or embodiments thereof the antisense oligomeric compounds are selected from the group of SEQ ID NO: 2-33 and fragments and variants thereof having at least 80%, 83%, 85%, 87%, 90%, 92%, 93%, 94%, 95%, 96%, 97%, 98%, 99%, 99.2%, 99.3%, 99.4%, 99.5%, 99.6%, 99.7% sequence identity to SEQ ID NO: 2-33.

The present invention is also directed to sequences that are at least 80% identical to SEQ ID NO: 2-33. Optionally at least 85% identical to SEQ ID NO: 2-33, more Optionally at least 88% identical to SEQ ID NO: 2-33, more Optionally at least 90% identical to SEQ ID NO: 2-33. more Optionally at least 91% identical to SEQ ID NO: 2-33, more Optionally at least 92% identical to SEQ ID NO: 2-33, more Optionally at least 93% identical to SEQ ID NO: 2-33, more Optionally at least 94% identical to SEQ ID NO: 2-33, more Optionally at least 95% identical to SEQ ID NO: 2-33, more Optionally at least 96% identical to SEQ ID NO: 2-33, more Optionally at least 97% identical to SEQ ID NO: 2-33, more Optionally at least 98% identical to SEQ ID NO: 2-33, more Optionally at least 99% identical to SEQ ID NO: 2-33.

Preferred antisense sequences are SEQ ID NO: 12, and SEQ ID NO:33 or sequences that are at least 80% identical thereto, Optionally at least 85% identical, more Optionally at least 88% identical, more Optionally at least 90% identical, more Optionally at least 91% identical, more Optionally at least 92% identical, more Optionally at least 93% identical, more Optionally at least 94% identical, more Optionally at least 95% identical, more Optionally at least 96% identical, more Optionally at least 97% identical, more Optionally at least 98% identical, more Optionally at least 99% identical to SEQ ID NO: 12, and/or 33.

Optionally of the invention and/or embodiments thereof of the present invention and/or embodiments thereof the antisense oligomeric compounds are selected from the group of fragments SEQ ID NO: 2-33, wherein the fragment is 16, 17, 18, 19, 20, 21, 22, 23, or 24 nucleotides long. Optionally of the invention and/or embodiments thereof of the present invention and/or embodiments thereof the antisense oligomeric compounds are selected from the group of fragments SEQ ID NO: 2-33, wherein the fragment is 17, 18, 19, 20, 21, or 22 nucleotides long. Optionally of the invention and/or embodiments thereof of the present invention and/or embodiments thereof the antisense oligomeric compounds are selected from the group of fragments SEQ ID NO: 2-33, wherein the fragment is 19, 20, or 21 nucleotides long.

The antisense oligomeric compounds may be selected from the group of SEQ ID NO: 41-540:

| Sequence in GAA cDNA to which AON anneals | AON sequence 5' -> 3' | Seq ID |
|---|---|---|
| c.-32-319_-300 | CCAAACAGCTGTCGCCTGGG | 41 |
| c.-32-299_-280 | AGGTAGACACTTGAAACAGG | 42 |
| c.-32-279_-260 | CCCAGGAAGACCAGCAAGGC | 43 |
| c.-32-259_-240 | TCAAACACGCTTAGAATGTC | 44 |
| c.-32-239_-220 | GTCTGCTAAAATGTTACAAA | 45 |
| c.-32-219_-200 | GAGTGCAGAGCACTTGCACA | 46 |
| c.-32-199_-180 | CGAGAAAGCTCCAGCAGGG | 47 |
| c.-32-179_-160 | GAGAGGGCCAGAAGGAAGGG | 48 |
| c.-32-159_-140 | GCCCTGCTGTCTAGACTGGG | 49 |
| c.-32-139_-120 | AGGTGGCCAGGGTGGGTGTT | 50 |
| c.-32-119_-100 | GCACCCAGGCAGGTGGGGTA | 51 |
| c.-32-99_-80 | CAACCGCGGCTGGCACTGCA | 52 |
| c.-32-79_-60 | TCAAAGCAGCTCTGAGACAT | 53 |
| c.-32-59_-40 | GGGCGGCACTCACGGGGCTC | 54 |
| c.-32-39_-20 | GCTCAGCAGGGAGGCGGGAG | 55 |
| c.-32-19_-0 | CCTGCGGGAGAAGAAAGCGG | 56 |
| c.-30_-12 | GCCTGGACAGCTCCTACAGG | 57 |
| c.-10_+9 | CACTCCCATGGTTGGAGATG | 58 |
| c.10_+29 | TGGGAGCAGGGCGGGTGCCT | 59 |
| c.30_+49 | CGCAGACGGCCAGGAGCCGG | 60 |
| c.50_+69 | GGTTGCCAAGGACACGAGGG | 61 |
| c.70_+89 | ATGTGCCCCAGGAGTGCAGC | 62 |
| c.90_+109 | GCAGGAAATCATGGAGTAGG | 63 |
| c.110_+129 | ACTCAGCTCTCGGGGAACCA | 64 |
| c.130_+149 | TCCAGGACTGGGGAGGAGCC | 65 |
| c.150_+169 | GGTGAGCTGGGTGAGTCTCC | 66 |
| c.170_+189 | TGGTCTGCTGGCTCCCTGCT | 67 |
| c.190_+209 | GCCTGGGCATCCCGGGGCCC | 68 |
| c.210_+229 | CTCTGGGACGGCCGGGGTGT | 69 |
| c.230_+249 | GTCGCACTGTGTGGGCACTG | 70 |
| c.250_+269 | AAGCGGCTGTTGGGGGGAC | 71 |
| c.270_+289 | CCTTGTCAGGGGCGCAATCG | 72 |

| | | |
|---|---|---|
| c.290_+309 | GCACTGTTCCTGGGTGATGG | 73 |
| c.310_+329 | TAGCAACAGCCGCGGGCCTC | 74 |
| c.330_+349 | GCCCCTGCTTTGCAGGGATG | 75 |
| c.350_+369 | CCCCATCTGGGCTCCCTGCA | 76 |
| c.370_+389 | GGGAAGAAGCACCAGGGCTG | 77 |
| c.390_+409 | TGTAGCTGGGGTAGCTGGGT | 78 |
| c.410_+429 | GGAGCTCAGGTTCTCCAGCT | 79 |
| c.430_+449 | GCCGTGTAGCCCATTTCAGA | 80 |
| c.450_+469 | GGGTGGTACGGGTCAGGGTG | 81 |
| c.470_+489 | GTCCTTGGGGAAGAAGGTGG | 82 |
| c.490_+509 | TCCAGCCGCAGGGTCAGGAT | 83 |
| c.510_+529 | TCTCAGTCTCCATCATCACG | 84 |
| c.530_+546 | GTGAAGTGGAGGCGGT | 85 |
| c.-32-225_-206 | AGAGCACTTGCACAGTCTGC | 86 |
| c.-32-223_-204 | GCAGAGCACTTGCACAGTCT | 87 |
| c.-32-221_-202 | GTGCAGAGCACTTGCACAGT | 88 |
| c.-32-217_-198 | GGGAGTGCAGAGCACTTGCA | 89 |
| c.-32-215_-196 | AGGGGAGTGCAGAGCACTTG | 90 |
| c.-32-213_-194 | GCAGGGGAGTGCAGAGCACT | 91 |
| c.-32-185_-166 | GCCAGAAGGAAGGGCGAGAA | 92 |
| c.-32-183_-164 | GGGCCAGAAGGAAGGGCGAG | 93 |
| c.-32-181_-162 | GAGGGCCAGAAGGAAGGGCG | 94 |
| c.-32-177_-158 | GGGAGAGGGCCAGAAGGAAG | 95 |
| c.-32-175_-156 | TGGGGAGAGGGCCAGAAGGA | 96 |
| c.-32-173_-154 | ACTGGGGAGAGGGCCAGAAG | 97 |

| variants that affect aberrant splicing of exon 2 caused by IVS1 in GAA exon 1-3 minigene system | AON sequence designed to block the region surrounding the identified splice element (5' -> 3') | Seq ID |
|---|---|---|
| c.-32-102C > T | CACCCAGGCAGGTGGGGTAAGGTGG | 98 |
| | AGCACCCAGGCAGGTGGGGTAAGGT | 99 |
| | GCAGCACCCAGGCAGGTGGGGTAAG | 100 |
| | CTGCAGCACCCAGGCAGGTGGGGTA | 101 |
| | CACTGCAGCACCCAGGCAGGTGGGG | 102 |
| | GGCACTGCAGCACCCAGGCAGGTGG | 103 |
| | CTGGCACTGCAGCACCCAGGCAGGT | 104 |
| | GGCTGGCACTGCAGCACCCAGGCAG | 105 |
| | GCGGCTGGCACTGCAGCACCCAGGC | 106 |
| | CCGCGGCTGGCACTGCAGCACCCAG | 107 |
| | TCAACCGCGGCTGGCACTGCAGCAC | 108 |
| | ACCCAGGCAGGTGGGGTAAGGTGGC | 109 |
| | GCACCCAGGCAGGTGGGGTAAGGTG | 110 |
| | CAGCACCCAGGCAGGTGGGGTAAGG | 111 |
| | TGCAGCACCCAGGCAGGTGGGGTAA | 112 |
| | ACTGCAGCACCCAGGCAGGTGGGGT | 113 |
| | GCACTGCAGCACCCAGGCAGGTGGG | 114 |
| | TGGCACTGCAGCACCCAGGCAGGTG | 115 |
| | GCTGGCACTGCAGCACCCAGGCAGG | 116 |
| | CGGCTGGCACTGCAGCACCCAGGCA | 117 |
| | CGCGGCTGGCACTGCAGCACCCAGG | 118 |

|   |   |   |
|---|---|---|
| | ACCGCGGCTGGCACTGCAGCACCCA | 119 |
| | CAACCGCGGCTGGCACTGCAGCACC | 120 |
| | ATCAACCGCGGCTGGCACTGCAGCA | 121 |
| c.-32-56C > T, c-32-46G > A, c.-32-28C > A, c.-32-28C >T, c.-32-21G > A | GGCTCTCAAAGCAGCTCTGAGACAT | 122 |
| | GGGGCTCTCAAAGCAGCTCTGAGAC | 123 |
| | ACGGGGCTCTCAAAGCAGCTCTGAG | 124 |
| | TCACGGGGCTCTCAAAGCAGCTCTG | 125 |
| | ACTCACGGGGCTCTCAAAGCAGCTC | 126 |
| | GCACTCACGGGGCTCTCAAAGCAGC | 127 |
| | CGGCACTCACGGGGCTCTCAAAGCA | 128 |
| | GGCGGCACTCACGGGGCTCTCAAAG | 129 |
| | GGGGCGGCACTCACGGGGCTCTCAA | 130 |
| | GAGGGGCGGCACTCACGGGGCTCTC | 131 |
| | GGGAGGGGCGGCACTCACGGGGCTC | 132 |
| | GCGGGAGGGGCGGCACTCACGGGGC | 133 |
| | AGGCGGGAGGGGCGGCACTCACGGG | 134 |
| | GGAGGCGGGAGGGGCGGCACTCACG | 135 |
| | AGGGAGGCGGGAGGGGCGGCACTCA | 136 |
| | GCAGGGAGGCGGGAGGGGCGGCACT | 137 |
| | CAGCAGGGAGGCGGGAGGGGCGGCA | 138 |
| | CTCAGCAGGGAGGCGGGAGGGGCGG | 139 |
| | GGCTCAGCAGGGAGGCGGGAGGGGC | 140 |
| | CGGGCTCAGCAGGGAGGCGGGAGGG | 141 |
| | AGCGGGCTCAGCAGGGAGGCGGGAG | 142 |
| | AAAGCGGGCTCAGCAGGGAGGCGGG | 143 |
| | AGAAAGCGGGCTCAGCAGGGAGGCG | 144 |
| | GAAGAAAGCGGGCTCAGCAGGGAGG | 145 |
| | GAGAAGAAAGCGGGCTCAGCAGGGA | 146 |
| | GGGAGAAGAAAGCGGGCTCAGCAGG | 147 |
| | GCGGGAGAAGAAAGCGGGCTCAGCA | 148 |
| | CTGCGGGAGAAGAAAGCGGGCTCAG | 149 |
| | GCCTGCGGGAGAAGAAAGCGGGCTC | 150 |
| | AGGCCTGCGGGAGAAGAAAGCGGGC | 151 |
| | ACTCCCATGGTTGGAGATGGCCTGG | 152 |
| | TCACTCCCATGGTTGGAGATGGCCT | 153 |
| | CCTCACTCCCATGGTTGGAGATGGC | 154 |
| | TGCCTCACTCCCATGGTTGGAGATG | 155 |
| | GGTGCCTCACTCCCATGGTTGGAGA | 156 |
| | CGGTGCCTCACTCCCATGGTTGGA | 157 |
| | GGCGGGTGCCTCACTCCCATGGTTG | 158 |
| | AGGGCGGGTGCCTCACTCCCATGGT | 159 |
| | GCAGGGCGGGTGCCTCACTCCCATG | 160 |
| | GAGCAGGGCGGGTGCCTCACTCCCA | 161 |
| | GGGAGCAGGGCGGGTGCCTCACTCC | 162 |
| | GTGGGAGCAGGGCGGGTGCCTCACT | 163 |
| | CGGTGGGAGCAGGGCGGGTGCCTCA | 164 |
| | GCCGGTGGGAGCAGGGCGGGTGCCT | 165 |
| | GAGCCGGTGGGAGCAGGGCGGGTGC | 166 |
| | AGGAGCCGGTGGGAGCAGGGCGGGT | 167 |
| | CCAGGAGCCGGTGGGAGCAGGGCGG | 168 |
| | GGCCAGGAGCCGGTGGGAGCAGGGC | 169 |
| | ACGGCCAGGAGCCGGTGGGAGCAGG | 170 |
| | AGACGGCCAGGAGCCGGTGGGAGCA | 171 |
| | GCAGACGGCCAGGAGCCGGTGGGAG | 172 |
| | GCGCAGACGGCCAGGAGCCGGTGGG | 173 |
| | GGGCGCAGACGGCCAGGAGCCGGTG | 174 |
| | GAGGGCGCAGACGGCCAGGAGCCGG | 175 |
| | ACGAGGGCGCAGACGGCCAGGAGCC | 176 |
| | ACACGAGGGCGCAGACGGCCAGGAG | 177 |
| | GGACACGAGGGCGCAGACGGCCAGG | 178 |
| | AAGGACACGAGGGCGCAGACGGCCA | 179 |
| | CCAAGGACACGAGGGCGCAGACGGC | 180 |
| | TGCCAAGGACACGAGGGCGCAGACG | 181 |
| | GCTCTCAAAGCAGCTCTGAGACATC | 182 |
| | GGGCTCTCAAAGCAGCTCTGAGACA | 183 |
| | CTCACGGGGCTCTCAAAGCAGCTCT | 184 |
| | CACTCACGGGGCTCTCAAAGCAGCT | 185 |
| | GGCACTCACGGGGCTCTCAAAGCAG | 186 |
| | GCGGCACTCACGGGGCTCTCAAAGC | 187 |
| | GGGCGGCACTCACGGGGCTCTCAAA | 188 |
| | AGGGGCGGCACTCACGGGGCTCTCA | 189 |
| | GGAGGGGCGGCACTCACGGGGCTCT | 190 |
| | CGGGAGGGGCGGCACTCACGGGGCT | 191 |
| | GCGGGAGGGGCGGCACTCACGGGG | 192 |
| | GAGGCGGGAGGGGCGGCACTCACGG | 193 |
| | GGGAGGCGGGAGGGGCGGCACTCAC | 194 |
| | CAGGGAGGCGGGAGGGGCGGCACTC | 195 |
| | AGCAGGGAGGCGGGAGGGGCGGCAC | 196 |

|  |  |  |
|---|---|---|
|  | TCAGCAGGGAGGCGGGAGGGGCGGC | 197 |
|  | GCTCAGCAGGGAGGCGGGAGGGGCG | 198 |
|  | GGGCTCAGCAGGGAGGCGGGAGGG | 199 |
|  | GCGGGCTCAGCAGGGAGGCGGGAGG | 200 |
|  | AAGCGGGCTCAGCAGGGAGGCGGGA | 201 |
|  | GAAAGCGGGCTCAGCAGGGAGGCGG | 202 |
|  | AAGAAAGCGGGCTCAGCAGGGAGGC | 203 |
|  | AGAAGAAAGCGGGCTCAGCAGGGAG | 204 |
|  | GGAGAAGAAAGCGGGCTCAGCAGGG | 205 |
|  | CGGGAGAAGAAAGCGGGCTCAGCAG | 206 |
|  | TGCGGGAGAAGAAAGCGGGCTCAGC | 207 |
|  | CCTGCGGGAGAAGAAAGCGGGCTCA | 208 |
|  | GGCCTGCGGGAGAAGAAAGCGGGCT | 209 |
|  | CAGGCCTGCGGGAGAAGAAAGCGGG | 210 |
|  | CGGGGCTCTCAAAGCAGCTCTGAGA | 211 |
|  | CACGGGGCTCTCAAAGCAGCTCTGA | 212 |
| c.7G > A, c.11G > A, c.15_17AAA, c.17C > T, c.19_21AAA, c.26_28AAA, c.33_35AAA, c.39G > A, c.42C > T | CTCCCATGGTTGGAGATGGCCTGGA | 213 |
|  | CACTCCCATGGTTGGAGATGGCCTG | 214 |
|  | CTCACTCCCATGGTTGGAGATGGCC | 215 |
|  | GCCTCACTCCCATGGTTGGAGATGG | 216 |
|  | GTGCCTCACTCCCATGGTTGGAGAT | 217 |
|  | GGGTGCCTCACTCCCATGGTTGGAG | 218 |
|  | GCGGGTGCCTCACTCCCATGGTTGG | 219 |
|  | GGGCGGGTGCCTCACTCCCATGGTT | 220 |
|  | CAGGGCGGGTGCCTCACTCCCATGG | 221 |
|  | AGCAGGGCGGGTGCCTCACTCCCAT | 222 |
|  | GGAGCAGGGCGGGTGCCTCACTCCC | 223 |
|  | TGGGAGCAGGGCGGGTGCCTCACTC | 224 |
|  | GGTGGGAGCAGGGCGGGTGCCTCAC | 225 |
|  | CCGGTGGGAGCAGGGCGGGTGCCTC | 226 |
|  | AGCCGGTGGGAGCAGGGCGGGTGCC | 227 |
|  | GGAGCCGGTGGGAGCAGGGCGGGTG | 228 |
|  | CAGGAGCCGGTGGGAGCAGGGCGGG | 229 |
|  | GCCAGGAGCCGGTGGGAGCAGGGCG | 230 |
|  | CGGCCAGGAGCCGGTGGGAGCAGGG | 231 |
|  | GACGGCCAGGAGCCGGTGGGAGCAG | 232 |
|  | CAGACGGCCAGGAGCCGGTGGGAGC | 233 |
|  | CGCAGACGGCCAGGAGCCGGTGGGA | 234 |
|  | GGCGCAGACGGCCAGGAGCCGGTGG | 235 |
|  | AGGGCGCAGACGGCCAGGAGCCGGT | 236 |
|  | CGAGGGCGCAGACGGCCAGGAGCCG | 237 |
|  | CACGAGGGCGCAGACGGCCAGGAGC | 238 |
|  | GACACGAGGGCGCAGACGGCCAGGA | 239 |
|  | AGGACACGAGGGCGCAGACGGCCAG | 240 |
|  | CAAGGACACGAGGGCGCAGACGGCC | 241 |
|  | GCCAAGGACACGAGGGCGCAGACGG | 242 |
|  | TTGCCAAGGACACGAGGGCGCAGAC | 243 |
| c.90C > T, c.112G > A, c.137C > T, c.164C > T | GGATGTGCCCCAGGAGTGCAGCGGT | 244 |
|  | TAGGATGTGCCCCAGGAGTGCAGCG | 245 |
|  | AGTAGGATGTGCCCCAGGAGTGCAG | 246 |
|  | GGAGTAGGATGTGCCCCAGGAGTGC | 247 |
|  | ATGGAGTAGGATGTGCCCCAGGAGT | 248 |
|  | TCATGGAGTAGGATGTGCCCCAGGA | 249 |
|  | AATCATGGAGTAGGATGTGCCCCAG | 250 |
|  | GAAATCATGGAGTAGGATGTGCCCC | 251 |
|  | AGGAAATCATGGAGTAGGATGTGCC | 252 |
|  | GCAGGAAATCATGGAGTAGGATGTG | 253 |
|  | CAGCAGGAAATCATGGAGTAGGATG | 254 |
|  | ACCAGCAGGAAATCATGGAGTAGGA | 255 |
|  | GAACCAGCAGGAAATCATGGAGTAG | 256 |
|  | GGGAACCAGCAGGAAATCATGGAGT | 257 |
|  | CGGGGAACCAGCAGGAAATCATGGA | 258 |
|  | CTCGGGGAACCAGCAGGAAATCATG | 259 |
|  | CTCTCGGGGAACCAGCAGGAAATCA | 260 |
|  | AGCTCTCGGGGAACCAGCAGGAAAT | 261 |
|  | TCAGCTCTCGGGGAACCAGCAGGAA | 262 |
|  | ACTCAGCTCTCGGGGAACCAGCAGG | 263 |
|  | CCACTCAGCTCTCGGGGAACCAGCA | 264 |
|  | AGCCACTCAGCTCTCGGGGAACCAG | 265 |
|  | GGAGCCACTCAGCTCTCGGGGAACC | 266 |
|  | GAGGAGCCACTCAGCTCTCGGGGAA | 267 |
|  | GGGAGGAGCCACTCAGCTCTCGGGG | 268 |
|  | TGGGGAGGAGCCACTCAGCTCTCGG | 269 |
|  | ACTGGGGAGGAGCCACTCAGCTCTC | 270 |
|  | GGACTGGGGAGGAGCCACTCAGCTC | 271 |
|  | CAGGACTGGGGAGGAGCCACTCAGC | 272 |
|  | TCCAGGACTGGGGAGGAGCCACTCA | 273 |

|  |  |  |
|---|---|---|
| | CCTCCAGGACTGGGGAGGAGCCACT | 274 |
| | CTCCTCCAGGACTGGGGAGGAGCCA | 275 |
| | GTCTCCTCCAGGACTGGGGAGGAGC | 276 |
| | GAGTCTCCTCCAGGACTGGGGAGGA | 277 |
| | GTGAGTCTCCTCCAGGACTGGGGAG | 278 |
| | GGGTGAGTCTCCTCCAGGACTGGGG | 279 |
| | CTGGGTGAGTCTCCTCCAGGACTGG | 280 |
| | AGCTGGGTGAGTCTCCTCCAGGACT | 281 |
| | TGAGCTGGGTGAGTCTCCTCCAGGA | 282 |
| | GGTGAGCTGGGTGAGTCTCCTCCAG | 283 |
| | CTGGTGAGCTGGGTGAGTCTCCTCC | 284 |
| | TGCTGGTGAGCTGGGTGAGTCTCCT | 285 |
| | CCTGCTGGTGAGCTGGGTGAGTCTC | 286 |
| | TCCCTGCTGGTGAGCTGGGTGAGTC | 287 |
| | GCTCCCTGCTGGTGAGCTGGGTGAG | 288 |
| | TGGCTCCCTGCTGGTGAGCTGGGTG | 289 |
| | GCTGGCTCCCTGCTGGTGAGCTGGG | 290 |
| | CTGCTGGCTCCCTGCTGGTGAGCTG | 291 |
| | GTCTGCTGGCTCCCTGCTGGTGAGC | 292 |
| | GATGTGCCCCAGGAGTGCAGCGGTT | 293 |
| | AGGATGTGCCCCAGGAGTGCAGCGG | 294 |
| | GTAGGATGTGCCCCAGGAGTGCAGC | 295 |
| | GAGTAGGATGTGCCCCAGGAGTGCA | 296 |
| | TGGAGTAGGATGTGCCCCAGGAGTG | 297 |
| | CATGGAGTAGGATGTGCCCCAGGAG | 298 |
| | ATCATGGAGTAGGATGTGCCCCAGG | 299 |
| | AAATCATGGAGTAGGATGTGCCCCA | 300 |
| | GGAAATCATGGAGTAGGATGTGCCC | 301 |
| | CAGGAAATCATGGAGTAGGATGTGC | 302 |
| | AGCAGGAAATCATGGAGTAGGATGT | 303 |
| | CCAGCAGGAAATCATGGAGTAGGAT | 304 |
| | AACCAGCAGGAAATCATGGAGTAGG | 305 |
| | GGAACCAGCAGGAAATCATGGAGTA | 306 |
| | GGGGAACCAGCAGGAAATCATGGAG | 307 |
| | TCGGGGAACCAGCAGGAAATCATGG | 308 |
| | TCTCGGGGAACCAGCAGGAAATCAT | 309 |
| | GCTCTCGGGGAACCAGCAGGAAATC | 310 |
| | CAGCTCTCGGGGAACCAGCAGGAAA | 311 |
| | CTCAGCTCTCGGGGAACCAGCAGGA | 312 |
| | CACTCAGCTCTCGGGGAACCAGCAG | 313 |
| | GCCACTCAGCTCTCGGGGAACCAGC | 314 |
| | GAGCCACTCAGCTCTCGGGGAACCA | 315 |
| | AGGAGCCACTCAGCTCTCGGGGAAC | 316 |
| | GGAGGAGCCACTCAGCTCTCGGGGA | 317 |
| | GGGGAGGAGCCACTCAGCTCTCGGG | 318 |
| | CTGGGGAGGAGCCACTCAGCTCTCG | 319 |
| | GACTGGGGAGGAGCCACTCAGCTCT | 320 |
| | AGGACTGGGGAGGAGCCACTCAGCT | 321 |
| | CCAGGACTGGGGAGGAGCCACTCAG | 322 |
| | CTCCAGGACTGGGGAGGAGCCACTC | 323 |
| | TCCTCCAGGACTGGGGAGGAGCCAC | 324 |
| | TCTCCTCCAGGACTGGGGAGGAGCC | 325 |
| | AGTCTCCTCCAGGACTGGGGAGGAG | 326 |
| | TGAGTCTCCTCCAGGACTGGGGAGG | 327 |
| | GGTGAGTCTCCTCCAGGACTGGGGA | 328 |
| | TGGGTGAGTCTCCTCCAGGACTGGG | 329 |
| | GCTGGGTGAGTCTCCTCCAGGACTG | 330 |
| | GAGCTGGGTGAGTCTCCTCCAGGAC | 331 |
| | GTGAGCTGGGTGAGTCTCCTCCAGG | 332 |
| | TGGTGAGCTGGGTGAGTCTCCTCCA | 333 |
| | GCTGGTGAGCTGGGTGAGTCTCCTC | 334 |
| | CTGCTGGTGAGCTGGGTGAGTCTCC | 335 |
| | CCCTGCTGGTGAGCTGGGTGAGTCT | 336 |
| | CTCCCTGCTGGTGAGCTGGGTGAGT | 337 |
| | GGCTCCCTGCTGGTGAGCTGGGTGA | 338 |
| | CTGGCTCCCTGCTGGTGAGCTGGGT | 339 |
| | TGCTGGCTCCCTGCTGGTGAGCTGG | 340 |
| | TCTGCTGGCTCCCTGCTGGTGAGCT | 341 |
| | GGTCTGCTGGCTCCCTGCTGGTGAG | 342 |
| c.348G > A, c.373C > T | AGCCCCTGCTTTGCAGGGATGTAGC | 343 |
| | GCAGCCCTGCTTTGCAGGGATGTA | 344 |
| | CTGCAGCCCTGCTTTGCAGGGATG | 345 |
| | CCCTGCAGCCCCTGCTTTGCAGGGA | 346 |
| | CTCCCTGCAGCCCCTGCTTTGCAGG | 347 |
| | GGCTCCCTGCAGCCCCTGCTTTGCA | 348 |
| | TGGGCTCCCTGCAGCCCCTGCTTTG | 349 |
| | TCTGGGCTCCCTGCAGCCCCTGCTT | 350 |
| | CATCTGGGCTCCCTGCAGCCCCTGC | 351 |

-continued

| | | |
|---|---|---|
| | CCCATCTGGGCTCCCTGCAGCCCCT | 352 |
| | GCCCCATCTGGGCTCCCTGCAGCCC | 353 |
| | CTGCCCCATCTGGGCTCCCTGCAGC | 354 |
| | GGCTGCCCCATCTGGGCTCCCTGCA | 355 |
| | AGGGCTGCCCCATCTGGGCTCCCTG | 356 |
| | CCAGGGCTGCCCCATCTGGGCTCCC | 357 |
| | CACCAGGGCTGCCCCATCTGGGCTC | 358 |
| | AGCACCAGGGCTGCCCCATCTGGGC | 359 |
| | GAAGCACCAGGGCTGCCCCATCTGG | 360 |
| | AAGAAGCACCAGGGCTGCCCCATCT | 361 |
| | GGAAGAAGCACCAGGGCTGCCCCAT | 362 |
| | TGGGAAGAAGCACCAGGGCTGCCCC | 363 |
| | GGTGGGAAGAAGCACCAGGGCTGCC | 364 |
| | TGGGTGGGAAGAAGCACCAGGGCTG | 365 |
| | GCTGGGTGGGAAGAAGCACCAGGGC | 366 |
| | GCCCCTGCTTTGCAGGGATGTAGCA | 367 |
| | CAGCCCCTGCTTTGCAGGGATGTAG | 368 |
| | TGCAGCCCCTGCTTTGCAGGGATGT | 369 |
| | CCTGCAGCCCCTGCTTTGCAGGGAT | 370 |
| | TCCCTGCAGCCCCTGCTTTGCAGGG | 371 |
| | GCTCCCTGCAGCCCCTGCTTTGCAG | 372 |
| | GGGCTCCCTGCAGCCCCTGCTTTGC | 373 |
| | CTGGGCTCCCTGCAGCCCCTGCTTT | 374 |
| | ATCTGGGCTCCCTGCAGCCCCTGCT | 375 |
| | CCATCTGGGCTCCCTGCAGCCCCTG | 376 |
| | CCCCATCTGGGCTCCCTGCAGCCCC | 377 |
| | TGCCCCATCTGGGCTCCCTGCAGCC | 378 |
| | GCTGCCCCATCTGGGCTCCCTGCAG | 379 |
| | GGGCTGCCCCATCTGGGCTCCCTGC | 380 |
| | CAGGGCTGCCCCATCTGGGCTCCCT | 381 |
| | ACCAGGGCTGCCCCATCTGGGCTCC | 382 |
| | GCACCAGGGCTGCCCCATCTGGGCT | 383 |
| | AAGCACCAGGGCTGCCCCATCTGGG | 384 |
| | AGAAGCACCAGGGCTGCCCCATCTG | 385 |
| | GAAGAAGCACCAGGGCTGCCCCATC | 386 |
| | GGGAAGAAGCACCAGGGCTGCCCCA | 387 |
| | GTGGGAAGAAGCACCAGGGCTGCCC | 388 |
| | GGGTGGGAAGAAGCACCAGGGCTGC | 389 |
| | CTGGGTGGGAAGAAGCACCAGGGCT | 390 |
| | AGCTGGGTGGGAAGAAGCACCAGGG | 391 |
| c.413T > A | CAGCTTGTAGCTGGGGTAGCTGGGT | 392 |
| | TCCAGCTTGTAGCTGGGGTAGCTGG | 393 |
| | TCTCCAGCTTGTAGCTGGGGTAGCT | 394 |
| | GTTCTCCAGCTTGTAGCTGGGGTAG | 395 |
| | AGGTTCTCCAGCTTGTAGCTGGGGT | 396 |
| | TCAGGTTCTCCAGCTTGTAGCTGGG | 397 |
| | GCTCAGGTTCTCCAGCTTGTAGCTG | 398 |
| | GAGCTCAGGTTCTCCAGCTTGTAGC | 399 |
| | AGGAGCTCAGGTTCTCCAGCTTGTA | 400 |
| | AGAGGAGCTCAGGTTCTCCAGCTTG | 401 |
| | TCAGAGGAGCTCAGGTTCTCCAGCT | 402 |
| | TTTCAGAGGAGCTCAGGTTCTCCAG | 403 |
| | AGCTTGTAGCTGGGGTAGCTGGGTG | 404 |
| | CCAGCTTGTAGCTGGGGTAGCTGGG | 405 |
| | CTCCAGCTTGTAGCTGGGGTAGCTG | 406 |
| | TTCTCCAGCTTGTAGCTGGGGTAGC | 407 |
| | GGTTCTCCAGCTTGTAGCTGGGGTA | 408 |
| | CAGGTTCTCCAGCTTGTAGCTGGGG | 409 |
| | CTCAGGTTCTCCAGCTTGTAGCTGG | 410 |
| | AGCTCAGGTTCTCCAGCTTGTAGCT | 411 |
| | GGAGCTCAGGTTCTCCAGCTTGTAG | 412 |
| | GAGGAGCTCAGGTTCTCCAGCTTGT | 413 |
| | CAGAGGAGCTCAGGTTCTCCAGCTT | 414 |
| | TTCAGAGGAGCTCAGGTTCTCCAGC | 415 |
| | ATTTCAGAGGAGCTCAGGTTCTCCA | 416 |
| c.469C > T, c.476T > C, | GGGGTGGTACGGGTCAGGGTGGCCG | 417 |
| c.476T > G, c.478T > G, | TGGGGGTGGTACGGGTCAGGGTGGC | 418 |
| c.482C > T | GGTGGGGGTGGTACGGGTCAGGGTG | 419 |
| | AAGGTGGGGGTGGTACGGGTCAGGG | 420 |
| | AGAAGGTGGGGGTGGTACGGGTCAG | 421 |
| | GAAGAAGGTGGGGGTGGTACGGGTC | 422 |
| | GGGAAGAAGGTGGGGGTGGTACGGG | 423 |
| | TGGGAAGAAGGTGGGGGTGGTACG | 424 |
| | CTTGGGGAAGAAGGTGGGGGTGGTA | 425 |
| | TCCTTGGGGAAGAAGGTGGGGGTGG | 426 |
| | TGTCCTTGGGGAAGAAGGTGGGGGT | 427 |
| | GATGTCCTTGGGGAAGAAGGTGGGG | 428 |

-continued

| | | |
|---|---|---|
| | AGGATGTCCTTGGGGAAGAAGGTGG | 429 |
| | TCAGGATGTCCTTGGGGAAGAAGGT | 430 |
| | GGTCAGGATGTCCTTGGGGAAGAAG | 431 |
| | AGGGTCAGGATGTCCTTGGGGAAGA | 432 |
| | GCAGGGTCAGGATGTCCTTGGGGAA | 433 |
| | CCGCAGGGTCAGGATGTCCTTGGGG | 434 |
| | AGCCGCAGGGTCAGGATGTCCTTGG | 435 |
| | GGGTGGTACGGGTCAGGGTGGCCGT | 436 |
| | GGGGGTGGTACGGGTCAGGGTGGCC | 437 |
| | GTGGGGGTGGTACGGGTCAGGGTGG | 438 |
| | AGGTGGGGGTGGTACGGGTCAGGGT | 439 |
| | GAAGGTGGGGGTGGTACGGGTCAGG | 440 |
| | AAGAAGGTGGGGGTGGTACGGGTCA | 441 |
| | GGAAGAAGGTGGGGGTGGTACGGGT | 442 |
| | GGGGAAGAAGGTGGGGGTGGTACGG | 443 |
| | TTGGGGAAGAAGGTGGGGGTGGTAC | 444 |
| | CCTTGGGGAAGAAGGTGGGGGTGGT | 445 |
| | GTCCTTGGGGAAGAAGGTGGGGGTG | 446 |
| | ATGTCCTTGGGGAAGAAGGTGGGGG | 447 |
| | GGATGTCCTTGGGGAAGAAGGTGGG | 448 |
| | CAGGATGTCCTTGGGGAAGAAGGTG | 449 |
| | GTCAGGATGTCCTTGGGGAAGAAGG | 450 |
| | GGGTCAGGATGTCCTTGGGGAAGAA | 451 |
| | CAGGGTCAGGATGTCCTTGGGGAAG | 452 |
| | CGCAGGGTCAGGATGTCCTTGGGGA | 453 |
| | GCCGCAGGGTCAGGATGTCCTTGGG | 454 |
| | CAGCCGCAGGGTCAGGATGTCCTTG | 455 |
| c.510C > T, c.515T > A, | CGTCCAGCCGCAGGGTCAGGATGTC | 456 |
| c.520G > A | CACGTCCAGCCGCAGGGTCAGGATG | 457 |
| | ATCACGTCCAGCCGCAGGGTCAGGA | 458 |
| | TCATCACGTCCAGCCGCAGGGTCAG | 459 |
| | CATCATCACGTCCAGCCGCAGGGTC | 460 |
| | TCCATCATCACGTCCAGCCGCAGGG | 461 |
| | TCTCCATCATCACGTCCAGCCGCAG | 462 |
| | AGTCTCCATCATCACGTCCAGCCGC | 463 |
| | TCAGTCTCCATCATCACGTCCAGCC | 464 |
| | TCTCAGTCTCCATCATCACGTCCAG | 465 |
| | GTTCTCAGTCTCCATCATCACGTCC | 466 |
| | CGGTTCTCAGTCTCCATCATCACGT | 467 |
| | GGCGGTTCTCAGTCTCCATCATCAC | 468 |
| | GAGGCGGTTCTCAGTCTCCATCATC | 469 |
| | TGGAGGCGGTTCTCAGTCTCCATCA | 470 |
| | AGTGGAGGCGGTTCTCAGTCTCCAT | 471 |
| | GAAGTGGAGGCGGTTCTCAGTCTCC | 472 |
| | GTCCAGCCGCAGGGTCAGGATGTCC | 473 |
| | ACGTCCAGCCGCAGGGTCAGGATGT | 474 |
| | TCACGTCCAGCCGCAGGGTCAGGAT | 475 |
| | CATCACGTCCAGCCGCAGGGTCAGG | 476 |
| | ATCATCACGTCCAGCCGCAGGGTCA | 477 |
| | CCATCATCACGTCCAGCCGCAGGGT | 478 |
| | CTCCATCATCACGTCCAGCCGCAGG | 479 |
| | GTCTCCATCATCACGTCCAGCCGCA | 480 |
| | CAGTCTCCATCATCACGTCCAGCCG | 481 |
| | CTCAGTCTCCATCATCACGTCCAGC | 482 |
| | TTCTCAGTCTCCATCATCACGTCCA | 483 |
| | GGTTCTCAGTCTCCATCATCACGTC | 484 |
| | GCGGTTCTCAGTCTCCATCATCACG | 485 |
| | AGGCGGTTCTCAGTCTCCATCATCA | 486 |
| | GGAGGCGGTTCTCAGTCTCCATCAT | 487 |
| | GTGGAGGCGGTTCTCAGTCTCCATC | 488 |
| | AAGTGGAGGCGGTTCTCAGTCTCCA | 489 |
| | TGAAGTGGAGGCGGTTCTCAGTCTC | 490 |
| c.546+11C > T, | TGCCCTGCCCACCGTGAAGTGGAGG | 491 |
| c.546+14G > A, | CCTGCCCTGCCCACCGTGAAGTGGA | 492 |
| c.546+19G > A, | CCCCTGCCCTGCCCACCGTGAAGTG | 493 |
| c.546+23C > A | CGCCCCTGCCCTGCCCACCGTGAAG | 494 |
| | CCCGCCCCTGCCCTGCCCACCGTGA | 495 |
| | GCCCTGCCCACCGTGAAGTGGAGGC | 496 |
| | CTGCCCTGCCCACCGTGAAGTGGAG | 497 |
| | CCCTGCCCTGCCCACCGTGAAGTGG | 498 |
| | GCCCCTGCCCTGCCCACCGTGAAGT | 499 |
| | CCGCCCCTGCCCTGCCCACCGTGAA | 500 |
| | CCCCGCCCCTGCCCTGCCCACCGTG | 501 |
| | GCCCCGCCCCTGCCCTGCCCACCG | 502 |
| | CCGCCCCGCCCCTGCCCTGCCCAC | 503 |
| | CGCCGCCCCCGCCCCTGCCCTGCCC | 504 |
| | GCCGCCGCCCCCGCCCCTGCCCTGC | 505 |

-continued

| | | |
|---|---|---|
| | TGGCCGCCGCCCCCGCCCCTGCCCT | 506 |
| | CCTGGCCGCCGCCCCGCCCCTGCC | 507 |
| | GCCCTGGCCGCCGCCCCCGCCCCTG | 508 |
| | CTGCCCTGGCCGCCGCCCCCGCCCC | 509 |
| | CTCTGCCCTGGCCGCCGCCCCCGCC | 510 |
| | CCCTCTGCCCTGGCCGCCGCCCCCG | 511 |
| | CACCCTCTGCCCTGGCCGCCGCCCC | 512 |
| | CGCACCCTCTGCCCTGGCCGCCGCC | 513 |
| | CGCGCACCCTCTGCCCTGGCCGCCG | 514 |
| | CCCCCGCCCCTGCCCTGCCCACCGT | 515 |
| | CGCCCCCGCCCCTGCCCTGCCCACC | 516 |
| | GCCGCCCCCGCCCCTGCCCTGCCCA | 517 |
| | CCGCCGCCCCCGCCCCTGCCCTGCC | 518 |
| | GGCCGCCGCCCCCGCCCCTGCCCTG | 519 |
| | CTGGCCGCCGCCCCCGCCCCTGCCC | 520 |
| | CCCTGGCCGCCGCCCCCGCCCCTGC | 521 |
| | TGCCCTGGCCGCCGCCCCCGCCCCT | 522 |
| | TCTGCCCTGGCCGCCGCCCCCGCCC | 523 |
| | CCTCTGCCCTGGCCGCCGCCCCCGC | 524 |
| | ACCCTCTGCCCTGGCCGCCGCCCCC | 525 |
| | GCACCCTCTGCCCTGGCCGCCGCCC | 526 |
| | GCGCACCCTCTGCCCTGGCCGCCGC | 527 |
| c.547-6 | AGAGATGGGGGTTTATTGATGTTCC | 528 |
| | GAAGAGATGGGGGTTTATTGATGTT | 529 |
| | TAGAAGAGATGGGGGTTTATTGATG | 530 |
| | TCTAGAAGAGATGGGGGTTTATTGA | 531 |
| | GATCTAGAAGAGATGGGGGTTTATT | 532 |
| | TTGATCTAGAAGAGATGGGGGTTTA | 533 |
| | CTTTGATCTAGAAGAGATGGGGGTT | 534 |
| | ATCTTTGATCTAGAAGAGATGGGGG | 535 |
| | GGATCTTTGATCTAGAAGAGATGGG | 536 |
| | CTGGATCTTTGATCTAGAAGAGATG | 537 |
| | AGCTGGATCTTTGATCTAGAAGAGA | 538 |
| | TTAGCTGGATCTTTGATCTAGAAGA | 539 |
| | TGTTAGCTGGATCTTTGATCTAGAA | 540 |

In the above examples the sequences are 25 nucleotides long however longer variants or shorter fragment are also envisioned. Optionally of the invention and/or embodiments thereof of the present invention and/or embodiments thereof the antisense oligomeric compounds are selected from the group of SEQ ID NO: 41-540 and fragments and variants thereof having at least 80% sequence identity. Optionally of the invention and/or embodiments thereof of the present invention and/or embodiments thereof the antisense oligomeric compounds are selected from the group of SEQ ID NO: 41-540 and fragments and variants thereof having at least 80%, 83%, 85%, 87%, 90%, 92%, 93%, 94%, 95%, 96%, 97%, 98%, 99%, 99.2%, 99.3%, 99.4%, 99.5%, 99.6%, 99.7% sequence identity to SEQ ID NO: 41-540.

The present invention is also directed to sequences that are at least 80% identical to SEQ ID NO: 41-540. Optionally at least 85% identical to SEQ ID NO: 41-540, more Optionally at least 88% identical to SEQ ID NO: 41-540, more Optionally at least 90% identical to SEQ ID NO: 41-540, more Optionally at least 91% identical to SEQ ID NO: 41-540, more Optionally at least 92% identical to SEQ ID NO: 41-540, more Optionally at least 93% identical to SEQ ID NO: 41-540, more Optionally at least 94% identical to SEQ ID NO: 41-540, more Optionally at least 95% identical to SEQ ID NO: 41-540, more Optionally at least 96% identical to SEQ ID NO: 41-540, more Optionally at least 97% identical to SEQ ID NO: 41-540, more Optionally at least 98% identical to SEQ ID NO: 41-540, more Optionally at least 99% identical to SEQ ID NO: 41-540.

Optionally of the invention and/or embodiments thereof of the present invention and/or embodiments thereof the antisense oligomeric compounds are selected from the group of fragments SEQ ID NO: 41-540, wherein the fragment is 16, 17, 18, 19, 20, 21, 22, 23, or 24 nucleotides long. Optionally of the invention and/or embodiments thereof of the present invention and/or embodiments thereof the antisense oligomeric compounds are selected from the group of fragments SEQ ID NO: 41-540, wherein the fragment is 17, 18, 19, 20, 21, or 22 nucleotides long. Optionally of the invention and/or embodiments thereof of the present invention and/or embodiments thereof the antisense oligomeric compounds are selected from the group of fragments SEQ ID NO: 41-540, wherein the fragment is 19, 20, or 21 nucleotides long.

Optionally of the invention and/or embodiments thereof the target sequence provides exclusion of intron 6. It was found that SEQ ID NO: 1584 provides the target sequence for exclusion of intron 6.

Optionally of the invention and/or embodiments thereof of an aspect and/or embodiments of the invention the target sequence is the AACCCCAGAGCTGCTTCCCTTCCAGATGTGGTCCTGCAGCCGAGCCCT GCCCTTAGCTGGAGGTCGACAGGTGGGATCCTGGATGTCTACATCTTC CTGGGCCCAGAGCCCAAGAGCGTGGTGCAGCAGTACCTGGACGTTGTG GGTAGGGCCTGCTCCCTGGCCGCGGCCCCCGCCCCAAGGCTCCCTCCT CCCTCCCTCATGAAGTCGGCGTTGGCCTGCAGGATACCCGTTCATGCC GCCATACTGGGGCCTGGGCTTCCACCTGTGCCGCTGGGGCTACTCCTC CACCGCTATCACCCGCCAGGTGGTGGAGAACATGACCAGGGCCCACTT CCCCCTGGTGAGTTGGGGTGGTGGCAGGGGAG (SEQ ID NO: 1584). It should be noted that also naturally occurring single nucleotide polymorphism are included.

Also the following genomic sequences are target sequences for exclusion of intron 6 of GAA:

| Sequence in cDNA to which antisense oligomeric compound anneals* | sequence of region (5'-> 3'): | Seq ID |
|---|---|---|
| c.956-25_1194+25 | AACCCCAGAGCTGCTTCCCTTCCAGATGTGGTCCTGC AGCCGAGCCCTGCCCTTAGCTGGAGGTCGACAGGTG GGATCCTGGATGTCTACATCTTCCTGGGCCCAGAGC CCAAGAGCGTGGTGCAGCAGTACCTGGACGTTGTGG GTAGGGCCTGCTCCCTGGCCGCGGCCCCCGCCCCAA GGCTCCCTCCTCCCTCCCTCATGAAGTCGGCGTTGG CCTGCAGGATACCCGTTCATGCCGCCATACTGGGGC CTGGGCTTCCACCTGTGCCGCTGGGGCTACTCCTCC ACCGCTATCACCCGCCAGGTGGTGGAGAACATGACC AGGGCCCACTTCCCCCTGGTGAGTTGGGGTGGTGGC AGGGGAG | 1584 |
| c.956-25_1004 | AACCCCAGAGCTGCTTCCCTTCCAGATGTGGTCCTGC AGCCGAGCCCTGCCCTTAGCTGGAGGTCGACAGGTGG | 1585 |
| c.1005_1075+3 | GATCCTGGATGTCTACATCTTCCTGGGCCCAGAGCC CAAGAGCGTGGTGCAGCAGTACCTGGACGTTGTGGG TA | 1586 |
| c.1075+4_1076-2 | GGGCCTGCTCCCTGGCCGCGGCCCCCGCCCCAAGGC TCCCTCCTCCCTCCCTCATGAAGTCGGCGTTGGCCTGC | 1587 |
| c.1076-2_1147 | AGGATACCCGTTCATGCCGCCATACTGGGGCCTGGG CTTCCACCTGTGCCGCTGGGGCTACTCCTCCACCGCTA | 1588 |
| c.1148_1194+25 | TCACCCGCCAGGTGGTGGAGAACATGACCAGGGCCC ACTTCCCCCTGGTGAGTTGGGGTGGTGGCAGGGGAG | 1589 |

It is to be noted that targeting means that at least part of the sequence SEQ ID NO: 1584-1589 is targeted, e.g. by a sequence that hybridizes with at least a part or by the sequence SEQ ID NO: 1584-1589, or that binds to at least a part of SEQ ID NO: 1584-1589. Sequences that target may be shorter or longer than the target sequence.

Optionally the sequences targeting SEQ ID NO: 1584-1589 hybridize with at least a part of SEQ ID NO: 1584-1589. Sequences that hybridize may be shorter or longer than the target sequence. Nucleotide sequences SEQ ID NO: 541-1583 are oligomers that are able to enhance GAA intron 6 exclusion.

In one aspect or embodiment of aspects and/or embodiments thereof, the invention is directed to an antisense oligomeric compound selected from the group comprising SEQ ID NO: 541-1583 and variants and fragments having at least 80% identity thereof. The antisense oligomeric compound may also target single nucleotide polymorphism of SEQ ID NO: 1584-1589. It should be noted that it may not necessary to have the full length of SEQ ID NO: 541-1583, fragments having a shorter or longer sequence are also envisioned. The inventors have found the target genomic sequence which enables the exclusion of intron 6 and a skilled person is capable of finding suitable sequences that target this target genomic sequence, such as SEQ ID NO: 1584-1589 and single nucleotide polymorphisms thereof. Exemplary sequences that target this target genomic sequence, such as SEQ ID NO: 1584-1589 may be SEQ ID NO: 541-1583, but also variants and fragments having at least 80% identity thereof. In particular shorter fragments such as fragments with 18, 19, 20, 21, 22, 23, or 24 nucleotides of SEQ ID NO: 541-1583 are envisioned.

In one aspect or embodiment of aspects and/or embodiments thereof, the invention is directed to an antisense oligomeric compound complementary to a polynucleotide having a sequence selected from the group comprising SEQ ID NO: 1584-1589 and single nucleotide polymorphisms thereof. Also sequences having at least 80% identity to antisense oligomeric compound complementary to a polynucleotide having a sequence selected from the group comprising SEQ ID NO: 1584-1589 are envisioned. Antisense oligomeric compound that target one or more than one single nucleotide polymorphisms may be designed.

In one aspect or embodiment of aspects and/or embodiments thereof, the invention is directed to an antisense oligomeric compound targeting a sequence selected from the group comprising the genomic sequence c.956-25_1194+25.

In one aspect or embodiment of aspects and/or embodiments thereof, the invention is directed to an antisense oligomeric compound comprising sequences selected from the group comprising SEQ ID NO: 41-1583, 1590-1594 and sequences having at least 80% identity thereof.

In one aspect or embodiment of aspects and/or embodiments thereof, the invention is directed to antisense oligomeric compound comprising a sequences selected from the group comprising SEQ ID NO: 541-1583, 1590-1594.

Antisense oligomeric compounds targeting SEQ ID NO: 1584 are a very suitable to treat Pompe patients. Exemplary antisense oligomeric compounds targeting SEQ ID NO: 1584 are SEQ ID NO: 541-1853. However the invention is not limited to these sequences. A skilled person is capable of designing antisense oligomeric compounds against target sequence SEQ ID NO: 1584, 1885, 1586, 1587, 1588, 1589. The antisense oligomeric compounds against target sequenced SEQ ID NO: 1584, 1885, 1586, 1587, 1588, or 1589 may have length of 10 to 100 nucleotides, Optionally 11 to 75 nucleotides, Optionally 12 to 73 nucleotides, Optionally 13 to 70 nucleotides, Optionally 14 to 65 nucleotides, Optionally 15 to 60 nucleotides, Optionally 16 to 55 nucleotides, Optionally 17 to 50 nucleotides, Optionally 18 to 45 nucleotides, Optionally 19 to 40 nucleotides, Optionally 20 to 38 nucleotides, Optionally 21 to 35 nucleotides, Optionally 22 to 33 nucleotides, Optionally 23 to 30 nucleotides, Optionally 24 to 29 nucleotides, Optionally 25 to 28 nucleotides, Optionally 26 to 27 nucleotides.

The antisense oligomeric compounds may be selected from the group of SEQ ID NO541-1583:

| Sequence in cDNA to which AON anneals for intron 6 exclusion | AON sequence 5' -> 3' | Seq ID |
|---|---|---|
| c.956-25_-1 | CTGGAAGGGAAGCAGCTCTGGGGTT | 541 |
| c.956-24_956 | TCTGGAAGGGAAGCAGCTCTGGGT | 542 |
| c.956-23_957 | ATCTGGAAGGGAAGCAGCTCTGGG | 543 |
| c.956-22_958 | CATCTGGAAGGGAAGCAGCTCTGG | 544 |
| c.956-21_959 | ACATCTGGAAGGGAAGCAGCTCTG | 545 |
| c.956-20_960 | CACATCTGGAAGGGAAGCAGCTCT | 546 |
| c.956-19_961 | CCACATCTGGAAGGGAAGCAGCTCT | 547 |
| c.956-18_962 | ACCACATCTGGAAGGGAAGCAGCTC | 548 |
| c.956-17_963 | GACCACATCTGGAAGGGAAGCAGCT | 549 |
| c.956-16_964 | GGACCACATCTGGAAGGGAAGCAGC | 550 |
| c.956-15_965 | AGGACCACATCTGGAAGGGAAGCAG | 551 |
| c.956-14_966 | CAGGACCACATCTGGAAGGGAAGCA | 552 |
| c.956-13_967 | GCAGGACCACATCTGGAAGGGAAGC | 553 |
| c.956-12_968 | TGCAGGACCACATCTGGAAGGGAAG | 554 |
| c.956-11_969 | CTGCAGGACCACATCTGGAAGGGAA | 555 |
| c.956-10_970 | GCTGCAGGACCACATCTGGAAGGGA | 556 |
| c.956-9_971 | GGCTGCAGGACCACATCTGGAAGGG | 557 |
| c.956-8_972 | CGGCTGCAGGACCACATCTGGAAGG | 558 |
| c.956-7_973 | TCGGCTGCAGGACCACATCTGGAAG | 559 |
| c.956-6_974 | CTCGGCTGCAGGACCACATCTGGAA | 560 |
| c.956-5_975 | GCTCGGCTGCAGGACCACATCTGGA | 561 |
| c.956-4_976 | GGCTCGGCTGCAGGACCACATCTGG | 562 |
| c.956-3_977 | GGGCTCGGCTGCAGGACCACATCTG | 563 |
| c.956-2_978 | AGGGCTCGGCTGCAGGACCACATCT | 564 |
| c.956-1_979 | CAGGGCTCGGCTGCAGGACCACATC | 565 |
| c.956_980 | GCAGGGCTCGGCTGCAGGACCACAT | 566 |
| c.957_981 | GGCAGGGCTCGGCTGCAGGACCACA | 567 |
| c.958_982 | GGGCAGGGCTCGGCTGCAGGACCAC | 568 |
| c.959_983 | AGGGCAGGGCTCGGCTGCAGGACCA | 569 |
| c.960_984 | AAGGGCAGGGCTCGGCTGCAGGACC | 570 |
| c.961_985 | TAAGGGCAGGGCTCGGCTGCAGGAC | 571 |
| c.962_986 | CTAAGGGCAGGGCTCGGCTGCAGGA | 572 |
| c.963_987 | GCTAAGGGCAGGGCTCGGCTGCAGG | 573 |
| c.964_988 | AGCTAAGGGCAGGGCTCGGCTGCAG | 574 |
| c.965_989 | CAGCTAAGGGCAGGGCTCGGCTGCA | 575 |
| c.966_990 | CCAGCTAAGGGCAGGGCTCGGCTGC | 576 |
| c.967_991 | TCCAGCTAAGGGCAGGGCTCGGCTG | 577 |
| c.968_992 | CTCCAGCTAAGGGCAGGGCTCGGCT | 578 |
| c.969_993 | CCTCCAGCTAAGGGCAGGGCTCGGC | 579 |
| c.970_994 | ACCTCCAGCTAAGGGCAGGGCTCGG | 580 |
| c.971_995 | GACCTCCAGCTAAGGGCAGGGCTCG | 581 |
| c.972_996 | CGACCTCCAGCTAAGGGCAGGGCTC | 582 |
| c.973_997 | TCGACCTCCAGCTAAGGGCAGGGCT | 583 |
| c.974_998 | GTCGACCTCCAGCTAAGGGCAGGGC | 584 |
| c.975_999 | TGTCGACCTCCAGCTAAGGGCAGGG | 585 |
| c.976_1000 | CTGTCGACCTCCAGCTAAGGGCAGG | 586 |
| c.977_1001 | CCTGTCGACCTCCAGCTAAGGGCAG | 587 |
| c.978_1002 | ACCTGTCGACCTCCAGCTAAGGGCA | 588 |
| c.979_1003 | CACCTGTCGACCTCCAGCTAAGGGC | 589 |
| c.980_1004 | CCACCTGTCGACCTCCAGCTAAGGG | 590 |
| c.981_1005 | CCCACCTGTCGACCTCCAGCTAAGG | 591 |
| c.982_1006 | TCCCACCTGTCGACCTCCAGCTAAG | 592 |
| c.983_1007 | ATCCCACCTGTCGACCTCCAGCTAA | 593 |
| c.984_1008 | GATCCCACCTGTCGACCTCCAGCTA | 594 |
| c.985_1009 | GGATCCCACCTGTCGACCTCCAGCT | 595 |
| c.986_1010 | AGGATCCCACCTGTCGACCTCCAGC | 596 |
| c.987_1011 | CAGGATCCCACCTGTCGACCTCCAG | 597 |
| c.988_1012 | CCAGGATCCCACCTGTCGACCTCCA | 598 |
| c.989_1013 | TCCAGGATCCCACCTGTCGACCTCC | 599 |
| c.990_1014 | ATCCAGGATCCCACCTGTCGACCTC | 600 |
| c.991_1015 | CATCCAGGATCCCACCTGTCGACCT | 601 |
| c.992_1016 | ACATCCAGGATCCCACCTGTCGACC | 602 |
| c.993_1017 | GACATCCAGGATCCCACCTGTCGAC | 603 |
| c.994_1018 | AGACATCCAGGATCCCACCTGTCGA | 604 |
| c.995_1019 | TAGACATCCAGGATCCCACCTGTCG | 605 |
| c.996_1020 | GTAGACATCCAGGATCCCACCTGTC | 606 |
| c.997_1021 | TGTAGACATCCAGGATCCCACCTGT | 607 |
| c.998_1022 | ATGTAGACATCCAGGATCCCACCTG | 608 |
| c.999_1023 | GATGTAGACATCCAGGATCCCACCT | 609 |
| c.1000_1024 | AGATGTAGACATCCAGGATCCCACC | 610 |
| c.1001_1025 | AAGATGTAGACATCCAGGATCCCAC | 611 |
| c.1002_1026 | GAAGATGTAGACATCCAGGATCCCA | 612 |

-continued

| Sequence in cDNA to which AON anneals for intron 6 exclusion | AON sequence 5' -> 3' | Seq ID |
|---|---|---|
| c.1003_1027 | GGAAGATGTAGACATCCAGGATCCC | 613 |
| c.1004_1028 | AGGAAGATGTAGACATCCAGGATCC | 614 |
| c.1005_1029 | CAGGAAGATGTAGACATCCAGGATC | 615 |
| c.1006_1030 | CCAGGAAGATGTAGACATCCAGGAT | 616 |
| c.1007_1031 | CCCAGGAAGATGTAGACATCCAGGA | 617 |
| c.1008_1032 | GCCCAGGAAGATGTAGACATCCAGG | 618 |
| c.1009_1033 | GGCCCAGGAAGATGTAGACATCCAG | 619 |
| c.1010_1034 | GGGCCCAGGAAGATGTAGACATCCA | 620 |
| c.1011_1035 | TGGGCCCAGGAAGATGTAGACATCC | 621 |
| c.1012_1036 | CTGGGCCCAGGAAGATGTAGACATC | 622 |
| c.1013_1037 | TCTGGGCCCAGGAAGATGTAGACAT | 623 |
| c.1014_1038 | CTCTGGGCCCAGGAAGATGTAGACA | 624 |
| c.1015_1039 | GCTCTGGGCCCAGGAAGATGTAGAC | 625 |
| c.1016_1040 | GGCTCTGGGCCCAGGAAGATGTAGA | 626 |
| c.1017_1041 | GGGCTCTGGGCCCAGGAAGATGTAG | 627 |
| c.1018_1042 | TGGGCTCTGGGCCCAGGAAGATGTA | 628 |
| c.1019_1043 | TTGGGCTCTGGGCCCAGGAAGATGT | 629 |
| c.1020_1044 | CTTGGGCTCTGGGCCCAGGAAGATG | 630 |
| c.1021_1045 | TCTTGGGCTCTGGGCCCAGGAAGAT | 631 |
| c.1022_1046 | CTCTTGGGCTCTGGGCCCAGGAAGA | 632 |
| c.1023_1047 | GCTCTTGGGCTCTGGGCCCAGGAAG | 633 |
| c.1024_1048 | CGCTCTTGGGCTCTGGGCCCAGGAA | 634 |
| c.1025_1049 | ACGCTCTTGGGCTCTGGGCCCAGGA | 635 |
| c.1026_1050 | CACGCTCTTGGGCTCTGGGCCCAGG | 636 |
| c.1027_1051 | CCACGCTCTTGGGCTCTGGGCCCAG | 637 |
| c.1028_1052 | ACCACGCTCTTGGGCTCTGGGCCCA | 638 |
| c.1029_1053 | CACCACGCTCTTGGGCTCTGGGCCC | 639 |
| c.1030_1054 | GCACCACGCTCTTGGGCTCTGGGCC | 640 |
| c.1031_1055 | TGCACCACGCTCTTGGGCTCTGGGC | 641 |
| c.1032_1056 | CTGCACCACGCTCTTGGGCTCTGGG | 642 |
| c.1033_1057 | GCTGCACCACGCTCTTGGGCTCTGG | 643 |
| c.1034_1058 | TGCTGCACCACGCTCTTGGGCTCTG | 644 |
| c.1035_1059 | CTGCTGCACCACGCTCTTGGGCTCT | 645 |
| c.1036_1060 | ACTGCTGCACCACGCTCTTGGGCTC | 646 |
| c.1037_1061 | TACTGCTGCACCACGCTCTTGGGCT | 647 |
| c.1038_1062 | GTACTGCTGCACCACGCTCTTGGGC | 648 |
| c.1039_1063 | GGTACTGCTGCACCACGCTCTTGGG | 649 |
| c.1040_1064 | AGGTACTGCTGCACCACGCTCTTGG | 650 |
| c.1041_1065 | CAGGTACTGCTGCACCACGCTCTTG | 651 |
| c.1042_1066 | CCAGGTACTGCTGCACCACGCTCTT | 652 |
| c.1043_1067 | TCCAGGTACTGCTGCACCACGCTCT | 653 |
| c.1044_1068 | GTCCAGGTACTGCTGCACCACGCTC | 654 |
| c.1045_1069 | CGTCCAGGTACTGCTGCACCACGCT | 655 |
| c.1046_1070 | ACGTCCAGGTACTGCTGCACCACGC | 656 |
| c.1047_1071 | AACGTCCAGGTACTGCTGCACCACG | 657 |
| c.1048_1072 | CAACGTCCAGGTACTGCTGCACCAC | 658 |
| c.1049_1073 | ACAACGTCCAGGTACTGCTGCACCA | 659 |
| c.1050_1074 | CACAACGTCCAGGTACTGCTGCACC | 660 |
| c.1051_1075 | CCACAACGTCCAGGTACTGCTGCAC | 661 |
| c.1052_1075+1 | CCCACAACGTCCAGGTACTGCTGCA | 662 |
| c.1053_1075+2 | ACCCACAACGTCCAGGTACTGCTGC | 663 |
| c.1054_1075+3 | TACCCACAACGTCCAGGTACTGCTG | 664 |
| c.1055_1075+4 | CTACCCACAACGTCCAGGTACTGCT | 665 |
| c.1056_1075+5 | CCTACCCACAACGTCCAGGTACTGC | 666 |
| c.1057_1075+6 | CCCTACCCACAACGTCCAGGTACTG | 667 |
| c.1058_1075+7 | GCCCTACCCACAACGTCCAGGTACT | 668 |
| c.1059_1075+8 | GGCCCTACCCACAACGTCCAGGTAC | 669 |
| c.1060_1075+9 | AGGCCCTACCCACAACGTCCAGGTA | 670 |
| c.1061_1075+10 | CAGGCCCTACCCACAACGTCCAGGT | 671 |
| c.1062_1075+11 | GCAGGCCCTACCCACAACGTCCAGG | 672 |
| c.1063_1075+12 | AGCAGGCCCTACCCACAACGTCCAG | 673 |
| c.1064_1075+13 | GAGCAGGCCCTACCCACAACGTCCA | 674 |
| c.1065_1075+14 | GGAGCAGGCCCTACCCACAACGTCC | 675 |
| c.1066_1075+15 | GGGAGCAGGCCCTACCCACAACGTC | 676 |
| c.1067_1075+16 | AGGGAGCAGGCCCTACCCACAACGT | 677 |
| c.1068_1075+17 | CAGGGAGCAGGCCCTACCCACAACG | 678 |
| c.1069_1075+18 | CCAGGGAGCAGGCCCTACCCACAAC | 679 |
| c.1070_1075+19 | GCCAGGGAGCAGGCCCTACCCACAA | 680 |
| c.1071_1075+20 | GGCCAGGGAGCAGGCCCTACCCACA | 681 |
| c.1072_1075+21 | CGGCCAGGGAGCAGGCCCTACCCAC | 682 |
| c.1073_1075+22 | GCGGCCAGGGAGCAGGCCCTACCCA | 683 |
| c.1074_1075+23 | CGCGGCCAGGGAGCAGGCCCTACCC | 684 |
| c.1075_1075+24 | CCGCGGCCAGGGAGCAGGCCCTACC | 685 |
| C.1075+1_+25 | GCCGCGGCCAGGGAGCAGGCCCTAC | 686 |

| Sequence in cDNA to which AON anneals for intron 6 exclusion | AON sequence 5' -> 3' | Seq ID |
|---|---|---|
| c.1075+2_+26 | GGCCGCGGCCAGGGAGCAGGCCCTA | 687 |
| c.1075+3_+27 | GGGCCGCGGCCAGGGAGCAGGCCCT | 688 |
| c.1075+4_+28 | GGGGCCGCGGCCAGGGAGCAGGCCC | 689 |
| c.1075+5_+29 | GGGGGCCGCGGCCAGGGAGCAGGCC | 690 |
| c.1075+6_+30 | CGGGGGCCGCGGCCAGGGAGCAGGC | 691 |
| c.1075+7_+31 | GCGGGGGCCGCGGCCAGGGAGCAGG | 692 |
| c.1075+8_+32 | GGCGGGGGCCGCGGCCAGGGAGCAG | 693 |
| c.1075+9_+33 | GGGCGGGGGCCGCGGCCAGGGAGCA | 694 |
| c.1075+10_+34 | GGGGCGGGGGCCGCGGCCAGGGAGC | 695 |
| c.1075+11_+35 | TGGGGCGGGGGCCGCGGCCAGGGAG | 696 |
| c.1075+12_+36 | TTGGGGCGGGGGCCGCGGCCAGGGA | 697 |
| c.1075+13_+37 | CTTGGGGCGGGGGCCGCGGCCAGGG | 698 |
| c.1075+14_+38 | CCTTGGGGCGGGGGCCGCGGCCAGG | 699 |
| c.1075+15_+39 | GCCTTGGGGCGGGGGCCGCGGCCAG | 700 |
| c.1075+16_+40 | AGCCTTGGGGCGGGGGCCGCGGCCA | 701 |
| c.1075+17_1076-39 | GAGCCTTGGGGCGGGGGCCGCGGCC | 702 |
| c.1075+18_1076-38 | GGAGCCTTGGGGCGGGGGCCGCGGC | 703 |
| c.1075+19_1076-37 | GGGAGCCTTGGGGCGGGGGCCGCGG | 704 |
| c.1075+20_1076-36 | AGGGAGCCTTGGGGCGGGGGCCGCG | 705 |
| c.1075+21_1076-35 | GAGGGAGCCTTGGGGCGGGGGCCGC | 706 |
| c.1075+22_1076-34 | GGAGGGAGCCTTGGGGCGGGGGCCG | 707 |
| c.1075+23_1076-33 | AGGAGGGAGCCTTGGGGCGGGGGCC | 708 |
| c.1075+24_1076-32 | GAGGAGGGAGCCTTGGGGCGGGGGC | 709 |
| c.1075+25_1076-31 | GGAGGAGGGAGCCTTGGGGCGGGGG | 710 |
| c.1075+26_1076-30 | GGGAGGAGGGAGCCTTGGGGCGGGG | 711 |
| c.1075+27_1076-29 | AGGGAGGAGGGAGCCTTGGGGCGGG | 712 |
| c.1075+28_1076-28 | GAGGGAGGAGGGAGCCTTGGGGCGG | 713 |
| c.1075+29_1076-27 | GGAGGGAGGAGGGAGCCTTGGGGCG | 714 |
| c.1075+30_1076-26 | GGGAGGGAGGAGGGAGCCTTGGGGC | 715 |
| c.1075+31_1076-25 | AGGGAGGGAGGAGGGAGCCTTGGGG | 716 |
| c.1075+32_1076-24 | GAGGGAGGGAGGAGGGAGCCTTGGG | 717 |
| c.1075+33_1076-23 | TGAGGGAGGGAGGAGGGAGCCTTGG | 718 |
| c.1075+34_1076-22 | ATGAGGGAGGGAGGAGGGAGCCTTG | 719 |
| c.1075+35_1076-21 | CATGAGGGAGGGAGGAGGGAGCCTT | 720 |
| c.1075+36_1076-20 | TCATGAGGGAGGGAGGAGGGAGCCT | 721 |
| c.1075+37_1076-19 | TTCATGAGGGAGGGAGGAGGGAGCC | 722 |
| c.1075+38_1076-18 | CTTCATGAGGGAGGGAGGAGGGAGC | 723 |
| c.1075+39_1076-17 | ACTTCATGAGGGAGGGAGGAGGGAG | 724 |
| c.1075+40_1076-16 | GACTTCATGAGGGAGGGAGGAGGGA | 725 |
| c.1076-39_-15 | CGACTTCATGAGGGAGGGAGGAGGG | 726 |
| c.1076-38_-14 | CCGACTTCATGAGGGAGGGAGGAGG | 727 |
| c.1076-37_-13 | GCCGACTTCATGAGGGAGGGAGGAG | 728 |
| c.1076-36_-12 | CGCCGACTTCATGAGGGAGGGAGGA | 729 |
| c.1076-35_-11 | ACGCCGACTTCATGAGGGAGGGAGG | 730 |
| c.1076-34_-10 | AACGCCGACTTCATGAGGGAGGGAG | 731 |
| c.1076-33_-9 | CAACGCCGACTTCATGAGGGAGGGA | 732 |
| c.1076-32_-8 | CCAACGCCGACTTCATGAGGGAGGG | 733 |
| c.1076-31_-7 | GCCAACGCCGACTTCATGAGGGAGG | 734 |
| c.1076-30_-6 | GGCCAACGCCGACTTCATGAGGGAG | 735 |
| c.1076-29_-5 | AGGCCAACGCCGACTTCATGAGGGA | 736 |
| c.1076-28_-4 | CAGGCCAACGCCGACTTCATGAGGG | 737 |
| c.1076-27_-3 | GCAGGCCAACGCCGACTTCATGAGG | 738 |
| c.1076-26_-2 | TGCAGGCCAACGCCGACTTCATGAG | 739 |
| c.1076-25_-1 | CTGCAGGCCAACGCCGACTTCATGA | 740 |
| c.1076-24_1076 | CCTGCAGGCCAACGCCGACTTCATG | 741 |
| c.1076-23_1077 | TCCTGCAGGCCAACGCCGACTTCAT | 742 |
| c.1076-22_1078 | ATCCTGCAGGCCAACGCCGACTTCA | 743 |
| c.1076-21_1079 | TATCCTGCAGGCCAACGCCGACTTC | 744 |
| c.1076-20_1080 | GTATCCTGCAGGCCAACGCCGACTT | 745 |
| c.1076-19_1081 | GGTATCCTGCAGGCCAACGCCGACT | 746 |
| c.1076-18_1082 | GGGTATCCTGCAGGCCAACGCCGAC | 747 |
| c.1076-17_1083 | CGGGTATCCTGCAGGCCAACGCCGA | 748 |
| c.1076-16_1084 | ACGGGTATCCTGCAGGCCAACGCCG | 749 |
| c.1076-15_1085 | AACGGGTATCCTGCAGGCCAACGCC | 750 |
| c.1076-14_1086 | GAACGGGTATCCTGCAGGCCAACGC | 751 |
| c.1076-13_1087 | TGAACGGGTATCCTGCAGGCCAACG | 752 |
| c.1076-12_1088 | ATGAACGGGTATCCTGCAGGCCAAC | 753 |
| c.1076-11_1089 | CATGAACGGGTATCCTGCAGGCCAA | 754 |
| c.1076-10_1090 | GCATGAACGGGTATCCTGCAGGCCA | 755 |
| c.1076-9_1091 | GGCATGAACGGGTATCCTGCAGGCC | 756 |
| c.1076-8_1092 | CGGCATGAACGGGTATCCTGCAGGC | 757 |
| c.1076-7_1093 | GCGGCATGAACGGGTATCCTGCAGG | 758 |
| c.1076-6_1094 | GGCGGCATGAACGGGTATCCTGCAG | 759 |
| c.1076-5_1095 | TGGCGGCATGAACGGGTATCCTGCA | 760 |

| Sequence in cDNA to which AON anneals for intron 6 exclusion | AON sequence 5' -> 3' | Seq ID |
| --- | --- | --- |
| c.1076-4_1096 | ATGGCGGCATGAACGGGTATCCTGC | 761 |
| c.1076-3_1097 | TATGGCGGCATGAACGGGTATCCTG | 762 |
| c.1076-2_1098 | GTATGGCGGCATGAACGGGTATCCT | 763 |
| c.1076-1_1099 | AGTATGGCGGCATGAACGGGTATCC | 764 |
| c.1076_1100 | CAGTATGGCGGCATGAACGGGTATC | 765 |
| c.1077_1101 | CCAGTATGGCGGCATGAACGGGTAT | 766 |
| c.1078_1102 | CCCAGTATGGCGGCATGAACGGGTA | 767 |
| c.1079_1103 | CCCCAGTATGGCGGCATGAACGGGT | 768 |
| c.1080_1104 | GCCCCAGTATGGCGGCATGAACGGG | 769 |
| c.1081_1105 | GGCCCCAGTATGGCGGCATGAACGG | 770 |
| c.1082_1106 | AGGCCCCAGTATGGCGGCATGAACG | 771 |
| c.1083_1107 | CAGGCCCCAGTATGGCGGCATGAAC | 772 |
| c.1084_1108 | CCAGGCCCCAGTATGGCGGCATGAA | 773 |
| c.1085_1109 | CCCAGGCCCCAGTATGGCGGCATGA | 774 |
| c.1086_1110 | GCCCAGGCCCCAGTATGGCGGCATG | 775 |
| c.1087_1111 | AGCCCAGGCCCCAGTATGGCGGCAT | 776 |
| c.1088_1112 | AAGCCCAGGCCCCAGTATGGCGGCA | 777 |
| c.1089_1113 | GAAGCCCAGGCCCCAGTATGGCGGC | 778 |
| c.1090_1114 | GGAAGCCCAGGCCCCAGTATGGCGG | 779 |
| c.1091_1115 | TGGAAGCCCAGGCCCCAGTATGGCG | 780 |
| c.1092_1116 | GTGGAAGCCCAGGCCCCAGTATGGC | 781 |
| c.1093_1117 | GGTGGAAGCCCAGGCCCCAGTATGG | 782 |
| c.1094_1118 | AGGTGGAAGCCCAGGCCCCAGTATG | 783 |
| c.1095_1119 | CAGGTGGAAGCCCAGGCCCCAGTAT | 784 |
| c.1096_1120 | ACAGGTGGAAGCCCAGGCCCCAGTA | 785 |
| c.1097_1121 | CACAGGTGGAAGCCCAGGCCCCAGT | 786 |
| c.1098_1122 | GCACAGGTGGAAGCCCAGGCCCCAG | 787 |
| c.1099_1123 | GGCACAGGTGGAAGCCCAGGCCCCA | 788 |
| c.1100_1124 | CGGCACAGGTGGAAGCCCAGGCCCC | 789 |
| c.1101_1125 | GCGGCACAGGTGGAAGCCCAGGCCC | 790 |
| c.1102_1126 | AGCGGCACAGGTGGAAGCCCAGGCC | 791 |
| c.1103_1127 | CAGCGGCACAGGTGGAAGCCCAGGC | 792 |
| c.1104_1128 | CCAGCGGCACAGGTGGAAGCCCAGG | 793 |
| c.1105_1129 | CCCAGCGGCACAGGTGGAAGCCCAG | 794 |
| c.1106_1130 | CCCCAGCGGCACAGGTGGAAGCCCA | 795 |
| c.1107_1131 | GCCCCAGCGGCACAGGTGGAAGCCC | 796 |
| c.1108_1132 | AGCCCCAGCGGCACAGGTGGAAGCC | 797 |
| c.1109_1133 | TAGCCCCAGCGGCACAGGTGGAAGC | 798 |
| c.1110_1134 | GTAGCCCCAGCGGCACAGGTGGAAG | 799 |
| c.1111_1135 | AGTAGCCCCAGCGGCACAGGTGGAA | 800 |
| c.1112_1136 | GAGTAGCCCCAGCGGCACAGGTGGA | 801 |
| c.1113_1137 | GGAGTAGCCCCAGCGGCACAGGTGG | 802 |
| c.1114_1138 | AGGAGTAGCCCCAGCGGCACAGGTG | 803 |
| c.1115_1139 | GAGGAGTAGCCCCAGCGGCACAGGT | 804 |
| c.1116_1140 | GGAGGAGTAGCCCCAGCGGCACAGG | 805 |
| c.1117_1141 | TGGAGGAGTAGCCCCAGCGGCACAG | 806 |
| c.1118_1142 | GTGGAGGAGTAGCCCCAGCGGCACA | 807 |
| c.1119_1143 | GGTGGAGGAGTAGCCCCAGCGGCAC | 808 |
| c.1120_1144 | CGGTGGAGGAGTAGCCCCAGCGGCA | 809 |
| c.1121_1145 | GCGGTGGAGGAGTAGCCCCAGCGGC | 810 |
| c.1122_1146 | AGCGGTGGAGGAGTAGCCCCAGCGG | 811 |
| c.1123_1147 | TAGCGGTGGAGGAGTAGCCCCAGCG | 812 |
| c.1124_1148 | ATAGCGGTGGAGGAGTAGCCCCAGC | 813 |
| c.1125_1149 | GATAGCGGTGGAGGAGTAGCCCCAG | 814 |
| c.1126_1150 | TGATAGCGGTGGAGGAGTAGCCCCA | 815 |
| c.1127_1151 | GTGATAGCGGTGGAGGAGTAGCCCC | 816 |
| c.1128_1152 | GGTGATAGCGGTGGAGGAGTAGCCC | 817 |
| c.1129_1153 | GGGTGATAGCGGTGGAGGAGTAGCC | 818 |
| c.1130_1154 | CGGGTGATAGCGGTGGAGGAGTAGC | 819 |
| c.1131_1155 | GCGGGTGATAGCGGTGGAGGAGTAG | 820 |
| c.1132_1156 | GGCGGGTGATAGCGGTGGAGGAGTA | 821 |
| c.1133_1157 | TGGCGGGTGATAGCGGTGGAGGAGT | 822 |
| c.1134_1158 | CTGGCGGGTGATAGCGGTGGAGGAG | 823 |
| c.1135_1159 | CCTGGCGGGTGATAGCGGTGGAGGA | 824 |
| c.1136_1160 | ACCTGGCGGGTGATAGCGGTGGAGG | 825 |
| c.1137_1161 | CACCTGGCGGGTGATAGCGGTGGAG | 826 |
| c.1138_1162 | CCACCTGGCGGGTGATAGCGGTGGA | 827 |
| c.1139_1163 | ACCACCTGGCGGGTGATAGCGGTGG | 828 |
| c.1140_1164 | CACCACCTGGCGGGTGATAGCGGTG | 829 |
| c.1141_1165 | CCACCACCTGGCGGGTGATAGCGGT | 830 |
| c.1142_1166 | TCCACCACCTGGCGGGTGATAGCGG | 831 |
| c.1143_1167 | CTCCACCACCTGGCGGGTGATAGCG | 832 |
| c.1144_1168 | TCTCCACCACCTGGCGGGTGATAGC | 833 |
| c.1145_1169 | TTCTCCACCACCTGGCGGGTGATAG | 834 |

| Sequence in cDNA to which AON anneals for intron 6 exclusion | AON sequence 5' -> 3' | Seq ID |
|---|---|---|
| c.1146_1170 | GTTCTCCACCACCTGGCGGGTGATA | 835 |
| c.1147_1171 | TGTTCTCCACCACCTGGCGGGTGAT | 836 |
| c.1148_1172 | ATGTTCTCCACCACCTGGCGGGTGA | 837 |
| c.1149_1173 | CATGTTCTCCACCACCTGGCGGGTG | 838 |
| c.1150_1174 | TCATGTTCTCCACCACCTGGCGGGT | 839 |
| c.1151_1175 | GTCATGTTCTCCACCACCTGGCGGG | 840 |
| c.1152_1176 | GGTCATGTTCTCCACCACCTGGCGG | 841 |
| c.1153_1177 | TGGTCATGTTCTCCACCACCTGGCG | 842 |
| c.1154_1178 | CTGGTCATGTTCTCCACCACCTGGC | 843 |
| c.1155_1179 | CCTGGTCATGTTCTCCACCACCTGG | 844 |
| c.1156_1180 | CCCTGGTCATGTTCTCCACCACCTG | 845 |
| c.1157_1181 | GCCCTGGTCATGTTCTCCACCACCT | 846 |
| c.1158_1182 | GGCCCTGGTCATGTTCTCCACCACC | 847 |
| c.1159_1183 | GGGCCCTGGTCATGTTCTCCACCAC | 848 |
| c.1160_1184 | TGGGCCCTGGTCATGTTCTCCACCA | 849 |
| c.1161_1185 | GTGGGCCCTGGTCATGTTCTCCACC | 850 |
| c.1162_1186 | AGTGGGCCCTGGTCATGTTCTCCAC | 851 |
| c.1163_1187 | AAGTGGGCCCTGGTCATGTTCTCCA | 852 |
| c.1164_1188 | GAAGTGGGCCCTGGTCATGTTCTCC | 853 |
| c.1165_1189 | GGAAGTGGGCCCTGGTCATGTTCTC | 854 |
| c.1166_1190 | GGGAAGTGGGCCCTGGTCATGTTCT | 855 |
| c.1167_1191 | GGGGAAGTGGGCCCTGGTCATGTTC | 856 |
| c.1168_1192 | GGGGGAAGTGGGCCCTGGTCATGTT | 857 |
| c.1169_1193 | AGGGGGAAGTGGGCCCTGGTCATGT | 858 |
| c.1170_1194 | CAGGGGGAAGTGGGCCCTGGTCATG | 859 |
| c.1171_1194+1 | CCAGGGGGAAGTGGGCCCTGGTCAT | 860 |
| c.1172_1194+2 | ACCAGGGGGAAGTGGGCCCTGGTCA | 861 |
| c.1173_1194+3 | CACCAGGGGGAAGTGGGCCCTGGTC | 862 |
| c.1174_1194+4 | TCACCAGGGGGAAGTGGGCCCTGGT | 863 |
| c.1175_1194+5 | CTCACCAGGGGGAAGTGGGCCCTGG | 864 |
| c.1176_1194+6 | ACTCACCAGGGGGAAGTGGGCCCTG | 865 |
| c.1177_1194+7 | AACTCACCAGGGGGAAGTGGGCCCT | 866 |
| c.1178_1194+8 | CAACTCACCAGGGGGAAGTGGGCCC | 867 |
| c.1179_1194+9 | CCAACTCACCAGGGGGAAGTGGGCC | 868 |
| c.1180_1194+10 | CCCAACTCACCAGGGGGAAGTGGGC | 869 |
| c.1181_1194+11 | CCCCAACTCACCAGGGGGAAGTGGG | 870 |
| c.1182_1194+12 | ACCCCAACTCACCAGGGGGAAGTGG | 871 |
| c.1183_1194+13 | CACCCCAACTCACCAGGGGGAAGTG | 872 |
| c.1184_1194+14 | CCACCCCAACTCACCAGGGGGAAGT | 873 |
| c.1185_1194+15 | ACCACCCCAACTCACCAGGGGGAAG | 874 |
| c.1186_1194+16 | CACCACCCCAACTCACCAGGGGGAA | 875 |
| c.1187_1194+17 | CCACCACCCCAACTCACCAGGGGGA | 876 |
| c.1188_1194+18 | GCCACCACCCCAACTCACCAGGGGG | 877 |
| c.1189_1194+19 | TGCCACCACCCCAACTCACCAGGGG | 878 |
| c.1190_1194+20 | CTGCCACCACCCCAACTCACCAGGG | 879 |
| c.1191_1194+21 | CCTGCCACCACCCCAACTCACCAGG | 880 |
| c.1192_1194+22 | CCCTGCCACCACCCCAACTCACCAG | 881 |
| c.1193_1194+23 | CCCCTGCCACCACCCCAACTCACCA | 882 |
| c.1194_1194+24 | TCCCCTGCCACCACCCCAACTCACC | 883 |
| c.1194+1_+25 | CTCCCCTGCCACCACCCCAACTCAC | 884 |
| c.956-25_-5 | AAGGGAAGCAGCTCTGGGTT | 885 |
| c.956-24_-4 | GAAGGGAAGCAGCTCTGGGT | 886 |
| c.956-23_-3 | GGAAGGGAAGCAGCTCTGGG | 887 |
| c.956-22_-2 | TGGAAGGGAAGCAGCTCTGG | 888 |
| c.956-21_-1 | CTGGAAGGGAAGCAGCTCTG | 889 |
| c.956-20_956 | TCTGGAAGGGAAGCAGCTCT | 890 |
| c.956-19_957 | ATCTGGAAGGGAAGCAGCTC | 891 |
| c.956-18_958 | CATCTGGAAGGGAAGCAGCTC | 892 |
| c.956-17_959 | ACATCTGGAAGGGAAGCAGCT | 893 |
| c.956-16_960 | CACATCTGGAAGGGAAGCAGC | 894 |
| c.956-15_961 | CCACATCTGGAAGGGAAGCAG | 895 |
| c.956-14_962 | ACCACATCTGGAAGGGAAGCA | 896 |
| c.956-13_963 | GACCACATCTGGAAGGGAAGC | 897 |
| c.956-12_964 | GGACCACATCTGGAAGGGAAG | 898 |
| c.956-11_965 | AGGACCACATCTGGAAGGGAA | 899 |
| c.956-10_966 | CAGGACCACATCTGGAAGGGA | 900 |
| c.956-9_967 | GCAGGACCACATCTGGAAGGG | 901 |
| c.956-8_968 | TGCAGGACCACATCTGGAAGG | 902 |
| c.956-7_969 | CTGCAGGACCACATCTGGAAG | 903 |
| c.956-6_970 | GCTGCAGGACCACATCTGGAA | 904 |
| c.956-5_971 | GGCTGCAGGACCACATCTGGA | 905 |
| c.956-4_972 | CGGCTGCAGGACCACATCTGG | 906 |
| c.956-3_973 | TCGGCTGCAGGACCACATCTG | 907 |
| c.956-2_974 | CTCGGCTGCAGGACCACATCT | 908 |

-continued

| Sequence in cDNA to which AON anneals for intron 6 exclusion | AON sequence 5' -> 3' | Seq ID |
|---|---|---|
| c.956-1_975 | GCTCGGCTGCAGGACCACATC | 909 |
| c.956_976 | GGCTCGGCTGCAGGACCACAT | 910 |
| c.957_977 | GGGCTCGGCTGCAGGACCACA | 911 |
| c.958_978 | AGGGCTCGGCTGCAGGACCAC | 912 |
| c.959_979 | CAGGGCTCGGCTGCAGGACCA | 913 |
| c.960_980 | GCAGGGCTCGGCTGCAGGACC | 914 |
| c.961_981 | GGCAGGGCTCGGCTGCAGGAC | 915 |
| c.962_982 | GGGCAGGGCTCGGCTGCAGGA | 916 |
| c.963_983 | AGGGCAGGGCTCGGCTGCAGG | 917 |
| c.964_984 | AAGGGCAGGGCTCGGCTGCAG | 918 |
| c.965_985 | TAAGGGCAGGGCTCGGCTGCA | 919 |
| c.966_986 | CTAAGGGCAGGGCTCGGCTGC | 920 |
| c.967_987 | GCTAAGGGCAGGGCTCGGCTG | 921 |
| c.968_988 | AGCTAAGGGCAGGGCTCGGCT | 922 |
| c.969_989 | CAGCTAAGGGCAGGGCTCGGC | 923 |
| c.970_990 | CCAGCTAAGGGCAGGGCTCGG | 924 |
| c.971_991 | TCCAGCTAAGGGCAGGGCTCG | 925 |
| c.972_992 | CTCCAGCTAAGGGCAGGGCTC | 926 |
| c.973_993 | CCTCCAGCTAAGGGCAGGGCT | 927 |
| c.974_994 | ACCTCCAGCTAAGGGCAGGGC | 928 |
| c.975_995 | GACCTCCAGCTAAGGGCAGGG | 929 |
| c.976_996 | CGACCTCCAGCTAAGGGCAGG | 930 |
| c.977_997 | TCGACCTCCAGCTAAGGGCAG | 931 |
| c.978_998 | GTCGACCTCCAGCTAAGGGCA | 932 |
| c.979_999 | TGTCGACCTCCAGCTAAGGGC | 933 |
| c.980_1000 | CTGTCGACCTCCAGCTAAGGG | 934 |
| c.981_1001 | CCTGTCGACCTCCAGCTAAGG | 935 |
| c.982_1002 | ACCTGTCGACCTCCAGCTAAG | 936 |
| c.983_1003 | CACCTGTCGACCTCCAGCTAA | 937 |
| c.984_1004 | CCACCTGTCGACCTCCAGCTA | 938 |
| c.985_1005 | CCCACCTGTCGACCTCCAGCT | 939 |
| c.986_1006 | TCCCACCTGTCGACCTCCAGC | 940 |
| c.987_1007 | ATCCCACCTGTCGACCTCCAG | 941 |
| c.988_1008 | GATCCCACCTGTCGACCTCCA | 942 |
| c.989_1009 | GGATCCCACCTGTCGACCTCC | 943 |
| c.990_1010 | AGGATCCCACCTGTCGACCTC | 944 |
| c.991_1011 | CAGGATCCCACCTGTCGACCT | 945 |
| c.992_1012 | CCAGGATCCCACCTGTCGACC | 946 |
| c.993_1013 | TCCAGGATCCCACCTGTCGAC | 947 |
| c.994_1014 | ATCCAGGATCCCACCTGTCGA | 948 |
| c.995_1015 | CATCCAGGATCCCACCTGTCG | 949 |
| c.996_1016 | ACATCCAGGATCCCACCTGTC | 950 |
| c.997_1017 | GACATCCAGGATCCCACCTGT | 951 |
| c.998_1018 | AGACATCCAGGATCCCACCTG | 952 |
| c.999_1019 | TAGACATCCAGGATCCCACCT | 953 |
| c.1000_1020 | GTAGACATCCAGGATCCCACC | 954 |
| c.1001_1021 | TGTAGACATCCAGGATCCCAC | 955 |
| c.1002_1022 | ATGTAGACATCCAGGATCCCA | 956 |
| c.1003_1023 | GATGTAGACATCCAGGATCCC | 957 |
| c.1004_1024 | AGATGTAGACATCCAGGATCC | 958 |
| c.1005_1025 | AAGATGTAGACATCCAGGATC | 959 |
| c.1006_1026 | GAAGATGTAGACATCCAGGAT | 960 |
| c.1007_1027 | GGAAGATGTAGACATCCAGGA | 961 |
| c.1008_1028 | AGGAAGATGTAGACATCCAGG | 962 |
| c.1009_1029 | CAGGAAGATGTAGACATCCAG | 963 |
| c.1010_1030 | CCAGGAAGATGTAGACATCCA | 964 |
| c.1011_1031 | CCCAGGAAGATGTAGACATCC | 965 |
| c.1012_1032 | GCCCAGGAAGATGTAGACATC | 966 |
| c.1013_1033 | GGCCCAGGAAGATGTAGACAT | 967 |
| c.1014_1034 | GGGCCCAGGAAGATGTAGACA | 968 |
| c.1015_1035 | TGGGCCCAGGAAGATGTAGAC | 969 |
| c.1016_1036 | CTGGGCCCAGGAAGATGTAGA | 970 |
| c.1017_1037 | TCTGGGCCCAGGAAGATGTAG | 971 |
| c.1018_1038 | CTCTGGGCCCAGGAAGATGTA | 972 |
| c.1019_1039 | GCTCTGGGCCCAGGAAGATGT | 973 |
| c.1020_1040 | GGCTCTGGGCCCAGGAAGATG | 974 |
| c.1021_1041 | GGGCTCTGGGCCCAGGAAGAT | 975 |
| c.1022_1042 | TGGGCTCTGGGCCCAGGAAGA | 976 |
| c.1023_1043 | TTGGGCTCTGGGCCCAGGAAG | 977 |
| c.1024_1044 | CTTGGGCTCTGGGCCCAGGAA | 978 |
| c.1025_1045 | TCTTGGGCTCTGGGCCCAGGA | 979 |
| c.1026_1046 | CTCTTGGGCTCTGGGCCCAGG | 980 |
| c.1027_1047 | GCTCTTGGGCTCTGGGCCCAG | 981 |
| c.1028_1048 | CGCTCTTGGGCTCTGGGCCCA | 982 |

| Sequence in cDNA to which AON anneals for intron 6 exclusion | AON sequence 5' -> 3' | Seq ID |
|---|---|---|
| c.1029_1049 | ACGCTCTTGGGCTCTGGGCCC | 983 |
| c.1030_1050 | CACGCTCTTGGGCTCTGGGCC | 984 |
| c.1031_1051 | CCACGCTCTTGGGCTCTGGGC | 985 |
| c.1032_1052 | ACCACGCTCTTGGGCTCTGGG | 986 |
| c.1033_1053 | CACCACGCTCTTGGGCTCTGG | 987 |
| c.1034_1054 | GCACCACGCTCTTGGGCTCTG | 988 |
| c.1035_1055 | TGCACCACGCTCTTGGGCTCT | 989 |
| c.1036_1056 | CTGCACCACGCTCTTGGGCTC | 990 |
| c.1037_1057 | GCTGCACCACGCTCTTGGGCT | 991 |
| c.1038_1058 | TGCTGCACCACGCTCTTGGGC | 992 |
| c.1039_1059 | CTGCTGCACCACGCTCTTGGG | 993 |
| c.1040_1060 | ACTGCTGCACCACGCTCTTGG | 994 |
| c.1041_1061 | TACTGCTGCACCACGCTCTTG | 995 |
| c.1042_1062 | GTACTGCTGCACCACGCTCTT | 996 |
| c.1043_1063 | GGTACTGCTGCACCACGCTCT | 997 |
| c.1044_1064 | AGGTACTGCTGCACCACGCTC | 998 |
| c.1045_1065 | CAGGTACTGCTGCACCACGCT | 999 |
| c.1046_1066 | CCAGGTACTGCTGCACCACGC | 1000 |
| c.1047_1067 | TCCAGGTACTGCTGCACCACG | 1001 |
| c.1048_1068 | GTCCAGGTACTGCTGCACCAC | 1002 |
| c.1049_1069 | CGTCCAGGTACTGCTGCACCA | 1003 |
| c.1050_1070 | ACGTCCAGGTACTGCTGCACC | 1004 |
| c.1051_1071 | AACGTCCAGGTACTGCTGCAC | 1005 |
| c.1052_1072 | CAACGTCCAGGTACTGCTGCA | 1006 |
| c.1053_1073 | ACAACGTCCAGGTACTGCTGC | 1007 |
| c.1054_1074 | CACAACGTCCAGGTACTGCTG | 1008 |
| c.1055_1075 | CCACAACGTCCAGGTACTGCT | 1009 |
| c.1056_1075+1 | CCCACAACGTCCAGGTACTGC | 1010 |
| c.1057_1075+2 | ACCCACAACGTCCAGGTACTG | 1011 |
| c.1058_1075+3 | TACCCACAACGTCCAGGTACT | 1012 |
| c.1059_1075+4 | CTACCCACAACGTCCAGGTAC | 1013 |
| c.1060_1075+5 | CCTACCCACAACGTCCAGGTA | 1014 |
| c.1061_1075+6 | CCCTACCCACAACGTCCAGGT | 1015 |
| c.1062_1075+7 | GCCCTACCCACAACGTCCAGG | 1016 |
| c.1063_1075+8 | GGCCCTACCCACAACGTCCAG | 1017 |
| c.1064_1075+9 | AGGCCCTACCCACAACGTCCA | 1018 |
| c.1065_1075+10 | CAGGCCCTACCCACAACGTCC | 1019 |
| c.1066_1075+11 | GCAGGCCCTACCCACAACGTC | 1020 |
| c.1067_1075+12 | AGCAGGCCCTACCCACAACGT | 1021 |
| c.1068_1075+13 | GAGCAGGCCCTACCCACAACG | 1022 |
| c.1069_1075+14 | GGAGCAGGCCCTACCCACAAC | 1023 |
| c.1070_1075+15 | GGGAGCAGGCCCTACCCACAA | 1024 |
| c.1071_1075+16 | AGGGAGCAGGCCCTACCCACA | 1025 |
| c.1072_1075+17 | CAGGGAGCAGGCCCTACCCAC | 1026 |
| c.1073_1075+18 | CCAGGGAGCAGGCCCTACCCA | 1027 |
| c.1074_1075+19 | GCCAGGGAGCAGGCCCTACCC | 1028 |
| c.1075_1075+20 | GGCCAGGGAGCAGGCCCTACC | 1029 |
| c.1075+1_+21 | CGGCCAGGGAGCAGGCCCTAC | 1030 |
| c.1075+2_+22 | GCGGCCAGGGAGCAGGCCCTA | 1031 |
| c.1075+3_+23 | CGCGGCCAGGGAGCAGGCCCT | 1032 |
| c.1075+4_+24 | CCGCGGCCAGGGAGCAGGCCC | 1033 |
| c.1075+5_+25 | GCCGCGGCCAGGGAGCAGGCC | 1034 |
| c.1075+6_+26 | GGCCGCGGCCAGGGAGCAGGC | 1035 |
| c.1075+7_+27 | GGGCCGCGGCCAGGGAGCAGG | 1036 |
| c.1075+8_+28 | GGGGCCGCGGCCAGGGAGCAG | 1037 |
| c.1075+9_+29 | GGGGGCCGCGGCCAGGGAGCA | 1038 |
| c.1075+10_+30 | CGGGGGCCGCGGCCAGGGAGC | 1039 |
| c.1075+11_+31 | GCGGGGGCCGCGGCCAGGGAG | 1040 |
| c.1075+12_+32 | GGCGGGGGCCGCGGCCAGGGA | 1041 |
| c.1075+13_+33 | GGGCGGGGGCCGCGGCCAGGG | 1042 |
| c.1075+14_+34 | GGGGCGGGGGCCGCGGCCAGG | 1043 |
| c.1075+15_+35 | TGGGGCGGGGGCCGCGGCCAG | 1044 |
| c.1075+16_+36 | TTGGGGCGGGGGCCGCGGCCA | 1045 |
| c.1075+17_+37 | CTTGGGGCGGGGGCCGCGGCC | 1046 |
| c.1075+18_+38 | CCTTGGGGCGGGGGCCGCGG | 1047 |
| c.1075+19_+39 | GCCTTGGGGCGGGGGCCGCGG | 1048 |
| c.1075+20_+40 | AGCCTTGGGGCGGGGGCCGCG | 1049 |
| c.1075+21_1076-39 | GAGCCTTGGGGCGGGGGCCGC | 1050 |
| c.1075+22_1076-38 | GGAGCCTTGGGGCGGGGGCCG | 1051 |
| c.1075+23_1076-37 | GGGAGCCTTGGGGCGGGGGCC | 1052 |
| c.1075+24_1076-36 | AGGGAGCCTTGGGGCGGGGGC | 1053 |
| c.1075+25_1076-35 | GAGGGAGCCTTGGGGCGGGGG | 1054 |
| c.1075+26_1076-34 | GGAGGGAGCCTTGGGGCGGGG | 1055 |
| c.1075+27_1076-33 | AGGAGGGAGCCTTGGGGCGGG | 1056 |

| Sequence in cDNA to which AON anneals for intron 6 exclusion | AON sequence 5' -> 3' | Seq ID |
|---|---|---|
| c.1075+28_1076-32 | GAGGAGGGAGCCTTGGGCGG | 1057 |
| c.1075+29_1076-31 | GGAGGAGGGAGCCTTGGGCG | 1058 |
| c.1075+30_1076-30 | GGGAGGAGGGAGCCTTGGGC | 1059 |
| c.1075+31_1076-29 | AGGGAGGAGGGAGCCTTGGG | 1060 |
| c.1075+32_1076-28 | GAGGGAGGAGGGAGCCTTGG | 1061 |
| c.1075+33_1076-27 | GGAGGGAGGAGGGAGCCTTGG | 1062 |
| c.1075+34_1076-26 | GGGAGGGAGGAGGGAGCCTTG | 1063 |
| c.1075+35_1076-25 | AGGGAGGGAGGAGGGAGCCTT | 1064 |
| c.1075+36_1076-24 | GAGGGAGGGAGGAGGGAGCCT | 1065 |
| c.1075+37_1076-23 | TGAGGGAGGGAGGAGGGAGCC | 1066 |
| c.1075+38_1076-22 | ATGAGGGAGGGAGGAGGGAGC | 1067 |
| c.1075+39_1076-21 | CATGAGGGAGGGAGGAGGGAG | 1068 |
| c.1075+40_1076-20 | TCATGAGGGAGGGAGGAGGGA | 1069 |
| c.1076-39_-19 | TTCATGAGGGAGGGAGGAGGG | 1070 |
| c.1076-38_-18 | CTTCATGAGGGAGGGAGGAGG | 1071 |
| c.1076-37_-17 | ACTTCATGAGGGAGGGAGGAG | 1072 |
| c.1076-36_-16 | GACTTCATGAGGGAGGGAGGA | 1073 |
| c.1076-35_-15 | CGACTTCATGAGGGAGGGAGG | 1074 |
| c.1076-34_-14 | CCGACTTCATGAGGGAGGGAG | 1075 |
| c.1076-33_-13 | GCCGACTTCATGAGGGAGGGA | 1076 |
| c.1076-32_-12 | CGCCGACTTCATGAGGGAGGG | 1077 |
| c.1076-31_-11 | ACGCCGACTTCATGAGGGAGG | 1078 |
| c.1076-30_-10 | AACGCCGACTTCATGAGGGAG | 1079 |
| c.1076-29_-9 | CAACGCCGACTTCATGAGGGA | 1080 |
| c.1076-28_-8 | CCAACGCCGACTTCATGAGGG | 1081 |
| c.1076-27_-7 | GCCAACGCCGACTTCATGAGG | 1082 |
| c.1076-26_-6 | GGCCAACGCCGACTTCATGAG | 1083 |
| c.1076-25_-5 | AGGCCAACGCCGACTTCATGA | 1084 |
| c.1076-24_-4 | CAGGCCAACGCCGACTTCATG | 1085 |
| c.1076-23_-3 | GCAGGCCAACGCCGACTTCAT | 1086 |
| c.1076-22_-2 | TGCAGGCCAACGCCGACTTCA | 1087 |
| c.1076-21_-1 | CTGCAGGCCAACGCCGACTTC | 1088 |
| c.1076-20_1076 | CCTGCAGGCCAACGCCGACTT | 1089 |
| c.1076-19_1077 | TCCTGCAGGCCAACGCCGACT | 1090 |
| c.1076-18_1078 | ATCCTGCAGGCCAACGCCGAC | 1091 |
| c.1076-17_1079 | TATCCTGCAGGCCAACGCCGA | 1092 |
| c.1076-16_1080 | GTATCCTGCAGGCCAACGCCG | 1093 |
| c.1076-15_1081 | GGTATCCTGCAGGCCAACGCC | 1094 |
| c.1076-14_1082 | GGGTATCCTGCAGGCCAACGC | 1095 |
| c.1076-13_1083 | CGGGTATCCTGCAGGCCAACG | 1096 |
| c.1076-12_1084 | ACGGGTATCCTGCAGGCCAAC | 1097 |
| c.1076-11_1085 | AACGGGTATCCTGCAGGCCAA | 1098 |
| c.1076-10_1086 | GAACGGGTATCCTGCAGGCCA | 1099 |
| c.1076-9_1087 | TGAACGGGTATCCTGCAGGCC | 1100 |
| c.1076-8_1088 | ATGAACGGGTATCCTGCAGGC | 1101 |
| c.1076-7_1089 | CATGAACGGGTATCCTGCAGG | 1102 |
| c.1076-6_1090 | GCATGAACGGGTATCCTGCAG | 1103 |
| c.1076-5_1091 | GGCATGAACGGGTATCCTGCA | 1104 |
| c.1076-4_1092 | CGGCATGAACGGGTATCCTGC | 1105 |
| c.1076-3_1093 | GCGGCATGAACGGGTATCCTG | 1106 |
| c.1076-2_1094 | GGCGGCATGAACGGGTATCCT | 1107 |
| c.1076-1_1095 | TGGCGGCATGAACGGGTATCC | 1108 |
| c.1076_1096 | ATGGCGGCATGAACGGGTATC | 1109 |
| c.1077_1097 | TATGGCGGCATGAACGGGTAT | 1110 |
| c.1078_1098 | GTATGGCGGCATGAACGGGTA | 1111 |
| c.1079_1099 | AGTATGGCGGCATGAACGGGT | 1112 |
| c.1080_1100 | CAGTATGGCGGCATGAACGGG | 1113 |
| c.1081_1101 | CCAGTATGGCGGCATGAACGG | 1114 |
| c.1082_1102 | CCCAGTATGGCGGCATGAACG | 1115 |
| c.1083_1103 | CCCCAGTATGGCGGCATGAAC | 1116 |
| c.1084_1104 | GCCCCAGTATGGCGGCATGAA | 1117 |
| c.1085_1105 | GGCCCCAGTATGGCGGCATGA | 1118 |
| c.1086_1106 | AGGCCCCAGTATGGCGGCATG | 1119 |
| c.1087_1107 | CAGGCCCCAGTATGGCGGCAT | 1120 |
| c.1088_1108 | CCAGGCCCCAGTATGGCGGCA | 1121 |
| c.1089_1109 | CCCAGGCCCCAGTATGGCGGC | 1122 |
| c.1090_1110 | GCCCAGGCCCCAGTATGGCGG | 1123 |
| c.1091_1111 | AGCCCAGGCCCCAGTATGGCG | 1124 |
| c.1092_1112 | AAGCCCAGGCCCCAGTATGGC | 1125 |
| c.1093_1113 | GAAGCCCAGGCCCCAGTATGG | 1126 |
| c.1094_1114 | GGAAGCCCAGGCCCCAGTATG | 1127 |
| c.1095_1115 | TGGAAGCCCAGGCCCCAGTAT | 1128 |
| c.1096_1116 | GTGGAAGCCCAGGCCCCAGTA | 1129 |
| c.1097_1117 | GGTGGAAGCCCAGGCCCCAGT | 1130 |

| Sequence in cDNA to which AON anneals for intron 6 exclusion | AON sequence 5' -> 3' | Seq ID |
|---|---|---|
| c.1098_1118 | AGGTGGAAGCCCAGGCCCCAG | 1131 |
| c.1099_1119 | CAGGTGGAAGCCCAGGCCCCA | 1132 |
| c.1100_1120 | ACAGGTGGAAGCCCAGGCCCC | 1133 |
| c.1101_1121 | CACAGGTGGAAGCCCAGGCCC | 1134 |
| c.1102_1122 | GCACAGGTGGAAGCCCAGGCC | 1135 |
| c.1103_1123 | GGCACAGGTGGAAGCCCAGGC | 1136 |
| c.1104_1124 | CGGCACAGGTGGAAGCCCAGG | 1137 |
| c.1105_1125 | GCGGCACAGGTGGAAGCCCAG | 1138 |
| c.1106_1126 | AGCGGCACAGGTGGAAGCCCA | 1139 |
| c.1107_1127 | CAGCGGCACAGGTGGAAGCCC | 1140 |
| c.1108_1128 | CCAGCGGCACAGGTGGAAGCC | 1141 |
| c.1109_1129 | CCCAGCGGCACAGGTGGAAGC | 1142 |
| c.1110_1130 | CCCCAGCGGCACAGGTGGAAG | 1143 |
| c.1111_1131 | GCCCCAGCGGCACAGGTGGAA | 1144 |
| c.1112_1132 | AGCCCCAGCGGCACAGGTGGA | 1145 |
| c.1113_1133 | TAGCCCCAGCGGCACAGGTGG | 1146 |
| c.1114_1134 | GTAGCCCCAGCGGCACAGGTG | 1147 |
| c.1115_1135 | AGTAGCCCCAGCGGCACAGGT | 1148 |
| c.1116_1136 | GAGTAGCCCCAGCGGCACAGG | 1149 |
| c.1117_1137 | GGAGTAGCCCCAGCGGCACAG | 1150 |
| c.1118_1138 | AGGAGTAGCCCCAGCGGCACA | 1151 |
| c.1119_1139 | GAGGAGTAGCCCCAGCGGCAC | 1152 |
| c.1120_1140 | GGAGGAGTAGCCCCAGCGGCA | 1153 |
| c.1121_1141 | TGGAGGAGTAGCCCCAGCGGC | 1154 |
| c.1122_1142 | GTGGAGGAGTAGCCCCAGCGG | 1155 |
| c.1123_1143 | GGTGGAGGAGTAGCCCCAGCG | 1156 |
| c.1124_1144 | CGGTGGAGGAGTAGCCCCAGC | 1157 |
| c.1125_1145 | GCGGTGGAGGAGTAGCCCCAG | 1158 |
| c.1126_1146 | AGCGGTGGAGGAGTAGCCCCA | 1159 |
| c.1127_1147 | TAGCGGTGGAGGAGTAGCCCC | 1160 |
| c.1128_1148 | ATAGCGGTGGAGGAGTAGCCC | 1161 |
| c.1129_1149 | GATAGCGGTGGAGGAGTAGCC | 1162 |
| c.1130_1150 | TGATAGCGGTGGAGGAGTAGC | 1163 |
| c.1131_1151 | GTGATAGCGGTGGAGGAGTAG | 1164 |
| c.1132_1152 | GGTGATAGCGGTGGAGGAGTA | 1165 |
| c.1133_1153 | GGGTGATAGCGGTGGAGGAGT | 1166 |
| c.1134_1154 | CGGGTGATAGCGGTGGAGGAG | 1167 |
| c.1135_1155 | GCGGGTGATAGCGGTGGAGGA | 1168 |
| c.1136_1156 | GGCGGGTGATAGCGGTGGAGG | 1169 |
| c.1137_1157 | TGGCGGGTGATAGCGGTGGAG | 1170 |
| c.1138_1158 | CTGGCGGGTGATAGCGGTGGA | 1171 |
| c.1139_1159 | CCTGGCGGGTGATAGCGGTGG | 1172 |
| c.1140_1160 | ACCTGGCGGGTGATAGCGGTG | 1173 |
| c.1141_1161 | CACCTGGCGGGTGATAGCGGT | 1174 |
| c.1142_1162 | CCACCTGGCGGGTGATAGCGG | 1175 |
| c.1143_1163 | ACCACCTGGCGGGTGATAGCG | 1176 |
| c.1144_1164 | CACCACCTGGCGGGTGATAGC | 1177 |
| c.1145_1165 | CCACCACCTGGCGGGTGATAG | 1178 |
| c.1146_1166 | TCCACCACCTGGCGGGTGATA | 1179 |
| c.1147_1167 | CTCCACCACCTGGCGGGTGAT | 1180 |
| c.1148_1168 | TCTCCACCACCTGGCGGGTGA | 1181 |
| c.1149_1169 | TTCTCCACCACCTGGCGGGTG | 1182 |
| c.1150_1170 | GTTCTCCACCACCTGGCGGGT | 1183 |
| c.1151_1171 | TGTTCTCCACCACCTGGCGGG | 1184 |
| c.1152_1172 | ATGTTCTCCACCACCTGGCGG | 1185 |
| c.1153_1173 | CATGTTCTCCACCACCTGGCG | 1186 |
| c.1154_1174 | TCATGTTCTCCACCACCTGGC | 1187 |
| c.1155_1175 | GTCATGTTCTCCACCACCTGG | 1188 |
| c.1156_1176 | GGTCATGTTCTCCACCACCTG | 1189 |
| c.1157_1177 | TGGTCATGTTCTCCACCACCT | 1190 |
| c.1158_1178 | CTGGTCATGTTCTCCACCACC | 1191 |
| c.1159_1179 | CCTGGTCATGTTCTCCACCAC | 1192 |
| c.1160_1180 | CCCTGGTCATGTTCTCCACCA | 1193 |
| c.1161_1181 | GCCCTGGTCATGTTCTCCACC | 1194 |
| c.1162_1182 | GGCCCTGGTCATGTTCTCCAC | 1195 |
| c.1163_1183 | GGGCCCTGGTCATGTTCTCCA | 1196 |
| c.1164_1184 | TGGGCCCTGGTCATGTTCTCC | 1197 |
| c.1165_1185 | GTGGGCCCTGGTCATGTTCTC | 1198 |
| c.1166_1186 | AGTGGGCCCTGGTCATGTTCT | 1199 |
| c.1167_1187 | AAGTGGGCCCTGGTCATGTTC | 1200 |
| c.1168_1188 | GAAGTGGGCCCTGGTCATGTT | 1201 |
| c.1169_1189 | GGAAGTGGGCCCTGGTCATGT | 1202 |
| c.1170_1190 | GGGAAGTGGGCCCTGGTCATG | 1203 |
| c.1171_1191 | GGGGAAGTGGGCCCTGGTCAT | 1204 |

-continued

| Sequence in cDNA to which AON anneals for intron 6 exclusion | AON sequence 5' -> 3' | Seq ID |
|---|---|---|
| c.1172_1192 | GGGGGAAGTGGGCCCTGGTCA | 1205 |
| c.1173_1193 | AGGGGGAAGTGGGCCCTGGTC | 1206 |
| c.1174_1194 | CAGGGGGAAGTGGGCCCTGGT | 1207 |
| c.1175_1194+1 | CCAGGGGGAAGTGGGCCCTGG | 1208 |
| c.1176_1194+2 | ACCAGGGGGAAGTGGGCCCTG | 1209 |
| c.1177_1194+3 | CACCAGGGGGAAGTGGGCCCT | 1210 |
| c.1178_1194+4 | TCACCAGGGGGAAGTGGGCCC | 1211 |
| c.1179_1194+5 | CTCACCAGGGGGAAGTGGGCC | 1212 |
| c.1180_1194+6 | ACTCACCAGGGGGAAGTGGGC | 1213 |
| c.1181_1194+7 | AACTCACCAGGGGGAAGTGGG | 1214 |
| c.1182_1194+8 | CAACTCACCAGGGGGAAGTGG | 1215 |
| c.1183_1194+9 | CCAACTCACCAGGGGGAAGTG | 1216 |
| c.1184_1194+10 | CCCAACTCACCAGGGGGAAGT | 1217 |
| c.1185_1194+11 | CCCCAACTCACCAGGGGGAAG | 1218 |
| c.1186_1194+12 | ACCCCAACTCACCAGGGGGAA | 1219 |
| c.1187_1194+13 | CACCCCAACTCACCAGGGGGA | 1220 |
| c.1188_1194+14 | CCACCCCAACTCACCAGGGGG | 1221 |
| c.1189_1194+15 | ACCACCCCAACTCACCAGGGG | 1222 |
| c.1190_1194+16 | CACCACCCCAACTCACCAGGG | 1223 |
| c.1191_1194+17 | CCACCACCCCAACTCACCAGG | 1224 |
| c.1192_1194+18 | GCCACCACCCCAACTCACCAG | 1225 |
| c.1193_1194+19 | TGCCACCACCCCAACTCACCA | 1226 |
| c.1194_1194+20 | CTGCCACCACCCCAACTCACC | 1227 |
| c.1194+1_+21 | CCTGCCACCACCCCAACTCAC | 1228 |
| c.1194+2_+22 | CCCTGCCACCACCCCAACTCA | 1229 |
| c.1194+3_+23 | CCCCTGCCACCACCCCAACTC | 1230 |
| c.1194+4_+24 | TCCCCTGCCACCACCCCAACT | 1231 |
| c.1194+5_+25 | CTCCCCTGCCACCACCCCAAC | 1232 |
| c.956-25_-8 | GGAAGCAGCTCTGGGGTT | 1233 |
| c.956-24_-7 | GGGAAGCAGCTCTGGGGT | 1234 |
| c.956-23_-6 | AGGGAAGCAGCTCTGGGG | 1235 |
| c.956-22_-5 | AAGGGAAGCAGCTCTGGG | 1236 |
| c.956-21_-4 | GAAGGGAAGCAGCTCTGG | 1237 |
| c.956-20_-3 | GGAAGGGAAGCAGCTCTG | 1238 |
| c.956-19_-2 | TGGAAGGGAAGCAGCTCT | 1239 |
| c.956-18_-1 | CTGGAAGGGAAGCAGCTC | 1240 |
| c.956-17_956 | TCTGGAAGGGAAGCAGCT | 1241 |
| c.956-16_957 | ATCTGGAAGGGAAGCAGC | 1242 |
| c.956-15_958 | CATCTGGAAGGGAAGCAG | 1243 |
| c.956-14_959 | ACATCTGGAAGGGAAGCA | 1244 |
| c.956-13_960 | CACATCTGGAAGGGAAGC | 1245 |
| c.956-12_961 | CCACATCTGGAAGGGAAG | 1246 |
| c.956-11_962 | ACCACATCTGGAAGGGAA | 1247 |
| c.956-10_963 | GACCACATCTGGAAGGGA | 1248 |
| c.956-9_964 | GGACCACATCTGGAAGGG | 1249 |
| c.956-8_965 | AGGACCACATCTGGAAGG | 1250 |
| c.956-7_966 | CAGGACCACATCTGGAAG | 1251 |
| c.956-6_967 | GCAGGACCACATCTGGAA | 1252 |
| c.956-5_968 | TGCAGGACCACATCTGGA | 1253 |
| c.956-4_969 | CTGCAGGACCACATCTGG | 1254 |
| c.956-3_970 | GCTGCAGGACCACATCTG | 1255 |
| c.956-2_971 | GGCTGCAGGACCACATCT | 1256 |
| c.956-1_972 | CGGCTGCAGGACCACATC | 1257 |
| c.956_973 | TCGGCTGCAGGACCACAT | 1258 |
| c.957_974 | CTCGGCTGCAGGACCACA | 1259 |
| c.958_975 | GCTCGGCTGCAGGACCAC | 1260 |
| c.959_976 | GGCTCGGCTGCAGGACCA | 1261 |
| c.960_977 | GGGCTCGGCTGCAGGACC | 1262 |
| c.961_978 | AGGGCTCGGCTGCAGGAC | 1263 |
| c.962_979 | CAGGGCTCGGCTGCAGGA | 1264 |
| c.963_980 | GCAGGGCTCGGCTGCAGG | 1265 |
| c.964_981 | GGCAGGGCTCGGCTGCAG | 1266 |
| c.965_982 | GGGCAGGGCTCGGCTGCA | 1267 |
| c.966_983 | AGGGCAGGGCTCGGCTGC | 1268 |
| c.967_984 | AAGGGCAGGGCTCGGCTG | 1269 |
| c.968_985 | TAAGGGCAGGGCTCGGCT | 1270 |
| c.969_986 | CTAAGGGCAGGGCTCGGC | 1271 |
| c.970_987 | GCTAAGGGCAGGGCTCGG | 1272 |
| c.971_988 | AGCTAAGGGCAGGGCTCG | 1273 |
| c.972_989 | CAGCTAAGGGCAGGGCTC | 1274 |
| c.973_990 | CCAGCTAAGGGCAGGGCT | 1275 |
| c.974_991 | TCCAGCTAAGGGCAGGGC | 1276 |
| c.975_992 | CTCCAGCTAAGGGCAGGG | 1277 |
| c.976_993 | CCTCCAGCTAAGGGCAGG | 1278 |

| Sequence in cDNA to which AON anneals for intron 6 exclusion | AON sequence 5' -> 3' | Seq ID | Sequence in cDNA to which AON anneals for intron 6 exclusion | AON sequence 5' -> 3' | Seq ID |
|---|---|---|---|---|---|
| c.977_994 | ACCTCCAGCTAAGGGCAG | 1279 | c.1014_1031 | CCCAGGAAGATGTAGACA | 1316 |
| c.978_995 | GACCTCCAGCTAAGGGCA | 1280 | c.1015_1032 | GCCCAGGAAGATGTAGAC | 1317 |
| c.979_996 | CGACCTCCAGCTAAGGGC | 1281 | c.1016_1033 | GGCCCAGGAAGATGTAGA | 1318 |
| c.980_997 | TCGACCTCCAGCTAAGGG | 1282 | c.1017_1034 | GGGCCCAGGAAGATGTAG | 1319 |
| c.981_998 | GTCGACCTCCAGCTAAGG | 1283 | c.1018_1035 | TGGGCCCAGGAAGATGTA | 1320 |
| c.982_999 | TGTCGACCTCCAGCTAAG | 1284 | c.1019_1036 | CTGGGCCCAGGAAGATGT | 1321 |
| c.983_1000 | CTGTCGACCTCCAGCTAA | 1285 | c.1020_1037 | TCTGGGCCCAGGAAGATG | 1322 |
| c.984_1001 | CCTGTCGACCTCCAGCTA | 1286 | c.1021_1038 | CTCTGGGCCCAGGAAGAT | 1323 |
| c.985_1002 | ACCTGTCGACCTCCAGCT | 1287 | c.1022_1039 | GCTCTGGGCCCAGGAAGA | 1324 |
| c.986_1003 | CACCTGTCGACCTCCAGC | 1288 | c.1023_1040 | GGCTCTGGGCCCAGGAAG | 1325 |
| c.987_1004 | CCACCTGTCGACCTCCAG | 1289 | c.1024_1041 | GGGCTCTGGGCCCAGGAA | 1326 |
| c.988_1005 | CCCACCTGTCGACCTCCA | 1290 | c.1025_1042 | TGGGCTCTGGGCCCAGGA | 1327 |
| c.989_1006 | TCCCACCTGTCGACCTCC | 1291 | c.1026_1043 | TTGGGCTCTGGGCCCAGG | 1328 |
| c.990_1007 | ATCCCACCTGTCGACCTC | 1292 | c.1027_1044 | CTTGGGCTCTGGGCCCAG | 1329 |
| c.991_1008 | GATCCCACCTGTCGACCT | 1293 | c.1028_1045 | TCTTGGGCTCTGGGCCCA | 1330 |
| c.992_1009 | GGATCCCACCTGTCGACC | 1294 | c.1029_1046 | CTCTTGGGCTCTGGGCCC | 1331 |
| c.993_1010 | AGGATCCCACCTGTCGAC | 1295 | c.1030_1047 | GCTCTTGGGCTCTGGGCC | 1332 |
| c.994_1011 | CAGGATCCCACCTGTCGA | 1296 | c.1031_1048 | CGCTCTTGGGCTCTGGGC | 1333 |
| c.995_1012 | CCAGGATCCCACCTGTCG | 1297 | c.1032_1049 | ACGCTCTTGGGCTCTGGG | 1334 |
| c.996_1013 | TCCAGGATCCCACCTGTC | 1298 | c.1033_1050 | CACGCTCTTGGGCTCTGG | 1335 |
| c.997_1014 | ATCCAGGATCCCACCTGT | 1299 | c.1034_1051 | CCACGCTCTTGGGCTCTG | 1336 |
| c.998_1015 | CATCCAGGATCCCACCTG | 1300 | c.1035_1052 | ACCACGCTCTTGGGCTCT | 1337 |
| c.999_1016 | ACATCCAGGATCCCACCT | 1301 | c.1036_1053 | CACCACGCTCTTGGGCTC | 1338 |
| c.1000_1017 | GACATCCAGGATCCCACC | 1302 | c.1037_1054 | GCACCACGCTCTTGGGCT | 1339 |
| c.1001_1018 | AGACATCCAGGATCCCAC | 1303 | c.1038_1055 | TGCACCACGCTCTTGGGC | 1340 |
| c.1002_1019 | TAGACATCCAGGATCCCA | 1304 | c.1039_1056 | CTGCACCACGCTCTTGGG | 1341 |
| c.1003_1020 | GTAGACATCCAGGATCCC | 1305 | c.1040_1057 | GCTGCACCACGCTCTTGG | 1342 |
| c.1004_1021 | TGTAGACATCCAGGATCC | 1306 | c.1041_1058 | TGCTGCACCACGCTCTTG | 1343 |
| c.1005_1022 | ATGTAGACATCCAGGATC | 1307 | c.1042_1059 | CTGCTGCACCACGCTCTT | 1344 |
| c.1006_1023 | GATGTAGACATCCAGGAT | 1308 | c.1043_1060 | ACTGCTGCACCACGCTCT | 1345 |
| c.1007_1024 | AGATGTAGACATCCAGGA | 1309 | c.1044_1061 | TACTGCTGCACCACGCTC | 1346 |
| c.1008_1025 | AAGATGTAGACATCCAGG | 1310 | c.1045_1062 | GTACTGCTGCACCACGCT | 1347 |
| c.1009_1026 | GAAGATGTAGACATCCAG | 1311 | c.1046_1063 | GGTACTGCTGCACCACGC | 1348 |
| c.1010_1027 | GGAAGATGTAGACATCCA | 1312 | c.1047_1064 | AGGTACTGCTGCACCACG | 1349 |
| c.1011_1028 | AGGAAGATGTAGACATCC | 1313 | c.1048_1065 | CAGGTACTGCTGCACCAC | 1350 |
| c.1012_1029 | CAGGAAGATGTAGACATC | 1314 | c.1049_1066 | CCAGGTACTGCTGCACCA | 1351 |
| c.1013_1030 | CCAGGAAGATGTAGACAT | 1315 | c.1050_1067 | TCCAGGTACTGCTGCACC | 1352 |

| Sequence in cDNA to which AON anneals for intron 6 exclusion | AON sequence 5' -> 3' | Seq ID |
| --- | --- | --- |
| c.1051_1068 | GTCCAGGTACTGCTGCAC | 1353 |
| c.1052_1069 | CGTCCAGGTACTGCTGCA | 1354 |
| c.1053_1070 | ACGTCCAGGTACTGCTGC | 1355 |
| c.1054_1071 | AACGTCCAGGTACTGCTG | 1356 |
| c.1055_1072 | CAACGTCCAGGTACTGCT | 1357 |
| c.1056_1073 | ACAACGTCCAGGTACTGC | 1358 |
| c.1057_1074 | CACAACGTCCAGGTACTG | 1359 |
| c.1058_1075 | CCACAACGTCCAGGTACT | 1360 |
| c.1059_1075+1 | CCCACAACGTCCAGGTAC | 1361 |
| c.1060_1075+2 | ACCCACAACGTCCAGGTA | 1362 |
| c.1061_1075+3 | TACCCACAACGTCCAGGT | 1363 |
| c.1062_1075+4 | CTACCCACAACGTCCAGG | 1364 |
| c.1063_1075+5 | CCTACCCACAACGTCCAG | 1365 |
| c.1064_1075+6 | CCCTACCCACAACGTCCA | 1366 |
| c.1065_1075+7 | GCCCTACCCACAACGTCC | 1367 |
| c.1066_1075+8 | GGCCCTACCCACAACGTC | 1368 |
| c.1067_1075+9 | AGGCCCTACCCACAACGT | 1369 |
| c.1068_1075+10 | CAGGCCCTACCCACAACG | 1370 |
| c.1069_1075+11 | GCAGGCCCTACCCACAAC | 1371 |
| c.1070_1075+12 | AGCAGGCCCTACCCACAA | 1372 |
| c.1071_1075+13 | GAGCAGGCCCTACCCACA | 1373 |
| c.1072_1075+14 | GGAGCAGGCCCTACCCAC | 1374 |
| c.1073_1075+15 | GGGAGCAGGCCCTACCCA | 1375 |
| c.1074_1075+16 | AGGGAGCAGGCCCTACCC | 1376 |
| c.1075_1075+17 | CAGGGAGCAGGCCCTACC | 1377 |
| c.1075+1_+18 | CCAGGGAGCAGGCCCTAC | 1378 |
| c.1075+2_+19 | GCCAGGGAGCAGGCCCTA | 1379 |
| c.1075+3_+20 | GGCCAGGGAGCAGGCCCT | 1380 |
| c.1075+4_+21 | CGGCCAGGGAGCAGGCCC | 1381 |
| c.1075+5_+22 | GCGGCCAGGGAGCAGGCC | 1382 |
| c.1075+6_+23 | CGCGGCCAGGGAGCAGGC | 1383 |
| c.1075+7_+24 | CCGCGGCCAGGGAGCAGG | 1384 |
| c.1075+8_+25 | GCCGCGGCCAGGGAGCAG | 1385 |
| c.1075+9_+26 | GGCCGCGGCCAGGGAGCA | 1386 |
| c.1075+10_+27 | GGGCCGCGGCCAGGGAGC | 1387 |
| c.1075+11_+28 | GGGGCCGCGGCCAGGGAG | 1388 |
| c.1075+12_+29 | GGGGGCCGCGGCCAGGGA | 1389 |
| c.1075+13_+30 | CGGGGGCCGCGGCCAGGG | 1390 |
| c.1075+14_+31 | GCGGGGGCCGCGGCCAGG | 1391 |
| c.1075+15_+32 | GGCGGGGGCCGCGGCCAG | 1392 |
| c.1075+16_+33 | GGGCGGGGGCCGCGGCCA | 1393 |
| c.1075+17_+34 | GGGGCGGGGGCCGCGGCC | 1394 |
| c.1075+18_+35 | TGGGGCGGGGGCCGCGGC | 1395 |
| c.1075+19_+36 | TTGGGGCGGGGGCCGCGG | 1396 |
| c.1075+20_+37 | CTTGGGGCGGGGGCCGCG | 1397 |
| c.1075+21_+38 | CCTTGGGGCGGGGGCCGC | 1398 |
| c.1075+22_+39 | GCCTTGGGGCGGGGGCCG | 1399 |
| c.1075+23_+40 | AGCCTTGGGGCGGGGGCC | 1400 |
| c.1075+24_1076-39 | GAGCCTTGGGGCGGGGGC | 1401 |
| c.1075+25_1076-38 | GGAGCCTTGGGGCGGGGG | 1402 |
| c.1075+26_1076-37 | GGGAGCCTTGGGGCGGGG | 1403 |
| c.1075+27_1076-36 | AGGGAGCCTTGGGGCGGG | 1404 |
| c.1075+28_1076-35 | GAGGGAGCCTTGGGGCGG | 1405 |
| c.1075+29_1076-34 | GGAGGGAGCCTTGGGGCG | 1406 |
| c.1075+30_1076-33 | AGGAGGGAGCCTTGGGGC | 1407 |
| c.1075+31_1076-32 | GAGGAGGGAGCCTTGGGG | 1408 |
| c.1075+32_1076-31 | GGAGGAGGGAGCCTTGGG | 1409 |
| c.1075+33_1076-30 | GGGAGGAGGGAGCCTTGG | 1410 |
| c.1075+34_1076-29 | AGGGAGGAGGGAGCCTTG | 1411 |
| c.1075+35_1076-28 | GAGGGAGGAGGGAGCCTT | 1412 |
| c.1075+36_1076-27 | GGAGGGAGGAGGGAGCCT | 1413 |
| c.1075+37_1076-26 | GGGAGGGAGGAGGGAGCC | 1414 |
| c.1075+38_1076-25 | AGGGAGGGAGGAGGGAGC | 1415 |
| c.1075+39_1076-24 | GAGGGAGGGAGGAGGGAG | 1416 |
| c.1075+40_1076-23 | TGAGGGAGGGAGGAGGGA | 1417 |
| c.1076-39_-22 | ATGAGGGAGGGAGGAGGG | 1418 |
| c.1076-38_-21 | CATGAGGGAGGGAGGAGG | 1419 |
| c.1076-37_-20 | TCATGAGGGAGGGAGGAG | 1420 |
| c.1076-36_-19 | TTCATGAGGGAGGGAGGA | 1421 |
| c.1076-35_-18 | CTTCATGAGGGAGGGAGG | 1422 |
| c.1076-34_-17 | ACTTCATGAGGGAGGGAG | 1423 |
| c.1076-33_-16 | GACTTCATGAGGGAGGGA | 1424 |
| c.1076-32_-15 | CGACTTCATGAGGGAGGG | 1425 |
| c.1076-31_-14 | CCGACTTCATGAGGGAGG | 1426 |

| Sequence in cDNA to which AON anneals for intron 6 exclusion | AON sequence 5' -> 3' | Seq ID | Sequence in cDNA to which AON anneals for intron 6 exclusion | AON sequence 5' -> 3' | Seq ID |
|---|---|---|---|---|---|
| c.1076-30_-13 | GCCGACTTCATGAGGGAG | 1427 | c.1083_1100 | CAGTATGGCGGCATGAAC | 1464 |
| c.1076-29_-12 | CGCCGACTTCATGAGGGA | 1428 | c.1084_1101 | CCAGTATGGCGGCATGAA | 1465 |
| c.1076-28_-11 | ACGCCGACTTCATGAGGG | 1429 | c.1085_1102 | CCCAGTATGGCGGCATGA | 1466 |
| c.1076-27_-10 | AACGCCGACTTCATGAGG | 1430 | c.1086_1103 | CCCCAGTATGGCGGCATG | 1467 |
| c.1076-26_-9 | CAACGCCGACTTCATGAG | 1431 | c.1087_1104 | GCCCCAGTATGGCGGCAT | 1468 |
| c.1076-25_-8 | CCAACGCCGACTTCATGA | 1432 | c.1088_1105 | GGCCCCAGTATGGCGGCA | 1469 |
| c.1076-24_-7 | GCCAACGCCGACTTCATG | 1433 | c.1089_1106 | AGGCCCCAGTATGGCGGC | 1470 |
| c.1076-23_-6 | GGCCAACGCCGACTTCAT | 1434 | c.1090_1107 | CAGGCCCCAGTATGGCGG | 1471 |
| c.1076-22_-5 | AGGCCAACGCCGACTTCA | 1435 | c.1091_1108 | CCAGGCCCCAGTATGGCG | 1472 |
| c.1076-21_-4 | CAGGCCAACGCCGACTTC | 1436 | c.1092_1109 | CCCAGGCCCCAGTATGGC | 1473 |
| c.1076-20_-3 | GCAGGCCAACGCCGACTT | 1437 | c.1093_1110 | GCCCAGGCCCCAGTATGG | 1474 |
| c.1076-19_-2 | TGCAGGCCAACGCCGACT | 1438 | c.1094_1111 | AGCCCAGGCCCCAGTATG | 1475 |
| c.1076-18_-1 | CTGCAGGCCAACGCCGAC | 1439 | c.1095_1112 | AAGCCCAGGCCCCAGTAT | 1476 |
| c.1076-17_1076 | CCTGCAGGCCAACGCCGA | 1440 | c.1096_1113 | GAAGCCCAGGCCCCAGTA | 1477 |
| c.1076-16_1077 | TCCTGCAGGCCAACGCCG | 1441 | c.1097_1114 | GGAAGCCCAGGCCCCAGT | 1478 |
| c.1076-15_1078 | ATCCTGCAGGCCAACGCC | 1442 | c.1098_1115 | TGGAAGCCCAGGCCCCAG | 1479 |
| c.1076-14_1079 | TATCCTGCAGGCCAACGC | 1443 | c.1099_1116 | GTGGAAGCCCAGGCCCCA | 1480 |
| c.1076-13_1080 | GTATCCTGCAGGCCAACG | 1444 | c.1100_1117 | GGTGGAAGCCCAGGCCCC | 1481 |
| c.1076-12_1081 | GGTATCCTGCAGGCCAAC | 1445 | c.1101_1118 | AGGTGGAAGCCCAGGCCC | 1482 |
| c.1076-11_1082 | GGGTATCCTGCAGGCCAA | 1446 | c.1102_1119 | CAGGTGGAAGCCCAGGCC | 1483 |
| c.1076-10_1083 | CGGGTATCCTGCAGGCCA | 1447 | c.1103_1120 | ACAGGTGGAAGCCCAGGC | 1484 |
| c.1076-9_1084 | ACGGGTATCCTGCAGGCC | 1448 | c.1104_1121 | CACAGGTGGAAGCCCAGG | 1485 |
| c.1076-8_1085 | AACGGGTATCCTGCAGGC | 1449 | c.1105_1122 | GCACAGGTGGAAGCCCAG | 1486 |
| c.1076-7_1086 | GAACGGGTATCCTGCAGG | 1450 | c.1106_1123 | GGCACAGGTGGAAGCCCA | 1487 |
| c.1076-6_1087 | TGAACGGGTATCCTGCAG | 1451 | c.1107_1124 | CGGCACAGGTGGAAGCCC | 1488 |
| c.1076-5_1088 | ATGAACGGGTATCCTGCA | 1452 | c.1108_1125 | GCGGCACAGGTGGAAGCC | 1489 |
| c.1076-4_1089 | CATGAACGGGTATCCTGC | 1453 | c.1109_1126 | AGCGGCACAGGTGGAAGC | 1490 |
| c.1076-3_1090 | GCATGAACGGGTATCCTG | 1454 | c.1110_1127 | CAGCGGCACAGGTGGAAG | 1491 |
| c.1076-2_1091 | GGCATGAACGGGTATCCT | 1455 | c.1111_1128 | CCAGCGGCACAGGTGGAA | 1492 |
| c.1076-1_1092 | CGGCATGAACGGGTATCC | 1456 | c.1112_1129 | CCCAGCGGCACAGGTGGA | 1493 |
| c.1076_1093 | GCGGCATGAACGGGTATC | 1457 | c.1113_1130 | CCCCAGCGGCACAGGTGG | 1494 |
| c.1077_1094 | GGCGGCATGAACGGGTAT | 1458 | c.1114_1131 | GCCCCAGCGGCACAGGTG | 1495 |
| c.1078_1095 | TGGCGGCATGAACGGGTA | 1459 | c.1115_1132 | AGCCCCAGCGGCACAGGT | 1496 |
| c.1079_1096 | ATGGCGGCATGAACGGGT | 1460 | c.1116_1133 | TAGCCCCAGCGGCACAGG | 1497 |
| c.1080_1097 | TATGGCGGCATGAACGGG | 1461 | c.1117_1134 | GTAGCCCCAGCGGCACAG | 1498 |
| c.1081_1098 | GTATGGCGGCATGAACGG | 1462 | c.1118_1135 | AGTAGCCCCAGCGGCACA | 1499 |
| c.1082_1099 | AGTATGGCGGCATGAACG | 1463 | c.1119_1136 | GAGTAGCCCCAGCGGCAC | 1500 |

-continued

| Sequence in cDNA to which AON anneals for intron 6 exclusion | AON sequence 5' -> 3' | Seq ID |
|---|---|---|
| c.1120_1137 | GGAGTAGCCCCAGCGGCA | 1501 |
| c.1121_1138 | AGGAGTAGCCCCAGCGGC | 1502 |
| c.1122_1139 | GAGGAGTAGCCCCAGCGG | 1503 |
| c.1123_1140 | GGAGGAGTAGCCCCAGCG | 1504 |
| c.1124_1141 | TGGAGGAGTAGCCCCAGC | 1505 |
| c.1125_1142 | GTGGAGGAGTAGCCCCAG | 1506 |
| c.1126_1143 | GGTGGAGGAGTAGCCCCA | 1507 |
| c.1127_1144 | CGGTGGAGGAGTAGCCCC | 1508 |
| c.1128_1145 | GCGGTGGAGGAGTAGCCC | 1509 |
| c.1129_1146 | AGCGGTGGAGGAGTAGCC | 1510 |
| c.1130_1147 | TAGCGGTGGAGGAGTAGC | 1511 |
| c.1131_1148 | ATAGCGGTGGAGGAGTAG | 1512 |
| c.1132_1149 | GATAGCGGTGGAGGAGTA | 1513 |
| c.1133_1150 | TGATAGCGGTGGAGGAGT | 1514 |
| c.1134_1151 | GTGATAGCGGTGGAGGAG | 1515 |
| c.1135_1152 | GGTGATAGCGGTGGAGGA | 1516 |
| c.1136_1153 | GGGTGATAGCGGTGGAGG | 1517 |
| c.1137_1154 | CGGGTGATAGCGGTGGAG | 1518 |
| c.1138_1155 | GCGGGTGATAGCGGTGGA | 1519 |
| c.1139_1156 | GGCGGGTGATAGCGGTGG | 1520 |
| c.1140_1157 | TGGCGGGTGATAGCGGTG | 1521 |
| c.1141_1158 | CTGGCGGGTGATAGCGGT | 1522 |
| c.1142_1159 | CCTGGCGGGTGATAGCGG | 1523 |
| c.1143_1160 | ACCTGGCGGGTGATAGCG | 1524 |
| c.1144_1161 | CACCTGGCGGGTGATAGC | 1525 |
| c.1145_1162 | CCACCTGGCGGGTGATAG | 1526 |
| c.1146_1163 | ACCACCTGGCGGGTGATA | 1527 |
| c.1147_1164 | CACCACCTGGCGGGTGAT | 1528 |
| c.1148_1165 | CCACCACCTGGCGGGTGA | 1529 |
| c.1149_1166 | TCCACCACCTGGCGGGTG | 1530 |
| c.1150_1167 | CTCCACCACCTGGCGGGT | 1531 |
| c.1151_1168 | TCTCCACCACCTGGCGGG | 1532 |
| c.1152_1169 | TTCTCCACCACCTGGCGG | 1533 |
| c.1153_1170 | GTTCTCCACCACCTGGCG | 1534 |
| c.1154_1171 | TGTTCTCCACCACCTGGC | 1535 |
| c.1155_1172 | ATGTTCTCCACCACCTGG | 1536 |
| c.1156_1173 | CATGTTCTCCACCACCTG | 1537 |

-continued

| Sequence in cDNA to which AON anneals for intron 6 exclusion | AON sequence 5' -> 3' | Seq ID |
|---|---|---|
| c.1157_1174 | TCATGTTCTCCACCACCT | 1538 |
| c.1158_1175 | GTCATGTTCTCCACCACC | 1539 |
| c.1159_1176 | GGTCATGTTCTCCACCAC | 1540 |
| c.1160_1177 | TGGTCATGTTCTCCACCA | 1541 |
| c.1161_1178 | CTGGTCATGTTCTCCACC | 1542 |
| c.1162_1179 | CCTGGTCATGTTCTCCAC | 1543 |
| c.1163_1180 | CCCTGGTCATGTTCTCCA | 1544 |
| c.1164_1181 | GCCCTGGTCATGTTCTCC | 1545 |
| c.1165_1182 | GGCCCTGGTCATGTTCTC | 1546 |
| c.1166_1183 | GGGCCCTGGTCATGTTCT | 1547 |
| c.1167_1184 | TGGGCCCTGGTCATGTTC | 1548 |
| c.1168_1185 | GTGGGCCCTGGTCATGTT | 1549 |
| c.1169_1186 | AGTGGGCCCTGGTCATGT | 1550 |
| c.1170_1187 | AAGTGGGCCCTGGTCATG | 1551 |
| c.1171_1188 | GAAGTGGGCCCTGGTCAT | 1552 |
| c.1172_1189 | GGAAGTGGGCCCTGGTCA | 1553 |
| c.1173_1190 | GGGAAGTGGGCCCTGGTC | 1554 |
| c.1174_1191 | GGGGAAGTGGGCCCTGGT | 1555 |
| c.1175_1192 | GGGGGAAGTGGGCCCTGG | 1556 |
| c.1176_1193 | AGGGGGAAGTGGGCCCTG | 1557 |
| c.1177_1194 | CAGGGGGAAGTGGGCCCT | 1558 |
| c.1178_1194+1 | CCAGGGGGAAGTGGGCCC | 1559 |
| c.1179_1194+2 | ACCAGGGGGAAGTGGGCC | 1560 |
| c.1180_1194+3 | CACCAGGGGGAAGTGGGC | 1561 |
| c.1181_1194+4 | TCACCAGGGGGAAGTGGG | 1562 |
| c.1182_1194+5 | CTCACCAGGGGGAAGTGG | 1563 |
| c.1183_1194+6 | ACTCACCAGGGGGAAGTG | 1564 |
| c.1184_1194+7 | AACTCACCAGGGGGAAGT | 1565 |
| c.1185_1194+8 | CAACTCACCAGGGGGAAG | 1566 |
| c.1186_1194+9 | CCAACTCACCAGGGGGAA | 1567 |
| c.1187_1194+10 | CCCAACTCACCAGGGGGA | 1568 |
| c.1188_1194+11 | CCCCAACTCACCAGGGGG | 1569 |
| c.1189_1194+12 | ACCCCAACTCACCAGGGG | 1570 |
| c.1190_1194+13 | CACCCCAACTCACCAGGG | 1571 |
| c.1191_1194+14 | CCACCCCAACTCACCAGG | 1572 |
| c.1192_1194+15 | ACCACCCCAACTCACCAG | 1573 |
| c.1193_1194+16 | CACCACCCCAACTCACCA | 1574 |

| Sequence in cDNA to which AON anneals for intron 6 exclusion | AON sequence 5' -> 3' | Seq ID |
|---|---|---|
| c.1194_1194+17 | CCACCACCCCAACTCACC | 1575 |
| c.1194+1_+18 | GCCACCACCCCAACTCAC | 1576 |
| c.1194+2_+19 | TGCCACCACCCCAACTCA | 1577 |
| c.1194+3_+20 | CTGCCACCACCCCAACTC | 1578 |
| c.1194+4_+21 | CCTGCCACCACCCCAACT | 1579 |
| c.1194+5_+22 | CCCTGCCACCACCCCAAC | 1580 |
| c.1194+6_+23 | CCCCTGCCACCACCCCAA | 1581 |
| c.1194+7_+24 | TCCCCTGCCACCACCCCA | 1582 |
| c.1194+8_+25 | CTCCCCTGCCACCACCCC | 1583 |
| GAA_c.2190-357_-333 | TCAGTCAAGTATCTGGAAAGTACGA | 1590 |
| GAA_c.2190-355_-335 | AGTCAAGTATCTGGAAAGTAC | 1591 |
| GAA_c.1249_1273 | GGAAGTCCCGGAAGCCAACCTTGTT | 1592 |
| GAA_c.1552-46_-26 | TGACTCTGCCCAGAGTGAGGA | 1593 |
| GAA_c.1755-112_-88 | AGCTTTCTGGGATGAGGCAGAGGCT | 1594 |

In the above examples the sequences are 18, 21 and 25 nucleotides long however longer variants or shorter fragment are also envisioned. Optionally of the invention and/or embodiments thereof of the present invention and/or embodiments thereof the antisense oligomeric compounds are selected from the group of SEQ ID NO: 541-1583, 1590-1594 and fragments and variants thereof having at least 80% sequence identity. Optionally of the invention and/or embodiments thereof of the present invention and/or embodiments thereof the antisense oligomeric compounds are selected from the group of SEQ ID NO: 541-1583, 1590-1594 and fragments and variants thereof having at least 80%,83%, 85%, 87%, 90%, 92%, 93%, 94%, 95%, 96%, 97%, 98%, 99%, 99.2%, 99.3%, 99.4%, 99.5%, 99.6%, 99.7% sequence identity to SEQ ID NO: 541-1583, 1590-1594.

Or sequences that are at least 80% identical to SEQ ID NO: 541-1583, 1590-1594. Optionally at least 85% identical to SEQ ID NO: 541-1583, 1590-1594, more Optionally at least 88% identical to SEQ ID NO: 541-1583, 1590-1594, more Optionally at least 90% identical to SEQ ID NO: 541-1583, 1590-1594. more Optionally at least 91% identical to SEQ ID NO: 541-1583, 1590-1594, more Optionally at least 92% identical to SEQ ID NO: 541-1583, 1590-1594, more Optionally at least 93% identical to SEQ ID NO: 541-1583, 1590-1594, more Optionally at least 94% identical to SEQ ID NO: 541-1583, 1590-1594, more Optionally at least 95% identical to SEQ ID NO: 541-1583, 1590-1594, more Optionally at least 96% identical to SEQ ID NO: 541-1583, 1590-1594, more Optionally at least 97% identical to SEQ ID NO: 541-1583, 1590-1594, more Optionally at least 98% identical to SEQ ID NO: 541-1583, 1590-1594, more Optionally at least 99% identical to SEQ ID NO: 541-1583, 1590-1594.

Optionally of the invention and/or embodiments thereof of the present invention and/or embodiments thereof the antisense oligomeric compounds are selected from the group of fragments SEQ ID NO: 541-1583, 1590-1594, wherein the fragment is 16, 17, 18, 19, 20, 21, 22, 23, or 24 nucleotides long. Optionally of the invention and/or embodiments thereof of the present invention and/or embodiments thereof the antisense oligomeric compounds are selected from the group of fragments SEQ ID NO: 541-1583, 1590-1594, wherein the fragment is 17, 18, 19, 20, 21, or 22 nucleotides long. Optionally of the invention and/or embodiments thereof of the present invention and/or embodiments thereof the antisense oligomeric compounds are selected from the group of fragments SEQ ID NO: 541-1583, 1590-1594, wherein the fragment is 19, 20, or 21 nucleotides long.

The antisense oligomeric compound may be also be complementary to a genomic nucleic acid sequence of GAA gene targeting the location that comprises the position of a mutation selected from the group
c.-32-13T>G (IVS1), c.1636+5G>T, c.525delT, c.-32-3C>G, c. 1551+1G>A, c.1075G>A, c.1552-3C>G, c.1437G>A, c.1256A>T, c.1551+1G>T.

Optionally the genomic nucleic acid sequence is pre-mRNA.

Optionally of the invention and/or embodiments thereof, the antisense oligomeric compound may be also be complementary to a genomic nucleic acid sequence of GAA gene targeting the location that comprises the position of a mutation selected from the group comprising c.-32-3C>G, c.-32-13T>G, c.-32-102T>C, c.-32-56C>T, c.-32-46G>A, c.-32-28C>A, c.-32-28C>T, c.-32-21G>A, c.7G>A, c.11G>A, c.15_17AAA, c.17C>T, c.19_21AAA, c.26_28AAA, c.33_35AAA, c.39G>A, c.42C>T, c.90C>T, c.112G>A, c.137C>T, c.164C>T, c.348G>A, c.373C>T, c.413T>A, c.469C>T, c.476T>C, c.476T>G, c.478T>G, c.482C>T, c.510C>T, c.515T>A, c.520G>A, c.546+11C>T, c.546+14G>A, c.546+19G>A, c.546+23C>A, c.547-6, c.1071, c.1254, and c.1552-30.

Optionally the genomic nucleic acid sequence is pre-mRNA

Optionally of the invention and/or embodiments thereof, the antisense oligomeric compound may be also be complementary to a genomic nucleic acid sequence of GAA gene targeting the location that comprises the position of a mutation selected from the group comprising c.17C>T c.469C>T c.546+23C>A, c.-32-102T>C c.-32-56C>T c.11G>A c.112G>A c.137C>T.

Optionally of the invention and/or embodiments thereof, the antisense oligomeric compound may be also be complementary to a genomic nucleic acid sequence of GAA gene targeting the location that comprises the position of a mutation selected from the group comprising c.17C>T c.469C>T c.546+23C>A.

Optionally of the invention and/or embodiments thereof, the antisense oligomeric compound may be also be complementary to a genomic nucleic acid sequence of GAA gene targeting the location that comprises the position of a mutation selected from the group comprising c.-32-102T>C c.-32-56C>T c.11G>A c.112G>A c.137C>T.

Most preferred are antisense oligomeric compounds that are complementary to a genomic nucleic acid sequence of GAA gene targeting the location that comprises the position of a mutation c.-32-13T>G (IVS1).

Most preferred are antisense oligomeric compounds that are complementary to a genomic nucleic acid sequence of GAA gene targeting the location that comprises the position of a mutation c.-32-3C>G, c.1256A>T, c.1551+1G>T, c.546G>T.

Most preferred are antisense oligomeric compounds that are complementary to a genomic nucleic acid sequence of GAA gene targeting the location that comprises the position of a mutation c.-32-3C>G.

Most preferred are antisense oligomeric compounds that are complementary to a genomic nucleic acid sequence of GAA gene targeting SEQ ID NO: 1.

```
                                              (SEQ ID NO: 1)
GCTCTGCACTCCCCTGCTGGAGCTTTTCTCGCCCTTCCTTCTGGCCCTCT

CCCCA.
```

Optionally of the invention and/or embodiments thereof, the antisense oligomeric compound are 8 to 80 nucleotides in length, 9 to 50 nucleotides in length, 10 to 30 nucleotides in length, 12 to 30 nucleotides in length, 15 to 25 nucleotides in length or about 20 nucleotides in length. One of ordinary skill in the art will appreciate that this comprehends antisense compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides.

In one embodiment of the invention and/or embodiments thereof, the antisense compounds comprise 13 to 80 nucleotides. One having ordinary skill in the art will appreciate that this embodies antisense compounds of 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides.

In one embodiment of the invention and/or embodiments thereof, the antisense compounds comprise 13 to 50 nucleotides. One having ordinary skill in the art will appreciate that this embodies antisense compounds of 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, or 50 nucleotides.

In one embodiment of the invention and/or embodiments thereof, the antisense compounds comprise 13 to 30 nucleotides. One having ordinary skill in the art will appreciate that this embodies antisense compounds of 13, 14, 15, 16, 17, 18, 19, 20, 21, 22, 23, 24, 25, 26, 27, 28, 29 or 30 nucleotides.

In one embodiment of the invention and/or embodiments thereof, the antisense compounds comprise 20 to 30 nucleotides. One having ordinary skill in the art will appreciate that this embodies antisense compounds of 20, 21, 22, 23, 24, 25, 26, 27, 28, 29, or 30 nucleotides. In one embodiment of the invention and/or embodiments thereof, the antisense compounds comprise 15 to 25 nucleotides. One having ordinary skill in the art will appreciate that this embodies antisense compounds of 15, 16, 17, 18, 19, 20, 21, 22, 23, 24 or 25.

In one embodiment of the invention and/or embodiments thereof, the antisense compounds comprise 20 nucleotides.

In one embodiment of the invention and/or embodiments thereof, the antisense compounds comprise 19 nucleotides.

In one embodiment of the invention and/or embodiments thereof, the antisense compounds comprise 18 nucleotides.

In one embodiment of the invention and/or embodiments thereof, the antisense compounds comprise 17 nucleotides.

In one embodiment of the invention and/or embodiments thereof, the antisense compounds comprise 16 nucleotides.

In one embodiment of the invention and/or embodiments thereof, the antisense compounds comprise 15 nucleotides.

In one embodiment of the invention and/or embodiments thereof, the antisense compounds comprise 14 nucleotides.

In one embodiment of the invention and/or embodiments thereof, the antisense compounds comprise 13 nucleotides.

In one embodiment of the invention and/or embodiments thereof, compounds include oligonucleotide sequences that comprise at least the 8 consecutive nucleotides from one of the antisense compounds as claimed. Optionally at least 9 consecutive nucleotides from one of the antisense compounds as claimed, more Optionally at least 10 consecutive nucleotides from one of the antisense compounds as claimed, more Optionally at least 11 consecutive nucleotides from one of the antisense compounds as claimed, more Optionally at least 12 consecutive nucleotides from one of the antisense compounds as claimed, more Optionally at least 13 consecutive nucleotides from one of the antisense compounds as claimed, more Optionally at least 14 consecutive nucleotides from one of the antisense compounds as claimed, more Optionally at least 15 consecutive nucleotides from one of the antisense compounds as claimed, more Optionally at least 16 consecutive nucleotides from one of the antisense compounds as claimed, more Optionally at least 17 consecutive nucleotides from one of the antisense compounds as claimed, more Optionally at least 18 consecutive nucleotides from one of the antisense compounds as claimed, more Optionally at least 19 consecutive nucleotides from one of the antisense compounds as claimed, more Optionally at least 20 consecutive nucleotides from one of the antisense compounds as claimed.

Any remaining nucleotides from the oligonuclotides may be oligonucleotides that improve resistance to Rnase H, cell-targeting sequences, cell penetrating sequences, marker sequences or any other sequences.

One having skill in the art armed with the antisense compounds disclosed herein will be able, without undue experimentation, to identify further antisense compounds.

In order for an antisense oligonucleotide to achieve therapeutic success, oligonucleotide chemistry must allow for adequate cellular uptake (Kurreck, J. (2003) Eur. J. Biochem. 270:1628-1644). Splicing oligonucleotides have traditionally been comprised of uniform modifications that render the oligonucleotide RNA-like, and thus resistant to cleavage by RNase H, which is critical to achieve modulation of splicing. Provided herein are antisense compounds for modulation of splicing.

Optionally of the invention and/or embodiments thereof, the antisense compounds are chimeric, with regions of RNA-like and DNA-like chemistry. Despite regions of DNA-like chemistry, the chimeric compounds are Optionally RNase H-resistant and effectively modulate splicing of target mRNA in vitro and in vivo. In another preferred embodiment the disclosed antisense oligomeric compounds show enhanced cellular uptake and greater pharmacologic activity compared with uniformly modified oligonucleotides.

Contemplated herein are antisense oligomeric compound which are targeted to a splice site of a target mRNA or to splicing repressor sequences, or to splicing enhancer sequences, Optionally to splicing repressor sequences. Splice sites include aberrant and cryptic splice sites.

One skilled in the art recognizes that the inclusion of mismatches is possible without eliminating the activity of the antisense compound. Compounds provided herein are therefore directed to those antisense compounds that may contain up to about 20% nucleotides that disrupt base pairing of the antisense compound to the target. Optionally the compounds contain no more than about 15%, more Optionally not more than about 10%, most Optionally not more than 5% or no mismatches. The remaining nucleotides do not disrupt hybridization (e.g., universal bases).

It is understood in the art that incorporation of nucleotide affinity modifications may allow for a greater number of mismatches compared to an unmodified compound. Similarly, certain oligonucleotide sequences may be more tolerant to mismatches than other oligonucleotide sequences. One of the skill in the art is capable of determining an appropriate number of mismatches between oligonucleotides, or between an oligonucleotide and a target nucleic acid, such as by determining melting temperature.

It is known by a skilled person that hybridization to a target mRNA depends on the conditions. "Stringent hybridization conditions" or "stringent conditions" refer to conditions under which an oligomeric compound will hybridize to its target sequence, but to a minimal number of other sequences. Stringent conditions are sequence-dependent and will be different in different circumstances, and "stringent conditions" under which oligomeric compounds hybridize to a target sequence are determined by the nature and composition of the oligomeric compounds and the assays in which they are being investigated.

Antisense compounds, or a portion thereof, may have a defined percent identity to a SEQ ID NO, or a compound having a specific Isis number. As used herein, a sequence is identical to the sequence disclosed herein if it has the same nucleobase pairing ability. For example, a RNA which contains uracil in place of thymidine in the disclosed sequences would be considered identical as they both pair with adenine. This identity may be over the entire length of the oligomeric compound, or in a portion of the antisense compound (e.g., nucleotides 1-20 of a 27-mer may be compared to a 20-mer to determine percent identity of the oligomeric compound to the SEQ ID NO.) It is understood by those skilled in the art that an antisense compound need not have an identical sequence to those described herein to function similarly to the antisense compound described herein. Shortened versions of antisense compound taught herein, or non-identical versions of the antisense compound taught herein are also contemplated. Non-identical versions are those wherein each base does not have the same pairing activity as the antisense compounds disclosed herein. Bases do not have the same pairing activity by being shorter or having at least one abasic site. Alternatively, a non-identical version can include at least one base replaced with a different base with different pairing activity (e.g., G can be replaced by C, A, or T). Percent identity is calculated according to the number of bases that have identical base pairing corresponding to the SEQ ID NO or antisense compound to which it is being compared. The non-identical bases may be adjacent to each other, dispersed through out the oligonucleotide, or both.

For example, a 16-mer having the same sequence as nucleotides 2-17 of a 20-mer is 80% identical to the 20-mer. Alternatively, a 20-mer containing four nucleotides not identical to the 20-mer is also 80% identical to the 20-mer. A 14-mer having the same sequence as nucleotides 1-14 of an 18-mer is 78% identical to the 18-mer. Such calculations are well within the ability of those skilled in the art.

The percent identity is based on the percent of nucleotides in the original sequence present in a portion of the modified sequence. Therefore, a 30 nucleobase antisense compound comprising the full sequence of the complement of a 20 nucleobase active target segment would have a portion of 100% identity with the complement of the 20 nucleobase active target segment, while further comprising an additional 10 nucleobase portion. The complement of an active target segment may constitute a single portion. Optionally of the invention and/or embodiments thereof, the oligonucleotides are at least about 80%, more Optionally at least about 85%, even more Optionally at least about 90%, most Optionally at least 95% identical to at least a portion of the complement of the active target segments presented herein.

It is well known by those skilled in the art that it is possible to increase or decrease the length of an antisense compound and/or introduce mismatch bases without eliminating activity. For example, in Woolf et al. (Proc. Natl. Acad. Sci. USA 89:7305-7310, 1992, incorporated herein by reference), a series of antisense oligomeric compounds of 13-25 nucleotides in length were tested for their ability to induce cleavage of a target RNA. Antisense oligomeric compounds of 25 nucleotides in length with 8 or 11 mismatch bases near the ends of the antisense oligomeric compounds were able to direct specific cleavage of the target mRNA, albeit to a lesser extent than the antisense oligomeric compounds that contained no mismatches. Similarly, target specific cleavage was achieved using a 13 nucleobase antisense oligomeric compounds, including those with 1 or 3 mismatches. Maher and Dolnick (Nuc. Acid. Res. 16:3341-3358, 1988, incorporated herein by reference) tested a series of tandem 14 nucleobase antisense oligomeric compounds, and a 28 and 42 nucleobase antisense oligomeric compounds comprised of the sequence of two or three of the tandem antisense oligomeric compounds, respectively, for their ability to arrest translation of human DHFR in a rabbit reticulocyte assay. Each of the three 14 nucleobase antisense oligomeric compounds alone were able to inhibit translation, albeit at a more modest level than the 28 or 42 nucleobase antisense oligomeric compounds. It is understood that antisense compounds can vary in length and percent complementarity to the target provided that they maintain the desired activity. Methods to determine desired activity are disclosed herein and well known to those skilled in the art. Optionally of the invention and/or embodiments thereof, the antisense oligomeric compounds have at least 80% complementarity to the target mRNA, more Optionally at least 85% complementarity to the target mRNA, more Optionally at least 90% complementarity to the target mRNA, more Optionally at least 95% complementarity to the target mRNA, more Optionally at least 96% complementarity to the target mRNA, more Optionally at least 97% complementarity to the target mRNA, more Optionally at least 98% complementarity to the target mRNA, more Optionally at least 99% complementarity to the target mRNA, more Optionally at least 100% complementarity to the target mRNA.

As is known in the art, a nucleoside is a base-sugar combination. The base portion of the nucleoside is normally a heterocyclic base (sometimes referred to as a "nucleobase" or simply a "base"). The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. In forming oligonucleotides, the phosphate groups covalently link adjacent nucleosides to one another to form a linear polymeric compound. Within oligonucleotides, the phosphate groups are commonly referred to as forming the internucleoside backbone of the oligonucleotide. The normal linkage or backbone of RNA and DNA is a 3' to 5' phosphodiester linkage. It is often preferable to include chemical modifications in oligonucleotides to alter their activity. Chemical modifications can alter oligonucleotide activity by, for example: increasing affinity of an antisense oligonucleotide for its target RNA, increasing nuclease resistance, and/or altering the pharmacokinetics of the oligonucleotide. The use of chemistries that increase the affinity of an oligonucleotide for its target can allow for the use of shorter oligonucleotide compounds.

Antisense compounds provided herein may also contain one or more nucleosides having modified sugar moieties. The furanosyl sugar ring of a nucleoside can be modified in a number of ways including, but not limited to, addition of a substituent group, bridging of two non-geminal ring atoms to form a bicyclic nucleic acid (BNA) and substitution of an atom or group such as —S—, —N(R)— or —C($R_1$)($R_2$) for the ring oxygen at the 4'-position. Modified sugar moieties are well known and can be used to alter, typically increase, the affinity of the antisense compound for its target and/or increase nuclease resistance. A representative list of preferred modified sugars includes but is not limited to bicyclic modified sugars (BNA's), including LNA and ENA (4'-(CH2)2-O-2' bridge); and substituted sugars, especially 2'-substituted sugars having a 2'-F, 2'-OCH2 or a 2'-O(CH2) 2-OCH3 substituent group. Sugars can also be replaced with sugar mimetic groups among others. Methods for the preparations of modified sugars are well known to those skilled in the art. Suitable compounds can comprise one of the following at the 2' position: OH; F; O—, S—, or N-alkyl; O—, S—, or N-alkenyl; O—, S- or N-alkynyl; or O-alkyl-O-alkyl, wherein the alkyl, alkenyl and alkynyl may be substituted or unsubstituted C1 to C10 alkyl or C2 to C10 alkenyl and alkynyl. Also suitable are O((CH2)nO)mCH3, O(CH2)nOCH3, O(CH2)nNH2, O(CH2)nCH3, O(CH2) nONH2, and O(CH2)nON((CH2)nCH3)2, where n and m are from 1 to about 10. Other oligonucleotides comprise one of the following at the 2' position: C1 to C10 lower alkyl, substituted lower alkyl, alkenyl, alkynyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, poly-alkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. One modification includes 2'-methoxyethoxy (2'-O—CH2CH2OCH3, also known as 2'-O-(2-methoxyethyl) or 2'-MOE) (Martin et al., Helv. Chim. Acta, 1995, 78, 486-504), i.e., an alkoxyalkoxy group. A further modification includes 2'-dimethylaminooxyethoxy, i.e., a O(CH2)20N (CH3)2 group, also known as 2'-DMAOE, and 2'-dimethylaminoethoxyethoxy (also known in the art as 2'-O-dimethyl-amino-ethoxy-ethyl or 2'-DMAEOE), i.e., 2'-O—(CH2)2-O—(CH2)2-N(CH3)2. Other modifications include 2'-methoxy (2'-O—CH3), 2'-aminopropoxy (2'-OCH2CH2CH2NH2), 2'-allyl (2'-CH2-CH—CH2), 2'-O-allyl (2'-O—CH2-CH—CH2) and 2'-fluoro (2'-F). The 2'-modification may be in the arabino (up) position or ribo (down) position. One 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Antisense compounds may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920; and, 6,147,200.

In one aspect of the present invention oligomeric compounds include nucleosides modified to induce a 3'-endo sugar conformation. A nucleoside can incorporate modifications of the heterocyclic base, the sugar moiety or both to induce a desired 3'-endo sugar conformation. These modified nucleosides are used to mimic RNA-like nucleosides so that particular properties of an oligomeric compound can be enhanced while maintaining the desirable 3'-endo conformational geometry.

In the present invention there is a preference for an RNA type duplex (A form helix, predominantly 3'-endo) as they are RnasH resistant. Properties that are enhanced by using more stable 3'-endo nucleosides include but are not limited to: modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage.

Nucleoside conformation is influenced by various factors including substitution at the 2', 3' or 4'-positions of the pentofuranosyl sugar. Electronegative substituents generally prefer the axial positions, while sterically demanding substituents generally prefer the equatorial positions (Principles of Nucleic Acid Structure, Wolfgang Sanger, 1984, Springer-Verlag.) Modification of the 2' position to favor the 3'-endo conformation can be achieved while maintaining the 2'-OH as a recognition element (Gallo et al., Tetrahedron (2001), 57, 5707-5713. Harry-O'kuru et al., J. Org. Chem., (1997), 62(6), 1754-1759 and Tang et al., J. Org. Chem. (1999), 64, 747-754.) Alternatively, preference for the 3'-endo conformation can be achieved by deletion of the 2'-OH as exemplified by 2' deoxy-2'F-nucleosides (Kawasaki et al., J. Med. Chem. (1993), 36, 831-841), which adopts the 3'-endo conformation positioning the electronegative fluorine atom in the axial position. Representative 2'-substituent groups amenable to the present invention that give A-form conformational properties (3'-endo) to the resultant duplexes include 2'-O-alkyl, 2'-O-substituted alkyl and 2'-fluoro substituent groups. Other suitable substituent groups are various alkyl and aryl ethers and thioethers, amines and monoalkyl and dialkyl substituted amines.

Other modifications of the ribose ring, for example substitution at the 4'-position to give 4'-F modified nucleosides (Guillerm et al., Bioorganic and Medicinal Chemistry Letters (1995), 5, 1455-1460 and Owen et al., J. Org. Chem. (1976), 41, 3010-3017), or for example modification to yield methanocarba nucleoside analogs (Jacobson et al., J. Med. Chem. Lett. (2000), 43, 2196-2203 and Lee et al., Bioorganic and Medicinal Chemistry Letters (2001), 11, 1333-1337) also induce preference for the 3'-endo conformation. Along similar lines, one or more nucleosides may be modified in such a way that conformation is locked into a C3'-endo type conformation, i.e. Locked Nucleic Acid (LNA, Singh et al, Chem. Commun. (1998), 4, 455-456), and ethylene bridged Nucleic Acids (ENA(TM), Morita et al, Bioorganic & Medicinal Chemistry Letters (2002), 12, 73-76.)

Preferred modification of the sugar are selected from the group consisting of 2'-O-methyl 2'-O-methoxyethyl, 2'-fluoro, 2'-dimethylaminooxyethoxy, 2'-dimethylaminoethoxyethoxy, 2'-guanidinium, 2'-O-guanidinium ethyl, 2'-carbamate, 2'-aminooxy, 2'-acetamido and locked nucleic acid. In one preferred embodiment, the sugar modification is 2'-O-methyl or 2'-O-methoxyethyl.

Oligomeric compounds can also include nucleobase (often referred to in the art as heterocyclic base or simply as "base") modifications or substitutions. As used herein, "unmodified" or "natural" nucleotides include the purine bases adenine (A) and guanine (G), and the pyrimidine bases thymine (T), cytosine (C) and uracil (U). A "substitution" is the replacement of an unmodified or natural base with another unmodified or natural base. "Modified" nucleotides mean other synthetic and natural nucleotides such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C[identical to]C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleotides include tricyclic pyrimidines such as phenoxazine cytidine(1H-pyrimido(5,4-b)(1,4)benzoxazin-2 (3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido (5,4-b)(1,4)benzoxazin-2(3H)-one), carbazole cytidine (2H-pyrimido(4,5-b)indol-2-one), pyridoindole cytidine (H-pyrido(3',2':4,5)pyrrolo[2,3-d]pyrimidin-2-one). Modified nucleotides may also include those in which the purine or pyrimidine base is replaced with other heterocycles, for example 7-deaza-adenine, 7-deazaguanosine, 2-aminopyridine and 2-pyridone. Further nucleotides include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleotides are known to those skilled in the art as suitable for increasing the binding affinity of the compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently suitable base substitutions, even more particularly when combined with 2'-O-methoxyethyl sugar modifications. It is understood in the art that modification of the base does not entail such chemical modifications as to produce substitutions in a nucleic acid sequence. Representative United States patents that teach the preparation of certain of the above noted modified nucleotides as well as other modified nucleotides include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; 5,681,941; and 5,750,692.

Oligomeric compounds of the present invention may also include polycyclic heterocyclic compounds in place of one or more of the naturally-occurring heterocyclic base moieties. A number of tricyclic heterocyclic compounds have been previously reported. These compounds are routinely used in antisense applications to increase the binding properties of the modified strand to a target strand. The most studied modifications are targeted to guanosines hence they have been termed G-clamps or cytidine analogs. Representative cytosine analogs that make 3 hydrogen bonds with a guanosine in a second strand include 1,3-diazaphenoxazine-2-one (Kurchavov, et al., Nucleosides and Nucleotides, 1997, 16, 1837-1846), 1,3-diazaphenothiazine-2-one, (Lin, K.-Y.; Jones, R. J.; Matteucci, M. J. Am. Chem. Soc. 1995, 117, 3873-3874) and 6,7,8,9-tetrafluoro-1,3-diazaphenoxazine-2-one (Wang, J.; Lin, K.-Y., Matteucci, M. Tetrahedron Lett. 1998, 39, 8385-8388). Incorporated into oligonucleotides these base modifications were shown to hybridize with complementary guanine and the latter was also shown to hybridize with adenine and to enhance helical thermal stability by extended stacking interactions (also see U.S. Pre-Grant Publications 20030207804 and 20030175906).

Further helix-stabilizing properties have been observed when a cytosine analog/substitute has an aminoethoxy moiety attached to the rigid 1,3-diazaphenoxazine-2-one scaffold (Lin, K.-Y.; Matteucci, M. J. Am. Chem. Soc. 1998, 120, 8531-8532). Binding studies demonstrated that a single incorporation could enhance the binding affinity of a model oligonucleotide to its complementary target DNA or RNA with a ΔTm of up to 18° C. relative to 5-methyl cytosine, which is a high affinity enhancement for a single modification. On the other hand, the gain in helical stability does not compromise the specificity of the oligonucleotides.

Further tricyclic heterocyclic compounds and methods of using them that are amenable to use in the present invention are disclosed in U.S. Pat. Nos. 6,028,183, and 6,007,992.

The enhanced binding affinity of the phenoxazine derivatives together with their uncompromised sequence specificity makes them valuable nucleobase analogs for the development of more potent antisense-based drugs. In fact, promising data have been derived from in vitro experiments demonstrating that heptanucleotides containing phenoxazine substitutions are capable to activate RNase H, enhance cellular uptake and exhibit an increased antisense activity (Lin, K-Y; Matteucci, M. J. Am. Chem. Soc. 1998, 120, 8531-8532). The activity enhancement was even more pronounced in case of G-clamp, as a single substitution was shown to significantly improve the in vitro potency of a 20 mer 2'-deoxyphosphorothioate oligonucleotides (Flanagan, W. M.; Wolf, J. J.; Olson, P.; Grant, D.; Lin, K.-Y.; Wagner, R. W.; Matteucci, M. Proc. Natl. Acad. Sci. USA, 1999, 96, 3513-3518).

Further modified polycyclic heterocyclic compounds useful as heterocyclic bases are disclosed in but not limited to, the above noted U.S. Pat. No. 3,687,808, as well as U.S. Pat. Nos. 4,845,205; 5,130,302; 5,134,066; 5,175,273; 5,367, 066; 5,432,272; 5,434,257; 5,457,187; 5,459,255; 5,484, 908; 5,502,177; 5,525,711; 5,552,540; 5,587,469; 5,594, 121, 5,596,091; 5,614,617; 5,645,985; 5,646,269; 5,750, 692; 5,830,653; 5,763,588; 6,005,096; and 5,681,941, and U.S. Pre-Grant Publication 20030158403.

The compounds described herein may include internucleoside linking groups that link the nucleosides or otherwise modified monomer units together thereby forming an antisense compound. The two main classes of internucleoside linking groups are defined by the presence or absence of a phosphorus atom. Representative phosphorus containing internucleoside linkages include, but are not limited to, phosphodiesters, phosphotriesters, methylphosphonates, phosphoramidate, and phosphorothioates. Representative non-phosphorus containing internucleoside linking groups include, but are not limited to, methylenemethylimino (—CH2-N(CH3)-O—CH2-), thiodiester (—O—C(O)—S—), thionocarbamate (—O—C(O)(NH)—S—); siloxane (—O—Si(H)2-O—); and N,N'-dimethylhydrazine (—CH2-N(CH3)-N(CH3)-). Modified internucleoside linkages, compared to natural phosphodiester linkages, can be used to alter, typically increase, nuclease resistance of the antisense compound.

Internucleoside linkages having a chiral atom may be prepared racemic, chiral, or as a mixture. Representative chiral internucleoside linkages include, but are not limited to, alkylphosphonates and phosphorothioates. Methods of preparation of phosphorous-containing and non-phosphorous-containing linkages are well known to those skilled in the art.

Suitable modified internucleoside linking groups are for example, phosphorothioates, chiral phosphorothioates, phosphorodithioates, phosphotriesters, aminoalkyl-phosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkyl-phosphonates, thionoalkylphosphotriesters, phosphonoacetate and thiophosphonoacetate (see Sheehan et al., Nucleic Acids Research, 2003, 31(14), 4109-4118 and Dellinger et al., J. Am. Chem. Soc., 2003, 125, 940-950), selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity comprise a single 3' to 3' linkage at the 3'-most internucleotide linkage, i.e., a single inverted nucleoside residue which may be abasic (the nucleobase is missing or has a hydroxyl group in place thereof). Various salts, mixed salts and free acid forms are also included.

N3'-P5'-phosphoramidates have been reported to exhibit both a high affinity towards a complementary RNA strand and nuclease resistance (Gryaznov et al., J. Am. Chem. Soc., 1994, 116, 3143-3144). N3'-P5'-phosphoramidates have been studied with some success in vivo to specifically down regulate the expression of the c-myc gene (Skorski et al., Proc. Natl. Acad. Sci., 1997, 94, 3966-3971; and Faira et al., Nat. Biotechnol., 2001, 19, 40-44).

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050.

In some embodiments of the invention, oligomeric compounds may have one or more phosphorothioate and/or heteroatom internucleoside linkages, in particular —CH2-NH—O—CH2-, —CH2-N(CH3)-O—CH2- (known as a methylene (methylimino) or MMI backbone), —CH2-O—N(CH3)-CH2-, —CH2-N(CH3)-N(CH3)-CH2- and —O—N(CH3)-CH2-CH2- (wherein the native phosphodiester internucleotide linkage is represented as —O—P(—O)(OH)—O—CH2-). The MMI type internucleoside linkages are disclosed in the above referenced U.S. Pat. No. 5,489,677. Amide internucleoside linkages are disclosed in the above referenced U.S. Pat. No. 5,602,240.

Some oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH2 component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439.

In some embodiments of the invention, the backbone of the antisense oligomeric compound is selected from the group consisting of phosphodiester ODN, phosphoramidate, phosphorothioate, Locked nucleic acids, 2'O methoxyethyl, 2'-deoxy-2'-fluoro-D-arabinose, S-constrained-ethyl, Tricyclo DNA, Morpholino, Vivo-morpholino, Peptide nucleic acids, Unlocked Nucleic Acid, 2'-O,4'-C-ethylene-bridged nucleic acids, 2',4'-bridged nucleic acid, multi-targeting oligonucleotides, 2'-Deoxy-2',4'-difluorouridine, 2'-deoxy-2'-fluoroarabinonucleic acid, 2'-O,4'-C-spirocyclopropylene bridged nucleic acid, amido-bridged nucleic acid, gamma-CF2-aminopropylglycine PNA, constrained altritol nucleic acids, Mixed backbone antisense glucosylceramide synthase oligonucleotide, 3'-fluoro hexitol nucleic acid, positively charged phosphorodiamidate morpholino oligomers, trans-4-hydroxy-L-proline phosphono peptide nucleic acid, constrained methoxyethyl.

Optionally of the invention and/or embodiments thereof the internucleoside linkage is phosphorothioate, or phosphorodiamidate It is further intended that multiple modifications can be made to one or more of the oligomeric compounds of the invention at multiple sites of one or more monomeric subunits (nucleosides are suitable) and/or internucleoside linkages to enhance properties such as but not limited to activity in a selected application.

The synthesis of numerous of the modified nucleosides amenable to the present invention are known in the art (see for example, Chemistry of Nucleosides and Nucleotides Vol 1-3, ed. Leroy B. Townsend, 1988, Plenum press). The conformation of modified nucleosides and their oligomers can be estimated by various methods routine to those skilled in the art such as molecular dynamics calculations, nuclear magnetic resonance spectroscopy and CD measurements.

Optionally of the invention and/or embodiments thereof, the oligomeric compounds of the present invention are morpholino phosphorothioates, or phosphorodiamidate morpholino.

Another group of oligomeric compounds includes oligonucleotide mimetics. As used herein the term "mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target. Representative examples of a sugar mimetic include, but are not limited to, cyclohexenyl or morpholino. Representative examples of a mimetic for a sugar-internucleoside linkage combination include, but are not limited to, peptide nucleic acids (PNA) and morpholino groups linked by uncharged achiral linkages. In some instances a mimetic is used in place of the nucleobase. Representative nucleobase mimetics are well known in the art and include, but are not limited to, tricyclic phenoxazine analogs and universal bases (Berger et al., Nuc Acid Res. 2000, 28:2911-14, incorporated herein by reference). Methods of synthesis of sugar, nucleoside and nucleobase mimetics are well known to those skilled in the art. The heterocyclic base moiety or a modified heterocyclic base moiety is Optionally maintained for hybridization with an appropriate target nucleic acid.

The compounds described herein may contain one or more asymmetric centers and thus give rise to enantiomers, diastereomers, and other stereoisomeric configurations that may be defined, in terms of absolute stereochemistry, as (R) or (S), [alpha] or [beta], or as (D) or (L) such as for amino acids et al. The present disclosure is meant to include all such possible isomers, as well as their racemic and optically pure forms.

One such oligomeric compound, an oligonucleotide mimetic that has been shown to have excellent hybridization properties, is referred to as a peptide nucleic acid (PNA) (Nielsen et al., Science, 1991, 254, 1497-1500). PNAs have favorable hybridization properties, high biological stability and are electrostatically neutral molecules. PNA compounds have been used to correct aberrant splicing in a transgenic mouse model (Sazani et al., Nat. Biotechnol., 2002, 20, 1228-1233). In PNA oligomeric compounds, the sugar-backbone of an oligonucleotide is replaced with an amide containing backbone, in particular an aminoethylglycine backbone. The nucleotides are bound directly or indirectly to aza nitrogen atoms of the amide portion of the backbone. Representative United States patents that teach the preparation of PNA oligomeric compounds include, but are not limited to, U.S. Pat. Nos. 5,539,082; 5,714,331; and 5,719, 262. PNA compounds can be obtained commercially from Applied Biosystems (Foster City, Calif., USA). Numerous modifications to the basic PNA backbone are known in the art; particularly useful are PNA compounds with one or more amino acids conjugated to one or both termini. For example, 1-8 lysine or arginine residues are useful when conjugated to the end of a PNA molecule. A polyarginine tail may be a suitable for enhancing cell penetration.

Another class of oligonucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups have been selected to give a non-ionic oligomeric compound. Morpholino-based oligomeric compounds are non-ionic mimetics of oligo-nucleotides which are less likely to form undesired interactions with cellular proteins (Dwaine A. Braasch and David R. Corey, Biochemistry, 2002, 41(14), 4503-4510). Morpholino-based oligomeric compounds have been studied in zebrafish embryos (see: Genesis, volume 30, issue 3, 2001 and Heasman, J., Dev. Biol., 2002, 243, 209-214). Further studies of morpholino-based oligomeric compounds have also been reported (Nasevicius et al., Nat. Genet., 2000, 26, 216-220; and Lacerra et al., Proc. Natl. Acad. Sci., 2000, 97, 9591-9596). Morpholino-based oligomeric compounds are disclosed in U.S. Pat. No. 5,034,506. The morpholino class of oligomeric compounds have been prepared having a variety of different linking groups joining the monomeric subunits. Linking groups can be varied from chiral to achiral, and from charged to neutral. U.S. Pat. No. 5,166,315 discloses linkages including —O—P(—O)(N(CH3)2)-O—; U.S. Pat. No. 5,034,506 discloses achiral intermorpholino linkages; and U.S. Pat. No. 5,185,444 discloses phosphorus containing chiral intermorpholino linkages.

A further class of oligonucleotide mimetic is referred to as cyclohexene nucleic acids (CeNA). In CeNA oligonucleotides, the furanose ring normally present in a DNA or RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (Wang et al., J. Am. Chem. Soc., 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation. Furthermore the incorporation of CeNA into a sequence targeting RNA was stable to serum and able to activate E. coli RNase H resulting in cleavage of the target RNA strand.

A further modification includes bicyclic sugar moieties such as "Locked Nucleic Acids" (LNAs) in which the 2'-hydroxyl group of the ribosyl sugar ring is linked to the 4' carbon atom of the sugar ring thereby forming a 2'-C,4'-C-oxymethylene linkage to form the bicyclic sugar moiety (reviewed in Elayadi et al., Curr. Opinion Invens. Drugs, 2001, 2, 558-561; Braasch et al., Chem. Biol., 2001, 8 1-7; and Orum et al., Curr. Opinion Mol. Ther., 2001, 3, 239-243; see also U.S. Pat. Nos. 6,268,490 and 6,670,461). The linkage can be a methylene (—CH2-) group bridging the 2' oxygen atom and the 4' carbon atom, for which the term LNA is used for the bicyclic moiety; in the case of an ethylene group in this position, the term ENA(TM) is used (Singh et al., Chem. Commun., 1998, 4, 455-456; ENA (TM): Morita et al., Bioorganic Medicinal Chemistry, 2003, 11, 2211-2226). LNA and other bicyclic sugar analogs display very high duplex thermal stabilities with complementary DNA and RNA (Tm=+3 to +10[deg.] C.), stability towards 3'-exonucleolytic degradation and good solubility properties. LNAs are commercially available from ProLigo (Paris, France and Boulder, Colo., USA).

An isomer of LNA that has also been studied is alpha-L-LNA which has been shown to have superior stability against a 3'-exonuclease. The alpha-L-LNAs were incorporated into antisense gapmers and chimeras that showed potent antisense activity (Frieden et al., Nucleic Acids Research, 2003, 21, 6365-6372).

Another similar bicyclic sugar moiety that has been prepared and studied has the bridge going from the 3'-hydroxyl group via a single methylene group to the 4' carbon atom of the sugar ring thereby forming a 3'-C,4'-C-oxymethylene linkage (see U.S. Pat. No. 6,043,060).

LNA has been shown to form exceedingly stable LNA: LNA duplexes (Koshkin et al., J. Am. Chem. Soc., 1998, 120, 13252-13253). LNA:LNA hybridization was shown to be the most thermally stable nucleic acid type duplex system, and the RNA-mimicking character of LNA was established at the duplex level. Introduction of 3 LNA monomers (T or A) significantly increased melting points (Tm=+15/+11[deg.] C.) toward DNA complements. The universality of LNA-mediated hybridization has been stressed by the formation of exceedingly stable LNA:LNA duplexes. The RNA-mimicking of LNA was reflected with regard to the N-type conformational restriction of the monomers and to the secondary structure of the LNA:RNA duplex.

LNAs also form duplexes with complementary DNA, RNA or LNA with high thermal affinities. Circular dichroism (CD) spectra show that duplexes involving fully modified LNA (esp. LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watson-Crick base pairing rules with generally improved selectivity compared to the corresponding unmodified reference strands. DNA-LNA chimeras have been shown to efficiently inhibit gene expression when targeted to a variety of regions (5'-untranslated region, region of the start codon or coding region) within the luciferase mRNA (Braasch et al., Nucleic Acids Research, 2002, 30, 5160-5167).

Potent and nontoxic antisense oligonucleotides containing LNAs have been described (Wahlestedt et al., Proc. Natl. Acad. Sc U.S.A., 2000, 97, 5633-5638). The authors have demonstrated that LNAs confer several desired properties. LNA/DNA copolymers were not degraded readily in blood serum and cell extracts. LNA/DNA copolymers exhibited potent antisense activity in assay systems as disparate as G-protein-coupled receptor signaling in living rat brain and detection of reporter genes in *Escherichia coli*. Lipofectin-mediated efficient delivery of LNA into living human breast cancer cells has also been accomplished. Further successful in vivo studies involving LNA's have shown knock-down of the rat delta opioid receptor without toxicity (Wahlestedt et al., Proc. Natl. Acad. Sci., 2000, 97, 5633-5638) and in another study showed a blockage of the translation of the large subunit of RNA polymerase II (Fluiter et al., Nucleic Acids Res., 2003, 31, 953-962).

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

Analogs of LNA, phosphorothioate-LNA and 2'-thio-LNAs, have also been prepared (Kumar et al., Bioorg. Med. Chem. Lett., 1998, 8, 2219-2222). Preparation of locked nucleoside analogs containing oligodeoxyribonucleotide duplexes as substrates for nucleic acid polymerases has also been described (Wengel et al., WO 99/14226). Furthermore, synthesis of 2'-amino-LNA, a novel conformationally restricted high-affinity oligonucleotide analog has been described in the art (Singh et al., J. Org. Chem., 1998, 63, 10035-10039). In addition, 2'-Amino- and 2'-methylamino-LNA's have been prepared and the thermal stability of their duplexes with complementary RNA and DNA strands has been previously reported.

Another oligonucleotide mimetic that has been prepared and studied is threose nucleic acid. This oligonucleotide mimetic is based on threose nucleosides instead of ribose nucleosides. Initial interest in (3',2')-alpha-L-threose nucleic acid (TNA) was directed to the question of whether a DNA polymerase existed that would copy the TNA. It was found that certain DNA polymerases are able to copy limited stretches of a TNA template (reported in Chemical and Engineering News, 2003, 81, 9). In another study it was determined that TNA is capable of antiparallel Watson-Crick base pairing with complementary DNA, RNA and TNA oligonucleotides (Chaput et al., J. Am. Chem. Soc., 2003, 125, 856-857).

In one study (3',2')-alpha-L-threose nucleic acid was prepared and compared to the 2' and 3' amidate analogs (Wu et al., Organic Letters, 2002, 4(8), 1279-1282). The amidate analogs were shown to bind to RNA and DNA with comparable strength to that of RNA/DNA.

Further oligonucleotide mimetics have been prepared to include bicyclic and tricyclic nucleoside analogs (see Steffens et al., Helv. Chim. Acta, 1997, 80, 2426-2439; Steffens et al., J. Am. Chem. Soc., 1999, 121, 3249-3255; Renneberg et al., J. Am. Chem. Soc., 2002, 124, 5993-6002; and Renneberg et al., Nucleic acids res., 2002, 30, 2751-2757). These modified nucleoside analogs have been oligomerized using the phosphoramidite approach and the resulting oligomeric compounds containing tricyclic nucleoside analogs have shown increased thermal stabilities (Tm's) when hybridized to DNA, RNA and itself. Oligomeric compounds containing bicyclic nucleoside analogs have shown thermal stabilities approaching that of DNA duplexes.

Another class of oligonucleotide mimetic is referred to as phosphonomonoester nucleic acids which incorporate a phosphorus group in the backbone. This class of oligonucleotide mimetic is reported to have useful physical and biological and pharmacological properties in the areas of inhibiting gene expression (antisense oligonucleotides, sense oligonucleotides and triplex-forming oligonucleotides), as probes for the detection of nucleic acids and as auxiliaries for use in molecular biology. Further oligonucleotide mimetics amenable to the present invention have been prepared wherein a cyclobutyl ring replaces the naturally occurring furanosyl ring.

Another modification of the oligomeric compounds of the invention involves chemically linking to the oligomeric compound one or more moieties or conjugates which enhance the properties of the oligomeric compound, such as to enhance the activity, cellular distribution or cellular uptake of the oligomeric compound. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention.

Representative conjugate groups are disclosed in International Patent Application PCT/US92/09196, filed Oct. 23, 1992, and U.S. Pat. Nos. 6,287,860 and 6,762,169.

Conjugate moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethyl-ammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Oligomeric compounds of the invention may also be conjugated to drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. Pat. No. 6,656,730.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Oligomeric compounds can also be modified to have one or more stabilizing groups that are generally attached to one or both termini of an oligomeric compound to enhance properties such as for example nuclease stability. Included in stabilizing groups are cap structures. By "cap structure or terminal cap moiety" is meant chemical modifications, which have been incorporated at either terminus of oligonucleotides (see for example Wincott et al., WO 97/26270). These terminal modifications protect the oligomeric compounds having terminal nucleic acid molecules from exonuclease degradation, and can improve delivery and/or localization within a cell. The cap can be present at either the 5'-terminus (5'-cap) or at the 3'-terminus (3'-cap) or can be present on both termini of a single strand, or one or more termini of both strands of a double-stranded compound. This cap structure is not to be confused with the inverted methylguanosine "5' cap" present at the 5' end of native mRNA molecules. In non-limiting examples, the 5'-cap includes inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Wincott et al., International PCT publication No. WO 97/26270).

Particularly suitable 3'-cap structures include, for example 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Tyer, 1993, Tetrahedron 49, 1925).

Further 3' and 5'-stabilizing groups that can be used to cap one or both ends of an oligomeric compound to impart nuclease stability include those disclosed in WO 03/004602 published on Jan. 16, 2003.

In certain embodiments, oligomeric compounds, may be conjugated with a wide variety of different positively charged polymers. Examples of positively charged polymers include peptides, such as argine rich peptides (Examples of positively charged peptides that may be used in the practice of the invention include R9F2C; (RXR)4 XB (where X can be any amino acid); R5F2R4c; (RFF)3; Tat proteins, such as TAT sequence CYGRKKRRQRRR; and (RFF)3R), cationic polymers, such as dendrimeric octaguanindine polymer, and other positively charged molecules as known in the art for conjugation to antisense oligonucleotide compounds. In one embodiment of the invention and/or embodiments thereof, the antisense oligonucleotides are conjugated with positively charged polymer comprising a polymer having a molecular weight that is from about 1,000 to 20,000 Daltons, and Optionally from about 5,000 to 10,000 Daltons. Another example of positively charged polymers is polyethylenimine (PEI) with multiple positively charged amine groups in its branched or unbranched chains. PEI has else been widely used as gene and oligomer delivery vesicle.

Optionally of the invention and/or embodiments thereof the oligomeric compounds are modified with cell penetrating sequences.

Suitable cell penetrating sequences include cell penetrating peptides, such as TAT peptide, MPG, Pep-1, MAP, fusogenic, antimicrobial peptides (AMPS), bacteriocidal peptides, fungicidal peptides, virucidal peptides, Cell-penetrating peptides (CPPs) are short peptides that facilitate cellular uptake of the particles of the invention. The particle of the invention is associated with the CPP peptides either through chemical linkage via covalent bonds or through non-covalent interactions. The function of the CPPs are to deliver the particles into cells, a process that commonly occurs through endocytosis with the cargo delivered to the endosomes of living mammalian cells. CPPs typically have an amino acid composition that either contains a high relative abundance of positively charged amino acids such as lysine or arginine or has sequences that contain an alternating pattern of polar/charged amino acids and non-polar, hydrophobic amino acids. These two types of structures are referred to as polycationic or amphipathic, respectively. A third class of CPPs are the hydrophobic peptides, containing only a polar residues, with low net charge or have hydrophobic amino acid groups that are crucial for cellular uptake.

An exemplary cell penetrating peptide is the trans-activating transcriptional activator (Tat) from Human Immunodeficiency Virus 1 (HIV-1) could be efficiently taken up from the surrounding media by numerous cell types in culture. Other cell penetrating peptides are MPG, Pep-1, transportan, penetratin, CADY, TP, TP10, arginine octamer. polyarginine sequences, Arg8, VP22 HSV-1 structural protein, SAP Proline-rich motifs, Vectocell® peptides, hCT (9-32), SynB, Pvec, and PPTG1. Cell penetrating peptides may be cationic, essentially containing clusters of polyarginine in their primary sequence or amphipathic. CPPs are generally peptides of less than 30 amino acids, derived from natural or unnatural protein or chimeric sequences.

Optionally the oligomeric compounds are derivatised with conjugates selected from the group consisting of Pip6a, PEG12, (R/W)9, H5WYG, GalNAc or GN3, M12, PEI-LA, RGD, endosomolytic peptide, peptide, Pep-3, CADY, C6, MPEG-PCL-CH2R$_4$H2C, (RXR)4XB, R9F2, TAT, (KFF) 3K, (RFF)3RXB, (RFF)3R, F-3, Pip2a, B-peptide, B-MSP, Pip5e, PKKKRKV, Penetratin, Lys4, SPACE, Tat-DRBD, (RXR)4, (RxR)3RXB, (KFF)3K, T-cell-derived CPP, PEG-Pep-3, MPG-8, MPG-8-Chol, PepFect6, P5RHH, R15, Chol-R9.

Optionally the oligomeric compounds, enzyme, and/or nucleic acid encoding for the enzyme are incorporated or otherwise associated with nanoparticles. Nanoparticles may optionally be modified for targeting specific cells and optimised for penetrating cells. A skilled person is aware of methods to employ nanoparticles for oligomeric compounds delivery to cells.

Suitable particle are gold particles, silver particle.

Optionally the nanoparticles are made from material selected from the group consisting of gelatine, hydrophilic gelatine, Arg-Gly-Asp-Polyethylenglycol-stearic acid-chitosan, mesoporous silica.

Optionally the nanoparticles are made from protein selected from the group consisting of Hematoporphyrin-Bovine serum albumin, Heat-liable enterotoxin subunit B-Bovine serum albumin, Apotransferin-Bovine serum albumin, Apotransferrin-Lactoferrin, Chitosan-retinoic acid-Albumin, 30Kc19-human-serum-albumin.

Optionally the nanoparticles are made from a polymer selected from the group consisting of Poly(lactic-co-glyoclic acid), Poly(lactic-co-glyoclic acid)-Chitosan, Poly(lactic-co-glyoclic acid)-eudragit, Poly (lactic acid)-F127-Poly (lactic acid), Polycaprolactone-eudragit RS, Polyacrylic acid, Thiolated Polyacrylic acid, Chitosan, Chitosan-Hydroxy propyl Methyl cellulose Phthalate, Chitosan-PGA-DTPA, Trimethyl chitosan-cysteine conjugate, Lauryl-succinyl-Chitosan, Dextran-poloxamer-Chitosan-albumin, Dextran sulfate-Chitosan, Cholic acid modified dextran sulfate, Alginate-dextran sulfate-Chitosan-albumin, Alginate, Thiolated-Eudragit, Poly-N-isopropylacrylamide, Poly(lactic-co-glyoclic acid), Polyethylenglycol-dithiodipropionate-hyaluronic acid, polycaprolactone, Galactose-Chitosan, O-carboxymethyl-chitosan-Galactose, hyaluronic acid-Galactose, Galactosylated-chitosan-polycaprolactone, Galactosylated-chitosan, poly(alkylene oxide)-poly(propylacrylic acid), Poly (lactic acid), (poly(ethylene imine)), Poly(lactic-co-glyoclic acid).

Optionally the oligomeric compounds, enzyme, and/or nucleic acid encoding for the enzyme are incorporated or otherwise associated with extracellular vesicles (EV). Extracellular vesicles (EVs) are small vesicles, which are secreted by prokaryotic and eukaryotic cells One may distinguish between three classes of EVs, namely apoptotic bodies (ABs), microvesicles (MVs) and exosomes. Exosomes or extracellular vesicles are derived from cells. The cells may any kind of cell that is capable of producing exosomes. The cells may be patient derived or from donors, cells in culture or heterologous systems from animals or plants. Preferably the exosomes or extracellular vesicles are derived from the human cells. Several approaches may be used for the loading of exosomal or extracellular vesical carriers with therapeutic cargo (A) loading naïve exosomes or extracellular vesicles isolated from parental cells ex vitro;

(B) loading parental cells with enzyme, nucleic acid encoding the enzyme and/or antisense oligomeric compound, which is then released in exosomes or extracellular vesicles; and finally, (C) transfecting/infecting parental cells with DNA encoding enzyme, and/or antisense oligomeric compound, which are then released in exosomes or extracellular vesicles. Exosomes possess an intrinsic ability to cross biological barriers, including the most difficult to penetrate: the blood brain barrier (BBB).

Optionally the exosomes or extracellular vesicles comprise the enzyme or GAA. Optionally the exosomes or extracellular vesicles comprise the mRNA for the enzyme or GAA. Optionally the exosomes or extracellular vesicles comprise the antisense oligomeric compound. Optionally the exosomes or extracellular vesicles comprise a DNA construct encoding for the antisense oligomeric compound.

Optionally the oligomeric compounds, enzyme, and/or nucleic acid encoding for the enzyme are incorporated or otherwise associated with micelles.

Optionally the oligomeric compounds, enzyme, and/or nucleic acid encoding for the enzyme are incorporated or otherwise associated with liposomes.

Optionally the oligomeric compounds, enzyme, and/or nucleic acid encoding for the enzyme are incorporated or otherwise associated with microparticles.

Optionally, the oligomeric compounds are modified with an endosomal escape agent moiety. The endocytic pathway is a major uptake mechanism of cells. Compounds taken up by the endocytic pathway become entrapped in endosomes and may be degraded by specific enzymes in the lysosome. This may be desired or not desired depending on the purpose. If taken up by the endosomes is not desired, endosomal escape agent may be used. Suitable endosomal escape agents may be chloroquine, TAT peptide.

It is not necessary for all positions in a given oligomeric compound to be uniformly modified, and in fact more than one of the aforementioned modifications may be incorporated in a single compound or even within a single nucleoside within an oligomeric compound.

The present invention also includes oligomeric compounds which are chimeric compounds. "Chimeric" oligomeric compounds or "chimeras," in the context of this invention, are single- or double-stranded oligomeric compounds, such as oligonucleotides, which contain two or more chemically distinct regions, each comprising at least one monomer unit, i.e., a nucleotide in the case of an oligonucleotide compound. Chimeric antisense oligonucleotides are one form of oligomeric compound. These oligonucleotides typically contain at least one region which is modified so as to confer upon the oligonucleotide increased resistance to nuclease degradation, increased cellular uptake, alteration of charge, increased stability and/or increased binding affinity for the target nucleic acid.

Chimeric oligomeric compounds of the invention can be formed as composite structures of two or more oligonucleotides, modified oligonucleotides, oligonucleosides, oligonucleotide mimetics, or regions or portions thereof. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922.

Oligomerization of modified and unmodified nucleosides can be routinely performed according to literature procedures for DNA (Protocols for Oligonucleotides and Analogs, Ed. Agrawal (1993), Humana Press) and/or RNA (Scaringe, Methods (2001), 23, 206-217. Gait et al., Applications of Chemically synthesized RNA in RNA: Protein Interactions, Ed. Smith (1998), 1-36. Gallo et al., Tetrahedron (2001), 57, 5707-5713).

Oligomeric compounds of the present invention can be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The following precursor compounds, including amidites and their intermediates can be prepared by methods routine to those skilled in the art; 5'-O-Dimethoxytrityl-thymidine intermediate for 5-methyl dC amidite, 5'-O-Dimethoxytrityl-2'-deoxy-5-methylcytidine intermediate for 5-methyl-dC amidite, 5'-O-Dimethoxytityl-2'-deoxy-N4-benzoyl-5-methylcytidine penultimate intermediate for 5-methyl dC amidite, (5'-O-(4,4'-Dimethoxytriphenylmethyl)-2'-deoxy-N4-benzoyl-5-methylcytidin-3'-O-yl)-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, (5'-O-(4,4'-Dimethoxytriphenylmethyl)-2'-O-(2-methoxyethyl)-5-methyluridin-3'-O-yl)-2-cyanoethyl-N,N-diisopropylphosphoramidite (MOE T amidite), 5'-O-Dimethoxytrityl-2'-O-(2-methoxyethyl)-5-methylcytidine intermediate, 5'-O-dimethoxytrityl-2'-O-(2-methoxyethyl)-N<4>-benzoyl-5-methyl-cytidine penultimate intermediate, (5'-O-(4,4'-Dimethoxytriphenylmethyl)-2'-O-(2-methoxyethyl)-N<4>-benzoyl-5-methylcytidin-3'-O-yl)-2-cyanoethyl-N,N-diisopropylphosphoramidite (MOE 5-Me-C amidite), (5'-O-(4,4'-Dimethoxytriphenylmethyl)-2'-O-(2-methoxyethyl)-N<6>-benzoyladenosin-3'-O-yl)-2-cyanoethyl-N,N-diisopropylphosphoramidite (MOE A amdite), (5'-0-(4,4'-Dimethoxytriphenylmethyl)-2'-O-(2-methoxyethyl)-N<4>-isobutyrylguanosin-3'-O-yl)-2-cyanoethyl-N,N-diisopropylphosphoramidite (MOE G amidite), 2'-O-(Aminooxyethyl) nucleoside amidites and 2'-O-(dimethylaminooxyethyl) nucleoside amidites, 2'-(Dimethylaminooxyethoxy) nucleoside amidites, 5'-O-tert-Butyldiphenylsilyl-0<2>-2'-anhydro-5-methyluridine, 5'-O-tert-Butyldiphenylsilyl-2'-O-(2-hydroxyethyl)-5-methyluridine, 2'-O-((2-phthalimidoxy)ethyl)-5'-t-butyldiphenylsilyl-5-methyluridine, 5'-O-tert-butyldiphenylsilyl-2'-O-((2-formadoximinooxy)ethyl)-5-methyluridine, 5'-O-tert-Butyldiphenylsilyl-2'-O—(N,N dimethylaminooxyethyl)-5-methyluridine, 2'-O-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-((2-cyanoethyl)-N,N-diisopropylphosphoramidite), 2'-(Aminooxyethoxy) nucleoside amidites, N2-isobutyryl-6-O-diphenylcarbamoyl-2'-O-(2-ethylacetyl)-5'-O-(4,4'-dimethoxytrityl)guanosine-3'-((2-cyanoethyl)-N,N-diisopropylphosphoramidite), 2'-dimethylaminoethoxyethoxy (2'-DMAEOE) nucleoside amidites, 2'-O-(2(2-N,N-dimethylaminoethoxy)ethyl)-5-methyl uridine, 5'-O-dimethoxytrityl-2'-O-(2(2-N,N-dimethylaminoethoxy)-ethyl))-5-methyl uridine and 5'-O-Dimethoxytrityl-2'-O-(2(2-N,N-dimethylaminoethoxy)-ethyl))-5-methyl uridine-3'-O-(cyanoethyl-N,N-diisopropyl)phosphoramidite.

The preparation of such precursor compounds for oligonucleotide synthesis are routine in the art and disclosed in U.S. Pat. No. 6,426,220 and published PCT WO 02/36743.

2'-Deoxy and 2'-methoxy beta-cyanoethyldiisopropyl phosphoramidites can be purchased from commercial sources (e.g. Chemgenes, Needham, Mass. or Glen Research, Inc. Sterling, Va.). Other 2'-O-alkoxy substituted nucleoside amidites can be prepared as described in U.S. Pat. No. 5,506,351.

Oligonucleotides containing 5-methyl-2'-deoxycytidine (5-Me-C) nucleotides can be synthesized routinely according to published methods (Sanghvi, et. al., Nucleic Acids Research, 1993, 21, 3197-3203) using commercially available phosphoramidites (Glen Research, Sterling Va. or ChemGenes, Needham, Mass.).

2'-fluoro oligonucleotides can be synthesized routinely as described (Kawasaki, et. al., J. Med. Chem., 1993, 36, 831-841) and U.S. Pat. No. 5,670,633.

2'-O-Methoxyethyl-substituted nucleoside amidites can be prepared routinely as per the methods of Martin, P., Helvetica Chimica Acta, 1995, 78, 486-504.

Aminooxyethyl and dimethylaminooxyethyl amidites can be prepared routinely as per the methods of U.S. Pat. No. 6,127,533.

Phosphorothioate-containing oligonucleotides (P—S) can be synthesized by methods routine to those skilled in the art (see, for example, Protocols for Oligonucleotides and Analogs, Ed. Agrawal (1993), Humana Press). Phosphinate oligonucleotides can be prepared as described in U.S. Pat. No. 5,508,270.

Alkyl phosphonate oligonucleotides can be prepared as described in U.S. Pat. No. 4,469,863.

3'-Deoxy-3'-methylene phosphonate oligonucleotides can be prepared as described in U.S. Pat. No. 5,610,289 or 5,625,050.

Phosphoramidite oligonucleotides can be prepared as described in U.S. Pat. No. 5,256,775 or 5,366,878.

Alkylphosphonothioate oligonucleotides can be prepared as described in published PCT applications PCT/US94/00902 and PCT/US93/06976 (published as WO 94/17093 and WO 94/02499, respectively).

3'-Deoxy-3'-amino phosphoramidate oligonucleotides can be prepared as described in U.S. Pat. No. 5,476,925.

Phosphotriester oligonucleotides can be prepared as described in U.S. Pat. No. 5,023,243.

Borano phosphate oligonucleotides can be prepared as described in U.S. Pat. Nos. 5,130,302 and 5,177,198.

4'-thio-containing oligonucleotides can be synthesized as described in U.S. Pat. No. 5,639,873.

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P—O or P—S linkages can be prepared as described in U.S. Pat. Nos. 5,378,825, 5,386,023, 5,489,677, 5,602,240 and 5,610,289.

Formacetal and thioformacetal linked oligonucleosides can be prepared as described in U.S. Pat. Nos. 5,264,562 and 5,264,564.

Ethylene oxide linked oligonucleosides can be prepared as described in U.S. Pat. No. 5,223,618.

Peptide nucleic acids (PNAs) can be prepared in accordance with any of the various procedures referred to in Peptide Nucleic Acids (PNA): Synthesis, Properties and Potential Applications, Bioorganic & Medicinal Chemistry, 1996, 4, 5-23. They may also be prepared in accordance with U.S. Pat. Nos. 5,539,082, 5,700,922, 5,719,262, 6,559,279 and 6,762,281.

Oligomeric compounds incorporating at least one 2'-O-protected nucleoside by methods routine in the art. After incorporation and appropriate deprotection the 2'-O-protected nucleoside will be converted to a ribonucleoside at the position of incorporation. The number and position of the 2-ribonucleoside units in the final oligomeric compound may vary from one at any site or the strategy can be used to prepare up to a full 2'-OH modified oligomeric compound.

The main RNA synthesis strategies that are presently being used commercially include 5'-[beta]-DMT-2'-O-t-butyldimethylsilyl (TBDMS), 5'-O-DMT-2'-[1(2-fluorophenyl)-4-methoxypiperidin-4-yl] (FPMP), 2'-O-[(triisopropylsilyl)oxy]methyl (2'-O—CH2-O—Si(iPr)3 (TOM), and the 5'-O-silyl ether-2'-ACE (5'-O-bis(trimethylsiloxy)cyclododecyloxysilyl ether (DOD)-2'-O-bis(2-acetoxyethoxy) methyl (ACE). Some companies currently offering RNA products include Pierce Nucleic Acid Technologies (Milwaukee, Wis.), Dharmacon Research Inc. (a subsidiary of Fisher Scientific, Lafayette, Colo.), and Integrated DNA Technologies, Inc. (Coralville, Iowa). One company, Princeton Separations, markets an RNA synthesis activator advertised to reduce coupling times especially with TOM and TBDMS chemistries. Such an activator would also be amenable to the oligomeric compounds of the present invention.

All of the aforementioned RNA synthesis strategies are amenable to the oligomeric compounds of the present invention. Strategies that would be a hybrid of the above e.g. using a 5'-protecting group from one strategy with a 2'-O-protecting from another strategy is also contemplated herein.

Chimeric oligonucleotides, chimeric oligonucleosides and mixed chimeric oligonucleotides/oligonucleosides can be synthesized according to U.S. Pat. No. 5,623,065.

Chimeric oligomeric compounds exhibiting enhanced cellular uptake and greater pharmacologic activity may be made in accordance to U.S. Pat. No. 8,501,703.

Another form of oligomeric compounds comprise tricyclo-DNA (tc-DNA) antisense oligonucleotides. Tricyclo-DNA nucleotides are nucleotides modified by the introduction of a cyclopropane ring to restrict conformational flexibility of the backbone and to optimize the backbone geometry of the torsion angle γ. Homobasic adenine- and thymine-containing tc-DNAs form extraordinarily stable A-T base pairs with complementary RNAs. Antisense oligomeric compound that contains between 6-22 tricyclo nucleotides in length, in particular between 8-20 tricyclo nucleotides, more particularly between 10 and 18 or between 11 and 18 tricyclo nucleotides are suitable. See e.g. WO2010115993 for examples of tricyclo-DNA (tc-DNA) antisense oligonucleotides.

Oligomerization of modified and unmodified nucleosides can be routinely performed according to literature procedures for DNA (Protocols for Oligonucleotides and Analogs, Ed. Agrawal (1993), Humana Press) and/or RNA (Scaringe, Methods (2001), 23, 206-217. Gait et al., Applications of Chemically synthesized RNA in RNA: Protein Interactions, Ed. Smith (1998), 1-36. Gallo et al., Tetrahedron (2001), 57, 5707-5713).

Antisense compounds can be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives. The disclosure is not limited by the method of antisense compound synthesis.

Methods of oligonucleotide purification and analysis are known to those skilled in the art. Analysis methods include capillary electrophoresis (CE) and electrospray-mass spectroscopy. Such synthesis and analysis methods can be performed in multi-well plates. The methods described herein are not limited by the method of oligomer purification.

Optionally of the invention and/or embodiments thereof, the antisense compounds provided herein are resistant to RNase H degradation.

In one embodiment of the invention and/or embodiments thereof, the antisense compounds comprise at least one modified nucleotide. In another embodiment, the antisense compounds comprise a modified nucleotide at each position. In yet another embodiment, the antisense compounds are uniformly modified at each position.

Modulation of splicing can be assayed in a variety of ways known in the art. Target mRNA levels can be quantitated by, e.g., Northern blot analysis, competitive polymerase chain reaction (PCR), or real-time PCR. RNA analysis can be performed on total cellular RNA or poly(A)+mRNA by methods known in the art. Methods of RNA isolation are taught in, for example, Ausubel, F. M. et al., Current Protocols in Molecular Biology, Volume 1, pp. 4.1.1-4.2.9 and 4.5.1-4.5.3, John Wiley & Sons, Inc., 1993. Northern blot analysis is routine in the art and is taught in, for example, Ausubel, F. M. et al., Current Protocols in Molecular Biology, Volume 1, pp. 4.2.1-4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Levels of a protein encoded by a target mRNA can be quantitated in a variety of ways well known in the art, such as immunoprecipitation, Western blot analysis (immunoblotting), ELISA or fluorescence-activated cell sorting (FACS). Antibodies directed to a protein encoded by a target mRNA can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., Current Protocols in Molecular Biology, Volume 2, pp. 11.12.1-11.12.9, John Wiley & Sons, Inc., 1997. Preparation of monoclonal antibodies is taught in, for example, Ausubel, F. M. et al., Current Protocols in Molecular Biology, Volume 2, pp. 11.4.1-11.11.5, John Wiley & Sons, Inc., 1997.

Immunoprecipitation methods are standard in the art and can be found at, for example, Ausubel, F. M. et al., Current Protocols in Molecular Biology, Volume 2, pp. 10.16.1-10.16.11, John Wiley & Sons, Inc., 1998. Western blot (immunoblot) analysis is standard in the art and can be found at, for example, Ausubel, F. M. et al., Current Protocols in Molecular Biology, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., Current Protocols in Molecular Biology, Volume 2, pp. 11.2.1-11.2.22, John Wiley & Sons, Inc., 1991.

The effect of the oligomeric compounds of the present invention may be analysed by RT PCT, qPCR, flanking exon PCR and/or a method comprising flanking exon PCR on each internal exon corresponding to the mRNA to obtain one or more flanking exon amplification products, and detecting the presence and length of the said flanking exon amplification products, quantifying of each protein encoding exon of said mRNA.

The oligomeric compounds provided herein may be utilized for therapeutics or research. Furthermore, antisense compounds, which are able to inhibit gene expression or modulate splicing with specificity, may be used to elucidate the function of particular genes or gene products or to distinguish between functions of various members of a biological pathway. Optionally of the invention and/or embodiments thereof the oligomeric compounds are used for the treatment of Pompe disease. Optionally of the invention and/or embodiments thereof the oligomeric compounds are used in research of the function of the GAA gene.

Compounds described herein can be used to modulate splicing of a target mRNA in an metazoans, Optionally mammals Optionally human. In one non-limiting embodiment of the invention and/or embodiments thereof, the methods comprise the step of administering to said animal an effective amount of an antisense compound that modulates splicing of a target mRNA.

For example, modulation of splicing of a target mRNA can be measured by determining levels of mRNA splicing products in a bodily fluid, tissue, organ of cells of the animal. Bodily fluids include, but are not limited to, blood (serum or plasma), lymphatic fluid, cerebrospinal fluid, semen, urine, synovial fluid and saliva and can be obtained by methods routine to those skilled in the art. Tissues, organs or cells include, but are not limited to, blood (e.g., hematopoietic cells, such as human hematopoietic progenitor cells, human hematopoietic stem cells, CD34+ cells CD4+ cells), lymphocytes and other blood lineage cells, skin, bone marrow, spleen, thymus, lymph node, brain, spinal cord, heart, skeletal muscle, liver, connective tissue, pancreas, prostate, kidney, lung, oral mucosa, esophagus, stomach, ilium, small intestine, colon, bladder, cervix, ovary, testis, mammary gland, adrenal gland, and adipose (white and brown). Samples of tissues, organs and cells can be routinely obtained by biopsy. In some alternative situations, samples of tissues or organs can be recovered from an animal after death. Optionally of the invention and/or embodiments thereof modulation of splicing is measured in fibroblast, Optionally primary fibroblasts, Optionally primary fibroblasts from patients suffering from Pompe disease.

The effects of treatment with the oligomeric compounds can be assessed by measuring biomarkers associated with modulation of splicing of a target mRNA in the aforementioned fluids, tissues or organs, collected from an animal contacted with one or more compounds, by routine clinical methods known in the art. These biomarkers include but are not limited to: glucose, cholesterol, lipoproteins, triglycerides, free fatty acids and other markers of glucose and lipid metabolism; liver transaminases, bilirubin, albumin, blood urea nitrogen, creatine and other markers of kidney and liver function; interleukins, tumor necrosis factors, intracellular adhesion molecules, C-reactive protein and other markers of inflammation; testosterone, estrogen and other hormones; tumor markers; vitamins, minerals and electrolytes. Optionally of the invention and/or embodiments thereof the biomarker is glycogen.

The compounds disclosed herein can be utilized in pharmaceutical compositions by adding an effective amount of a compound to a suitable pharmaceutically acceptable diluent or carrier. The compounds can also be used in the manufacture of a medicament for the treatment of diseases and disorders related to alterations in splicing. Optionally of the invention and/or embodiments thereof, the disease is Pompe disease.

Methods whereby bodily fluids, organs or tissues are contacted with an effective amount of one or more of the antisense compounds or compositions of the disclosure are also contemplated. Bodily fluids, organs or tissues can be contacted with one or more of the compounds of the disclosure resulting in modulation of splicing of target mRNA in the cells of bodily fluids, organs or tissues. An effective amount can be determined by monitoring the modulatory effect of the antisense compound or compounds or compositions on target nucleic acids or their products by methods routine to the skilled artisan. Further contemplated are ex vivo methods of treatment whereby cells or tissues are isolated from a subject, contacted with an effective amount of the antisense compound or compounds or compositions and reintroduced into the subject by routine methods known to those skilled in the art.

A sufficient amount of an antisense oligomeric compound to be administered will be an amount that is sufficient to induce amelioration of unwanted disease symptoms. Such an amount may vary inter alia depending on such factors as the gender, age, weight, overall physical condition, of the patient, etc. and may be determined on a case by case basis. The amount may also vary according to the type of condition being treated, and the other components of a treatment protocol (e.g. administration of other medicaments such as steroids, etc.). The amount may also vary according to the method of administration such as systemically or locally.

Typical dosage amounts of the antisense oligonucleotide molecules in pharmaceutical formulations may range from about 0.05 to 1000 mg/kg body weight, and in particular from about 5 to 500 mg/kg body weight. In one embodiment of the invention and/or embodiments thereof, the dosage amount is from about 50 to 300 mg/kg body weight once in 2 weeks, or once or twice a week, or any frequency required to achieve therapeutic effect. Optionally amounts are from 3-50 mg/kg, more Optionally 10-40 mg/kg, more Optionally 15-25 mg/kg.

The dosage administered will, of course, vary depending on the use and known factors such as the pharmacodynamic characteristics of the active ingredient; age, health, and weight of the recipient; nature and extent of symptoms, kind of concurrent treatment, frequency of treatment, and the effect desired. The recipient may be any type of mammal, but is Optionally a human. In one embodiment of the invention and/or embodiments thereof, dosage forms (compositions) of the inventive pharmaceutical composition may contain about 1 microgram to 50,000 micrograms of active ingredient per unit, and in particular, from about 10 to 10,000 micrograms of active ingredient per unit. (if here a unit means a vial or one package for one injection, then it will be much higher, up to 15 g if the weight of a patient is 50 kg) For intravenous delivery, a unit dose of the pharmaceutical formulation will generally contain from 0.5 to 500 micrograms per kg body weight and Optionally will contain from 5 to 300 micrograms, in particular 10, 15, 20, 30, 40, 50, 100, 200, or 300 micrograms per kg body weight ([mu]g/kg body weight) of the antisense oligonucleotide molecule. Preferred intravenous dosage ranges from 10 ng to 2000 microg, Optionally 3 to 300 [mg, more Optionally 10 to 100 [mu]g of compound per kg of body weight. Alternatively the unit dose may contain from 2 to 20 milligrams of the antisense oligonucleotide molecule and be administered in multiples, if desired, to give the preceding daily dose. In these pharmaceutical compositions, the antisense oligonucleotide molecule will ordinarily be present in an amount of about 0.5-95% by weight based on the total weight of the composition.

In one particular embodiment, it should be recognized that the dosage can be raised or lowered based on individual patient response. It will be appreciated that the actual amounts of antisense oligonucleotide molecule used will vary according to the specific antisense oligonucleotide molecule being utilized, the particular compositions formulated, the mode of application, and the particular site of administration.

Optionally the compounds are administered daily, once every 2 days, once every 3 days, once a week, once every two weeks, or once every month.

In another preferred embodiment the administration is only one time, e.g. when using a viral vector.

If a viral-based delivery of antisense oligomeric compounds is chosen, suitable doses will depend on different factors such as the viral strain that is employed, the route of delivery (intramuscular, intravenous, intra-arterial or other), Those of skill in the art will recognize that such parameters are normally worked out during clinical trials. Further, those of skill in the art will recognize that, while disease symptoms may be completely alleviated by the treatments described herein, this need not be the case. Even a partial or intermittent relief of symptoms may be of great benefit to the recipient. In addition, treatment of the patient is usually not a single event. Rather, the antisense oligomeric compounds of the invention will likely be administered on multiple occasions, that may be, depending on the results obtained, several days apart, several weeks apart, or several months apart, or even several years apart.

Those of skill in the art will recognize that there are many ways to determine or measure a level of functionality of a protein, and to determine a level of increase or decrease of functionality e.g. in response to a treatment protocol. Such methods include but are not limited to measuring or detecting an activity of the protein, etc. Such measurements are generally made in comparison to a standard or control or "normal" sample. In addition, when the protein's lack of functionality is involved in a disease process, disease symptoms may be monitored and/or measured in order to indirectly detect the presence or absence of a correctly functioning protein, or to gauge the success of a treatment protocol intended to remedy the lack of functioning of the protein. In preferred embodiment the functionality of the GAA protein is measured. This is Optionally performed with an enzymatic activity assays as is well known to a skilled person.

In a particular embodiment of the invention and/or embodiments thereof; antisense oligonucleotides of the invention may be delivered in vivo alone or in association with a vector. In its broadest sense, a "vector" is any vehicle capable of facilitating the transfer of the antisense oligonucleotide of the invention to the cells. Optionally, the vector transports the nucleic acid to cells with reduced degradation relative to the extent of degradation that would result in the absence of the vector. In general, the vectors useful in the invention include, but are not limited to, naked plasmids, non viral delivery systems (electroporation, sonoporation, cationic transfection agents, liposomes, etc. . . . ), phagemids, viruses, other vehicles derived from viral or bacterial sources that have been manipulated by the insertion or incorporation of the antisense oligonucleotide nucleic acid sequences. Viral vectors are a preferred type of vector and include, but are not limited to nucleic acid sequences from the following viruses: R A viruses such as a retrovirus (as for example moloney murine leukemia virus and lentiviral derived vectors), harvey murine sarcoma virus, murine mammary tumor virus, and rous sarcoma virus; adenovirus, adeno-associated virus; SV40-type viruses; polyoma viruses; Epstein-Barr viruses; papilloma viruses; herpes virus; vaccinia virus; polio virus. One can readily employ other vectors not named but known to the art.

Preferred viral vectors according to the invention include adenoviruses and adeno-associated (AAV) viruses, which are DNA viruses that have already been approved for human use in gene therapy. Actually 12 different AAV serotypes (AAVI to 12) are known, each with different tissue tropisms (Wu, Z Mol Ther 2006; 14:316-27). Recombinant AAV are derived from the dependent parvovirus AAV (Choi, V W J Virol 2005; 79:6801-07). The adeno-associated virus type 1 to 12 can be engineered to be replication deficient and is capable of infecting a wide range of cell types and species (Wu, Z Mol Ther 2006; 14:316-27). It further has advantages such as, heat and lipid solvent stability; high transduction frequencies in cells of diverse lineages, including hemopoietic cells; and lack of superinfection inhibition thus allowing multiple series of transductions. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g. Sambrook et al, 1989. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by, intranasal sprays or drops, rectal suppository and orally.

Optionally, said DNA plasmid is injected intramuscular, or intravenous. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

Optionally of the invention and/or embodiments thereof, the antisense oligonucleotide nucleic acid sequence is under the control of a heterologous regulatory region, e.g., a heterologous promoter. The promoter can also be, e.g., a viral promoter, such as CMV promoter or any synthetic promoters. Optionally of the invention and/or embodiments thereof, the vector may code for more than one antisense oligomeric compound. Each antisense oligomeric compound is directed to different targets.

Pharmaceutical composition comprising the antisense compounds described herein may comprise any pharmaceutically acceptable salts, esters, or salts of such esters, or any other functional chemical equivalent which, upon administration to an animal including a human, is capable of providing (directly or indirectly) the biologically active metabolite or residue thereof. Accordingly, for example, the disclosure is also drawn to prodrugs and pharmaceutically acceptable salts of the antisense compounds, pharmaceutically acceptable salts of such prodrugs, and other bioequivalents.

The term "prodrug" indicates a therapeutic agent that is prepared in an inactive or less active form that is converted to an active form (i.e., drug) within the body or cells thereof by the action of endogenous enzymes, chemicals, and/or conditions. In particular, prodrug versions of the oligonucleotides are prepared as SATE ((S-acetyl-2-thioethyl) phosphate) derivatives according to the methods disclosed in WO 93/24510 or WO 94/26764. Prodrugs can also include antisense compounds wherein one or both ends comprise nucleotides that are cleaved (e.g., by incorporating phosphodiester backbone linkages at the ends) to produce the active compound.

The term "pharmaceutically acceptable salts" refers to physiologically and pharmaceutically acceptable salts of the compounds: i.e., salts that retain the desired biological activity of the parent compound and do not impart undesired toxicological effects thereto. Sodium salts of antisense oligonucleotides are useful and are well accepted for therapeutic administration to humans. In another embodiment of the invention and/or embodiments thereof, sodium salts of dsRNA compounds are also provided.

The antisense compounds described herein may also be admixed, encapsulated, conjugated or otherwise associated with other molecules, molecule structures or mixtures of compounds.

The present disclosure also includes pharmaceutical compositions and formulations which include the antisense compounds described herein. The pharmaceutical compositions may be administered in a number of ways depending upon whether local or systemic treatment is desired and upon the area to be treated. Optionally of the invention and/or embodiments thereof, administration is intramuscular or intravenous.

The pharmaceutical formulations, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers, finely divided solid carriers, or both, and then, if necessary, shaping the product (e.g., into a specific particle size for delivery). Optionally of the invention and/or embodiments thereof, the pharmaceutical formulations are prepared for intramuscular administration in an appropriate solvent, e.g., water or normal saline, possibly in a sterile formulation, with carriers or other agents.

A "pharmaceutical carrier" or "excipient" can be a pharmaceutically acceptable solvent, suspending agent or any other pharmacologically inert vehicle for delivering one or more nucleic acids to an animal and are known in the art. The excipient may be liquid or solid and is selected, with the planned manner of administration in mind, so as to provide for the desired bulk, consistency, etc., when combined with a nucleic acid and the other components of a given pharmaceutical composition.

Compositions provided herein may contain two or more antisense compounds. In another related embodiment, compositions may contain one or more antisense compounds, particularly oligonucleotides, targeted to a first nucleic acid and one or more additional antisense compounds targeted to a second nucleic acid target. Alternatively, compositions provided herein can contain two or more antisense compounds targeted to different regions of the same nucleic acid target. Two or more combined compounds may be used together or sequentially. Compositions can also be combined with other non-antisense compound therapeutic agents.

The antisense oligomeric compound described herein may be in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. Aqueous suspensions may also contain one or more preservatives, for example ethyl, or n-propyl p-hydroxybenzoate. Dispersible powders and granules suitable for preparation of an aqueous suspension by the addition of water provide the active ingredient in admixture with a dispersing or wetting agent, suspending agent and one or more preservatives. antisense oligomeric compound compositions may be in the form of a sterile injectable aqueous or oleaginous suspension. Suspensions may be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono or diglycerides. In addition, fatty acids such as oleic acid find use in the preparation of injectables.

The present disclosure also includes antisense oligomeric compound compositions prepared for storage or administration that include a pharmaceutically effective amount of the desired compounds in a pharmaceutically acceptable carrier or diluent. Acceptable carriers or diluents for therapeutic use are well known in the pharmaceutical art, and are described, for example, in Remington's Pharmaceutical Sciences (Mack Publishing Co., A. R. Gennaro edit., 1985). For example, preservatives and stabilizers can be provided. These include sodium benzoate, sorbic acid and esters of p-hydroxybenzoic acid. In addition, antioxidants and suspending agents can be used.

Pharmaceutical compositions of this disclosure can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxy ethylene sorbitan monooleate.

The antisense oligomeric compound of this disclosure may be administered to a patient by any standard means, with or without stabilizers, buffers, or the like, to form a composition suitable for treatment. When it is desired to use a liposome delivery mechanism, standard protocols for formation of liposomes can be followed. Thus the antisense oligomeric compound of the present disclosure may be administered in any form, for example intramuscular or by local, systemic, or intrathecal injection.

This disclosure also features the use of antisense oligomeric compound compositions comprising surface-modified liposomes containing poly(ethylene glycol) lipids (PEG-modif[iota]ed, or long-circulating liposomes or stealth liposomes). These formulations offer a method for increasing the accumulation of antisense oligomeric compound in target tissues. This class of drug carriers resists opsonization and elimination by the mononuclear phagocytic system (MPS or RES), thereby enabling longer blood circulation times and enhanced tissue exposure for the encapsulated antisense oligomeric compound (Lasic et al, Chem. Rev. 95:2601-2627 (1995) and Ishiwata et al, Chem. Pharm. Bull. 43:1005-1011 (1995). Long-circulating liposomes enhance the pharmacokinetics and pharmacodynamics of antisense oligomeric compound, particularly compared to conventional cationic liposomes which are known to accumulate in tissues of the MPS (Liu et al, J. Biol. Chem. 42:24864-24870 (1995); Choi et al, PCT Publication No. WO 96/10391; Ansell et al, PCT Publication No. WO 96/10390; Holland et al, PCT Publication No. WO 96/10392). Long-circulating liposomes are also likely to protect antisense oligomeric compound from nuclease degradation to a greater extent compared to cationic liposomes, based on their ability to avoid accumulation in metabolically aggressive MPS tissues such as the liver and spleen.

Following administration of the antisense oligomeric compound compositions according to the formulations and methods of this disclosure, test subjects will exhibit about a 10% up to about a 99% reduction in one or more symptoms associated with the disease or disorder being treated, as compared to placebo-treated or other suitable control subjects.

The invention claimed is:

1. A method of treating Pompe disease, comprising administration of an enzyme or nucleic acid encoding for said enzyme suitable for Enzyme Replacement Therapy for Pompe disease in combination with the administration of an antisense oligomeric compound that modulates the splicing of acid alpha-glucosidase (GAA) pre-mRNA, wherein said enzyme suitable for Enzyme Replacement Therapy is an GAA enzyme, or any modification, variant, analogue, or functional derivative thereof.

2. The method according to claim 1, wherein the antisense oligomeric compound modulates aberrant splicing of acid alpha-glucosidase (GAA) enzyme gene, optionally by an activity selected from the group consisting of promotion of exon inclusion, inhibition of a cryptic splicing site, inhibition of intron inclusion, recovering of reading frame, inhibition of splicing silencer sequence, activation of splicing enhancer sequence or any combination thereof.

3. The method according to claim 1, wherein the antisense oligomeric compound targets a nucleic acid sequence of the GAA gene selected from the group consisting of SEQ ID NO: 1, 37-40, 1584-1589 or targets a single nucleotide polymorphisms of SEQ ID NO: 1, 37-40, 1584-1589.

4. The method according to claim 1, wherein said enzyme or said nucleic acid encoding for said enzyme is administered once every 1 week, or once every 2 weeks, or once every 3 weeks.

5. The method according to claim 1, wherein said antisense oligomeric compound is administered once every week, once every 2 week, once every 4 weeks, or once every 6 weeks.

6. The method according to claim 1, wherein said enzyme or said nucleic acid encoding for said enzyme is administered in a dose of about 1-100 mg/kg, optionally 2-90 mg/kg, 3-80 mg/kg, 5-75 mg/kg, 7-70 mg/kg, 10-60 mg/kg, 12-55 mg/kg, 15-50 mg/kg, 17-45 mg/kg, 20-40 mg/kg, 22-35 mg/kg, or 25-30 mg/kg.

7. The method according to claim 1, wherein said antisense oligomeric compound is administered in a dose of about 0.05 to 1000 mg/kg, about 0.1 to 900 mg/kg, 1-800 mg/kg, 2-750 mg/kg, 3-700 mg/kg, 4-600 mg/kg, 5-500 mg/kg, 7 to 450 mg/kg, 10 to 400 mg/kg, 12 to 350 mg/kg, 15 to 300 mg/kg, 17 to 250 mg/kg, 20 to 220 mg/kg, 22 to 200 mg/kg, 25 to 180 mg/kg, 30 to 150 mg/kg, 35 to 125 mg/kg, 40 to 100 mg/kg, 45 to 75 mg/kg, or 50-70 mg/kg.

8. The method according to claim 1, wherein said enzyme or said nucleic acid encoding for said enzyme, or said antisense oligomeric compound is administered in combination with a chaperone, such as an Active Site-Specific Chaperone (ASSC).

9. The method according to claim 1, wherein the administration is in combination with genistein, or in combination with cell penetrating peptides.

10. The method according to claim 1, wherein said enzyme is selected from the group consisting of a recombinant human GAA, Myozyme, Lumizyme, neoGAA, Gilt GAA (BMN-701), and OXY2810.

11. The method according to claim 1, wherein the antisense oligomeric compound is selected from the group consisting of SEQ ID NO: 2-33, 541-1583, 1590-1594, and sequences having at least 80% identity thereof.

* * * * *

SEQUENCE LISTING

```
<160> NUMBER OF SEQ ID NOS: 1594

<210> SEQ ID NO 1
<211> LENGTH: 55
<212> TYPE: DNA
<213> ORGANISM: Artificial Sequence
<220> FEATURE:
<223> OTHER INFORMATION: Sequence in cDNA to which AON anneals

<400> SEQUENCE: 1
gctctgcact ccctgctgg agcttttctc gcccttcctt ctggccctct cccca            55

<210> SEQ ID NO 2
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 2
tggggagagg gccagaagga agggc                                            25

<210> SEQ ID NO 3
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 3
ggggagaggg ccagaaggaa gggcg                                            25
```

```
<210> SEQ ID NO 4
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 4
gggagagggc cagaaggaag ggcga                                         25

<210> SEQ ID NO 5
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 5
ggagagggcc agaaggaagg gcgag                                         25

<210> SEQ ID NO 6
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 6
gagagggcca gaaggaaggg cgaga                                         25

<210> SEQ ID NO 7
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 7
agagggccag aaggaagggc gagaa                                         25

<210> SEQ ID NO 8
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 8
gagggccaga aggaagggcg agaaa                                         25

<210> SEQ ID NO 9
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 9
agggccagaa ggaagggcga gaaaa                                         25

<210> SEQ ID NO 10
<211> LENGTH: 25
<212> TYPE: DNA
<213> ORGANISM: Artificial Sequence
<220> FEATURE:
<223> OTHER INFORMATION: sequence of AON (5'-> 3')
```

```
<400> SEQUENCE: 10
gggccagaag gaagggcgag aaaag                                       25

<210> SEQ ID NO 11
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 11
ggccagaagg aagggcgaga aaagc                                       25

<210> SEQ ID NO 12
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 12
gccagaagga agggcgagaa aagct                                       25

<210> SEQ ID NO 13
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 13
ccagaaggaa gggcgagaaa agctc                                       25

<210> SEQ ID NO 14
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 14
cagaaggaag ggcgagaaaa gctcc                                       25

<210> SEQ ID NO 15
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 15
agaaggaagg gcgagaaaag ctcca                                       25

<210> SEQ ID NO 16
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 16
gaaggaaggg cgagaaaagc tccag                                       25

<210> SEQ ID NO 17
```

```
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 17
aaggaagggc gagaaaagct ccagc                                             25

<210> SEQ ID NO 18
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 18
aggaagggcg agaaaagctc cagca                                             25

<210> SEQ ID NO 19
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 19
ggaagggcga gaaaagctcc agcag                                             25

<210> SEQ ID NO 20
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 20
gaagggcgag aaaagctcca gcagg                                             25

<210> SEQ ID NO 21
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 21
aagggcgaga aaagctccag caggg                                             25

<210> SEQ ID NO 22
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 22
agggcgagaa aagctccagc agggg                                             25

<210> SEQ ID NO 23
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 23
```

-continued gggcgagaaa agctccagca gggga                                25

<210> SEQ ID NO 24
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 24
ggcgagaaaa gctccagcag gggag                                25

<210> SEQ ID NO 25
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 25
gcgagaaaag ctccagcagg ggagt                                25

<210> SEQ ID NO 26
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 26
cgagaaaagc tccagcaggg gagtg                                25

<210> SEQ ID NO 27
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 27
gagaaaagct ccagcagggg agtgc                                25

<210> SEQ ID NO 28
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 28
agaaaagctc cagcagggga gtgca                                25

<210> SEQ ID NO 29
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 29
gaaaagctcc agcaggggag tgcag                                25

<210> SEQ ID NO 30
<211> LENGTH: 25
<212> TYPE: DNA

```
<213> ORGANISM: Artificial Sequence
<220> FEATURE:
<223> OTHER INFORMATION: sequence of AON (5'-> 3')

<400> SEQUENCE: 30
aaaagctcca gcaggggagt gcaga                                              25

<210> SEQ ID NO 31
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 31
aaagctccag cagggagtg cagag                                               25

<210> SEQ ID NO 32
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 32
aagctccagc aggggagtgc agagc                                              25

<210> SEQ ID NO 33
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 33
ccagaaggaa gggcgagaaa a                                                  21

<210> SEQ ID NO 34
<211> LENGTH: 24
<212> TYPE: DNA
<213> ORGANISM: Artificial Sequence
<220> FEATURE:
<223> OTHER INFORMATION: fake sequence to maintain correct numbering

<400> SEQUENCE: 34
aaaaaaaaaa aaaaaaaaaa aaaa                                               24

<210> SEQ ID NO 35
<211> LENGTH: 24
<212> TYPE: DNA
<213> ORGANISM: Artificial Sequence
<220> FEATURE:
<223> OTHER INFORMATION: fake sequence to maintain correct numbering

<400> SEQUENCE: 35
aaaaaaaaaa aaaaaaaaaa aaaa                                               24

<210> SEQ ID NO 36
<211> LENGTH: 24
<212> TYPE: DNA
<213> ORGANISM: Artificial Sequence
<220> FEATURE:
<223> OTHER INFORMATION: fake sequence to maintain correct numbering

<400> SEQUENCE: 36
aaaaaaaaaa aaaaaaaaaa aaaa                                               24
```

```
<210> SEQ ID NO 37
<211> LENGTH: 45
<212> TYPE: DNA
<213> ORGANISM: Artificial Sequence
<220> FEATURE:
<223> OTHER INFORMATION: Sequence in cDNA to which AON anneals

<400> SEQUENCE: 37
gctctgcact cccctgctgg agcttttctc gcccttcctt ctggc            45

<210> SEQ ID NO 38
<211> LENGTH: 31
<212> TYPE: DNA
<213> ORGANISM: Artificial Sequence
<220> FEATURE:
<223> OTHER INFORMATION: Sequence in cDNA to which AON anneals

<400> SEQUENCE: 38
tgcactcccc tgctggagct tttctcgccc t                           31

<210> SEQ ID NO 39
<211> LENGTH: 36
<212> TYPE: DNA
<213> ORGANISM: Artificial Sequence
<220> FEATURE:
<223> OTHER INFORMATION: Sequence in cDNA to which AON anneals

<400> SEQUENCE: 39
tgcactcccc tgctggagct tttctcgccc ttcctt                      36

<210> SEQ ID NO 40
<211> LENGTH: 31
<212> TYPE: DNA
<213> ORGANISM: Artificial Sequence
<220> FEATURE:
<223> OTHER INFORMATION: Sequence in cDNA to which AON anneals

<400> SEQUENCE: 40
tcccctgctg gagcttttct cgcccttcct t                           31

<210> SEQ ID NO 41
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 41
ccaaacagct gtcgcctggg                                        20

<210> SEQ ID NO 42
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 42
aggtagacac ttgaaacagg                                        20

<210> SEQ ID NO 43
<211> LENGTH: 20
<212> TYPE: DNA
<213> ORGANISM: Artificial Sequence
<220> FEATURE:
```

<223> OTHER INFORMATION: AON sequence 5' -> 3'

<400> SEQUENCE: 43
cccaggaaga ccagcaaggc                                                     20

<210> SEQ ID NO 44
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 44
tcaaacacgc ttagaatgtc                                                     20

<210> SEQ ID NO 45
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 45
gtctgctaaa atgttacaaa                                                     20

<210> SEQ ID NO 46
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 46
gagtgcagag cacttgcaca                                                     20

<210> SEQ ID NO 47
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 47
cgagaaaagc tccagcaggg                                                     20

<210> SEQ ID NO 48
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 48
gagagggcca gaaggaaggg                                                     20

<210> SEQ ID NO 49
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 49
gccctgctgt ctagactggg                                                     20

```
<210> SEQ ID NO 50
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 50
aggtggccag ggtgggtgtt                                                    20

<210> SEQ ID NO 51
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 51
gcacccaggc aggtggggta                                                    20

<210> SEQ ID NO 52
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 52
caaccgcggc tggcactgca                                                    20

<210> SEQ ID NO 53
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 53
tcaaagcagc tctgagacat                                                    20

<210> SEQ ID NO 54
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 54
gggcggcact cacggggctc                                                    20

<210> SEQ ID NO 55
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 55
gctcagcagg gaggcgggag                                                    20

<210> SEQ ID NO 56
<211> LENGTH: 20
<212> TYPE: DNA
<213> ORGANISM: Artificial Sequence
<220> FEATURE:
<223> OTHER INFORMATION: AON sequence 5' -> 3'
```

```
<400> SEQUENCE: 56
cctgcgggag aagaaagcgg                                               20

<210> SEQ ID NO 57
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 57
gcctggacag ctcctacagg                                               20

<210> SEQ ID NO 58
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 58
cactcccatg gttggagatg                                               20

<210> SEQ ID NO 59
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 59
tgggagcagg gcgggtgcct                                               20

<210> SEQ ID NO 60
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 60
cgcagacggc caggagccgg                                               20

<210> SEQ ID NO 61
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 61
ggttgccaag gacacgaggg                                               20

<210> SEQ ID NO 62
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 62
atgtgcccca ggagtgcagc                                               20

<210> SEQ ID NO 63
<211> LENGTH: 20
```

```
<212> TYPE: DNA
<213> ORGANISM: Artificial Sequence
<220> FEATURE:
<223> OTHER INFORMATION: AON sequence 5' -> 3'

<400> SEQUENCE: 63
gcaggaaatc atggagtagg                                               20

<210> SEQ ID NO 64
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 64
actcagctct cggggaacca                                               20

<210> SEQ ID NO 65
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 65
tccaggactg gggaggagcc                                               20

<210> SEQ ID NO 66
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 66
ggtgagctgg gtgagtctcc                                               20

<210> SEQ ID NO 67
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 67
tggtctgctg gctccctgct                                               20

<210> SEQ ID NO 68
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 68
gcctgggcat cccggggccc                                               20

<210> SEQ ID NO 69
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 69
```

```
ctctgggacg gccggggtgt                                              20

<210> SEQ ID NO 70
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 70
gtcgcactgt gtgggcactg                                              20

<210> SEQ ID NO 71
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 71
aagcggctgt tggggggggac                                             20

<210> SEQ ID NO 72
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 72
ccttgtcagg ggcgcaatcg                                              20

<210> SEQ ID NO 73
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 73
gcactgttcc tgggtgatgg                                              20

<210> SEQ ID NO 74
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 74
tagcaacagc cgcgggcctc                                              20

<210> SEQ ID NO 75
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 75 gccctgctt tgcagggatg                                               20

<210> SEQ ID NO 76
<211> LENGTH: 20
<212> TYPE: DNA
<213> ORGANISM: Artificial Sequence
```

```
<220> FEATURE:
<223> OTHER INFORMATION: AON sequence 5' -> 3'

<400> SEQUENCE: 76
ccccatctgg gctccctgca                                                   20

<210> SEQ ID NO 77
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 77
gggaagaagc accagggctg                                                   20

<210> SEQ ID NO 78
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 78
tgtagctggg gtagctgggt                                                   20

<210> SEQ ID NO 79
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 79
ggagctcagg ttctccagct                                                   20

<210> SEQ ID NO 80
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 80
gccgtgtagc ccatttcaga                                                   20

<210> SEQ ID NO 81
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 81
gggtggtacg ggtcagggtg                                                   20

<210> SEQ ID NO 82
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 82
gtccttgggg aagaaggtgg                                                   20
```

```
<210> SEQ ID NO 83
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 83
tccagccgca gggtcaggat                                                   20

<210> SEQ ID NO 84
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 84
tctcagtctc catcatcacg                                                   20

<210> SEQ ID NO 85
<211> LENGTH: 16
<212> TYPE: DNA
<213> ORGANISM: Artificial Sequence
<220> FEATURE:
<223> OTHER INFORMATION: AON sequence 5' -> 3'

<400> SEQUENCE: 85
gtgaagtgga ggcggt                                                       16

<210> SEQ ID NO 86
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 86
agagcacttg cacagtctgc                                                   20

<210> SEQ ID NO 87
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 87
gcagagcact tgcacagtct                                                   20

<210> SEQ ID NO 88
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 88
gtgcagagca cttgcacagt                                                   20

<210> SEQ ID NO 89
<211> LENGTH: 20
<212> TYPE: DNA
<213> ORGANISM: Artificial Sequence
<220> FEATURE:
<223> OTHER INFORMATION: AON sequence 5' -> 3'
```

-continued

```
<400> SEQUENCE: 89
gggagtgcag agcacttgca                                                      20

<210> SEQ ID NO 90
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 90
aggggagtgc agagcacttg                                                      20

<210> SEQ ID NO 91
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 91
gcaggggagt gcagagcact                                                      20

<210> SEQ ID NO 92
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 92
gccagaagga agggcgagaa                                                      20

<210> SEQ ID NO 93
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 93
gggccagaag gaagggcgag                                                      20

<210> SEQ ID NO 94
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 94
gagggccaga aggaagggcg                                                      20

<210> SEQ ID NO 95
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 95
gggagagggc cagaaggaag                                                      20

<210> SEQ ID NO 96
```

```
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 96
tggggagagg gccagaagga                                              20

<210> SEQ ID NO 97
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 97
actggggaga gggccagaag                                              20

<210> SEQ ID NO 98
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 98
cacccaggca ggtggggtaa ggtgg                                        25

<210> SEQ ID NO 99
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 99
agcacccagg caggtggggt aaggt                                        25

<210> SEQ ID NO 100
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 100
gcagcaccca ggcaggtggg gtaag                                        25

<210> SEQ ID NO 101
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 101
ctgcagcacc caggcaggtg gggta                                        25

<210> SEQ ID NO 102
<211> LENGTH: 25
<212> TYPE: DNA
<213> ORGANISM: Artificial Sequence
```

```
<220> FEATURE:
<223> OTHER INFORMATION: AON sequence designed to block the region
      surrounding the identified splice element (5' -> 3')

<400> SEQUENCE: 102
cactgcagca cccaggcagg tgggg                                              25

<210> SEQ ID NO 103
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 103
ggcactgcag cacccaggca ggtgg                                              25

<210> SEQ ID NO 104
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 104
ctggcactgc agcacccagg caggt                                              25

<210> SEQ ID NO 105
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 105
ggctggcact gcagcaccca ggcag                                              25

<210> SEQ ID NO 106
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 106
gcggctggca ctgcagcacc caggc                                              25

<210> SEQ ID NO 107
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 107
ccgcggctgg cactgcagca cccag                                              25

<210> SEQ ID NO 108
<211> LENGTH: 25
<212> TYPE: DNA
<213> ORGANISM: Artificial Sequence
<220> FEATURE:
```

```
<223> OTHER INFORMATION: AON sequence designed to block the region
      surrounding the identified splice element (5' -> 3')

<400> SEQUENCE: 108
tcaaccgcgg ctggcactgc agcac                                          25

<210> SEQ ID NO 109
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 109
acccaggcag gtggggtaag gtggc                                          25

<210> SEQ ID NO 110
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 110
gcacccaggc aggtggggta aggtg                                          25

<210> SEQ ID NO 111
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 111
cagcacccag gcaggtgggg taagg                                          25

<210> SEQ ID NO 112
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 112
tgcagcaccc aggcaggtgg ggtaa                                          25

<210> SEQ ID NO 113
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 113
actgcagcac ccaggcaggt ggggt                                          25

<210> SEQ ID NO 114
<211> LENGTH: 25
<212> TYPE: DNA
<213> ORGANISM: Artificial Sequence
<220> FEATURE:
<223> OTHER INFORMATION: AON sequence designed to block the region
```

-continued surrounding the identified splice element (5' -> 3')

<400> SEQUENCE: 114
gcactgcagc acccaggcag gtggg                                      25

<210> SEQ ID NO 115
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 115
tggcactgca gcacccaggc aggtg                                      25

<210> SEQ ID NO 116
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 116
gctggcactg cagcacccag gcagg                                      25

<210> SEQ ID NO 117
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 117
cggctggcac tgcagcaccc aggca                                      25

<210> SEQ ID NO 118
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 118
cgcggctggc actgcagcac ccagg                                      25

<210> SEQ ID NO 119
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 119
accgcggctg gcactgcagc accca                                      25

<210> SEQ ID NO 120
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 120
caaccgcggc tggcactgca gcacc                                              25

<210> SEQ ID NO 121
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 121
atcaaccgcg gctggcactg cagca                                              25

<210> SEQ ID NO 122
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 122
ggctctcaaa gcagctctga gacat                                              25

<210> SEQ ID NO 123
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 123
ggggctctca aagcagctct gagac                                              25

<210> SEQ ID NO 124
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 124
acggggctct caaagcagct ctgag                                              25

<210> SEQ ID NO 125
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 125
tcacggggct ctcaaagcag ctctg                                              25

<210> SEQ ID NO 126
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

```
<400> SEQUENCE: 126
actcacgggg ctctcaaagc agctc                                          25

<210> SEQ ID NO 127
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 127
gcactcacgg ggctctcaaa gcagc                                          25

<210> SEQ ID NO 128
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 128
cggcactcac ggggctctca aagca                                          25

<210> SEQ ID NO 129
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 129
ggcggcactc acggggctct caaag                                          25

<210> SEQ ID NO 130
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 130
ggggcggcac tcacggggct ctcaa                                          25

<210> SEQ ID NO 131
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 131
gaggggcggc actcacgggg ctctc                                          25

<210> SEQ ID NO 132
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 132
```
gggaggggcg gcactcacgg ggctc        25

<210> SEQ ID NO 133
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 133
gcgggagggg cggcactcac gggc        25

<210> SEQ ID NO 134
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 134
aggcgggagg ggcggcactc acggg        25

<210> SEQ ID NO 135
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 135
ggaggcggga ggggcggcac tcacg        25

<210> SEQ ID NO 136
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 136
agggaggcgg gagggggcggc actca        25

<210> SEQ ID NO 137
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 137
gcagggaggc gggaggggcg gcact        25

<210> SEQ ID NO 138
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 138
cagcagggag gcgggagggg cggca                                              25

<210> SEQ ID NO 139
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 139
ctcagcaggg aggcgggagg ggcgg                                              25

<210> SEQ ID NO 140
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 140
ggctcagcag ggaggcggga ggggc                                              25

<210> SEQ ID NO 141
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 141
cgggctcagc agggaggcgg gaggg                                              25

<210> SEQ ID NO 142
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 142
agcgggctca gcagggaggc gggag                                              25

<210> SEQ ID NO 143
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 143
aaagcgggct cagcagggag gcggg                                              25

<210> SEQ ID NO 144
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 144
agaaagcggg ctcagcaggg aggcg                                              25

<210> SEQ ID NO 145
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 145
gaagaaagcg ggctcagcag ggagg                                       25

<210> SEQ ID NO 146
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 146
gagaagaaag cgggctcagc aggga                                       25

<210> SEQ ID NO 147
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 147
gggagaagaa agcgggctca gcagg                                       25

<210> SEQ ID NO 148
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 148
gcgggagaag aaagcgggct cagca                                       25

<210> SEQ ID NO 149
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 149
ctgcgggaga agaaagcggg ctcag                                       25

<210> SEQ ID NO 150
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 150
gcctgcggga gaagaaagcg ggctc                                       25

-continued

```
<210> SEQ ID NO 151
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 151
aggcctgcgg gagaagaaag cgggc                                               25

<210> SEQ ID NO 152
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 152
actcccatgg ttggagatgg cctgg                                               25

<210> SEQ ID NO 153
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 153
tcactcccat ggttggagat ggcct                                               25

<210> SEQ ID NO 154
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 154
cctcactccc atggttggag atggc                                               25

<210> SEQ ID NO 155
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 155
tgcctcactc ccatggttgg agatg                                               25

<210> SEQ ID NO 156
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 156
ggtgcctcac tcccatggtt ggaga                                               25
```

```
<210> SEQ ID NO 157
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 157
cgggtgcctc actcccatgg ttgga                                          25

<210> SEQ ID NO 158
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 158
ggcgggtgcc tcactcccat ggttg                                          25

<210> SEQ ID NO 159
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 159
agggcgggtg cctcactccc atggt                                          25

<210> SEQ ID NO 160
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 160
gcagggcggg tgcctcactc ccatg                                          25

<210> SEQ ID NO 161
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 161
gagcagggcg ggtgcctcac tccca                                          25

<210> SEQ ID NO 162
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 162
gggagcaggg cgggtgcctc actcc                                          25

<210> SEQ ID NO 163
```

-continued

```
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 163
gtgggagcag ggcgggtgcc tcact                                              25

<210> SEQ ID NO 164
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 164
cggtgggagc agggcgggtg cctca                                              25

<210> SEQ ID NO 165
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 165
gccggtggga gcagggcggg tgcct                                              25

<210> SEQ ID NO 166
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 166
gagccggtgg gagcagggcg gtgc                                               25

<210> SEQ ID NO 167
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 167
aggagccggt gggagcaggg cgggt                                              25

<210> SEQ ID NO 168
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 168
ccaggagccg gtgggagcag gcgg                                               25

<210> SEQ ID NO 169
<211> LENGTH: 25
```

```
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 169
ggccaggagc cggtgggagc agggc                                            25

<210> SEQ ID NO 170
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 170
acggccagga gccggtggga gcagg                                            25

<210> SEQ ID NO 171
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 171
agacggccag gagccggtgg gagca                                            25

<210> SEQ ID NO 172
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 172
gcagacggcc aggagccggt gggag                                            25

<210> SEQ ID NO 173
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 173
gcgcagacgg ccaggagccg gtggg                                            25

<210> SEQ ID NO 174
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 174
gggcgcagac ggccaggagc cggtg                                            25

<210> SEQ ID NO 175
<211> LENGTH: 25
<212> TYPE: DNA
```

```
<213> ORGANISM: Artificial Sequence
<220> FEATURE:
<223> OTHER INFORMATION: AON sequence designed to block the region
      surrounding the identified splice element (5' -> 3')

<400> SEQUENCE: 175
gagggcgcag acggccagga gccgg                                              25

<210> SEQ ID NO 176
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 176
acgagggcgc agacggccag gagcc                                              25

<210> SEQ ID NO 177
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 177
acacgagggc gcagacggcc aggag                                              25

<210> SEQ ID NO 178
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 178
ggacacgagg gcgcagacgg ccagg                                              25

<210> SEQ ID NO 179
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 179
aaggacacga gggcgcagac ggcca                                              25

<210> SEQ ID NO 180
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 180
ccaaggacac gagggcgcag acggc                                              25

<210> SEQ ID NO 181
<211> LENGTH: 25
<212> TYPE: DNA
<213> ORGANISM: Artificial Sequence
```

-continued

```
<220> FEATURE:
<223> OTHER INFORMATION: AON sequence designed to block the region
      surrounding the identified splice element (5' -> 3')

<400> SEQUENCE: 181
tgccaaggac acgagggcgc agacg                                              25

<210> SEQ ID NO 182
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 182
gctctcaaag cagctctgag acatc                                              25

<210> SEQ ID NO 183
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 183
gggctctcaa agcagctctg agaca                                              25

<210> SEQ ID NO 184
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 184
ctcacggggc tctcaaagca gctct                                              25

<210> SEQ ID NO 185
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 185
cactcacggg gctctcaaag cagct                                              25

<210> SEQ ID NO 186
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 186
ggcactcacg gggctctcaa agcag                                              25

<210> SEQ ID NO 187
<211> LENGTH: 25
<212> TYPE: DNA
<213> ORGANISM: Artificial Sequence
<220> FEATURE:
```

```
<223> OTHER INFORMATION: AON sequence designed to block the region
      surrounding the identified splice element (5' -> 3')

<400> SEQUENCE: 187
gcggcactca cggggctctc aaagc                                          25

<210> SEQ ID NO 188
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 188
gggcggcact cacggggctc tcaaa                                          25

<210> SEQ ID NO 189
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 189
aggggcggca ctcacggggc tctca                                          25

<210> SEQ ID NO 190
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 190
ggaggggcgg cactcacggg gctct                                          25

<210> SEQ ID NO 191
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 191
cgggaggggc ggcactcacg gggct                                          25

<210> SEQ ID NO 192
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 192
ggcgggaggg gcggcactca cgggg                                          25

<210> SEQ ID NO 193
<211> LENGTH: 25
<212> TYPE: DNA
<213> ORGANISM: Artificial Sequence
<220> FEATURE:
<223> OTHER INFORMATION: AON sequence designed to block the region
```

-continued surrounding the identified splice element (5' -> 3')

<400> SEQUENCE: 193
gaggcgggag gggcggcact cacgg                                              25

<210> SEQ ID NO 194
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 194
gggaggcggg aggggcggca ctcac                                              25

<210> SEQ ID NO 195
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 195
cagggaggcg ggaggggcgg cactc                                              25

<210> SEQ ID NO 196
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 196
agcagggagg cgggaggggc ggcac                                              25

<210> SEQ ID NO 197
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 197
tcagcaggga ggcgggaggg gcggc                                              25

<210> SEQ ID NO 198
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 198
gctcagcagg gaggcgggag gggcg                                              25

<210> SEQ ID NO 199
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 199
gggctcagca gggaggcggg agggg                                                 25

<210> SEQ ID NO 200
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 200
gcgggctcag cagggaggcg ggagg                                                 25

<210> SEQ ID NO 201
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 201
aagcgggctc agcagggagg cggga                                                 25

<210> SEQ ID NO 202
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 202
gaaagcgggc tcagcaggga ggcgg                                                 25

<210> SEQ ID NO 203
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 203
aagaaagcgg gctcagcagg gaggc                                                 25

<210> SEQ ID NO 204
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 204
agaagaaagc gggctcagca gggag                                                 25

<210> SEQ ID NO 205
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

```
<400> SEQUENCE: 205
ggagaagaaa gcgggctcag caggg                                         25

<210> SEQ ID NO 206
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 206
cgggagaaga aagcgggctc agcag                                         25

<210> SEQ ID NO 207
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 207
tgcgggagaa gaaagcgggc tcagc                                         25

<210> SEQ ID NO 208
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 208
cctgcgggag aagaaagcgg gctca                                         25

<210> SEQ ID NO 209
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 209
ggcctgcggg agaagaaagc gggct                                         25

<210> SEQ ID NO 210
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 210
caggcctgcg ggagaagaaa gcggg                                         25

<210> SEQ ID NO 211
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 211
```

```
cggggctctc aaagcagctc tgaga                                         25
```

<210> SEQ ID NO 212
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 212

```
cacggggctc tcaaagcagc tctga                                         25
```

<210> SEQ ID NO 213
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 213

```
ctcccatggt tggagatggc ctgga                                         25
```

<210> SEQ ID NO 214
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 214

```
cactcccatg gttggagatg gcctg                                         25
```

<210> SEQ ID NO 215
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 215

```
ctcactccca tggttggaga tggcc                                         25
```

<210> SEQ ID NO 216
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 216

```
gcctcactcc catggttgga gatgg                                         25
```

<210> SEQ ID NO 217
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 217
gtgcctcact cccatggttg gagat         25

<210> SEQ ID NO 218
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 218
gggtgcctca ctcccatggt tggag         25

<210> SEQ ID NO 219
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 219
gcgggtgcct cactcccatg gttgg         25

<210> SEQ ID NO 220
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 220
gggcgggtgc ctcactccca tggtt         25

<210> SEQ ID NO 221
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 221
cagggcgggt gcctcactcc catgg         25

<210> SEQ ID NO 222
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 222
agcagggcgg gtgcctcact cccat         25

<210> SEQ ID NO 223
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 223
ggagcagggc gggtgcctca ctccc         25

<210> SEQ ID NO 224
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 224
tgggagcagg gcgggtgcct cactc                                    25

<210> SEQ ID NO 225
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 225
ggtgggagca gggcgggtgc ctcac                                    25

<210> SEQ ID NO 226
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 226
ccggtgggag cagggcgggt gcctc                                    25

<210> SEQ ID NO 227
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 227
agccggtggg agcagggcgg gtgcc                                    25

<210> SEQ ID NO 228
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 228
ggagccggtg ggagcagggc gggtg                                    25

<210> SEQ ID NO 229
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 229
caggagccgg tgggagcagg gcggg                                    25

<210> SEQ ID NO 230
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 230
gccaggagcc ggtgggagca gggcg                                          25

<210> SEQ ID NO 231
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 231
cggccaggag ccggtgggag caggg                                          25

<210> SEQ ID NO 232
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 232
gacggccagg agccggtggg agcag                                          25

<210> SEQ ID NO 233
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 233
cagacggcca ggagccggtg ggagc                                          25

<210> SEQ ID NO 234
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 234
cgcagacggc caggagccgg tggga                                          25

<210> SEQ ID NO 235
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 235
ggcgcagacg gccaggagcc ggtgg                                          25

```
<210> SEQ ID NO 236
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 236
agggcgcaga cggccaggag ccggt                                            25

<210> SEQ ID NO 237
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 237
cgagggcgca gacggccagg agccg                                            25

<210> SEQ ID NO 238
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 238
cacgagggcg cagacggcca ggagc                                            25

<210> SEQ ID NO 239
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 239
gacacgaggg cgcagacggc cagga                                            25

<210> SEQ ID NO 240
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 240
aggacacgag ggcgcagacg gccag                                            25

<210> SEQ ID NO 241
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 241
caaggacacg agggcgcaga cggcc                                            25

<210> SEQ ID NO 242
```

```
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 242
gccaaggaca cgagggcgca gacgg                                          25

<210> SEQ ID NO 243
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 243
ttgccaagga cacgagggcg cagac                                          25

<210> SEQ ID NO 244
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 244
ggatgtgccc caggagtgca gcggt                                          25

<210> SEQ ID NO 245
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 245
taggatgtgc cccaggagtg cagcg                                          25

<210> SEQ ID NO 246
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 246
agtaggatgt gccccaggag tgcag                                          25

<210> SEQ ID NO 247
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 247
ggagtaggat gtgccccagg agtgc                                          25

<210> SEQ ID NO 248
<211> LENGTH: 25
```

```
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 248
atggagtagg atgtgcccca ggagt                                          25

<210> SEQ ID NO 249
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 249
tcatggagta ggatgtgccc cagga                                          25

<210> SEQ ID NO 250
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 250
aatcatggag taggatgtgc cccag                                          25

<210> SEQ ID NO 251
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 251
gaaatcatgg agtaggatgt gcccc                                          25

<210> SEQ ID NO 252
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 252
aggaaatcat ggagtaggat gtgcc                                          25

<210> SEQ ID NO 253
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 253
gcaggaaatc atggagtagg atgtg                                          25

<210> SEQ ID NO 254
<211> LENGTH: 25
<212> TYPE: DNA
```

```
<213> ORGANISM: Artificial Sequence
<220> FEATURE:
<223> OTHER INFORMATION: AON sequence designed to block the region
      surrounding the identified splice element (5' -> 3')

<400> SEQUENCE: 254
cagcaggaaa tcatggagta ggatg                                              25

<210> SEQ ID NO 255
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 255
accagcagga aatcatggag tagga                                              25

<210> SEQ ID NO 256
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 256
gaaccagcag gaaatcatgg agtag                                              25

<210> SEQ ID NO 257
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 257
gggaaccagc aggaaatcat ggagt                                              25

<210> SEQ ID NO 258
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 258
cggggaacca gcaggaaatc atgga                                              25

<210> SEQ ID NO 259
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 259
ctcggggaac cagcaggaaa tcatg                                              25

<210> SEQ ID NO 260
<211> LENGTH: 25
<212> TYPE: DNA
<213> ORGANISM: Artificial Sequence
```

```
<220> FEATURE:
<223> OTHER INFORMATION: AON sequence designed to block the region
      surrounding the identified splice element (5' -> 3')

<400> SEQUENCE: 260
ctctcgggga accagcagga aatca                                          25

<210> SEQ ID NO 261
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 261
agctctcggg gaaccagcag gaaat                                          25

<210> SEQ ID NO 262
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 262
tcagctctcg gggaaccagc aggaa                                          25

<210> SEQ ID NO 263
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 263
actcagctct cggggaacca gcagg                                          25

<210> SEQ ID NO 264
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 264
ccactcagct ctcggggaac cagca                                          25

<210> SEQ ID NO 265
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 265
agccactcag ctctcgggga accag                                          25

<210> SEQ ID NO 266
<211> LENGTH: 25
<212> TYPE: DNA
<213> ORGANISM: Artificial Sequence
<220> FEATURE:
```

<223> OTHER INFORMATION: AON sequence designed to block the region
      surrounding the identified splice element (5' -> 3')

<400> SEQUENCE: 266
ggagccactc agctctcggg gaacc                                            25

<210> SEQ ID NO 267
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 267
gaggagccac tcagctctcg gggaa                                            25

<210> SEQ ID NO 268
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 268
gggaggagcc actcagctct cgggg                                            25

<210> SEQ ID NO 269
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 269
tggggaggag ccactcagct ctcgg                                            25

<210> SEQ ID NO 270
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 270
actggggagg agccactcag ctctc                                            25

<210> SEQ ID NO 271
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 271
ggactgggga ggagccactc agctc                                            25

<210> SEQ ID NO 272
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 272
caggactggg gaggagccac tcagc                                              25

<210> SEQ ID NO 273
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 273
tccaggactg gggaggagcc actca                                              25

<210> SEQ ID NO 274
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 274
cctccaggac tggggaggag ccact                                              25

<210> SEQ ID NO 275
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 275
ctcctccagg actggggagg agcca                                              25

<210> SEQ ID NO 276
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 276
gtctcctcca ggactgggga ggagc                                              25

<210> SEQ ID NO 277
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 277
gagtctcctc caggactggg gagga                                              25

<210> SEQ ID NO 278
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

```
<400> SEQUENCE: 278
gtgagtctcc tccaggactg gggag                                              25

<210> SEQ ID NO 279
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 279
gggtgagtct cctccaggac tgggg                                              25

<210> SEQ ID NO 280
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 280
ctgggtgagt ctcctccagg actgg                                              25

<210> SEQ ID NO 281
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 281
agctgggtga gtctcctcca ggact                                              25

<210> SEQ ID NO 282
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 282
tgagctgggt gagtctcctc cagga                                              25

<210> SEQ ID NO 283
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 283
ggtgagctgg gtgagtctcc tccag                                              25

<210> SEQ ID NO 284
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')
```

-continued

<400> SEQUENCE: 284
ctggtgagct gggtgagtct cctcc                                            25

<210> SEQ ID NO 285
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 285
tgctggtgag ctgggtgagt ctcct                                            25

<210> SEQ ID NO 286
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 286
cctgctggtg agctgggtga gtctc                                            25

<210> SEQ ID NO 287
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 287
tccctgctgg tgagctgggt gagtc                                            25

<210> SEQ ID NO 288
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 288
gctccctgct ggtgagctgg gtgag                                            25

<210> SEQ ID NO 289
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 289
tggctccctg ctggtgagct gggtg                                            25

<210> SEQ ID NO 290
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 290

```
gctggctccc tgctggtgag ctggg                                         25
```

<210> SEQ ID NO 291
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 291

```
ctgctggctc cctgctggtg agctg                                         25
```

<210> SEQ ID NO 292
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 292

```
gtctgctggc tccctgctgg tgagc                                         25
```

<210> SEQ ID NO 293
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 293

```
gatgtgcccc aggagtgcag cggtt                                         25
```

<210> SEQ ID NO 294
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 294

```
aggatgtgcc ccaggagtgc agcgg                                         25
```

<210> SEQ ID NO 295
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 295

```
gtaggatgtg ccccaggagt gcagc                                         25
```

<210> SEQ ID NO 296
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 296
gagtaggatg tgccccagga gtgca                                          25

<210> SEQ ID NO 297
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 297
tggagtagga tgtgccccag gagtg                                          25

<210> SEQ ID NO 298
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 298
catggagtag gatgtgcccc aggag                                          25

<210> SEQ ID NO 299
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 299
atcatggagt aggatgtgcc ccagg                                          25

<210> SEQ ID NO 300
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 300
aaatcatgga gtaggatgtg cccca                                          25

<210> SEQ ID NO 301
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 301
ggaaatcatg gagtaggatg tgccc                                          25

<210> SEQ ID NO 302
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 302
caggaaatca tggagtagga tgtgc                                          25

<210> SEQ ID NO 303
<211> LENGTH: 25
<212> TYPE: DNA
<213> ORGANISM: Artificial Sequence
<220> FEATURE:
<223> OTHER INFORMATION: AON sequence designed to block the region
    surrounding the identified splice element (5' -> 3')

<400> SEQUENCE: 303
agcaggaaat catggagtag gatgt                                            25

<210> SEQ ID NO 304
<211> LENGTH: 25
<212> TYPE: DNA
<213> ORGANISM: Artificial Sequence
<220> FEATURE:
<223> OTHER INFORMATION: AON sequence designed to block the region
    surrounding the identified splice element (5' -> 3')

<400> SEQUENCE: 304
ccagcaggaa atcatggagt aggat                                            25

<210> SEQ ID NO 305
<211> LENGTH: 25
<212> TYPE: DNA
<213> ORGANISM: Artificial Sequence
<220> FEATURE:
<223> OTHER INFORMATION: AON sequence designed to block the region
    surrounding the identified splice element (5' -> 3')

<400> SEQUENCE: 305
aaccagcagg aaatcatgga gtagg                                            25

<210> SEQ ID NO 306
<211> LENGTH: 25
<212> TYPE: DNA
<213> ORGANISM: Artificial Sequence
<220> FEATURE:
<223> OTHER INFORMATION: AON sequence designed to block the region
    surrounding the identified splice element (5' -> 3')

<400> SEQUENCE: 306
ggaaccagca ggaaatcatg gagta                                            25

<210> SEQ ID NO 307
<211> LENGTH: 25
<212> TYPE: DNA
<213> ORGANISM: Artificial Sequence
<220> FEATURE:
<223> OTHER INFORMATION: AON sequence designed to block the region
    surrounding the identified splice element (5' -> 3')

<400> SEQUENCE: 307
ggggaaccag caggaaatca tggag                                            25

<210> SEQ ID NO 308
<211> LENGTH: 25
<212> TYPE: DNA
<213> ORGANISM: Artificial Sequence
<220> FEATURE:
<223> OTHER INFORMATION: AON sequence designed to block the region
    surrounding the identified splice element (5' -> 3')

<400> SEQUENCE: 308
tcggggaacc agcaggaaat catgg                                            25

```
<210> SEQ ID NO 309
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 309
tctcggggaa ccagcaggaa atcat                                          25

<210> SEQ ID NO 310
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 310
gctctcgggg aaccagcagg aaatc                                          25

<210> SEQ ID NO 311
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 311
cagctctcgg ggaaccagca ggaaa                                          25

<210> SEQ ID NO 312
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 312
ctcagctctc ggggaaccag cagga                                          25

<210> SEQ ID NO 313
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 313
cactcagctc tcggggaacc agcag                                          25

<210> SEQ ID NO 314
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 314
gccactcagc tctcggggaa ccagc                                          25
```

```
<210> SEQ ID NO 315
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 315
gagccactca gctctcgggg aacca                                              25

<210> SEQ ID NO 316
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 316
aggagccact cagctctcgg ggaac                                              25

<210> SEQ ID NO 317
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 317
ggaggagcca ctcagctctc gggga                                              25

<210> SEQ ID NO 318
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 318
ggggaggagc cactcagctc tcggg                                              25

<210> SEQ ID NO 319
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 319
ctggggagga gccactcagc tctcg                                              25

<210> SEQ ID NO 320
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 320
gactggggag gagccactca gctct                                              25

<210> SEQ ID NO 321
```

```
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 321
aggactgggg aggagccact cagct                                            25

<210> SEQ ID NO 322
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 322
ccaggactgg ggaggagcca ctcag                                            25

<210> SEQ ID NO 323
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 323
ctccaggact ggggaggagc cactc                                            25

<210> SEQ ID NO 324
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 324
tcctccagga ctggggagga gccac                                            25

<210> SEQ ID NO 325
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 325
tctcctccag gactggggag gagcc                                            25

<210> SEQ ID NO 326
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 326
agtctcctcc aggactgggg aggag                                            25

<210> SEQ ID NO 327
<211> LENGTH: 25
```

-continued

<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 327
tgagtctcct ccaggactgg ggagg                                          25

<210> SEQ ID NO 328
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 328
ggtgagtctc ctccaggact gggga                                          25

<210> SEQ ID NO 329
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 329
tgggtgagtc tcctccagga ctggg                                          25

<210> SEQ ID NO 330
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 330
gctgggtgag tctcctccag gactg                                          25

<210> SEQ ID NO 331
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 331
gagctgggtg agtctcctcc aggac                                          25

<210> SEQ ID NO 332
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 332
gtgagctggg tgagtctcct ccagg                                          25

<210> SEQ ID NO 333
<211> LENGTH: 25
<212> TYPE: DNA

```
<213> ORGANISM: Artificial Sequence
<220> FEATURE:
<223> OTHER INFORMATION: AON sequence designed to block the region
      surrounding the identified splice element (5' -> 3')

<400> SEQUENCE: 333
tggtgagctg ggtgagtctc ctcca                                              25

<210> SEQ ID NO 334
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 334
gctggtgagc tgggtgagtc tcctc                                              25

<210> SEQ ID NO 335
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 335
ctgctggtga gctgggtgag tctcc                                              25

<210> SEQ ID NO 336
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 336
ccctgctggt gagctgggtg agtct                                              25

<210> SEQ ID NO 337
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 337
ctccctgctg gtgagctggg tgagt                                              25

<210> SEQ ID NO 338
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 338
ggctccctgc tggtgagctg ggtga                                              25

<210> SEQ ID NO 339
<211> LENGTH: 25
<212> TYPE: DNA
<213> ORGANISM: Artificial Sequence
```

<220> FEATURE:
<223> OTHER INFORMATION: AON sequence designed to block the region
      surrounding the identified splice element (5' -> 3')

<400> SEQUENCE: 339
ctggctccct gctggtgagc tgggt                                    25

<210> SEQ ID NO 340
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 340
tgctggctcc ctgctggtga gctgg                                    25

<210> SEQ ID NO 341
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 341
tctgctggct ccctgctggt gagct                                    25

<210> SEQ ID NO 342
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 342
ggtctgctgg ctccctgctg gtgag                                    25

<210> SEQ ID NO 343
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 343
agcccctgct ttgcagggat gtagc                                    25

<210> SEQ ID NO 344
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 344
gcagcccctg ctttgcaggg atgta                                    25

<210> SEQ ID NO 345
<211> LENGTH: 25
<212> TYPE: DNA
<213> ORGANISM: Artificial Sequence
<220> FEATURE:

<223> OTHER INFORMATION: AON sequence designed to block the region
      surrounding the identified splice element (5' -> 3')

<400> SEQUENCE: 345
ctgcagcccc tgctttgcag ggatg                                            25

<210> SEQ ID NO 346
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 346
ccctgcagcc cctgctttgc aggga                                            25

<210> SEQ ID NO 347
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 347
ctccctgcag ccctgctttg cagg                                             25

<210> SEQ ID NO 348
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 348
ggctccctgc agcccctgct ttgca                                            25

<210> SEQ ID NO 349
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 349
tgggctccct gcagcccctg ctttg                                            25

<210> SEQ ID NO 350
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 350
tctgggctcc ctgcagcccc tgctt                                            25

<210> SEQ ID NO 351
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 351
catctgggct ccctgcagcc cctgc					25

<210> SEQ ID NO 352
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 352
cccatctggg ctccctgcag ccct					25

<210> SEQ ID NO 353
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 353
gccccatctg ggctccctgc agccc					25

<210> SEQ ID NO 354
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 354
ctgccccatc tgggctccct gcagc					25

<210> SEQ ID NO 355
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 355
ggctgcccca tctgggctcc ctgca					25

<210> SEQ ID NO 356
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 356
agggctgccc catctgggct ccctg					25

<210> SEQ ID NO 357
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 357
ccagggctgc cccatctggg ctccc                                              25

<210> SEQ ID NO 358
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 358
caccagggct gccccatctg ggctc                                              25

<210> SEQ ID NO 359
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 359
agcaccaggg ctgccccatc tgggc                                              25

<210> SEQ ID NO 360
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 360
gaagcaccag ggctgcccca tctgg                                              25

<210> SEQ ID NO 361
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 361
aagaagcacc agggctgccc catct                                              25

<210> SEQ ID NO 362
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 362
ggaagaagca ccagggctgc cccat                                              25

<210> SEQ ID NO 363
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 363
tgggaagaag caccagggct gcccc                                              25

<210> SEQ ID NO 364
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 364
ggtgggaaga agcaccaggg ctgcc                                              25

<210> SEQ ID NO 365
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 365
tgggtgggaa gaagcaccag ggctg                                              25

<210> SEQ ID NO 366
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 366
gctgggtggg aagaagcacc agggc                                              25

<210> SEQ ID NO 367
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 367
gcccctgctt tgcagggatg tagca                                              25

<210> SEQ ID NO 368
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 368
cagcccctgc tttgcaggga tgtag                                              25

<210> SEQ ID NO 369
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 369
tgcagcccct gctttgcagg gatgt                                        25

<210> SEQ ID NO 370
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 370
cctgcagccc ctgctttgca gggat                                        25

<210> SEQ ID NO 371
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 371
tccctgcagc ccctgctttg caggg                                        25

<210> SEQ ID NO 372
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 372
gctccctgca gccctgctt tgcag                                         25

<210> SEQ ID NO 373
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 373
gggctccctg cagccctgc tttgc                                         25

<210> SEQ ID NO 374
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 374
ctgggctccc tgcagcccct gcttt                                        25

<210> SEQ ID NO 375
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 375
atctgggctc cctgcagccc ctgct                                              25

<210> SEQ ID NO 376
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 376
ccatctgggc tccctgcagc ccctg                                              25

<210> SEQ ID NO 377
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 377
ccccatctgg gctccctgca gcccc                                              25

<210> SEQ ID NO 378
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 378
tgccccatct gggctccctg cagcc                                              25

<210> SEQ ID NO 379
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 379
gctgccccat ctgggctccc tgcag                                              25

<210> SEQ ID NO 380
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 380
gggctgcccc atctgggctc cctgc                                              25

<210> SEQ ID NO 381
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 381
cagggctgcc ccatctgggc tccct                                              25

<210> SEQ ID NO 382
<211> LENGTH: 25
<212> TYPE: DNA
<213> ORGANISM: Artificial Sequence
<220> FEATURE:
<223> OTHER INFORMATION: AON sequence designed to block the region
    surrounding the identified splice element (5' -> 3')

<400> SEQUENCE: 382
accagggctg ccccatctgg gctcc                                    25

<210> SEQ ID NO 383
<211> LENGTH: 25
<212> TYPE: DNA
<213> ORGANISM: Artificial Sequence
<220> FEATURE:
<223> OTHER INFORMATION: AON sequence designed to block the region
    surrounding the identified splice element (5' -> 3')

<400> SEQUENCE: 383
gcaccagggc tgccccatct gggct                                    25

<210> SEQ ID NO 384
<211> LENGTH: 25
<212> TYPE: DNA
<213> ORGANISM: Artificial Sequence
<220> FEATURE:
<223> OTHER INFORMATION: AON sequence designed to block the region
    surrounding the identified splice element (5' -> 3')

<400> SEQUENCE: 384
aagcaccagg gctgccccat ctggg                                    25

<210> SEQ ID NO 385
<211> LENGTH: 25
<212> TYPE: DNA
<213> ORGANISM: Artificial Sequence
<220> FEATURE:
<223> OTHER INFORMATION: AON sequence designed to block the region
    surrounding the identified splice element (5' -> 3')

<400> SEQUENCE: 385
agaagcacca gggctgcccc atctg                                    25

<210> SEQ ID NO 386
<211> LENGTH: 25
<212> TYPE: DNA
<213> ORGANISM: Artificial Sequence
<220> FEATURE:
<223> OTHER INFORMATION: AON sequence designed to block the region
    surrounding the identified splice element (5' -> 3')

<400> SEQUENCE: 386
gaagaagcac cagggctgcc ccatc                                    25

<210> SEQ ID NO 387
<211> LENGTH: 25
<212> TYPE: DNA
<213> ORGANISM: Artificial Sequence
<220> FEATURE:
<223> OTHER INFORMATION: AON sequence designed to block the region
    surrounding the identified splice element (5' -> 3')

<400> SEQUENCE: 387
gggaagaagc cagggctg cccca                                      25

<210> SEQ ID NO 388
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 388
gtgggaagaa gcaccagggc tgccc                                              25

<210> SEQ ID NO 389
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 389
gggtgggaag aagcaccagg gctgc                                              25

<210> SEQ ID NO 390
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 390
ctgggtggga agaagcacca gggct                                              25

<210> SEQ ID NO 391
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 391
agctgggtgg gaagaagcac caggg                                              25

<210> SEQ ID NO 392
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 392
cagcttgtag ctggggtagc tgggt                                              25

<210> SEQ ID NO 393
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 393
tccagcttgt agctggggta gctgg                                              25

```
<210> SEQ ID NO 394
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 394
tctccagctt gtagctgggg tagct                                              25

<210> SEQ ID NO 395
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 395
gttctccagc ttgtagctgg ggtag                                              25

<210> SEQ ID NO 396
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 396
aggttctcca gcttgtagct ggggt                                              25

<210> SEQ ID NO 397
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 397
tcaggttctc cagcttgtag ctggg                                              25

<210> SEQ ID NO 398
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 398
gctcaggttc tccagcttgt agctg                                              25

<210> SEQ ID NO 399
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 399
gagctcaggt tctccagctt gtagc                                              25

<210> SEQ ID NO 400
```

<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 400
aggagctcag gttctccagc ttgta                                    25

<210> SEQ ID NO 401
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 401
agaggagctc aggttctcca gcttg                                    25

<210> SEQ ID NO 402
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 402
tcagaggagc tcaggttctc cagct                                    25

<210> SEQ ID NO 403
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 403
tttcagagga gctcaggttc tccag                                    25

<210> SEQ ID NO 404
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 404
agcttgtagc tggggtagct gggtg                                    25

<210> SEQ ID NO 405
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 405
ccagcttgta gctggggtag ctggg                                    25

<210> SEQ ID NO 406
<211> LENGTH: 25

```
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 406
ctccagcttg tagctggggt agctg                                    25

<210> SEQ ID NO 407
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 407
ttctccagct tgtagctggg gtagc                                    25

<210> SEQ ID NO 408
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 408
ggttctccag cttgtagctg gggta                                    25

<210> SEQ ID NO 409
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 409
caggttctcc agcttgtagc tgggg                                    25

<210> SEQ ID NO 410
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 410
ctcaggttct ccagcttgta gctgg                                    25

<210> SEQ ID NO 411
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 411
agctcaggtt ctccagcttg tagct                                    25

<210> SEQ ID NO 412
<211> LENGTH: 25
<212> TYPE: DNA
```

```
<213> ORGANISM: Artificial Sequence
<220> FEATURE:
<223> OTHER INFORMATION: AON sequence designed to block the region
      surrounding the identified splice element (5' -> 3')

<400> SEQUENCE: 412
ggagctcagg ttctccagct tgtag                                            25

<210> SEQ ID NO 413
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 413
gaggagctca ggttctccag cttgt                                            25

<210> SEQ ID NO 414
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 414
cagaggagct caggttctcc agctt                                            25

<210> SEQ ID NO 415
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 415
ttcagaggag ctcaggttct ccagc                                            25

<210> SEQ ID NO 416
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 416
atttcagagg agctcaggtt ctcca                                            25

<210> SEQ ID NO 417
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 417
ggggtggtac gggtcagggt ggccg                                            25

<210> SEQ ID NO 418
<211> LENGTH: 25
<212> TYPE: DNA
<213> ORGANISM: Artificial Sequence
```

<220> FEATURE:
<223> OTHER INFORMATION: AON sequence designed to block the region
      surrounding the identified splice element (5' -> 3')

<400> SEQUENCE: 418
tgggggtggt acgggtcagg gtggc                                          25

<210> SEQ ID NO 419
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 419
ggtgggggtg gtacgggtca gggtg                                          25

<210> SEQ ID NO 420
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 420
aaggtggggg tggtacgggt caggg                                          25

<210> SEQ ID NO 421
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 421
agaaggtggg ggtggtacgg gtcag                                          25

<210> SEQ ID NO 422
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 422
gaagaaggtg ggggtggtac gggtc                                          25

<210> SEQ ID NO 423
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 423
gggaagaagg tggggtggt acggg                                           25

<210> SEQ ID NO 424
<211> LENGTH: 25
<212> TYPE: DNA
<213> ORGANISM: Artificial Sequence
<220> FEATURE:

```
<223> OTHER INFORMATION: AON sequence designed to block the region
      surrounding the identified splice element (5' -> 3')

<400> SEQUENCE: 424
tggggaagaa ggtgggggtg gtacg                                              25

<210> SEQ ID NO 425
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 425
cttggggaag aaggtggggg tggta                                              25

<210> SEQ ID NO 426
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 426
tccttgggga agaaggtggg ggtgg                                              25

<210> SEQ ID NO 427
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 427
tgtccttggg gaagaaggtg ggggt                                              25

<210> SEQ ID NO 428
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 428
gatgtccttg gggaagaagg tgggg                                              25

<210> SEQ ID NO 429
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 429
aggatgtcct tggggaagaa ggtgg                                              25

<210> SEQ ID NO 430
<211> LENGTH: 25
<212> TYPE: DNA
<213> ORGANISM: Artificial Sequence
<220> FEATURE:
<223> OTHER INFORMATION: AON sequence designed to block the region
``` surrounding the identified splice element (5' -> 3')

<400> SEQUENCE: 430
tcaggatgtc cttggggaag aaggt					25

<210> SEQ ID NO 431
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 431
ggtcaggatg tccttgggga agaag					25

<210> SEQ ID NO 432
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 432
agggtcagga tgtccttggg gaaga					25

<210> SEQ ID NO 433
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 433
gcagggtcag gatgtccttg gggaa					25

<210> SEQ ID NO 434
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 434
ccgcagggtc aggatgtcct tgggg					25

<210> SEQ ID NO 435
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 435
agccgcaggg tcaggatgtc cttgg					25

<210> SEQ ID NO 436
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 436
gggtggtacg ggtcagggtg gccgt                                          25

<210> SEQ ID NO 437
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 437
gggggtggta cgggtcaggg tggcc                                          25

<210> SEQ ID NO 438
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 438 gtggggtgg tacgggtcag ggtgg                                           25

<210> SEQ ID NO 439
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 439 aggtggggt ggtacgggtc agggt                                           25

<210> SEQ ID NO 440
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 440
gaaggtgggg gtggtacggg tcagg                                          25

<210> SEQ ID NO 441
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 441
aagaaggtgg gggtggtacg ggtca                                          25

<210> SEQ ID NO 442
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

```
<400> SEQUENCE: 442
ggaagaaggt gggggtggta cgggt                                        25

<210> SEQ ID NO 443
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 443
ggggaagaag gtgggggtgg tacgg                                        25

<210> SEQ ID NO 444
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 444
ttggggaaga aggtgggggt ggtac                                        25

<210> SEQ ID NO 445
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 445
ccttggggaa gaaggtgggg gtggt                                        25

<210> SEQ ID NO 446
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 446
gtccttgggg aagaaggtgg gggtg                                        25

<210> SEQ ID NO 447
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 447
atgtccttgg ggaagaaggt ggggg                                        25

<210> SEQ ID NO 448
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 448
```

```
ggatgtcctt ggggaagaag gtggg                                          25
```

<210> SEQ ID NO 449
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 449

```
caggatgtcc ttggggaaga aggtg                                          25
```

<210> SEQ ID NO 450
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 450

```
gtcaggatgt ccttggggaa gaagg                                          25
```

<210> SEQ ID NO 451
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 451

```
gggtcaggat gtccttgggg aagaa                                          25
```

<210> SEQ ID NO 452
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 452

```
cagggtcagg atgtccttgg ggaag                                          25
```

<210> SEQ ID NO 453
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 453

```
cgcagggtca ggatgtcctt gggga                                          25
```

<210> SEQ ID NO 454
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 454

```
gccgcagggt caggatgtcc ttggg                                              25

<210> SEQ ID NO 455
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 455
cagccgcagg gtcaggatgt ccttg                                              25

<210> SEQ ID NO 456
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 456
cgtccagccg cagggtcagg atgtc                                              25

<210> SEQ ID NO 457
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 457
cacgtccagc cgcagggtca ggatg                                              25

<210> SEQ ID NO 458
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 458
atcacgtcca gccgcagggt cagga                                              25

<210> SEQ ID NO 459
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 459
tcatcacgtc cagccgcagg gtcag                                              25

<210> SEQ ID NO 460
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 460
catcatcacg tccagccgca gggtc                                              25
```

<210> SEQ ID NO 461
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 461
tccatcatca cgtccagccg caggg                                         25

<210> SEQ ID NO 462
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 462
tctccatcat cacgtccagc cgcag                                         25

<210> SEQ ID NO 463
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 463
agtctccatc atcacgtcca gccgc                                         25

<210> SEQ ID NO 464
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 464
tcagtctcca tcatcacgtc cagcc                                         25

<210> SEQ ID NO 465
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 465
tctcagtctc catcatcacg tccag                                         25

<210> SEQ ID NO 466
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 466
gttctcagtc tccatcatca cgtcc                                         25

<210> SEQ ID NO 467
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 467
cggttctcag tctccatcat cacgt                                           25

<210> SEQ ID NO 468
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 468
ggcggttctc agtctccatc atcac                                           25

<210> SEQ ID NO 469
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 469
gaggcggttc tcagtctcca tcatc                                           25

<210> SEQ ID NO 470
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 470
tggaggcggt tctcagtctc catca                                           25

<210> SEQ ID NO 471
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 471
agtggaggcg gttctcagtc tccat                                           25

<210> SEQ ID NO 472
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 472
gaagtggagg cggttctcag tctcc                                           25

```
<210> SEQ ID NO 473
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 473
gtccagccgc agggtcagga tgtcc                                         25

<210> SEQ ID NO 474
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 474
acgtccagcc gcagggtcag gatgt                                         25

<210> SEQ ID NO 475
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 475
tcacgtccag ccgcagggtc aggat                                         25

<210> SEQ ID NO 476
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 476
catcacgtcc agccgcaggg tcagg                                         25

<210> SEQ ID NO 477
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 477
atcatcacgt ccagccgcag ggtca                                         25

<210> SEQ ID NO 478
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 478
ccatcatcac gtccagccgc agggt                                         25

<210> SEQ ID NO 479
```

```
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 479
ctccatcatc acgtccagcc gcagg                                          25

<210> SEQ ID NO 480
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 480
gtctccatca tcacgtccag ccgca                                          25

<210> SEQ ID NO 481
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 481
cagtctccat catcacgtcc agccg                                          25

<210> SEQ ID NO 482
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 482
ctcagtctcc atcatcacgt ccagc                                          25

<210> SEQ ID NO 483
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 483
ttctcagtct ccatcatcac gtcca                                          25

<210> SEQ ID NO 484
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 484
ggttctcagt ctccatcatc acgtc                                          25

<210> SEQ ID NO 485
<211> LENGTH: 25
```

```
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 485
gcggttctca gtctccatca tcacg                                             25

<210> SEQ ID NO 486
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 486
aggcggttct cagtctccat catca                                             25

<210> SEQ ID NO 487
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 487
ggaggcggtt ctcagtctcc atcat                                             25

<210> SEQ ID NO 488
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 488
gtggaggcgg ttctcagtct ccatc                                             25

<210> SEQ ID NO 489
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 489
aagtggaggc ggttctcagt ctcca                                             25

<210> SEQ ID NO 490
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 490
tgaagtggag gcggttctca gtctc                                             25

<210> SEQ ID NO 491
<211> LENGTH: 25
<212> TYPE: DNA
```

```
<213> ORGANISM: Artificial Sequence
<220> FEATURE:
<223> OTHER INFORMATION: AON sequence designed to block the region
      surrounding the identified splice element (5' -> 3')

<400> SEQUENCE: 491
tgccctgccc accgtgaagt ggagg                                           25

<210> SEQ ID NO 492
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 492
cctgccctgc ccaccgtgaa gtgga                                           25

<210> SEQ ID NO 493
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 493
cccctgccct gcccaccgtg aagtg                                           25

<210> SEQ ID NO 494
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 494 cgccctgcc ctgcccaccg tgaag                                            25

<210> SEQ ID NO 495
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 495
cccgcccctg ccctgcccac cgtga                                           25

<210> SEQ ID NO 496
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 496
gccctgccca ccgtgaagtg gaggc                                           25

<210> SEQ ID NO 497
<211> LENGTH: 25
<212> TYPE: DNA
<213> ORGANISM: Artificial Sequence
```

<220> FEATURE:
<223> OTHER INFORMATION: AON sequence designed to block the region
      surrounding the identified splice element (5' -> 3')

<400> SEQUENCE: 497
ctgccctgcc caccgtgaag tggag                                              25

<210> SEQ ID NO 498
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 498
ccctgccctg cccaccgtga agtgg                                              25

<210> SEQ ID NO 499
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 499 gccctgccc tgcccaccgt gaagt                                               25

<210> SEQ ID NO 500
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 500 ccgccctgc cctgcccacc gtgaa                                               25

<210> SEQ ID NO 501
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 501
ccccgcccct gccctgccca ccgtg                                              25

<210> SEQ ID NO 502
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 502
gcccccgccc ctgccctgcc caccg                                              25

<210> SEQ ID NO 503
<211> LENGTH: 25
<212> TYPE: DNA
<213> ORGANISM: Artificial Sequence
<220> FEATURE:

```
<223> OTHER INFORMATION: AON sequence designed to block the region
      surrounding the identified splice element (5' -> 3')

<400> SEQUENCE: 503 ccgccccgc ccctgccctg cccac                                          25

<210> SEQ ID NO 504
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 504
cgccgccccc gccctgccc tgccc                                          25

<210> SEQ ID NO 505
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 505
gccgccgccc ccgcccctgc cctgc                                         25

<210> SEQ ID NO 506
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 506
tggccgccgc ccccgcccct gccct                                         25

<210> SEQ ID NO 507
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 507
cctggccgcc gccccgccc ctgcc                                          25

<210> SEQ ID NO 508
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 508
gccctggccg ccgccccgc ccctg                                          25

<210> SEQ ID NO 509
<211> LENGTH: 25
<212> TYPE: DNA
<213> ORGANISM: Artificial Sequence
<220> FEATURE:
<223> OTHER INFORMATION: AON sequence designed to block the region
``` surrounding the identified splice element (5' -> 3')

<400> SEQUENCE: 509
ctgccctggc cgccgccccc gcccc                                               25

<210> SEQ ID NO 510
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 510
ctctgccctg gccgccgccc ccgcc                                               25

<210> SEQ ID NO 511
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 511
ccctctgccc tggccgccgc ccccg                                               25

<210> SEQ ID NO 512
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 512
caccctctgc cctggccgcc gcccc                                               25

<210> SEQ ID NO 513
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 513
cgcaccctct gccctggccg ccgcc                                               25

<210> SEQ ID NO 514
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 514
cgcgcaccct ctgccctggc cgccg                                               25

<210> SEQ ID NO 515
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

-continued

<400> SEQUENCE: 515
cccccgcccc tgccctgccc accgt                                              25

<210> SEQ ID NO 516
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 516
cgcccccgcc cctgccctgc ccacc                                              25

<210> SEQ ID NO 517
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 517
gccgcccccg ccctgccct gccca                                               25

<210> SEQ ID NO 518
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 518
ccgccgcccc cgcccctgcc ctgcc                                              25

<210> SEQ ID NO 519
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 519
ggccgccgcc ccgcccctg ccctg                                               25

<210> SEQ ID NO 520
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 520
ctggccgccg ccccgcccc tgccc                                               25

<210> SEQ ID NO 521
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

```
<400> SEQUENCE: 521
ccctggccgc cgccccgcc cctgc                                              25

<210> SEQ ID NO 522
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 522
tgccctggcc gccgccccg ccct                                               25

<210> SEQ ID NO 523
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 523
tctgccctgg ccgccgcccc cgccc                                             25

<210> SEQ ID NO 524
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 524
cctctgccct ggccgccgcc cccgc                                             25

<210> SEQ ID NO 525
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 525
accctctgcc ctggccgccg ccccc                                             25

<210> SEQ ID NO 526
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 526
gcaccctctg ccctggccgc cgccc                                             25

<210> SEQ ID NO 527
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 527
```
gcgcaccctc tgccctggcc gccgc                                              25

<210> SEQ ID NO 528
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 528
agagatgggg gtttattgat gttcc                                              25

<210> SEQ ID NO 529
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 529
gaagagatgg gggtttattg atgtt                                              25

<210> SEQ ID NO 530
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 530
tagaagagat gggggtttat tgatg                                              25

<210> SEQ ID NO 531
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 531
tctagaagag atgggggttt attga                                              25

<210> SEQ ID NO 532
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 532
gatctagaag agatggggt ttatt                                               25

<210> SEQ ID NO 533
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 533
ttgatctaga agagatgggg gttta                                    25

<210> SEQ ID NO 534
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 534
ctttgatcta gaagagatgg gggtt                                    25

<210> SEQ ID NO 535
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 535
atctttgatc tagaagagat ggggg                                    25

<210> SEQ ID NO 536
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 536
ggatctttga tctagaagag atggg                                    25

<210> SEQ ID NO 537
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 537
ctggatcttt gatctagaag agatg                                    25

<210> SEQ ID NO 538
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 538
agctggatct tgatctaga agaga                                     25

<210> SEQ ID NO 539
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 539
ttagctggat ctttgatcta gaaga                                    25

<210> SEQ ID NO 540
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 540
tgttagctgg atctttgatc tagaa                                         25

<210> SEQ ID NO 541
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 541
ctggaaggga agcagctctg gggtt                                         25

<210> SEQ ID NO 542
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 542
tctggaaggg aagcagctct ggggt                                         25

<210> SEQ ID NO 543
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 543
atctggaagg gaagcagctc tgggg                                         25

<210> SEQ ID NO 544
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 544
catctggaag ggaagcagct ctggg                                         25

<210> SEQ ID NO 545
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 545
acatctggaa gggaagcagc tctgg                                         25

<210> SEQ ID NO 546
<211> LENGTH: 25
<212> TYPE: DNA
<213> ORGANISM: Artificial Sequence

```
<220> FEATURE:
<223> OTHER INFORMATION: AON sequence 5' -> 3'

<400> SEQUENCE: 546
cacatctgga agggaagcag ctctg                                              25

<210> SEQ ID NO 547
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 547
ccacatctgg aagggaagca gctct                                              25

<210> SEQ ID NO 548
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 548
accacatctg gaagggaagc agctc                                              25

<210> SEQ ID NO 549
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 549
gaccacatct ggaagggaag cagct                                              25

<210> SEQ ID NO 550
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 550
ggaccacatc tggaagggaa gcagc                                              25

<210> SEQ ID NO 551
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 551
aggaccacat ctggaaggga agcag                                              25

<210> SEQ ID NO 552
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 552
caggaccaca tctggaaggg aagca                                              25
```

<210> SEQ ID NO 553
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 553
gcaggaccac atctggaagg gaagc                                   25

<210> SEQ ID NO 554
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 554
tgcaggacca catctggaag ggaag                                   25

<210> SEQ ID NO 555
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 555
ctgcaggacc acatctggaa gggaa                                   25

<210> SEQ ID NO 556
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 556
gctgcaggac cacatctgga aggga                                   25

<210> SEQ ID NO 557
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 557
ggctgcagga ccacatctgg aaggg                                   25

<210> SEQ ID NO 558
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 558
cggctgcagg accacatctg gaagg                                   25

<210> SEQ ID NO 559
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 559
tcggctgcag gaccacatct ggaag                                    25

<210> SEQ ID NO 560
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 560
ctcggctgca ggaccacatc tggaa                                    25

<210> SEQ ID NO 561
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 561
gctcggctgc aggaccacat ctgga                                    25

<210> SEQ ID NO 562
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 562
ggctcggctg caggaccaca tctgg                                    25

<210> SEQ ID NO 563
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 563
gggctcggct gcaggaccac atctg                                    25

<210> SEQ ID NO 564
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 564
agggctcggc tgcaggacca catct                                    25

<210> SEQ ID NO 565
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 565
cagggctcgg ctgcaggacc acatc                                    25

<210> SEQ ID NO 566

```
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 566
gcagggctcg gctgcaggac cacat                                    25

<210> SEQ ID NO 567
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 567
ggcagggctc ggctgcagga ccaca                                    25

<210> SEQ ID NO 568
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 568
gggcagggct cggctgcagg accac                                    25

<210> SEQ ID NO 569
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 569
agggcagggc tcggctgcag gacca                                    25

<210> SEQ ID NO 570
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 570
aagggcaggg ctcggctgca ggacc                                    25

<210> SEQ ID NO 571
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 571
taagggcagg gctcggctgc aggac                                    25

<210> SEQ ID NO 572
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 572
```
ctaagggcag ggctcggctg cagga                          25

<210> SEQ ID NO 573
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 573
gctaagggca gggctcggct gcagg                          25

<210> SEQ ID NO 574
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 574
agctaagggc agggctcggc tgcag                          25

<210> SEQ ID NO 575
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 575
cagctaaggg cagggctcgg ctgca                          25

<210> SEQ ID NO 576
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 576
ccagctaagg gcagggctcg gctgc                          25

<210> SEQ ID NO 577
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 577
tccagctaag gcagggctc ggctg                           25

<210> SEQ ID NO 578
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 578
ctccagctaa gggcagggct cggct                          25

<210> SEQ ID NO 579
<211> LENGTH: 25
<212> TYPE: DNA

```
<213> ORGANISM: Artificial Sequence
<220> FEATURE:
<223> OTHER INFORMATION: AON sequence 5' -> 3'

<400> SEQUENCE: 579
cctccagcta agggcagggc tcggc                                              25

<210> SEQ ID NO 580
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 580
acctccagct aagggcaggg ctcgg                                              25

<210> SEQ ID NO 581
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 581
gacctccagc taagggcagg gctcg                                              25

<210> SEQ ID NO 582
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 582
gacctccagc taagggcagg gctcg                                              25

<210> SEQ ID NO 583
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 583
tcgacctcca gctaagggca gggct                                              25

<210> SEQ ID NO 584
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 584
gtcgacctcc agctaagggc agggc                                              25

<210> SEQ ID NO 585
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 585
tgtcgacctc cagctaaggg caggg                                              25
```

<210> SEQ ID NO 586
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 586
ctgtcgacct ccagctaagg gcagg 25

<210> SEQ ID NO 587
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 587
cctgtcgacc tccagctaag ggcag 25

<210> SEQ ID NO 588
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 588
acctgtcgac ctccagctaa gggca 25

<210> SEQ ID NO 589
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 589
cacctgtcga cctccagcta agggc 25

<210> SEQ ID NO 590
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 590
ccacctgtcg acctccagct aaggg 25

<210> SEQ ID NO 591
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 591
cccacctgtc gacctccagc taagg 25

<210> SEQ ID NO 592
<211> LENGTH: 25
<212> TYPE: DNA
<213> ORGANISM: Artificial Sequence
<220> FEATURE:

<223> OTHER INFORMATION: AON sequence 5' -> 3'

<400> SEQUENCE: 592
tcccacctgt cgacctccag ctaag                                    25

<210> SEQ ID NO 593
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 593
atcccacctg tcgacctcca gctaa                                    25

<210> SEQ ID NO 594
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 594
gatcccacct gtcgacctcc agcta                                    25

<210> SEQ ID NO 595
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 595
ggatcccacc tgtcgacctc cagct                                    25

<210> SEQ ID NO 596
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 596
aggatcccac tgtcgacct ccagc                                     25

<210> SEQ ID NO 597
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 597
caggatccca cctgtcgacc tccag                                    25

<210> SEQ ID NO 598
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 598
ccaggatccc acctgtcgac ctcca                                    25

-continued

```
<210> SEQ ID NO 599
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 599
tccaggatcc cacctgtcga cctcc                                              25

<210> SEQ ID NO 600
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 600
atccaggatc ccacctgtcg acctc                                              25

<210> SEQ ID NO 601
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 601
catccaggat cccacctgtc gacct                                              25

<210> SEQ ID NO 602
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 602
acatccagga tcccacctgt cgacc                                              25

<210> SEQ ID NO 603
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 603
gacatccagg atcccacctg tcgac                                              25

<210> SEQ ID NO 604
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 604
agacatccag gatcccacct gtcga                                              25

<210> SEQ ID NO 605
<211> LENGTH: 25
<212> TYPE: DNA
<213> ORGANISM: Artificial Sequence
<220> FEATURE:
<223> OTHER INFORMATION: AON sequence 5' -> 3'
```

```
<400> SEQUENCE: 605
tagacatcca ggatcccacc tgtcg                                          25

<210> SEQ ID NO 606
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 606
gtagacatcc aggatcccac ctgtc                                          25

<210> SEQ ID NO 607
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 607
tgtagacatc caggatccca cctgt                                          25

<210> SEQ ID NO 608
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 608
atgtagacat ccaggatccc acctg                                          25

<210> SEQ ID NO 609
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 609
gatgtagaca tccaggatcc cacct                                          25

<210> SEQ ID NO 610
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 610
agatgtagac atccaggatc ccacc                                          25

<210> SEQ ID NO 611
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 611
aagatgtaga catccaggat cccac                                          25

<210> SEQ ID NO 612
<211> LENGTH: 25
```

```
<212> TYPE: DNA
<213> ORGANISM: Artificial Sequence
<220> FEATURE:
<223> OTHER INFORMATION: AON sequence 5' -> 3'

<400> SEQUENCE: 612
gaagatgtag acatccagga tccca                                              25

<210> SEQ ID NO 613
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 613
ggaagatgta gacatccagg atccc                                              25

<210> SEQ ID NO 614
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 614
aggaagatgt agacatccag gatcc                                              25

<210> SEQ ID NO 615
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 615
caggaagatg tagacatcca ggatc                                              25

<210> SEQ ID NO 616
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 616
ccaggaagat gtagacatcc aggat                                              25

<210> SEQ ID NO 617
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 617
cccaggaaga tgtagacatc cagga                                              25

<210> SEQ ID NO 618
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 618
```
gcccaggaag atgtagacat ccagg                                         25

<210> SEQ ID NO 619
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 619
ggcccaggaa gatgtagaca tccag                                         25

<210> SEQ ID NO 620
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 620
gggcccagga agatgtagac atcca                                         25

<210> SEQ ID NO 621
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 621
tgggcccagg aagatgtaga catcc                                         25

<210> SEQ ID NO 622
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 622
ctgggcccag gaagatgtag acatc                                         25

<210> SEQ ID NO 623
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 623
tctgggccca ggaagatgta gacat                                         25

<210> SEQ ID NO 624
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 624
ctctgggccc aggaagatgt agaca                                         25

<210> SEQ ID NO 625
<211> LENGTH: 25
<212> TYPE: DNA
<213> ORGANISM: Artificial Sequence

```
<220> FEATURE:
<223> OTHER INFORMATION: AON sequence 5' -> 3'

<400> SEQUENCE: 625
gctctgggcc caggaagatg tagac                                              25

<210> SEQ ID NO 626
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 626
ggctctgggc ccaggaagat gtaga                                              25

<210> SEQ ID NO 627
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 627
gggctctggg cccaggaaga tgtag                                              25

<210> SEQ ID NO 628
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 628
tgggctctgg gcccaggaag atgta                                              25

<210> SEQ ID NO 629
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 629
ttgggctctg ggcccaggaa gatgt                                              25

<210> SEQ ID NO 630
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 630
cttgggctct gggcccagga agatg                                              25

<210> SEQ ID NO 631
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 631
tcttgggctc tgggcccagg aagat                                              25
```

<210> SEQ ID NO 632
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 632
ctcttgggct ctgggcccag gaaga                                              25

<210> SEQ ID NO 633
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 633
gctcttgggc tctgggccca ggaag                                              25

<210> SEQ ID NO 634
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 634
cgctcttggg ctctgggccc aggaa                                              25

<210> SEQ ID NO 635
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 635
acgctcttgg gctctgggcc cagga                                              25

<210> SEQ ID NO 636
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 636
cacgctcttg ggctctgggc ccagg                                              25

<210> SEQ ID NO 637
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 637
ccacgctctt gggctctggg cccag                                              25

<210> SEQ ID NO 638
<211> LENGTH: 25
<212> TYPE: DNA
<213> ORGANISM: Artificial Sequence
<220> FEATURE:
<223> OTHER INFORMATION: AON sequence 5' -> 3'

-continued

```
<400> SEQUENCE: 638
accacgctct tgggctctgg gccca                                              25

<210> SEQ ID NO 639
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 639
caccacgctc ttgggctctg ggccc                                              25

<210> SEQ ID NO 640
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 640
gcaccacgct cttgggctct gggcc                                              25

<210> SEQ ID NO 641
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 641
tgcaccacgc tcttgggctc tgggc                                              25

<210> SEQ ID NO 642
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 642
ctgcaccacg ctcttgggct ctggg                                              25

<210> SEQ ID NO 643
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 643
gctgcaccac gctcttgggc tctgg                                              25

<210> SEQ ID NO 644
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 644
tgctgcacca cgctcttggg ctctg                                              25

<210> SEQ ID NO 645
```

-continued

```
<210> SEQ ID NO 645
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 645
ctgctgcacc acgctcttgg gctct                                              25

<210> SEQ ID NO 646
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 646
actgctgcac cacgctcttg ggctc                                              25

<210> SEQ ID NO 647
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 647
tactgctgca ccacgctctt gggct                                              25

<210> SEQ ID NO 648
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 648
gtactgctgc accacgctct tgggc                                              25

<210> SEQ ID NO 649
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 649
ggtactgctg caccacgctc ttggg                                              25

<210> SEQ ID NO 650
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 650
aggtactgct gcaccacgct cttgg                                              25

<210> SEQ ID NO 651
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 651
```
caggtactgc tgcaccacgc tcttg                                        25

<210> SEQ ID NO 652
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 652
ccaggtactg ctgcaccacg ctctt                                        25

<210> SEQ ID NO 653
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 653
tccaggtact gctgcaccac gctct                                        25

<210> SEQ ID NO 654
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 654
gtccaggtac tgctgcacca cgctc                                        25

<210> SEQ ID NO 655
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 655
cgtccaggta ctgctgcacc acgct                                        25

<210> SEQ ID NO 656
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 656
acgtccaggt actgctgcac cacgc                                        25

<210> SEQ ID NO 657
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 657
aacgtccagg tactgctgca ccacg                                        25

<210> SEQ ID NO 658
<211> LENGTH: 25
<212> TYPE: DNA

```
<213> ORGANISM: Artificial Sequence
<220> FEATURE:
<223> OTHER INFORMATION: AON sequence 5' -> 3'

<400> SEQUENCE: 658
caacgtccag gtactgctgc accac                                              25

<210> SEQ ID NO 659
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 659
acaacgtcca ggtactgctg cacca                                              25

<210> SEQ ID NO 660
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 660
cacaacgtcc aggtactgct gcacc                                              25

<210> SEQ ID NO 661
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 661
ccacaacgtc caggtactgc tgcac                                              25

<210> SEQ ID NO 662
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 662
cccacaacgt ccaggtactg ctgca                                              25

<210> SEQ ID NO 663
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 663
acccacaacg tccaggtact gctgc                                              25

<210> SEQ ID NO 664
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 664
tacccacaac gtccaggtac tgctg                                              25
```

<210> SEQ ID NO 665
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 665
ctacccacaa cgtccaggta ctgct                                             25

<210> SEQ ID NO 666
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 666
cctacccaca acgtccaggt actgc                                             25

<210> SEQ ID NO 667
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 667
ccctacccac aacgtccagg tactg                                             25

<210> SEQ ID NO 668
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 668
gccctaccca caacgtccag gtact                                             25

<210> SEQ ID NO 669
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 669
ggccctaccc acaacgtcca ggtac                                             25

<210> SEQ ID NO 670
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 670
aggccctacc cacaacgtcc aggta                                             25

<210> SEQ ID NO 671
<211> LENGTH: 25
<212> TYPE: DNA
<213> ORGANISM: Artificial Sequence
<220> FEATURE:

<223> OTHER INFORMATION: AON sequence 5' -> 3'

<400> SEQUENCE: 671
caggccctac ccacaacgtc caggt                                     25

<210> SEQ ID NO 672
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 672
gcaggcccta cccacaacgt ccagg                                     25

<210> SEQ ID NO 673
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 673
agcaggccct acccacaacg tccag                                     25

<210> SEQ ID NO 674
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 674
gagcaggccc tacccacaac gtcca                                     25

<210> SEQ ID NO 675
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 675
ggagcaggcc ctacccacaa cgtcc                                     25

<210> SEQ ID NO 676
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 676
gggagcaggc cctacccaca acgtc                                     25

<210> SEQ ID NO 677
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 677
agggagcagg ccctacccac aacgt                                     25

```
<210> SEQ ID NO 678
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 678
cagggagcag gccctaccca caacg                                              25

<210> SEQ ID NO 679
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 679
ccagggagca ggccctaccc acaac                                              25

<210> SEQ ID NO 680
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 680
gccagggagc aggccctacc cacaa                                              25

<210> SEQ ID NO 681
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 681
ggccagggag caggccctac ccaca                                              25

<210> SEQ ID NO 682
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 682
cggccaggga gcaggcccta cccac                                              25

<210> SEQ ID NO 683
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 683
gcggccaggg agcaggccct accca                                              25

<210> SEQ ID NO 684
<211> LENGTH: 25
<212> TYPE: DNA
<213> ORGANISM: Artificial Sequence
<220> FEATURE:
<223> OTHER INFORMATION: AON sequence 5' -> 3'
```

```
<400> SEQUENCE: 684
cgcggccagg gagcaggccc taccc                                           25

<210> SEQ ID NO 685
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 685
ccgcggccag ggagcaggcc ctacc                                           25

<210> SEQ ID NO 686
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 686
gccgcggcca gggagcaggc cctac                                           25

<210> SEQ ID NO 687
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 687
ggccgcggcc agggagcagg ccta                                            25

<210> SEQ ID NO 688
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 688
gggccgcggc cagggagcag gccct                                           25

<210> SEQ ID NO 689
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 689
ggggccgcgg ccagggagca ggccc                                           25

<210> SEQ ID NO 690
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 690
gggggccgcg gccagggagc aggcc                                           25

<210> SEQ ID NO 691
<211> LENGTH: 25
```

```
<212> TYPE: DNA
<213> ORGANISM: Artificial Sequence
<220> FEATURE:
<223> OTHER INFORMATION: AON sequence 5' -> 3'

<400> SEQUENCE: 691 cggggggccgc ggccagggag caggc                                       25

<210> SEQ ID NO 692
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 692 gcggggggccg cggccaggga gcagg                                       25

<210> SEQ ID NO 693
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 693
ggcgggggcc gcggccaggg agcag                                        25

<210> SEQ ID NO 694
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 694 gggcggggggc cgcggccagg gagca                                       25

<210> SEQ ID NO 695
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 695
ggggcggggg ccgcggccag ggagc                                        25

<210> SEQ ID NO 696
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 696
tggggcgggg gccgcggcca gggag                                        25

<210> SEQ ID NO 697
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 697
```

```
ttggggcggg ggccgcggcc aggga                                              25

<210> SEQ ID NO 698
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 698
cttggggcgg gggccgcggc caggg                                              25

<210> SEQ ID NO 699
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 699
ccttggggcg ggggccgcgg ccagg                                              25

<210> SEQ ID NO 700
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 700
gccttggggc gggggccgcg gccag                                              25

<210> SEQ ID NO 701
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 701
agccttgggg cggggccgc ggcca                                               25

<210> SEQ ID NO 702
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 702
gagccttggg gcggggccg cggcc                                               25

<210> SEQ ID NO 703
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 703
ggagccttgg ggcggggcc gcggc                                               25

<210> SEQ ID NO 704
<211> LENGTH: 25
<212> TYPE: DNA
<213> ORGANISM: Artificial Sequence
```

```
<220> FEATURE:
<223> OTHER INFORMATION: AON sequence 5' -> 3'

<400> SEQUENCE: 704
gggagccttg gggcggggc cgcgg                                          25

<210> SEQ ID NO 705
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 705
agggagcctt ggggcggggg ccgcg                                         25

<210> SEQ ID NO 706
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 706
gagggagcct tggggcgggg gccgc                                         25

<210> SEQ ID NO 707
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 707
ggagggagcc ttggggcggg ggccg                                         25

<210> SEQ ID NO 708
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 708
aggagggagc cttggggcgg gggcc                                         25

<210> SEQ ID NO 709
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 709
gaggagggag ccttggggcg ggggc                                         25

<210> SEQ ID NO 710
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 710
ggaggaggga gccttggggc ggggg                                         25
```

```
<210> SEQ ID NO 711
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 711
gggaggaggg agccttgggg cgggg                                     25

<210> SEQ ID NO 712
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 712
agggaggagg gagccttggg gcggg                                     25

<210> SEQ ID NO 713
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 713
gagggaggag ggagccttgg ggcgg                                     25

<210> SEQ ID NO 714
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 714
ggagggagga gggagccttg gggcg                                     25

<210> SEQ ID NO 715
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 715
gggagggagg agggagcctt ggggc                                     25

<210> SEQ ID NO 716
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 716
agggagggag gagggagcct tgggg                                     25

<210> SEQ ID NO 717
<211> LENGTH: 25
<212> TYPE: DNA
<213> ORGANISM: Artificial Sequence
<220> FEATURE:
<223> OTHER INFORMATION: AON sequence 5' -> 3'
```

```
<400> SEQUENCE: 717
gagggaggga ggagggagcc ttggg                                              25

<210> SEQ ID NO 718
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 718
tgagggaggg aggagggagc cttgg                                              25

<210> SEQ ID NO 719
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 719
atgagggagg gaggagggag ccttg                                              25

<210> SEQ ID NO 720
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 720
catgagggag ggaggaggga gcctt                                              25

<210> SEQ ID NO 721
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 721
tcatgaggga gggaggaggg agcct                                              25

<210> SEQ ID NO 722
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 722
ttcatgaggg agggaggagg gagcc                                              25

<210> SEQ ID NO 723
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 723
cttcatgagg gagggaggag ggagc                                              25

<210> SEQ ID NO 724
```

```
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 724
acttcatgag ggagggagga gggag                                    25

<210> SEQ ID NO 725
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 725
gacttcatga gggagggagg aggga                                    25

<210> SEQ ID NO 726
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 726
cgacttcatg agggagggag gaggg                                    25

<210> SEQ ID NO 727
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 727
ccgacttcat gagggaggga ggagg                                    25

<210> SEQ ID NO 728
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 728
gccgacttca tgagggaggg aggag                                    25

<210> SEQ ID NO 729
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 729
cgccgacttc atgagggagg gagga                                    25

<210> SEQ ID NO 730
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 730
```
acgccgactt catgagggag ggagg                                           25

<210> SEQ ID NO 731
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 731
aacgccgact tcatgaggga gggag                                           25

<210> SEQ ID NO 732
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 732
caacgccgac ttcatgaggg aggga                                           25

<210> SEQ ID NO 733
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 733
ccaacgccga cttcatgagg gaggg                                           25

<210> SEQ ID NO 734
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 734
gccaacgccg acttcatgag ggagg                                           25

<210> SEQ ID NO 735
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 735
ggccaacgcc gacttcatga gggag                                           25

<210> SEQ ID NO 736
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 736
aggccaacgc cgacttcatg aggga                                           25

<210> SEQ ID NO 737
<211> LENGTH: 25
<212> TYPE: DNA

```
<213> ORGANISM: Artificial Sequence
<220> FEATURE:
<223> OTHER INFORMATION: AON sequence 5' -> 3'

<400> SEQUENCE: 737
caggccaacg ccgacttcat gaggg                                  25

<210> SEQ ID NO 738
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 738
gcaggccaac gccgacttca tgagg                                  25

<210> SEQ ID NO 739
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 739
tgcaggccaa cgccgacttc atgag                                  25

<210> SEQ ID NO 740
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 740
ctgcaggcca acgccgactt catga                                  25

<210> SEQ ID NO 741
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 741
cctgcaggcc aacgccgact tcatg                                  25

<210> SEQ ID NO 742
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 742
tcctgcaggc caacgccgac ttcat                                  25

<210> SEQ ID NO 743
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 743
atcctgcagg ccaacgccga cttca                                  25
```

<210> SEQ ID NO 744
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 744
tatcctgcag gccaacgccg acttc                                              25

<210> SEQ ID NO 745
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 745
gtatcctgca ggccaacgcc gactt                                              25

<210> SEQ ID NO 746
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 746
ggtatcctgc aggccaacgc cgact                                              25

<210> SEQ ID NO 747
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 747
gggtatcctg caggccaacg ccgac                                              25

<210> SEQ ID NO 748
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 748
cgggtatcct gcaggccaac gccga                                              25

<210> SEQ ID NO 749
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 749
acgggtatcc tgcaggccaa cgccg                                              25

<210> SEQ ID NO 750
<211> LENGTH: 25
<212> TYPE: DNA
<213> ORGANISM: Artificial Sequence
<220> FEATURE:

```
<223> OTHER INFORMATION: AON sequence 5' -> 3'

<400> SEQUENCE: 750
aacgggtatc ctgcaggcca acgcc                                              25

<210> SEQ ID NO 751
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 751
gaacgggtat cctgcaggcc aacgc                                              25

<210> SEQ ID NO 752
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 752
tgaacgggta tcctgcaggc caacg                                              25

<210> SEQ ID NO 753
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 753
atgaacgggt atcctgcagg ccaac                                              25

<210> SEQ ID NO 754
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 754
catgaacggg tatcctgcag gccaa                                              25

<210> SEQ ID NO 755
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 755
gcatgaacgg gtatcctgca ggcca                                              25

<210> SEQ ID NO 756
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 756
ggcatgaacg ggtatcctgc aggcc                                              25
```

```
<210> SEQ ID NO 757
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 757
cggcatgaac gggtatcctg caggc                                   25

<210> SEQ ID NO 758
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 758
gcggcatgaa cgggtatcct gcagg                                   25

<210> SEQ ID NO 759
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 759
ggcggcatga acgggtatcc tgcag                                   25

<210> SEQ ID NO 760
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 760
tggcggcatg aacgggtatc ctgca                                   25

<210> SEQ ID NO 761
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 761
atggcggcat gaacgggtat cctgc                                   25

<210> SEQ ID NO 762
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 762
tatggcggca tgaacgggta cctg                                    25

<210> SEQ ID NO 763
<211> LENGTH: 25
<212> TYPE: DNA
<213> ORGANISM: Artificial Sequence
<220> FEATURE:
<223> OTHER INFORMATION: AON sequence 5' -> 3'
```

<400> SEQUENCE: 763
gtatggcggc atgaacgggt atcct                                              25

<210> SEQ ID NO 764
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 764
agtatggcgg catgaacggg tatcc                                              25

<210> SEQ ID NO 765
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 765
cagtatggcg gcatgaacgg gtatc                                              25

<210> SEQ ID NO 766
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 766
ccagtatggc ggcatgaacg ggtat                                              25

<210> SEQ ID NO 767
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 767
cccagtatgg cggcatgaac gggta                                              25

<210> SEQ ID NO 768
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 768
ccccagtatg gcggcatgaa cgggt                                              25

<210> SEQ ID NO 769
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 769
gccccagtat ggcggcatga acggg                                              25

<210> SEQ ID NO 770
<211> LENGTH: 25

```
<212> TYPE: DNA
<213> ORGANISM: Artificial Sequence
<220> FEATURE:
<223> OTHER INFORMATION: AON sequence 5' -> 3'

<400> SEQUENCE: 770
ggccccagta tggcggcatg aacgg                                              25

<210> SEQ ID NO 771
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 771
aggccccagt atggcggcat gaacg                                              25

<210> SEQ ID NO 772
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 772
caggccccag tatggcggca tgaac                                              25

<210> SEQ ID NO 773
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 773
ccaggcccca gtatggcggc atgaa                                              25

<210> SEQ ID NO 774
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 774
cccaggcccc agtatggcgg catga                                              25

<210> SEQ ID NO 775
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 775
gcccaggccc cagtatggcg gcatg                                              25

<210> SEQ ID NO 776
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 776
```
agcccaggcc ccagtatggc ggcat        25

<210> SEQ ID NO 777
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 777
aagcccaggc cccagtatgg cggca        25

<210> SEQ ID NO 778
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 778
gaagcccagg ccccagtatg gcggc        25

<210> SEQ ID NO 779
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 779
ggaagcccag gccccagtat ggcgg        25

<210> SEQ ID NO 780
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 780
tggaagccca ggccccagta tggcg        25

<210> SEQ ID NO 781
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 781
gtggaagccc aggccccagt atggc        25

<210> SEQ ID NO 782
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 782
ggtggaagcc caggccccag tatgg        25

<210> SEQ ID NO 783
<211> LENGTH: 25
<212> TYPE: DNA
<213> ORGANISM: Artificial Sequence

```
<220> FEATURE:
<223> OTHER INFORMATION: AON sequence 5' -> 3'

<400> SEQUENCE: 783
aggtggaagc ccaggcccca gtatg                                              25

<210> SEQ ID NO 784
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 784
caggtggaag cccaggcccc agtat                                              25

<210> SEQ ID NO 785
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 785
acaggtggaa gcccaggccc cagta                                              25

<210> SEQ ID NO 786
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 786
cacaggtgga agcccaggcc ccagt                                              25

<210> SEQ ID NO 787
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 787
gcacaggtgg aagcccaggc cccag                                              25

<210> SEQ ID NO 788
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 788
ggcacaggtg gaagcccagg cccca                                              25

<210> SEQ ID NO 789
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 789
cggcacaggt ggaagcccag gcccc                                              25
```

<210> SEQ ID NO 790
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 790
gcggcacagg tggaagccca ggccc                                          25

<210> SEQ ID NO 791
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 791
agcggcacag gtggaagccc aggcc                                          25

<210> SEQ ID NO 792
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 792
cagcggcaca ggtggaagcc caggc                                          25

<210> SEQ ID NO 793
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 793
ccagcggcac aggtggaagc ccagg                                          25

<210> SEQ ID NO 794
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 794
cccagcggca caggtggaag cccag                                          25

<210> SEQ ID NO 795
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 795
ccccagcggc acaggtggaa gccca                                          25

<210> SEQ ID NO 796
<211> LENGTH: 25
<212> TYPE: DNA
<213> ORGANISM: Artificial Sequence
<220> FEATURE:
<223> OTHER INFORMATION: AON sequence 5' -> 3'

```
<400> SEQUENCE: 796
gccccagcgg cacaggtgga agccc                                      25

<210> SEQ ID NO 797
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 797
agccccagcg gcacaggtgg aagcc                                      25

<210> SEQ ID NO 798
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 798
tagccccagc ggcacaggtg gaagc                                      25

<210> SEQ ID NO 799
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 799
gtagccccag cggcacaggt ggaag                                      25

<210> SEQ ID NO 800
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 800
agtagcccca gcggcacagg tggaa                                      25

<210> SEQ ID NO 801
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 801
gagtagcccc agcggcacag gtgga                                      25

<210> SEQ ID NO 802
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 802
ggagtagccc cagcggcaca ggtgg                                      25

<210> SEQ ID NO 803
```

```
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 803
aggagtagcc ccagcggcac aggtg                                         25

<210> SEQ ID NO 804
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 804
gaggagtagc cccagcggca caggt                                         25

<210> SEQ ID NO 805
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 805
ggaggagtag ccccagcggc acagg                                         25

<210> SEQ ID NO 806
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 806
tggaggagta gccccagcgg cacag                                         25

<210> SEQ ID NO 807
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 807
gtggaggagt agccccagcg gcaca                                         25

<210> SEQ ID NO 808
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 808
ggtggaggag tagccccagc ggcac                                         25

<210> SEQ ID NO 809
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 809
```
cggtggagga gtagccccag cggca                              25

<210> SEQ ID NO 810
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 810
gcggtggagg agtagcccca gcggc                              25

<210> SEQ ID NO 811
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 811
agcggtggag gagtagcccc agcgg                              25

<210> SEQ ID NO 812
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 812
tagcggtgga ggagtagccc cagcg                              25

<210> SEQ ID NO 813
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 813
atagcggtgg aggagtagcc ccagc                              25

<210> SEQ ID NO 814
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 814
gatagcggtg gaggagtagc cccag                              25

<210> SEQ ID NO 815
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 815
tgatagcggt ggaggagtag cccca                              25

<210> SEQ ID NO 816
<211> LENGTH: 25
<212> TYPE: DNA

```
<213> ORGANISM: Artificial Sequence
<220> FEATURE:
<223> OTHER INFORMATION: AON sequence 5' -> 3'

<400> SEQUENCE: 816
gtgatagcgg tggaggagta gcccc                                        25

<210> SEQ ID NO 817
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 817
ggtgatagcg gtggaggagt agccc                                        25

<210> SEQ ID NO 818
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 818
gggtgatagc ggtggaggag tagcc                                        25

<210> SEQ ID NO 819
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 819
cgggtgatag cggtggagga gtagc                                        25

<210> SEQ ID NO 820
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 820
gcgggtgata gcggtggagg agtag                                        25

<210> SEQ ID NO 821
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 821
ggcgggtgat agcggtggag gagta                                        25

<210> SEQ ID NO 822
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 822
tggcgggtga tagcggtgga ggagt                                        25
```

<210> SEQ ID NO 823
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 823
ctggcgggtg atagcggtgg aggag                                              25

<210> SEQ ID NO 824
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 824
cctggcgggt gatagcggtg gagga                                              25

<210> SEQ ID NO 825
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 825
acctggcggg tgatagcggt ggagg                                              25

<210> SEQ ID NO 826
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 826
cacctggcgg gtgatagcgg tggag                                              25

<210> SEQ ID NO 827
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 827
ccacctggcg ggtgatagcg gtgga                                              25

<210> SEQ ID NO 828
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 828
accacctggc gggtgatagc ggtgg                                              25

<210> SEQ ID NO 829
<211> LENGTH: 25
<212> TYPE: DNA
<213> ORGANISM: Artificial Sequence
<220> FEATURE:

<223> OTHER INFORMATION: AON sequence 5' -> 3'

<400> SEQUENCE: 829
caccacctgg cgggtgatag cggtg                                     25

<210> SEQ ID NO 830
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 830
ccaccacctg gcgggtgata gcggt                                     25

<210> SEQ ID NO 831
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 831
tccaccacct ggcgggtgat agcgg                                     25

<210> SEQ ID NO 832
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 832
ctccaccacc tggcgggtga tagcg                                     25

<210> SEQ ID NO 833
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 833
tctccaccac ctggcgggtg atagc                                     25

<210> SEQ ID NO 834
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 834
ttctccacca cctggcgggt gatag                                     25

<210> SEQ ID NO 835
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 835
gttctccacc acctggcggg tgata                                     25

<210> SEQ ID NO 836
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 836
tgttctccac cacctggcgg gtgat                                         25

<210> SEQ ID NO 837
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 837
atgttctcca ccacctggcg ggtga                                         25

<210> SEQ ID NO 838
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 838
catgttctcc accacctggc gggtg                                         25

<210> SEQ ID NO 839
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 839
tcatgttctc caccacctgg cgggt                                         25

<210> SEQ ID NO 840
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 840
gtcatgttct ccaccacctg gcggg                                         25

<210> SEQ ID NO 841
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 841
ggtcatgttc tccaccacct ggcgg                                         25

<210> SEQ ID NO 842
<211> LENGTH: 25
<212> TYPE: DNA
<213> ORGANISM: Artificial Sequence
<220> FEATURE:
<223> OTHER INFORMATION: AON sequence 5' -> 3'

```
<400> SEQUENCE: 842
tggtcatgtt ctccaccacc tggcg                                              25

<210> SEQ ID NO 843
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 843
ctggtcatgt tctccaccac ctggc                                              25

<210> SEQ ID NO 844
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 844
cctggtcatg ttctccacca cctgg                                              25

<210> SEQ ID NO 845
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 845
ccctggtcat gttctccacc acctg                                              25

<210> SEQ ID NO 846
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 846
gccctggtca tgttctccac cacct                                              25

<210> SEQ ID NO 847
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 847
ggccctggtc atgttctcca ccacc                                              25

<210> SEQ ID NO 848
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 848
gggccctggt catgttctcc accac                                              25

<210> SEQ ID NO 849
<211> LENGTH: 25
```

```
<212> TYPE: DNA
<213> ORGANISM: Artificial Sequence
<220> FEATURE:
<223> OTHER INFORMATION: AON sequence 5' -> 3'

<400> SEQUENCE: 849
tgggccctgg tcatgttctc cacca                                25

<210> SEQ ID NO 850
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 850
gtgggccctg gtcatgttct ccacc                                25

<210> SEQ ID NO 851
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 851
agtgggccct ggtcatgttc tccac                                25

<210> SEQ ID NO 852
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 852
aagtgggccc tggtcatgtt ctcca                                25

<210> SEQ ID NO 853
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 853
gaagtgggcc ctggtcatgt tctcc                                25

<210> SEQ ID NO 854
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 854
ggaagtgggc cctggtcatg ttctc                                25

<210> SEQ ID NO 855
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 855
```

```
gggaagtgggc cctggtcat gttct                                          25
```

<210> SEQ ID NO 856
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 856

```
ggggaagtgg gccctggtca tgttc                                          25
```

<210> SEQ ID NO 857
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 857

```
gggggaagtg ggccctggtc atgtt                                          25
```

<210> SEQ ID NO 858
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 858

```
aggggggaagt gggccctggt catgt                                         25
```

<210> SEQ ID NO 859
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 859

```
caggggggaag tgggccctgg tcatg                                         25
```

<210> SEQ ID NO 860
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 860

```
ccaggggggaa gtgggccctg gtcat                                         25
```

<210> SEQ ID NO 861
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 861

```
accaggggga agtgggccct ggtca                                          25
```

<210> SEQ ID NO 862
<211> LENGTH: 25
<212> TYPE: DNA
<213> ORGANISM: Artificial Sequence

```
<220> FEATURE:
<223> OTHER INFORMATION: AON sequence 5' -> 3'

<400> SEQUENCE: 862
caccaggggg aagtgggccc tggtc                                           25

<210> SEQ ID NO 863
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 863
tcaccagggg gaagtgggcc ctggt                                           25

<210> SEQ ID NO 864
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 864
ctcaccaggg ggaagtgggc cctgg                                           25

<210> SEQ ID NO 865
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 865
actcaccagg gggaagtggg ccctg                                           25

<210> SEQ ID NO 866
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 866
aactcaccag ggggaagtgg gccct                                           25

<210> SEQ ID NO 867
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 867
caactcacca gggggaagtg ggccc                                           25

<210> SEQ ID NO 868
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 868
ccaactcacc aggggggaagt gggcc                                          25
```

```
<210> SEQ ID NO 869
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 869
cccaactcac cagggggaag tgggc                                              25

<210> SEQ ID NO 870
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 870
ccccaactca ccagggggaa gtggg                                              25

<210> SEQ ID NO 871
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 871
accccaactc accaggggga agtgg                                              25

<210> SEQ ID NO 872
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 872
caccccaact caccaggggg aagtg                                              25

<210> SEQ ID NO 873
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 873
ccaccccaac tcaccagggg gaagt                                              25

<210> SEQ ID NO 874
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 874
accaccccaa ctcaccaggg ggaag                                              25

<210> SEQ ID NO 875
<211> LENGTH: 25
<212> TYPE: DNA
<213> ORGANISM: Artificial Sequence
<220> FEATURE:
<223> OTHER INFORMATION: AON sequence 5' -> 3'
```

```
<400> SEQUENCE: 875
caccacccca actcaccagg gggaa                                              25

<210> SEQ ID NO 876
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 876
ccaccacccc aactcaccag gggga                                              25

<210> SEQ ID NO 877
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 877
gccaccaccc caactcacca ggggg                                              25

<210> SEQ ID NO 878
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 878
tgccaccacc ccaactcacc agggg                                              25

<210> SEQ ID NO 879
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 879
ctgccaccac cccaactcac caggg                                              25

<210> SEQ ID NO 880
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 880
cctgccacca ccccaactca ccagg                                              25

<210> SEQ ID NO 881
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 881
ccctgccacc accccaactc accag                                              25

<210> SEQ ID NO 882
```

```
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 882
cccctgccac caccccaact cacca                                    25

<210> SEQ ID NO 883
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 883 tccctgcca ccacccaac tcacc                                      25

<210> SEQ ID NO 884
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 884 ctccctgcc accaccccaa ctcac                                     25

<210> SEQ ID NO 885
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 885
aagggaagca gctctggggt t                                        21

<210> SEQ ID NO 886
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 886
gaagggaagc agctctgggg t                                        21

<210> SEQ ID NO 887
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 887
ggaagggaag cagctctggg g                                        21

<210> SEQ ID NO 888
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 888
```
tggaagggaa gcagctctgg g                                              21

<210> SEQ ID NO 889
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 889
ctggaaggga agcagctctg g                                              21

<210> SEQ ID NO 890
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 890
tctggaaggg aagcagctct g                                              21

<210> SEQ ID NO 891
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 891
atctggaagg gaagcagctc t                                              21

<210> SEQ ID NO 892
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 892
catctggaag ggaagcagct c                                              21

<210> SEQ ID NO 893
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 893
acatctggaa gggaagcagc t                                              21

<210> SEQ ID NO 894
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 894
cacatctgga agggaagcag c                                              21

<210> SEQ ID NO 895
<211> LENGTH: 21
<212> TYPE: DNA

```
<213> ORGANISM: Artificial Sequence
<220> FEATURE:
<223> OTHER INFORMATION: AON sequence 5' -> 3'

<400> SEQUENCE: 895
ccacatctgg aagggaagca g                                              21

<210> SEQ ID NO 896
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 896
accacatctg gaagggaagc a                                              21

<210> SEQ ID NO 897
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 897
gaccacatct ggaagggaag c                                              21

<210> SEQ ID NO 898
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 898
ggaccacatc tggaagggaa g                                              21

<210> SEQ ID NO 899
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 899
aggaccacat ctggaaggga a                                              21

<210> SEQ ID NO 900
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 900
caggaccaca tctggaaggg a                                              21

<210> SEQ ID NO 901
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 901
gcaggaccac atctggaagg g                                              21
```

<210> SEQ ID NO 902
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 902
tgcaggacca catctggaag g                                              21

<210> SEQ ID NO 903
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 903
ctgcaggacc acatctggaa g                                              21

<210> SEQ ID NO 904
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 904
gctgcaggac cacatctgga a                                              21

<210> SEQ ID NO 905
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 905
ggctgcagga ccacatctgg a                                              21

<210> SEQ ID NO 906
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 906
cggctgcagg accacatctg g                                              21

<210> SEQ ID NO 907
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 907
tcggctgcag gaccacatct g                                              21

<210> SEQ ID NO 908
<211> LENGTH: 21
<212> TYPE: DNA
<213> ORGANISM: Artificial Sequence
<220> FEATURE:

```
<223> OTHER INFORMATION: AON sequence 5' -> 3'

<400> SEQUENCE: 908
ctcggctgca ggaccacatc t                                              21

<210> SEQ ID NO 909
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 909
gctcggctgc aggaccacat c                                              21

<210> SEQ ID NO 910
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 910
ggctcggctg caggaccaca t                                              21

<210> SEQ ID NO 911
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 911
gggctcggct gcaggaccac a                                              21

<210> SEQ ID NO 912
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 912
agggctcggc tgcaggacca c                                              21

<210> SEQ ID NO 913
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 913
cagggctcgg ctgcaggacc a                                              21

<210> SEQ ID NO 914
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 914
gcagggctcg gctgcaggac c                                              21
```

```
<210> SEQ ID NO 915
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 915
ggcagggctc ggctgcagga c                                        21

<210> SEQ ID NO 916
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 916
gggcagggct cggctgcagg a                                        21

<210> SEQ ID NO 917
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 917
agggcagggc tcggctgcag g                                        21

<210> SEQ ID NO 918
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 918
aagggcaggg ctcggctgca g                                        21

<210> SEQ ID NO 919
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 919
taagggcagg gctcggctgc a                                        21

<210> SEQ ID NO 920
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 920
ctaagggcag ggctcggctg c                                        21

<210> SEQ ID NO 921
<211> LENGTH: 21
<212> TYPE: DNA
<213> ORGANISM: Artificial Sequence
<220> FEATURE:
<223> OTHER INFORMATION: AON sequence 5' -> 3'
```

-continued

<400> SEQUENCE: 921
gctaagggca gggctcggct g                                              21

<210> SEQ ID NO 922
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 922
agctaagggc agggctcggc t                                              21

<210> SEQ ID NO 923
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 923
cagctaaggg cagggctcgg c                                              21

<210> SEQ ID NO 924
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 924
ccagctaagg gcagggctcg g                                              21

<210> SEQ ID NO 925
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 925
tccagctaag ggcagggctc g                                              21

<210> SEQ ID NO 926
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 926
ctccagctaa gggcagggct c                                              21

<210> SEQ ID NO 927
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 927
cctccagcta agggcagggc t                                              21

<210> SEQ ID NO 928
<211> LENGTH: 21

```
<212> TYPE: DNA
<213> ORGANISM: Artificial Sequence
<220> FEATURE:
<223> OTHER INFORMATION: AON sequence 5' -> 3'

<400> SEQUENCE: 928
acctccagct aagggcaggg c                                               21

<210> SEQ ID NO 929
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 929
gacctccagc taagggcagg g                                               21

<210> SEQ ID NO 930
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 930
cgacctccag ctaagggcag g                                               21

<210> SEQ ID NO 931
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 931
tcgacctcca gctaagggca g                                               21

<210> SEQ ID NO 932
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 932
gtcgacctcc agctaagggc a                                               21

<210> SEQ ID NO 933
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 933
tgtcgacctc cagctaaggg c                                               21

<210> SEQ ID NO 934
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 934
```
ctgtcgacct ccagctaagg g                                        21

<210> SEQ ID NO 935
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 935
cctgtcgacc tccagctaag g                                        21

<210> SEQ ID NO 936
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 936
acctgtcgac ctccagctaa g                                        21

<210> SEQ ID NO 937
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 937
cacctgtcga cctccagcta a                                        21

<210> SEQ ID NO 938
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 938
ccacctgtcg acctccagct a                                        21

<210> SEQ ID NO 939
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 939
cccacctgtc gacctccagc t                                        21

<210> SEQ ID NO 940
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 940
tcccacctgt cgacctccag c                                        21

<210> SEQ ID NO 941
<211> LENGTH: 21
<212> TYPE: DNA
<213> ORGANISM: Artificial Sequence

```
<220> FEATURE:
<223> OTHER INFORMATION: AON sequence 5' -> 3'

<400> SEQUENCE: 941
atcccacctg tcgacctcca g                                              21

<210> SEQ ID NO 942
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 942
gatcccacct gtcgacctcc a                                              21

<210> SEQ ID NO 943
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 943
ggatcccacc tgtcgacctc c                                              21

<210> SEQ ID NO 944
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 944
aggatcccac ctgtcgacct c                                              21

<210> SEQ ID NO 945
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 945
caggatccca cctgtcgacc t                                              21

<210> SEQ ID NO 946
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 946
ccaggatccc acctgtcgac c                                              21

<210> SEQ ID NO 947
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 947
tccaggatcc cacctgtcga c                                              21
```

```
<210> SEQ ID NO 948
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 948
atccaggatc ccacctgtcg a                                              21

<210> SEQ ID NO 949
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 949
catccaggat cccacctgtc g                                              21

<210> SEQ ID NO 950
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 950
acatccagga tcccacctgt c                                              21

<210> SEQ ID NO 951
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 951
gacatccagg atcccacctg t                                              21

<210> SEQ ID NO 952
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 952
agacatccag gatcccacct g                                              21

<210> SEQ ID NO 953
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 953
tagacatcca ggatcccacc t                                              21

<210> SEQ ID NO 954
<211> LENGTH: 21
<212> TYPE: DNA
<213> ORGANISM: Artificial Sequence
<220> FEATURE:
<223> OTHER INFORMATION: AON sequence 5' -> 3'
```

```
<400> SEQUENCE: 954
gtagacatcc aggatcccac c                                              21

<210> SEQ ID NO 955
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 955
tgtagacatc caggatccca c                                              21

<210> SEQ ID NO 956
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 956
atgtagacat ccaggatccc a                                              21

<210> SEQ ID NO 957
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 957
gatgtagaca tccaggatcc c                                              21

<210> SEQ ID NO 958
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 958
agatgtagac atccaggatc c                                              21

<210> SEQ ID NO 959
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 959
aagatgtaga catccaggat c                                              21

<210> SEQ ID NO 960
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 960
gaagatgtag acatccagga t                                              21

<210> SEQ ID NO 961
```

-continued

```
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 961
ggaagatgta gacatccagg a                                              21

<210> SEQ ID NO 962
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 962
aggaagatgt agacatccag g                                              21

<210> SEQ ID NO 963
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 963
caggaagatg tagacatcca g                                              21

<210> SEQ ID NO 964
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 964
ccaggaagat gtagacatcc a                                              21

<210> SEQ ID NO 965
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 965
cccaggaaga tgtagacatc c                                              21

<210> SEQ ID NO 966
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 966
gcccaggaag atgtagacat c                                              21

<210> SEQ ID NO 967
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 967
```
ggcccaggaa gatgtagaca t                              21

<210> SEQ ID NO 968
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 968
gggcccagga agatgtagac a                              21

<210> SEQ ID NO 969
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 969
tgggcccagg aagatgtaga c                              21

<210> SEQ ID NO 970
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 970
ctgggcccag gaagatgtag a                              21

<210> SEQ ID NO 971
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 971
tctgggccca ggaagatgta g                              21

<210> SEQ ID NO 972
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 972
ctctgggccc aggaagatgt a                              21

<210> SEQ ID NO 973
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 973
gctctgggcc caggaagatg t                              21

<210> SEQ ID NO 974
<211> LENGTH: 21
<212> TYPE: DNA

```
<213> ORGANISM: Artificial Sequence
<220> FEATURE:
<223> OTHER INFORMATION: AON sequence 5' -> 3'

<400> SEQUENCE: 974
ggctctgggc ccaggaagat g                                               21

<210> SEQ ID NO 975
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 975
gggctctggg cccaggaaga t                                               21

<210> SEQ ID NO 976
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 976
tgggctctgg gcccaggaag a                                               21

<210> SEQ ID NO 977
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 977
ttgggctctg ggcccaggaa g                                               21

<210> SEQ ID NO 978
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 978
cttgggctct gggcccagga a                                               21

<210> SEQ ID NO 979
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 979
tcttgggctc tgggcccagg a                                               21

<210> SEQ ID NO 980
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 980
ctcttgggct ctgggcccag g                                               21
```

<210> SEQ ID NO 981
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 981
gctcttgggc tctgggccca g                                    21

<210> SEQ ID NO 982
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 982
cgctcttggg ctctgggccc a                                    21

<210> SEQ ID NO 983
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 983
acgctcttgg gctctgggcc c                                    21

<210> SEQ ID NO 984
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 984
cacgctcttg ggctctgggc c                                    21

<210> SEQ ID NO 985
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 985
ccacgctctt gggctctggg c                                    21

<210> SEQ ID NO 986
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 986
accacgctct tgggctctgg g                                    21

<210> SEQ ID NO 987
<211> LENGTH: 21
<212> TYPE: DNA
<213> ORGANISM: Artificial Sequence
<220> FEATURE:

```
<223> OTHER INFORMATION: AON sequence 5' -> 3'

<400> SEQUENCE: 987
caccacgctc ttgggctctg g                                              21

<210> SEQ ID NO 988
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 988
gcaccacgct cttgggctct g                                              21

<210> SEQ ID NO 989
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 989
tgcaccacgc tcttgggctc t                                              21

<210> SEQ ID NO 990
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 990
ctgcaccacg ctcttgggct c                                              21

<210> SEQ ID NO 991
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 991
gctgcaccac gctcttgggc t                                              21

<210> SEQ ID NO 992
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 992
tgctgcacca cgctcttggg c                                              21

<210> SEQ ID NO 993
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 993
ctgctgcacc acgctcttgg g                                              21
```

```
<210> SEQ ID NO 994
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 994
actgctgcac cacgctcttg g                                              21

<210> SEQ ID NO 995
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 995
tactgctgca ccacgctctt g                                              21

<210> SEQ ID NO 996
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 996
gtactgctgc accacgctct t                                              21

<210> SEQ ID NO 997
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 997
ggtactgctg caccacgctc t                                              21

<210> SEQ ID NO 998
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 998
aggtactgct gcaccacgct c                                              21

<210> SEQ ID NO 999
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 999
caggtactgc tgcaccacgc t                                              21

<210> SEQ ID NO 1000
<211> LENGTH: 21
<212> TYPE: DNA
<213> ORGANISM: Artificial Sequence
<220> FEATURE:
<223> OTHER INFORMATION: AON sequence 5' -> 3'
```

```
<400> SEQUENCE: 1000
ccaggtactg ctgcaccacg c                                              21

<210> SEQ ID NO 1001
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1001
tccaggtact gctgcaccac g                                              21

<210> SEQ ID NO 1002
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1002
gtccaggtac tgctgcacca c                                              21

<210> SEQ ID NO 1003
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1003
cgtccaggta ctgctgcacc a                                              21

<210> SEQ ID NO 1004
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1004
acgtccaggt actgctgcac c                                              21

<210> SEQ ID NO 1005
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1005
aacgtccagg tactgctgca c                                              21

<210> SEQ ID NO 1006
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1006
caacgtccag gtactgctgc a                                              21

<210> SEQ ID NO 1007
<211> LENGTH: 21
```

```
<212> TYPE: DNA
<213> ORGANISM: Artificial Sequence
<220> FEATURE:
<223> OTHER INFORMATION: AON sequence 5' -> 3'

<400> SEQUENCE: 1007
acaacgtcca ggtactgctg c                                          21

<210> SEQ ID NO 1008
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1008
cacaacgtcc aggtactgct g                                          21

<210> SEQ ID NO 1009
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1009
ccacaacgtc caggtactgc t                                          21

<210> SEQ ID NO 1010
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1010
cccacaacgt ccaggtactg c                                          21

<210> SEQ ID NO 1011
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1011
acccacaacg tccaggtact g                                          21

<210> SEQ ID NO 1012
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1012
tacccacaac gtccaggtac t                                          21

<210> SEQ ID NO 1013
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1013
```

-continued ctacccacaa cgtccaggta c                                            21

<210> SEQ ID NO 1014
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1014
cctacccaca acgtccaggt a                                            21

<210> SEQ ID NO 1015
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1015
ccctacccac aacgtccagg t                                            21

<210> SEQ ID NO 1016
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1016
gccctaccca caacgtccag g                                            21

<210> SEQ ID NO 1017
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1017
ggccctaccc acaacgtcca g                                            21

<210> SEQ ID NO 1018
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1018
aggccctacc cacaacgtcc a                                            21

<210> SEQ ID NO 1019
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1019
caggccctac ccacaacgtc c                                            21

<210> SEQ ID NO 1020
<211> LENGTH: 21
<212> TYPE: DNA
<213> ORGANISM: Artificial Sequence

```
<220> FEATURE:
<223> OTHER INFORMATION: AON sequence 5' -> 3'

<400> SEQUENCE: 1020
gcaggcccta cccacaacgt c                                              21

<210> SEQ ID NO 1021
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1021
agcaggccct acccacaacg t                                              21

<210> SEQ ID NO 1022
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1022
gagcaggccc tacccacaac g                                              21

<210> SEQ ID NO 1023
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1023
ggagcaggcc ctacccacaa c                                              21

<210> SEQ ID NO 1024
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1024
gggagcaggc cctacccaca a                                              21

<210> SEQ ID NO 1025
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1025
agggagcagg ccctacccac a                                              21

<210> SEQ ID NO 1026
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1026
cagggagcag gccctaccca c                                              21
```

<210> SEQ ID NO 1027
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1027
ccagggagca ggccctaccc a                                              21

<210> SEQ ID NO 1028
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1028
gccagggagc aggccctacc c                                              21

<210> SEQ ID NO 1029
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1029
ggccagggag caggccctac c                                              21

<210> SEQ ID NO 1030
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1030
cggccaggga gcaggcccta c                                              21

<210> SEQ ID NO 1031
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1031
gcggccaggg agcaggccct a                                              21

<210> SEQ ID NO 1032
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1032
cgcggccagg gagcaggccc t                                              21

<210> SEQ ID NO 1033
<211> LENGTH: 21
<212> TYPE: DNA
<213> ORGANISM: Artificial Sequence
<220> FEATURE:
<223> OTHER INFORMATION: AON sequence 5' -> 3'

-continued

<400> SEQUENCE: 1033
ccgcggccag ggagcaggcc c                                              21

<210> SEQ ID NO 1034
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1034
gccgcggcca gggagcaggc c                                              21

<210> SEQ ID NO 1035
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1035
ggccgcggcc agggagcagg c                                              21

<210> SEQ ID NO 1036
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1036
gggccgcggc cagggagcag g                                              21

<210> SEQ ID NO 1037
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1037
ggggccgcgg ccagggagca g                                              21

<210> SEQ ID NO 1038
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1038
gggggccgcg gccagggagc a                                              21

<210> SEQ ID NO 1039
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1039
cgggggccgc ggccagggag c                                              21

<210> SEQ ID NO 1040

```
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1040 gcggggccg cggccaggga g                                       21

<210> SEQ ID NO 1041
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1041 ggcggggcc gcggccaggg a                                       21

<210> SEQ ID NO 1042
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1042 gggcggggc cgcggccagg g                                       21

<210> SEQ ID NO 1043
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1043 ggggcgggg ccgcggccag g                                       21

<210> SEQ ID NO 1044
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1044
tggggcgggg gccgcggcca g                                      21

<210> SEQ ID NO 1045
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1045
ttggggcggg ggccgcggcc a                                      21

<210> SEQ ID NO 1046
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1046
```
cttggggcgg gggccgcggc c          21

<210> SEQ ID NO 1047
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1047
ccttggggcg ggggccgcgg c          21

<210> SEQ ID NO 1048
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1048
gccttggggc gggggccgcg g          21

<210> SEQ ID NO 1049
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1049
agccttgggg cggggccgc g          21

<210> SEQ ID NO 1050
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1050
gagccttggg gcgggggccg c          21

<210> SEQ ID NO 1051
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1051
ggagccttgg ggcggggggcc g          21

<210> SEQ ID NO 1052
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1052
gggagccttg gggcgggggc c          21

<210> SEQ ID NO 1053
<211> LENGTH: 21
<212> TYPE: DNA

```
<213> ORGANISM: Artificial Sequence
<220> FEATURE:
<223> OTHER INFORMATION: AON sequence 5' -> 3'

<400> SEQUENCE: 1053
agggagcctt ggggcggggg c                                              21

<210> SEQ ID NO 1054
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1054
gagggagcct tggggcgggg g                                              21

<210> SEQ ID NO 1055
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1055
ggagggagcc ttggggcggg g                                              21

<210> SEQ ID NO 1056
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1056
aggagggagc ttggggcgg g                                               21

<210> SEQ ID NO 1057
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1057
gaggagggag ccttggggcg g                                              21

<210> SEQ ID NO 1058
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1058
ggaggaggga gccttggggc g                                              21

<210> SEQ ID NO 1059
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1059
gggaggaggg agccttgggg c                                              21
```

<210> SEQ ID NO 1060
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1060
agggaggagg gagccttggg g                                              21

<210> SEQ ID NO 1061
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1061
gagggaggag ggagccttgg g                                              21

<210> SEQ ID NO 1062
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1062
ggagggagga gggagccttg g                                              21

<210> SEQ ID NO 1063
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1063
gggagggagg agggagcctt g                                              21

<210> SEQ ID NO 1064
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1064
agggagggag gagggagcct t                                              21

<210> SEQ ID NO 1065
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1065
gagggaggga ggagggagcc t                                              21

<210> SEQ ID NO 1066
<211> LENGTH: 21
<212> TYPE: DNA
<213> ORGANISM: Artificial Sequence
<220> FEATURE:

```
<223> OTHER INFORMATION: AON sequence 5' -> 3'

<400> SEQUENCE: 1066
tgagggaggg aggagggagc c                                              21

<210> SEQ ID NO 1067
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1067
atgagggagg gaggagggag c                                              21

<210> SEQ ID NO 1068
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1068
catgagggag ggaggaggga g                                              21

<210> SEQ ID NO 1069
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1069
tcatgaggga gggaggaggg a                                              21

<210> SEQ ID NO 1070
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1070
ttcatgaggg agggaggagg g                                              21

<210> SEQ ID NO 1071
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1071
cttcatgagg gagggaggag g                                              21

<210> SEQ ID NO 1072
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1072
acttcatgag ggagggagga g                                              21
```

```
<210> SEQ ID NO 1073
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1073
gacttcatga gggagggagg a                                              21

<210> SEQ ID NO 1074
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1074
cgacttcatg agggagggag g                                              21

<210> SEQ ID NO 1075
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1075
ccgacttcat gagggaggga g                                              21

<210> SEQ ID NO 1076
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1076
gccgacttca tgagggaggg a                                              21

<210> SEQ ID NO 1077
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1077
cgccgacttc atgagggagg g                                              21

<210> SEQ ID NO 1078
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1078
acgccgactt catgagggag g                                              21

<210> SEQ ID NO 1079
<211> LENGTH: 21
<212> TYPE: DNA
<213> ORGANISM: Artificial Sequence
<220> FEATURE:
<223> OTHER INFORMATION: AON sequence 5' -> 3'
```

<400> SEQUENCE: 1079
aacgccgact tcatgaggga g                                              21

<210> SEQ ID NO 1080
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1080
caacgccgac ttcatgaggg a                                              21

<210> SEQ ID NO 1081
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1081
ccaacgccga cttcatgagg g                                              21

<210> SEQ ID NO 1082
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1082
gccaacgccg acttcatgag g                                              21

<210> SEQ ID NO 1083
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1083
ggccaacgcc gacttcatga g                                              21

<210> SEQ ID NO 1084
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1084
aggccaacgc cgacttcatg a                                              21

<210> SEQ ID NO 1085
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1085
caggccaacg ccgacttcat g                                              21

<210> SEQ ID NO 1086
<211> LENGTH: 21

-continued

<212> TYPE: DNA
<213> ORGANISM: Artificial Sequence
<220> FEATURE:
<223> OTHER INFORMATION: AON sequence 5' -> 3'

<400> SEQUENCE: 1086
gcaggccaac gccgacttca t                                              21

<210> SEQ ID NO 1087
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1087
tgcaggccaa cgccgacttc a                                              21

<210> SEQ ID NO 1088
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1088
ctgcaggcca acgccgactt c                                              21

<210> SEQ ID NO 1089
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1089
cctgcaggcc aacgccgact t                                              21

<210> SEQ ID NO 1090
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1090
tcctgcaggc caacgccgac t                                              21

<210> SEQ ID NO 1091
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1091
atcctgcagg ccaacgccga c                                              21

<210> SEQ ID NO 1092
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1092

-continued tatcctgcag gccaacgccg a                                                         21

<210> SEQ ID NO 1093
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1093
gtatcctgca ggccaacgcc g                                                         21

<210> SEQ ID NO 1094
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1094
ggtatcctgc aggccaacgc c                                                         21

<210> SEQ ID NO 1095
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1095
gggtatcctg caggccaacg c                                                         21

<210> SEQ ID NO 1096
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1096
cgggtatcct gcaggccaac g                                                         21

<210> SEQ ID NO 1097
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1097
acgggtatcc tgcaggccaa c                                                         21

<210> SEQ ID NO 1098
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1098
aacgggtatc ctgcaggcca a                                                         21

<210> SEQ ID NO 1099
<211> LENGTH: 21
<212> TYPE: DNA
<213> ORGANISM: Artificial Sequence

```
<220> FEATURE:
<223> OTHER INFORMATION: AON sequence 5' -> 3'

<400> SEQUENCE: 1099
gaacgggtat cctgcaggcc a                                              21

<210> SEQ ID NO 1100
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1100
tgaacgggta tcctgcaggc c                                              21

<210> SEQ ID NO 1101
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1101
atgaacgggt atcctgcagg c                                              21

<210> SEQ ID NO 1102
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1102
catgaacggg tatcctgcag g                                              21

<210> SEQ ID NO 1103
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1103
gcatgaacgg gtatcctgca g                                              21

<210> SEQ ID NO 1104
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1104
ggcatgaacg ggtatcctgc a                                              21

<210> SEQ ID NO 1105
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1105
cggcatgaac gggtatcctg c                                              21
```

<210> SEQ ID NO 1106
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1106
gcggcatgaa cgggtatcct g                                              21

<210> SEQ ID NO 1107
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1107
ggcggcatga acgggtatcc t                                              21

<210> SEQ ID NO 1108
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1108
tggcggcatg aacgggtatc c                                              21

<210> SEQ ID NO 1109
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1109
atggcggcat gaacgggtat c                                              21

<210> SEQ ID NO 1110
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1110
tatggcggca tgaacgggta t                                              21

<210> SEQ ID NO 1111
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1111
gtatggcggc atgaacgggt a                                              21

<210> SEQ ID NO 1112
<211> LENGTH: 21
<212> TYPE: DNA
<213> ORGANISM: Artificial Sequence
<220> FEATURE:
<223> OTHER INFORMATION: AON sequence 5' -> 3'

```
<400> SEQUENCE: 1112
agtatggcgg catgaacggg t                                              21

<210> SEQ ID NO 1113
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1113
cagtatggcg gcatgaacgg g                                              21

<210> SEQ ID NO 1114
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1114
ccagtatggc ggcatgaacg g                                              21

<210> SEQ ID NO 1115
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1115
cccagtatgg cggcatgaac g                                              21

<210> SEQ ID NO 1116
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1116
ccccagtatg gcggcatgaa c                                              21

<210> SEQ ID NO 1117
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1117
gccccagtat ggcggcatga a                                              21

<210> SEQ ID NO 1118
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1118
ggccccagta tggcggcatg a                                              21

<210> SEQ ID NO 1119
```

```
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1119
aggccccagt atggcggcat g                                              21

<210> SEQ ID NO 1120
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1120
caggccccag tatggcggca t                                              21

<210> SEQ ID NO 1121
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1121
ccaggcccca gtatggcggc a                                              21

<210> SEQ ID NO 1122
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1122
cccaggcccc agtatggcgg c                                              21

<210> SEQ ID NO 1123
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1123
gcccaggccc cagtatggcg g                                              21

<210> SEQ ID NO 1124
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1124
agcccaggcc ccagtatggc g                                              21

<210> SEQ ID NO 1125
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1125
```
aagcccaggc cccagtatgg c                                         21

<210> SEQ ID NO 1126
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1126
gaagcccagg ccccagtatg g                                         21

<210> SEQ ID NO 1127
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1127
ggaagcccag gccccagtat g                                         21

<210> SEQ ID NO 1128
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1128
tggaagccca ggccccagta t                                         21

<210> SEQ ID NO 1129
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1129
gtggaagccc aggccccagt a                                         21

<210> SEQ ID NO 1130
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1130
ggtggaagcc caggcccag t                                          21

<210> SEQ ID NO 1131
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1131
aggtggaagc ccaggcccca g                                         21

<210> SEQ ID NO 1132
<211> LENGTH: 21
<212> TYPE: DNA

```
<213> ORGANISM: Artificial Sequence
<220> FEATURE:
<223> OTHER INFORMATION: AON sequence 5' -> 3'

<400> SEQUENCE: 1132
caggtggaag cccaggcccc a                                              21

<210> SEQ ID NO 1133
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1133
acaggtggaa gcccaggccc c                                              21

<210> SEQ ID NO 1134
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1134
cacaggtgga agcccaggcc c                                              21

<210> SEQ ID NO 1135
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1135
gcacaggtgg aagcccaggc c                                              21

<210> SEQ ID NO 1136
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1136
ggcacaggtg gaagcccagg c                                              21

<210> SEQ ID NO 1137
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1137
cggcacaggt ggaagcccag g                                              21

<210> SEQ ID NO 1138
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1138
gcggcacagg tggaagccca g                                              21
```

<210> SEQ ID NO 1139
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1139
agcggcacag gtggaagccc a                                              21

<210> SEQ ID NO 1140
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1140
cagcggcaca ggtggaagcc c                                              21

<210> SEQ ID NO 1141
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1141
ccagcggcac aggtggaagc c                                              21

<210> SEQ ID NO 1142
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1142
cccagcggca caggtggaag c                                              21

<210> SEQ ID NO 1143
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1143
ccccagcggc acaggtggaa g                                              21

<210> SEQ ID NO 1144
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1144
gccccagcgg cacaggtgga a                                              21

<210> SEQ ID NO 1145
<211> LENGTH: 21
<212> TYPE: DNA
<213> ORGANISM: Artificial Sequence
<220> FEATURE:

<223> OTHER INFORMATION: AON sequence 5' -> 3'

<400> SEQUENCE: 1145
agccccagcg gcacaggtgg a                                              21

<210> SEQ ID NO 1146
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1146
tagccccagc ggcacaggtg g                                              21

<210> SEQ ID NO 1147
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1147
gtagccccag cggcacaggt g                                              21

<210> SEQ ID NO 1148
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1148
agtagcccca gcggcacagg t                                              21

<210> SEQ ID NO 1149
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1149
gagtagcccc agcggcacag g                                              21

<210> SEQ ID NO 1150
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1150
ggagtagccc cagcggcaca g                                              21

<210> SEQ ID NO 1151
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1151
aggagtagcc ccagcggcac a                                              21

```
<210> SEQ ID NO 1152
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1152
gaggagtagc cccagcggca c                                              21

<210> SEQ ID NO 1153
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1153
ggaggagtag ccccagcggc a                                              21

<210> SEQ ID NO 1154
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1154
tggaggagta gccccagcgg c                                              21

<210> SEQ ID NO 1155
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1155
gtggaggagt agccccagcg g                                              21

<210> SEQ ID NO 1156
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1156
ggtggaggag tagccccagc g                                              21

<210> SEQ ID NO 1157
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1157
cggtggagga gtagccccag c                                              21

<210> SEQ ID NO 1158
<211> LENGTH: 21
<212> TYPE: DNA
<213> ORGANISM: Artificial Sequence
<220> FEATURE:
<223> OTHER INFORMATION: AON sequence 5' -> 3'
```

<400> SEQUENCE: 1158
gcggtggagg agtagcccca g                                              21

<210> SEQ ID NO 1159
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1159
agcggtggag gagtagcccc a                                              21

<210> SEQ ID NO 1160
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1160
tagcggtgga ggagtagccc c                                              21

<210> SEQ ID NO 1161
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1161
atagcggtgg aggagtagcc c                                              21

<210> SEQ ID NO 1162
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1162
gatagcggtg gaggagtagc c                                              21

<210> SEQ ID NO 1163
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1163
tgatagcggt ggaggagtag c                                              21

<210> SEQ ID NO 1164
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1164
gtgatagcgg tggaggagta g                                              21

<210> SEQ ID NO 1165
<211> LENGTH: 21

-continued

```
<212> TYPE: DNA
<213> ORGANISM: Artificial Sequence
<220> FEATURE:
<223> OTHER INFORMATION: AON sequence 5' -> 3'

<400> SEQUENCE: 1165
ggtgatagcg gtggaggagt a                                              21

<210> SEQ ID NO 1166
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1166
gggtgatagc ggtggaggag t                                              21

<210> SEQ ID NO 1167
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1167
cgggtgatag cggtggagga g                                              21

<210> SEQ ID NO 1168
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1168
gcgggtgata gcggtggagg a                                              21

<210> SEQ ID NO 1169
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1169
ggcgggtgat agcggtggag g                                              21

<210> SEQ ID NO 1170
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1170
tggcgggtga tagcggtgga g                                              21

<210> SEQ ID NO 1171
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1171
```
ctggcgggtg atagcggtgg a                                          21

<210> SEQ ID NO 1172
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1172
cctggcgggt gatagcggtg g                                          21

<210> SEQ ID NO 1173
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1173
acctggcggg tgatagcggt g                                          21

<210> SEQ ID NO 1174
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1174
cacctggcgg gtgatagcgg t                                          21

<210> SEQ ID NO 1175
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1175
ccacctggcg ggtgatagcg g                                          21

<210> SEQ ID NO 1176
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1176
accacctggc gggtgatagc g                                          21

<210> SEQ ID NO 1177
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1177
caccacctgg cgggtgatag c                                          21

<210> SEQ ID NO 1178
<211> LENGTH: 21
<212> TYPE: DNA
<213> ORGANISM: Artificial Sequence -continued
<220> FEATURE:
<223> OTHER INFORMATION: AON sequence 5' -> 3'

<400> SEQUENCE: 1178
ccaccacctg gcgggtgata g					21

<210> SEQ ID NO 1179
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1179
tccaccacct ggcgggtgat a					21

<210> SEQ ID NO 1180
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1180
ctccaccacc tggcgggtga t					21

<210> SEQ ID NO 1181
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1181
tctccaccac ctggcgggtg a					21

<210> SEQ ID NO 1182
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1182
ttctccacca cctggcgggt g					21

<210> SEQ ID NO 1183
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1183
gttctccacc acctggcggg t					21

<210> SEQ ID NO 1184
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1184
tgttctccac cacctggcgg g					21

<210> SEQ ID NO 1185
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1185
atgttctcca ccacctggcg g                                               21

<210> SEQ ID NO 1186
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1186
catgttctcc accacctggc g                                               21

<210> SEQ ID NO 1187
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1187
tcatgttctc caccacctgg c                                               21

<210> SEQ ID NO 1188
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1188
gtcatgttct ccaccacctg g                                               21

<210> SEQ ID NO 1189
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1189
ggtcatgttc tccaccacct g                                               21

<210> SEQ ID NO 1190
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1190
tggtcatgtt ctccaccacc t                                               21

<210> SEQ ID NO 1191
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1191
ctggtcatgt tctccaccac c                                              21

<210> SEQ ID NO 1192
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1192
cctggtcatg ttctccacca c                                              21

<210> SEQ ID NO 1193
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1193
ccctggtcat gttctccacc a                                              21

<210> SEQ ID NO 1194
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1194
gccctggtca tgttctccac c                                              21

<210> SEQ ID NO 1195
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1195
ggccctggtc atgttctcca c                                              21

<210> SEQ ID NO 1196
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1196
gggccctggt catgttctcc a                                              21

<210> SEQ ID NO 1197
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1197
tgggccctgg tcatgttctc c                                              21

<210> SEQ ID NO 1198

```
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1198
gtgggccctg gtcatgttct c                                              21

<210> SEQ ID NO 1199
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1199
agtgggccct ggtcatgttc t                                              21

<210> SEQ ID NO 1200
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1200
aagtgggccc tggtcatgtt c                                              21

<210> SEQ ID NO 1201
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1201
gaagtgggcc ctggtcatgt t                                              21

<210> SEQ ID NO 1202
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1202
ggaagtgggc cctggtcatg t                                              21

<210> SEQ ID NO 1203
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1203
gggaagtggg ccctggtcat g                                              21

<210> SEQ ID NO 1204
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1204
```

```
ggggaagtgg gccctggtca t                                              21

<210> SEQ ID NO 1205
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1205
gggggaagtg ggccctggtc a                                              21

<210> SEQ ID NO 1206
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1206 aggggggaagt gggccctggt c                                             21

<210> SEQ ID NO 1207
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1207 caggggggaag tgggccctgg t                                             21

<210> SEQ ID NO 1208
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1208
ccagggggaa gtgggccctg g                                              21

<210> SEQ ID NO 1209
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1209
accaggggga agtgggccct g                                              21

<210> SEQ ID NO 1210
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1210
caccaggggg aagtgggccc t                                              21

<210> SEQ ID NO 1211
<211> LENGTH: 21
<212> TYPE: DNA
```

```
<213> ORGANISM: Artificial Sequence
<220> FEATURE:
<223> OTHER INFORMATION: AON sequence 5' -> 3'

<400> SEQUENCE: 1211
tcaccagggg gaagtgggcc c                                              21

<210> SEQ ID NO 1212
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1212
ctcaccaggg ggaagtgggc c                                              21

<210> SEQ ID NO 1213
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1213
actcaccagg gggaagtggg c                                              21

<210> SEQ ID NO 1214
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1214
aactcaccag ggggaagtgg g                                              21

<210> SEQ ID NO 1215
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1215
caactcacca gggggaagtg g                                              21

<210> SEQ ID NO 1216
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1216
ccaactcacc aggggggaagt g                                             21

<210> SEQ ID NO 1217
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1217
cccaactcac caggggggaag t                                             21
```

```
<210> SEQ ID NO 1218
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1218
ccccaactca ccaggggaa g                                         21

<210> SEQ ID NO 1219
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1219
accccaactc accaggggga a                                        21

<210> SEQ ID NO 1220
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1220
caccccaact caccagggggg a                                       21

<210> SEQ ID NO 1221
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1221
ccaccccaac tcaccagggg g                                        21

<210> SEQ ID NO 1222
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1222
accaccccaa ctcaccaggg g                                        21

<210> SEQ ID NO 1223
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1223 caccaccccca actcaccagg g                                       21

<210> SEQ ID NO 1224
<211> LENGTH: 21
<212> TYPE: DNA
<213> ORGANISM: Artificial Sequence
<220> FEATURE:
```

<223> OTHER INFORMATION: AON sequence 5' -> 3'

<400> SEQUENCE: 1224
ccaccacccc aactcaccag g                                          21

<210> SEQ ID NO 1225
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1225
gccaccaccc caactcacca g                                          21

<210> SEQ ID NO 1226
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1226
tgccaccacc ccaactcacc a                                          21

<210> SEQ ID NO 1227
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1227
ctgccaccac cccaactcac c                                          21

<210> SEQ ID NO 1228
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1228
cctgccacca ccccaactca c                                          21

<210> SEQ ID NO 1229
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1229
ccctgccacc accccaactc a                                          21

<210> SEQ ID NO 1230
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1230
cccctgccac caccccaact c                                          21

-continued

```
<210> SEQ ID NO 1231
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1231
tcccctgcca ccaccccaac t                                              21

<210> SEQ ID NO 1232
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1232 ctccccctgcc accaccccaa c                                             21

<210> SEQ ID NO 1233
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1233
ggaagcagct ctggggtt                                                  18

<210> SEQ ID NO 1234
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1234
gggaagcagc tctggggt                                                  18

<210> SEQ ID NO 1235
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1235
agggaagcag ctctgggg                                                  18

<210> SEQ ID NO 1236
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1236
aagggaagca gctctggg                                                  18

<210> SEQ ID NO 1237
<211> LENGTH: 18
<212> TYPE: DNA
<213> ORGANISM: Artificial Sequence
<220> FEATURE:
<223> OTHER INFORMATION: AON sequence 5' -> 3'
```

```
<400> SEQUENCE: 1237
gaagggaagc agctctgg                                              18

<210> SEQ ID NO 1238
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1238
ggaagggaag cagctctg                                              18

<210> SEQ ID NO 1239
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1239
tggaagggaa gcagctct                                              18

<210> SEQ ID NO 1240
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1240
ctggaaggga agcagctc                                              18

<210> SEQ ID NO 1241
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1241
tctggaaggg aagcagct                                              18

<210> SEQ ID NO 1242
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1242
atctggaagg gaagcagc                                              18

<210> SEQ ID NO 1243
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1243
catctggaag ggaagcag                                              18

<210> SEQ ID NO 1244
<211> LENGTH: 18
```

```
<212> TYPE: DNA
<213> ORGANISM: Artificial Sequence
<220> FEATURE:
<223> OTHER INFORMATION: AON sequence 5' -> 3'

<400> SEQUENCE: 1244
acatctggaa gggaagca                                                   18

<210> SEQ ID NO 1245
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1245
cacatctgga agggaagc                                                   18

<210> SEQ ID NO 1246
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1246
ccacatctgg aagggaag                                                   18

<210> SEQ ID NO 1247
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1247
accacatctg gaagggaa                                                   18

<210> SEQ ID NO 1248
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1248
gaccacatct ggaaggga                                                   18

<210> SEQ ID NO 1249
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1249
ggaccacatc tggaaggg                                                   18

<210> SEQ ID NO 1250
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1250
```
aggaccacat ctggaagg                                                    18

<210> SEQ ID NO 1251
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1251
caggaccaca tctggaag                                                    18

<210> SEQ ID NO 1252
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1252
gcaggaccac atctggaa                                                    18

<210> SEQ ID NO 1253
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1253
tgcaggacca catctgga                                                    18

<210> SEQ ID NO 1254
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1254
ctgcaggacc acatctgg                                                    18

<210> SEQ ID NO 1255
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1255
gctgcaggac cacatctg                                                    18

<210> SEQ ID NO 1256
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1256
ggctgcagga ccacatct                                                    18

<210> SEQ ID NO 1257
<211> LENGTH: 18
<212> TYPE: DNA
<213> ORGANISM: Artificial Sequence

```
<220> FEATURE:
<223> OTHER INFORMATION: AON sequence 5' -> 3'

<400> SEQUENCE: 1257
cggctgcagg accacatc                                                 18

<210> SEQ ID NO 1258
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1258
tcggctgcag gaccacat                                                 18

<210> SEQ ID NO 1259
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1259
ctcggctgca ggaccaca                                                 18

<210> SEQ ID NO 1260
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1260
gctcggctgc aggaccac                                                 18

<210> SEQ ID NO 1261
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1261
ggctcggctg caggacca                                                 18

<210> SEQ ID NO 1262
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1262
gggctcggct gcaggacc                                                 18

<210> SEQ ID NO 1263
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1263
agggctcggc tgcaggac                                                 18
```

<210> SEQ ID NO 1264
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1264
cagggctcgg ctgcagga                                          18

<210> SEQ ID NO 1265
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1265
gcagggctcg gctgcagg                                          18

<210> SEQ ID NO 1266
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1266
ggcagggctc ggctgcag                                          18

<210> SEQ ID NO 1267
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1267
gggcagggct cggctgca                                          18

<210> SEQ ID NO 1268
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1268
agggcagggc tcggctgc                                          18

<210> SEQ ID NO 1269
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1269
aagggcaggg ctcggctg                                          18

<210> SEQ ID NO 1270
<211> LENGTH: 18
<212> TYPE: DNA
<213> ORGANISM: Artificial Sequence
<220> FEATURE:
<223> OTHER INFORMATION: AON sequence 5' -> 3'

```
<400> SEQUENCE: 1270
taagggcagg gctcggct                                                 18

<210> SEQ ID NO 1271
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1271
ctaagggcag ggctcggc                                                 18

<210> SEQ ID NO 1272
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1272
gctaagggca gggctcgg                                                 18

<210> SEQ ID NO 1273
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1273
agctaagggc agggctcg                                                 18

<210> SEQ ID NO 1274
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1274
cagctaaggg cagggctc                                                 18

<210> SEQ ID NO 1275
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1275
ccagctaagg gcagggct                                                 18

<210> SEQ ID NO 1276
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1276
tccagctaag ggcagggc                                                 18

<210> SEQ ID NO 1277
```

```
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1277
ctccagctaa gggcaggg                                              18

<210> SEQ ID NO 1278
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1278
cctccagcta agggcagg                                              18

<210> SEQ ID NO 1279
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1279
acctccagct aagggcag                                              18

<210> SEQ ID NO 1280
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1280
gacctccagc taagggca                                              18

<210> SEQ ID NO 1281
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1281
cgacctccag ctaagggc                                              18

<210> SEQ ID NO 1282
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1282
tcgacctcca gctaaggg                                              18

<210> SEQ ID NO 1283
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1283
```

-continued gtcgacctcc agctaagg                                            18

<210> SEQ ID NO 1284
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1284
tgtcgacctc cagctaag                                            18

<210> SEQ ID NO 1285
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1285
ctgtcgacct ccagctaa                                            18

<210> SEQ ID NO 1286
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1286
cctgtcgacc tccagcta                                            18

<210> SEQ ID NO 1287
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1287
acctgtcgac ctccagct                                            18

<210> SEQ ID NO 1288
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1288
cacctgtcga cctccagc                                            18

<210> SEQ ID NO 1289
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1289
ccacctgtcg acctccag                                            18

<210> SEQ ID NO 1290
<211> LENGTH: 18
<212> TYPE: DNA

<213> ORGANISM: Artificial Sequence
<220> FEATURE:
<223> OTHER INFORMATION: AON sequence 5' -> 3'

<400> SEQUENCE: 1290
cccacctgtc gacctcca                                                 18

<210> SEQ ID NO 1291
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1291
tcccacctgt cgacctcc                                                 18

<210> SEQ ID NO 1292
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1292
atcccacctg tcgacctc                                                 18

<210> SEQ ID NO 1293
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1293
gatcccacct gtcgacct                                                 18

<210> SEQ ID NO 1294
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1294
ggatcccacc tgtcgacc                                                 18

<210> SEQ ID NO 1295
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1295
aggatcccac ctgtcgac                                                 18

<210> SEQ ID NO 1296
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1296
caggatccca cctgtcga                                                 18

<210> SEQ ID NO 1297
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1297
ccaggatccc acctgtcg                                                 18

<210> SEQ ID NO 1298
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1298
tccaggatcc cacctgtc                                                 18

<210> SEQ ID NO 1299
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1299
atccaggatc ccacctgt                                                 18

<210> SEQ ID NO 1300
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1300
catccaggat cccacctg                                                 18

<210> SEQ ID NO 1301
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1301
acatccagga tcccacct                                                 18

<210> SEQ ID NO 1302
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1302
gacatccagg atcccacc                                                 18

<210> SEQ ID NO 1303
<211> LENGTH: 18
<212> TYPE: DNA
<213> ORGANISM: Artificial Sequence
<220> FEATURE:

```
<223> OTHER INFORMATION: AON sequence 5' -> 3'

<400> SEQUENCE: 1303
agacatccag gatcccac                                                 18

<210> SEQ ID NO 1304
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1304
tagacatcca ggatccca                                                 18

<210> SEQ ID NO 1305
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1305
gtagacatcc aggatccc                                                 18

<210> SEQ ID NO 1306
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1306
tgtagacatc caggatcc                                                 18

<210> SEQ ID NO 1307
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1307
atgtagacat ccaggatc                                                 18

<210> SEQ ID NO 1308
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1308
gatgtagaca tccaggat                                                 18

<210> SEQ ID NO 1309
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1309
agatgtagac atccagga
```

```
<210> SEQ ID NO 1310
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1310
aagatgtaga catccagg                                                 18

<210> SEQ ID NO 1311
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1311
gaagatgtag acatccag                                                 18

<210> SEQ ID NO 1312
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1312
ggaagatgta gacatcca                                                 18

<210> SEQ ID NO 1313
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1313
aggaagatgt agacatcc                                                 18

<210> SEQ ID NO 1314
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1314
caggaagatg tagacatc                                                 18

<210> SEQ ID NO 1315
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1315
ccaggaagat gtagacat                                                 18

<210> SEQ ID NO 1316
<211> LENGTH: 18
<212> TYPE: DNA
<213> ORGANISM: Artificial Sequence
<220> FEATURE:
<223> OTHER INFORMATION: AON sequence 5' -> 3'
```

```
<400> SEQUENCE: 1316
cccaggaaga tgtagaca                                                 18

<210> SEQ ID NO 1317
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1317
gcccaggaag atgtagac                                                 18

<210> SEQ ID NO 1318
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1318
ggcccaggaa gatgtaga                                                 18

<210> SEQ ID NO 1319
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1319
gggcccagga agatgtag                                                 18

<210> SEQ ID NO 1320
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1320
tgggcccagg aagatgta                                                 18

<210> SEQ ID NO 1321
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1321
ctgggcccag gaagatgt                                                 18

<210> SEQ ID NO 1322
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1322
tctgggccca ggaagatg                                                 18

<210> SEQ ID NO 1323
<211> LENGTH: 18
```

```
<212> TYPE: DNA
<213> ORGANISM: Artificial Sequence
<220> FEATURE:
<223> OTHER INFORMATION: AON sequence 5' -> 3'

<400> SEQUENCE: 1323
ctctgggccc aggaagat                                                 18

<210> SEQ ID NO 1324
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1324
gctctgggcc caggaaga                                                 18

<210> SEQ ID NO 1325
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1325
ggctctgggc ccaggaag                                                 18

<210> SEQ ID NO 1326
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1326
gggctctggg cccaggaa                                                 18

<210> SEQ ID NO 1327
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1327
tgggctctgg gcccagga                                                 18

<210> SEQ ID NO 1328
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1328
ttgggctctg ggcccagg                                                 18

<210> SEQ ID NO 1329
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1329
```

-continued cttgggctct gggcccag                                              18

<210> SEQ ID NO 1330
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1330
tcttgggctc tgggccca                                              18

<210> SEQ ID NO 1331
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1331
ctcttgggct ctgggccc                                              18

<210> SEQ ID NO 1332
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1332
gctcttgggc tctgggcc                                              18

<210> SEQ ID NO 1333
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1333
cgctcttggg ctctgggc                                              18

<210> SEQ ID NO 1334
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1334
acgctcttgg gctctggg                                              18

<210> SEQ ID NO 1335
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1335
cacgctcttg ggctctgg                                              18

<210> SEQ ID NO 1336
<211> LENGTH: 18
<212> TYPE: DNA
<213> ORGANISM: Artificial Sequence -continued

```
<220> FEATURE:
<223> OTHER INFORMATION: AON sequence 5' -> 3'

<400> SEQUENCE: 1336
ccacgctctt gggctctg                                                 18

<210> SEQ ID NO 1337
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1337
accacgctct tgggctct                                                 18

<210> SEQ ID NO 1338
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1338
caccacgctc ttgggctc                                                 18

<210> SEQ ID NO 1339
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1339
gcaccacgct cttgggct                                                 18

<210> SEQ ID NO 1340
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1340
tgcaccacgc tcttgggc                                                 18

<210> SEQ ID NO 1341
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1341
ctgcaccacg ctcttggg                                                 18

<210> SEQ ID NO 1342
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1342
gctgcaccac gctcttgg                                                 18
```

<210> SEQ ID NO 1343
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1343
tgctgcacca cgctcttg                                                 18

<210> SEQ ID NO 1344
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1344
ctgctgcacc acgctctt                                                 18

<210> SEQ ID NO 1345
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1345
actgctgcac cacgctct                                                 18

<210> SEQ ID NO 1346
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1346
tactgctgca ccacgctc                                                 18

<210> SEQ ID NO 1347
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1347
gtactgctgc accacgct                                                 18

<210> SEQ ID NO 1348
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1348
ggtactgctg caccacgc                                                 18

<210> SEQ ID NO 1349
<211> LENGTH: 18
<212> TYPE: DNA
<213> ORGANISM: Artificial Sequence
<220> FEATURE:
<223> OTHER INFORMATION: AON sequence 5' -> 3'

```
<400> SEQUENCE: 1349
aggtactgct gcaccacg                                                18

<210> SEQ ID NO 1350
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1350
caggtactgc tgcaccac                                                18

<210> SEQ ID NO 1351
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1351
ccaggtactg ctgcacca                                                18

<210> SEQ ID NO 1352
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1352
tccaggtact gctgcacc                                                18

<210> SEQ ID NO 1353
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1353
gtccaggtac tgctgcac                                                18

<210> SEQ ID NO 1354
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1354
cgtccaggta ctgctgca                                                18

<210> SEQ ID NO 1355
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1355
acgtccaggt actgctgc                                                18

<210> SEQ ID NO 1356
```

```
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1356
aacgtccagg tactgctg                                                 18

<210> SEQ ID NO 1357
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1357
caacgtccag gtactgct                                                 18

<210> SEQ ID NO 1358
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1358
acaacgtcca ggtactgc                                                 18

<210> SEQ ID NO 1359
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1359
cacaacgtcc aggtactg                                                 18

<210> SEQ ID NO 1360
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1360
ccacaacgtc caggtact                                                 18

<210> SEQ ID NO 1361
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1361
cccacaacgt ccaggtac                                                 18

<210> SEQ ID NO 1362
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1362
```
acccacaacg tccaggta                                            18

<210> SEQ ID NO 1363
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1363
tacccacaac gtccaggt                                            18

<210> SEQ ID NO 1364
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1364
ctacccacaa cgtccagg                                            18

<210> SEQ ID NO 1365
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1365
cctacccaca acgtccag                                            18

<210> SEQ ID NO 1366
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1366
ccctacccac aacgtcca                                            18

<210> SEQ ID NO 1367
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1367
gccctaccca caacgtcc                                            18

<210> SEQ ID NO 1368
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1368
ggccctaccc acaacgtc                                            18

<210> SEQ ID NO 1369
<211> LENGTH: 18
<212> TYPE: DNA

```
<213> ORGANISM: Artificial Sequence
<220> FEATURE:
<223> OTHER INFORMATION: AON sequence 5' -> 3'

<400> SEQUENCE: 1369
aggccctacc cacaacgt                                                 18

<210> SEQ ID NO 1370
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1370
caggccctac ccacaacg                                                 18

<210> SEQ ID NO 1371
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1371
gcaggcccta cccacaac                                                 18

<210> SEQ ID NO 1372
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1372
agcaggccct acccacaa                                                 18

<210> SEQ ID NO 1373
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1373
gagcaggccc tacccaca                                                 18

<210> SEQ ID NO 1374
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1374
ggagcaggcc ctacccac                                                 18

<210> SEQ ID NO 1375
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1375
gggagcaggc cctaccca                                                 18
```

<210> SEQ ID NO 1376
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1376
agggagcagg ccctaccc                    18

<210> SEQ ID NO 1377
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1377
cagggagcag gccctacc                    18

<210> SEQ ID NO 1378
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1378
ccagggagca ggccctac                    18

<210> SEQ ID NO 1379
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1379
gccagggagc aggcccta                    18

<210> SEQ ID NO 1380
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1380
ggccagggag caggccct                    18

<210> SEQ ID NO 1381
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1381
cggccaggga gcaggccc                    18

<210> SEQ ID NO 1382
<211> LENGTH: 18
<212> TYPE: DNA
<213> ORGANISM: Artificial Sequence
<220> FEATURE:

<223> OTHER INFORMATION: AON sequence 5' -> 3'

<400> SEQUENCE: 1382
gcggccaggg agcaggcc                                                 18

<210> SEQ ID NO 1383
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1383
cgcggccagg gagcaggc                                                 18

<210> SEQ ID NO 1384
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1384
ccgcggccag ggagcagg                                                 18

<210> SEQ ID NO 1385
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1385
gccgcggcca gggagcag                                                 18

<210> SEQ ID NO 1386
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1386
ggccgcggcc agggagca                                                 18

<210> SEQ ID NO 1387
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1387
gggccgcggc cagggagc                                                 18

<210> SEQ ID NO 1388
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1388
ggggccgcgg ccagggag                                                 18

<210> SEQ ID NO 1389
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1389
gggggccgcg gccaggga                                             18

<210> SEQ ID NO 1390
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1390 cggggccgc ggccaggg                                              18

<210> SEQ ID NO 1391
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1391 gcggggccg cggccagg                                              18

<210> SEQ ID NO 1392
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1392 ggcggggcc gcggccag                                              18

<210> SEQ ID NO 1393
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1393 gggcggggc cgcggcca                                              18

<210> SEQ ID NO 1394
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1394
ggggcggggg ccgcggcc                                             18

<210> SEQ ID NO 1395
<211> LENGTH: 18
<212> TYPE: DNA
<213> ORGANISM: Artificial Sequence
<220> FEATURE:
<223> OTHER INFORMATION: AON sequence 5' -> 3'

```
<400> SEQUENCE: 1395
tggggcgggg gccgcggc                                                 18

<210> SEQ ID NO 1396
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1396
ttggggcggg ggccgcgg                                                 18

<210> SEQ ID NO 1397
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1397
cttggggcgg gggccgcg                                                 18

<210> SEQ ID NO 1398
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1398
ccttggggcg ggggccgc                                                 18

<210> SEQ ID NO 1399
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1399
gccttggggc gggggccg                                                 18

<210> SEQ ID NO 1400
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1400
agccttgggg cggggggcc                                                18

<210> SEQ ID NO 1401
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1401
gagccttggg gcgggggc                                                 18

<210> SEQ ID NO 1402
<211> LENGTH: 18
```

```
<212> TYPE: DNA
<213> ORGANISM: Artificial Sequence
<220> FEATURE:
<223> OTHER INFORMATION: AON sequence 5' -> 3'

<400> SEQUENCE: 1402
ggagccttgg ggcggggg                                              18

<210> SEQ ID NO 1403
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1403
gggagccttg gggcgggg                                              18

<210> SEQ ID NO 1404
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1404
agggagcctt ggggcggg                                              18

<210> SEQ ID NO 1405
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1405
gagggagcct tggggcgg                                              18

<210> SEQ ID NO 1406
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1406
ggagggagcc ttggggcg                                              18

<210> SEQ ID NO 1407
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1407
aggagggagc cttggggc                                              18

<210> SEQ ID NO 1408
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1408
```

```
gaggagggag ccttgggg                                                 18

<210> SEQ ID NO 1409
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1409
ggaggaggga gccttggg                                                 18

<210> SEQ ID NO 1410
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1410
gggaggaggg agccttgg                                                 18

<210> SEQ ID NO 1411
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1411
agggaggagg gagccttg                                                 18

<210> SEQ ID NO 1412
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1412
gagggaggag ggagcctt                                                 18

<210> SEQ ID NO 1413
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1413
ggagggagga gggagcct                                                 18

<210> SEQ ID NO 1414
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1414
gggagggagg agggagcc                                                 18

<210> SEQ ID NO 1415
<211> LENGTH: 18
<212> TYPE: DNA
<213> ORGANISM: Artificial Sequence
```

-continued

```
<220> FEATURE:
<223> OTHER INFORMATION: AON sequence 5' -> 3'

<400> SEQUENCE: 1415
agggagggag gagggagc                                                 18

<210> SEQ ID NO 1416
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1416
gagggaggga ggagggag                                                 18

<210> SEQ ID NO 1417
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1417
tgagggaggg aggaggga                                                 18

<210> SEQ ID NO 1418
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1418
atgagggagg gaggaggg                                                 18

<210> SEQ ID NO 1419
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1419
catgagggag ggaggagg                                                 18

<210> SEQ ID NO 1420
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1420
tcatgaggga gggaggag                                                 18

<210> SEQ ID NO 1421
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1421
ttcatgaggg agggagga                                                 18
```

<210> SEQ ID NO 1422
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1422
cttcatgagg gagggagg                                                 18

<210> SEQ ID NO 1423
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1423
acttcatgag ggagggag                                                 18

<210> SEQ ID NO 1424
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1424
gacttcatga gggaggga                                                 18

<210> SEQ ID NO 1425
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1425
cgacttcatg agggaggg                                                 18

<210> SEQ ID NO 1426
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1426
ccgacttcat gagggagg                                                 18

<210> SEQ ID NO 1427
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1427
gccgacttca tgagggag                                                 18

<210> SEQ ID NO 1428
<211> LENGTH: 18
<212> TYPE: DNA
<213> ORGANISM: Artificial Sequence
<220> FEATURE:
<223> OTHER INFORMATION: AON sequence 5' -> 3'

```
<400> SEQUENCE: 1428
cgccgacttc atgaggga                                                    18

<210> SEQ ID NO 1429
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1429
acgccgactt catgaggg                                                    18

<210> SEQ ID NO 1430
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1430
aacgccgact tcatgagg                                                    18

<210> SEQ ID NO 1431
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1431
caacgccgac ttcatgag                                                    18

<210> SEQ ID NO 1432
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1432
ccaacgccga cttcatga                                                    18

<210> SEQ ID NO 1433
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1433
gccaacgccg acttcatg                                                    18

<210> SEQ ID NO 1434
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1434
ggccaacgcc gacttcat                                                    18

<210> SEQ ID NO 1435
```

```
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1435
aggccaacgc cgacttca                                              18

<210> SEQ ID NO 1436
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1436
caggccaacg ccgacttc                                              18

<210> SEQ ID NO 1437
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1437
gcaggccaac gccgactt                                              18

<210> SEQ ID NO 1438
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1438
tgcaggccaa cgccgact                                              18

<210> SEQ ID NO 1439
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1439
ctgcaggcca acgccgac                                              18

<210> SEQ ID NO 1440
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1440
cctgcaggcc aacgccga                                              18

<210> SEQ ID NO 1441
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1441
```

```
tcctgcaggc caacgccg                                                   18

<210> SEQ ID NO 1442
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1442
atcctgcagg ccaacgcc                                                   18

<210> SEQ ID NO 1443
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1443
tatcctgcag gccaacgc                                                   18

<210> SEQ ID NO 1444
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1444
gtatcctgca ggccaacg                                                   18

<210> SEQ ID NO 1445
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1445
ggtatcctgc aggccaac                                                   18

<210> SEQ ID NO 1446
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1446
gggtatcctg caggccaa                                                   18

<210> SEQ ID NO 1447
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1447
cgggtatcct gcaggcca                                                   18

<210> SEQ ID NO 1448
<211> LENGTH: 18
<212> TYPE: DNA
```

```
<213> ORGANISM: Artificial Sequence
<220> FEATURE:
<223> OTHER INFORMATION: AON sequence 5' -> 3'

<400> SEQUENCE: 1448
acgggtatcc tgcaggcc                                                 18

<210> SEQ ID NO 1449
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1449
aacgggtatc ctgcaggc                                                 18

<210> SEQ ID NO 1450
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1450
gaacgggtat cctgcagg                                                 18

<210> SEQ ID NO 1451
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1451
tgaacgggta tcctgcag                                                 18

<210> SEQ ID NO 1452
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1452
atgaacgggt atcctgca                                                 18

<210> SEQ ID NO 1453
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1453
catgaacggg tatcctgc                                                 18

<210> SEQ ID NO 1454
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1454
gcatgaacgg gtatcctg                                                 18
```

<210> SEQ ID NO 1455
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1455
ggcatgaacg ggtatcct                                                 18

<210> SEQ ID NO 1456
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1456
cggcatgaac gggtatcc                                                 18

<210> SEQ ID NO 1457
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1457
gcggcatgaa cgggtatc                                                 18

<210> SEQ ID NO 1458
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1458
ggcggcatga acgggtat                                                 18

<210> SEQ ID NO 1459
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1459
tggcggcatg aacgggta                                                 18

<210> SEQ ID NO 1460
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1460
atggcggcat gaacgggt                                                 18

<210> SEQ ID NO 1461
<211> LENGTH: 18
<212> TYPE: DNA
<213> ORGANISM: Artificial Sequence
<220> FEATURE:

<223> OTHER INFORMATION: AON sequence 5' -> 3'

<400> SEQUENCE: 1461
tatggcggca tgaacggg                                                    18

<210> SEQ ID NO 1462
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1462
gtatggcggc atgaacgg                                                    18

<210> SEQ ID NO 1463
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1463
agtatggcgg catgaacg                                                    18

<210> SEQ ID NO 1464
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1464
cagtatggcg gcatgaac                                                    18

<210> SEQ ID NO 1465
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1465
ccagtatggc ggcatgaa                                                    18

<210> SEQ ID NO 1466
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1466
cccagtatgg cggcatga                                                    18

<210> SEQ ID NO 1467
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1467
ccccagtatg gcggcatg                                                    18

```
<210> SEQ ID NO 1468
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1468
gccccagtat ggcggcat                                                 18

<210> SEQ ID NO 1469
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1469
ggccccagta tggcggca                                                 18

<210> SEQ ID NO 1470
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1470
aggccccagt atggcggc                                                 18

<210> SEQ ID NO 1471
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1471
caggccccag tatggcgg                                                 18

<210> SEQ ID NO 1472
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1472
ccaggcccca gtatggcg                                                 18

<210> SEQ ID NO 1473
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1473
cccaggcccc agtatggc                                                 18

<210> SEQ ID NO 1474
<211> LENGTH: 18
<212> TYPE: DNA
<213> ORGANISM: Artificial Sequence
<220> FEATURE:
<223> OTHER INFORMATION: AON sequence 5' -> 3'
```

<400> SEQUENCE: 1474
gcccaggccc cagtatgg                                                18

<210> SEQ ID NO 1475
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1475
agcccaggcc ccagtatg                                                18

<210> SEQ ID NO 1476
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1476
aagcccaggc cccagtat                                                18

<210> SEQ ID NO 1477
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1477
gaagcccagg ccccagta                                                18

<210> SEQ ID NO 1478
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1478
ggaagcccag gccccagt                                                18

<210> SEQ ID NO 1479
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1479
tggaagccca ggccccag                                                18

<210> SEQ ID NO 1480
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1480
gtggaagccc aggcccca                                                18

<210> SEQ ID NO 1481
<211> LENGTH: 18

```
<212> TYPE: DNA
<213> ORGANISM: Artificial Sequence
<220> FEATURE:
<223> OTHER INFORMATION: AON sequence 5' -> 3'

<400> SEQUENCE: 1481
ggtggaagcc caggcccc                                               18

<210> SEQ ID NO 1482
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1482
aggtggaagc ccaggccc                                               18

<210> SEQ ID NO 1483
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1483
caggtggaag cccaggcc                                               18

<210> SEQ ID NO 1484
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1484
acaggtggaa gcccaggc                                               18

<210> SEQ ID NO 1485
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1485
cacaggtgga agcccagg                                               18

<210> SEQ ID NO 1486
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1486
gcacaggtgg aagcccag                                               18

<210> SEQ ID NO 1487
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1487
```

```
ggcacaggtg gaagccca                                                 18

<210> SEQ ID NO 1488
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1488
cggcacaggt ggaagccc                                                 18

<210> SEQ ID NO 1489
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1489
gcggcacagg tggaagcc                                                 18

<210> SEQ ID NO 1490
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1490
agcggcacag gtggaagc                                                 18

<210> SEQ ID NO 1491
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1491
cagcggcaca ggtggaag                                                 18

<210> SEQ ID NO 1492
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1492
ccagcggcac aggtggaa                                                 18

<210> SEQ ID NO 1493
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1493
cccagcggca caggtgga                                                 18

<210> SEQ ID NO 1494
<211> LENGTH: 18
<212> TYPE: DNA
<213> ORGANISM: Artificial Sequence
```

```
<220> FEATURE:
<223> OTHER INFORMATION: AON sequence 5' -> 3'

<400> SEQUENCE: 1494
ccccagcggc acaggtgg                                                 18

<210> SEQ ID NO 1495
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1495
gccccagcgg cacaggtg                                                 18

<210> SEQ ID NO 1496
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1496
agccccagcg gcacaggt                                                 18

<210> SEQ ID NO 1497
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1497
tagccccagc ggcacagg                                                 18

<210> SEQ ID NO 1498
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1498
gtagccccag cggcacag                                                 18

<210> SEQ ID NO 1499
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1499
agtagcccca gcggcaca                                                 18

<210> SEQ ID NO 1500
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1500
gagtagcccc agcggcac                                                 18
```

```
<210> SEQ ID NO 1501
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1501
ggagtagccc cagcggca                                                 18

<210> SEQ ID NO 1502
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1502
aggagtagcc ccagcggc                                                 18

<210> SEQ ID NO 1503
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1503
gaggagtagc cccagcgg                                                 18

<210> SEQ ID NO 1504
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1504
ggaggagtag ccccagcg                                                 18

<210> SEQ ID NO 1505
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1505
tggaggagta gccccagc                                                 18

<210> SEQ ID NO 1506
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1506
gtggaggagt agccccag                                                 18

<210> SEQ ID NO 1507
<211> LENGTH: 18
<212> TYPE: DNA
<213> ORGANISM: Artificial Sequence
<220> FEATURE:
<223> OTHER INFORMATION: AON sequence 5' -> 3'
```

```
<400> SEQUENCE: 1507
ggtggaggag tagcccca                                             18

<210> SEQ ID NO 1508
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1508
cggtggagga gtagcccc                                             18

<210> SEQ ID NO 1509
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1509
gcggtggagg agtagccc                                             18

<210> SEQ ID NO 1510
<211> LENGTH: 36
<212> TYPE: DNA
<213> ORGANISM: Artificial Sequence
<220> FEATURE:
<223> OTHER INFORMATION: AON sequence 5' -> 3'

<400> SEQUENCE: 1510
agcggtggag gagtagccag cggtggagga gtagcc                         36

<210> SEQ ID NO 1511
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1511
tagcggtgga ggagtagc                                             18

<210> SEQ ID NO 1512
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1512
atagcggtgg aggagtag                                             18

<210> SEQ ID NO 1513
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1513
gatagcggtg gaggagta                                             18

<210> SEQ ID NO 1514
```

```
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1514
tgatagcggt ggaggagt                                                    18

<210> SEQ ID NO 1515
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1515
gtgatagcgg tggaggag                                                    18

<210> SEQ ID NO 1516
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1516
ggtgatagcg gtggagga                                                    18

<210> SEQ ID NO 1517
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1517
gggtgatagc ggtggagg                                                    18

<210> SEQ ID NO 1518
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1518
cgggtgatag cggtggag                                                    18

<210> SEQ ID NO 1519
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1519
gcgggtgata gcggtgga                                                    18

<210> SEQ ID NO 1520
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1520
```
ggcgggtgat agcggtgg                                                    18

<210> SEQ ID NO 1521
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1521
tggcgggtga tagcggtg                                                    18

<210> SEQ ID NO 1522
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1522
ctggcgggtg atagcggt                                                    18

<210> SEQ ID NO 1523
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1523
cctggcgggt gatagcgg                                                    18

<210> SEQ ID NO 1524
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1524
acctggcggg tgatagcg                                                    18

<210> SEQ ID NO 1525
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1525
cacctggcgg gtgatagc                                                    18

<210> SEQ ID NO 1526
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1526
ccacctggcg ggtgatag                                                    18

<210> SEQ ID NO 1527
<211> LENGTH: 18
<212> TYPE: DNA

```
<213> ORGANISM: Artificial Sequence
<220> FEATURE:
<223> OTHER INFORMATION: AON sequence 5' -> 3'

<400> SEQUENCE: 1527
accacctggc gggtgata                                               18

<210> SEQ ID NO 1528
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1528
caccacctgg cgggtgat                                               18

<210> SEQ ID NO 1529
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1529
ccaccacctg gcgggtga                                               18

<210> SEQ ID NO 1530
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1530
tccaccacct ggcgggtg                                               18

<210> SEQ ID NO 1531
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1531
ctccaccacc tggcgggt                                               18

<210> SEQ ID NO 1532
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1532
tctccaccac ctggcggg                                               18

<210> SEQ ID NO 1533
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1533
ttctccacca cctggcgg                                               18
```

```
<210> SEQ ID NO 1534
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1534
gttctccacc acctggcg                                                 18

<210> SEQ ID NO 1535
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1535
tgttctccac cacctggc                                                 18

<210> SEQ ID NO 1536
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1536
atgttctcca ccacctgg                                                 18

<210> SEQ ID NO 1537
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1537
catgttctcc accacctg                                                 18

<210> SEQ ID NO 1538
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1538
tcatgttctc caccacct                                                 18

<210> SEQ ID NO 1539
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1539
gtcatgttct ccaccacc                                                 18

<210> SEQ ID NO 1540
<211> LENGTH: 18
<212> TYPE: DNA
<213> ORGANISM: Artificial Sequence
<220> FEATURE:
```

<223> OTHER INFORMATION: AON sequence 5' -> 3'

<400> SEQUENCE: 1540
ggtcatgttc tccaccac                                              18

<210> SEQ ID NO 1541
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1541
tggtcatgtt ctccacca                                              18

<210> SEQ ID NO 1542
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1542
ctggtcatgt tctccacc                                              18

<210> SEQ ID NO 1543
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1543
cctggtcatg ttctccac                                              18

<210> SEQ ID NO 1544
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1544
ccctggtcat gttctcca                                              18

<210> SEQ ID NO 1545
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1545
gccctggtca tgttctcc                                              18

<210> SEQ ID NO 1546
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1546
ggccctggtc atgttctc                                              18

```
<210> SEQ ID NO 1547
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1547
gggccctggt catgttct                                              18

<210> SEQ ID NO 1548
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1548
tgggccctgg tcatgttc                                              18

<210> SEQ ID NO 1549
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1549
gtgggccctg gtcatgtt                                              18

<210> SEQ ID NO 1550
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1550
agtgggccct ggtcatgt                                              18

<210> SEQ ID NO 1551
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1551
aagtgggccc tggtcatg                                              18

<210> SEQ ID NO 1552
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1552
gaagtgggcc ctggtcat                                              18

<210> SEQ ID NO 1553
<211> LENGTH: 18
<212> TYPE: DNA
<213> ORGANISM: Artificial Sequence
<220> FEATURE:
<223> OTHER INFORMATION: AON sequence 5' -> 3'
```

```
<400> SEQUENCE: 1553
ggaagtgggc cctggtca                                                 18

<210> SEQ ID NO 1554
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1554
gggaagtggg ccctggtc                                                 18

<210> SEQ ID NO 1555
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1555
ggggaagtgg gccctggt                                                 18

<210> SEQ ID NO 1556
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1556
gggggaagtg ggccctgg                                                 18

<210> SEQ ID NO 1557
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1557
agggggaagt gggccctg                                                 18

<210> SEQ ID NO 1558
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1558
cagggggaag tgggccct                                                 18

<210> SEQ ID NO 1559
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1559
ccagggggaa gtgggccc                                                 18

<210> SEQ ID NO 1560
<211> LENGTH: 18
```

```
<212> TYPE: DNA
<213> ORGANISM: Artificial Sequence
<220> FEATURE:
<223> OTHER INFORMATION: AON sequence 5' -> 3'

<400> SEQUENCE: 1560
accaggggga agtgggcc                                                 18

<210> SEQ ID NO 1561
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1561
caccaggggg aagtgggc                                                 18

<210> SEQ ID NO 1562
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1562
tcaccagggg gaagtggg                                                 18

<210> SEQ ID NO 1563
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1563
ctcaccaggg ggaagtgg                                                 18

<210> SEQ ID NO 1564
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1564
actcaccagg gggaagtg                                                 18

<210> SEQ ID NO 1565
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1565
aactcaccag ggggaagt                                                 18

<210> SEQ ID NO 1566
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1566
```
caactcacca gggggaag                                          18

<210> SEQ ID NO 1567
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1567
ccaactcacc aggggaa                                           18

<210> SEQ ID NO 1568
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1568
cccaactcac caggggga                                          18

<210> SEQ ID NO 1569
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1569
ccccaactca ccaggggg                                          18

<210> SEQ ID NO 1570
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1570
accccaactc accagggg                                          18

<210> SEQ ID NO 1571
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1571
caccccaact caccaggg                                          18

<210> SEQ ID NO 1572
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1572
ccaccccaac tcaccagg                                          18

<210> SEQ ID NO 1573
<211> LENGTH: 18
<212> TYPE: DNA
<213> ORGANISM: Artificial Sequence

```
<220> FEATURE:
<223> OTHER INFORMATION: AON sequence 5' -> 3'

<400> SEQUENCE: 1573
accaccccaa ctcaccag                                                 18

<210> SEQ ID NO 1574
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1574
caccacccca actcacca                                                 18

<210> SEQ ID NO 1575
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1575
ccaccacccc aactcacc                                                 18

<210> SEQ ID NO 1576
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1576
gccaccaccc caactcac                                                 18

<210> SEQ ID NO 1577
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1577
tgccaccacc ccaactca                                                 18

<210> SEQ ID NO 1578
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1578
ctgccaccac cccaactc                                                 18

<210> SEQ ID NO 1579
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1579
cctgccacca ccccaact                                                 18
```

<210> SEQ ID NO 1580
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1580
ccctgccacc accccaac                                                 18

<210> SEQ ID NO 1581
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1581 ccctgccac caccccaa                                                  18

<210> SEQ ID NO 1582
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1582 tccctgcca ccacccca                                                  18

<210> SEQ ID NO 1583
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1583 ctccctgcc accaccc                                                   18

<210> SEQ ID NO 1584
<211> LENGTH: 368
<212> TYPE: DNA
<213> ORGANISM: Artificial Sequence
<220> FEATURE:
<223> OTHER INFORMATION: sequence of region (5'-> 3')

<400> SEQUENCE: 1584
aaccccagag ctgcttccct tccagatgtg gtcctgcagc cgagccctgc ccttagctgg    60
aggtcgacag gtgggatcct ggatgtctac atcttcctgg gcccagagcc caagagcgtg   120
gtgcagcagt acctggacgt tgtgggtagg gcctgctccc tggccgcggc ccccgcccca   180
aggctccctc ctccctccct catgaagtcg gcgttggcct gcaggatacc cgttcatgcc   240
gccatactgg ggcctgggct tccacctgtg ccgctggggc tactcctcca ccgctatcac   300
ccgccaggtg gtggagaaca tgaccagggc ccacttcccc ctggtgagtt ggggtggtgg   360
caggggag                                                            368

<210> SEQ ID NO 1585
<211> LENGTH: 74
<212> TYPE: DNA
<213> ORGANISM: Artificial Sequence
<220> FEATURE:
<223> OTHER INFORMATION: sequence of region (5'-> 3')

<400> SEQUENCE: 1585 aacccccagag ctgcttccct tccagatgtg gtcctgcagc cgagccctgc ccttagctgg    60
aggtcgacag gtgg                                                      74

<210> SEQ ID NO 1586
<211> LENGTH: 74
<212> TYPE: DNA
<213> ORGANISM: Artificial Sequence
<220> FEATURE:
<223> OTHER INFORMATION: sequence of region (5'-> 3')

<400> SEQUENCE: 1586
gatcctggat gtctacatct tcctgggccc agagcccaag agcgtggtgc agcagtacct    60
ggacgttgtg ggta                                                      74

<210> SEQ ID NO 1587
<211> LENGTH: 74
<212> TYPE: DNA
<213> ORGANISM: Artificial Sequence
<220> FEATURE:
<223> OTHER INFORMATION: sequence of region (5'-> 3')

<400> SEQUENCE: 1587
gggcctgctc cctggccgcg gccccccgccc caaggctccc tcctccctcc ctcatgaagt    60
cggcgttggc ctgc                                                      74

<210> SEQ ID NO 1588
<211> LENGTH: 74
<212> TYPE: DNA
<213> ORGANISM: Artificial Sequence
<220> FEATURE:
<223> OTHER INFORMATION: sequence of region (5'-> 3')

<400> SEQUENCE: 1588
aggatacccg ttcatgccgc catactgggg cctgggcttc cacctgtgcc gctggggcta    60
ctcctccacc gcta                                                      74

<210> SEQ ID NO 1589
<211> LENGTH: 72
<212> TYPE: DNA
<213> ORGANISM: Artificial Sequence
<220> FEATURE:
<223> OTHER INFORMATION: sequence of region (5'-> 3')

<400> SEQUENCE: 1589
tcacccgcca ggtggtggag aacatgacca gggcccactt cccccctggtg agttggggtg    60 gtggcagggg ag                                                        72

<210> SEQ ID NO 1590
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1590
tcagtcaagt atctggaaag tacga                                          25

<210> SEQ ID NO 1591
<211> LENGTH: 21
<212> TYPE: DNA

```
<213> ORGANISM: Artificial Sequence
<220> FEATURE:
<223> OTHER INFORMATION: AON sequence 5' -> 3'

<400> SEQUENCE: 1591
agtcaagtat ctggaaagta c                                              21

<210> SEQ ID NO 1592
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1592
ggaagtcccg gaagccaacc ttgtt                                          25

<210> SEQ ID NO 1593
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1593
tgactctgcc cagagtgagg a                                              21

<210> SEQ ID NO 1594
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1594
agctttctgg gatgaggcag aggct                                          25
```